(12) United States Patent
Hanaoka et al.

(10) Patent No.: US 7,671,226 B2
(45) Date of Patent: Mar. 2, 2010

(54) TRANSITION METAL COMPLEX, CATALYST FOR OLEFIN POLYMERIZATION, AND PROCESS FOR PRODUCING OLEFIN POLYMER WITH THE SAME

(75) Inventors: Hidenori Hanaoka, Suita (JP); Eiji Yoshikawa, Ibaraki (JP); Yuka Imamoto, Kitakatsuragi-gun (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 12/232,229

(22) Filed: Sep. 12, 2008

(65) Prior Publication Data

US 2009/0054607 A1    Feb. 26, 2009

Related U.S. Application Data

(62) Division of application No. 10/489,346, filed as application No. PCT/JP02/09314 on Sep. 12, 2002, now Pat. No. 7,439,379.

(30) Foreign Application Priority Data

| Sep. 14, 2001 | (JP) | ............................. 2001-279524 |
| Nov. 2, 2001 | (JP) | ............................. 2001-337581 |
| Nov. 2, 2001 | (JP) | ............................. 2001-337582 |
| Nov. 20, 2001 | (JP) | ............................. 2001-354234 |
| Nov. 30, 2001 | (JP) | ............................. 2001-366248 |
| Dec. 3, 2001 | (JP) | ............................. 2001-368236 |

(51) Int. Cl.
  *C07F 17/00* (2006.01)
  *B01J 31/22* (2006.01)
  *C08F 4/642* (2006.01)
  *C08F 4/6592* (2006.01)

(52) U.S. Cl. ............................. 556/53; 556/13; 556/32; 502/103; 502/155; 526/133; 526/134; 526/160; 526/161; 526/165; 526/943

(58) Field of Classification Search ................... 556/13, 556/32, 53; 502/103, 155; 526/133, 134, 526/160, 161, 165, 943
See application file for complete search history.

(56) References Cited

U.S. PATENT DOCUMENTS

| 5,621,126 A | 4/1997 | Canich et al. |
| 5,637,660 A | 6/1997 | Nagy et al. |
| 6,066,704 A | 5/2000 | Katayama et al. |
| 6,090,961 A | 7/2000 | Hanaoka et al. |
| 6,329,478 B1 | 12/2001 | Katayama et al. |
| 6,548,686 B2 | 4/2003 | Nabika et al. |
| 6,872,843 B2 | 3/2005 | Schottek et al. |

FOREIGN PATENT DOCUMENTS

| EP | 955304 | 11/1999 |
| JP | 2535249 | 6/1996 |
| JP | 9-87313 | 3/1997 |
| JP | 2000-38409 | 2/2000 |

OTHER PUBLICATIONS

Michinori Oki et al., "Isolation and Relative Reactivities in Chromium (VI) Oxide Oxidation of the Rotamers of 9-(2-Formyl-1-Naphthyl)Fluorene and Related Alcohols", Chemistry Letters, pp. 649-652, 1981.
Ryo Saito et al., "Reactivities of Stable Rotamers. XI. Rotamer Distributions and Some Addition Reactions to the Carbonyl in 9-[2-(Substituted carbonyl)-1-naphthyl]fluorene Rotamers", Bull. Chem. Soc. Jpn., 55, pp. 3273-3276, 1982.
Ronald N. Warrener et al., "Photodimers of Isobenzofuran: a Novel Application of Lanthanide Induced Shift Spectroscopy to Determine Stereochemistry", J. Chem. Soc., Chem. Commun., pp. 1195-1197, 1982.
Michael R. Buchmeiser et al., "Living Polymerization of Novel Conjugatively Spaced Ferrocenylacetylenes", Macromolecules, 31, pp. 3175-3183, 1998.
Robert W. Baker et al., "Central to axial chirality transfer via double bond migration: asymmetric synthesis and determination of the absolute configuration of axially chiral 1-(3'-indenyl)naphthalenes", Chem. Commun., pp. 2571-2572, 1996.

(Continued)

*Primary Examiner*—Caixia Lu
(74) *Attorney, Agent, or Firm*—Wenderoth, Lind & Ponack, LLP.

(57) ABSTRACT

The present invention relates to a transition metal complex represented by the formula (I):

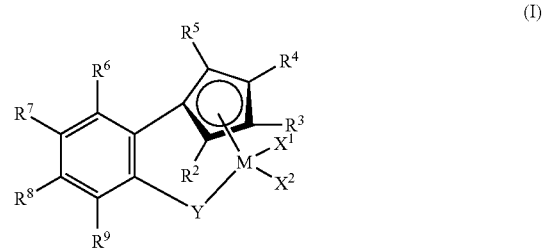

(I)

wherein M represents a Group 4 transition metal;
—Y— represents
  (a): —$C(R^1)(R^{20})$-A-,
  (b): —$C(R^1)(R^{20})$-$A^1(R^{30})$—,
  (c): —$C(R^1)$=$A^1$-, or
  (d): —$C(R^1)$=$A^1$-$A^2$-$R^{30}$;
A represents a Group 16 element and $A^1$ and $A^2$ each represents a Group 15 element;
$R^1$ to $R^9$, $R^{20}$, and $R^{30}$ are the same or different and each represents an optionally substituted hydrocarbon group, etc.; and $X^1$ and $X^2$ are the same or different and each represents a hydrogen atom, a halogen atom, an optionally substituted $C_{1-10}$ alkyl group, etc., and an intermediate product thereof, and a catalyst for olefin polymerization which comprises said transition metal complex as a component.

18 Claims, No Drawings

OTHER PUBLICATIONS

Michinori Oki et al., "Reactivities of Stable Rotamers. XVIII. Reactions of 9-[2-(1-Hydroxyethyl)-1-naphthyl] fluorene Rotamers with Sulfuric Acid and Thionyl Chloride", Bull. Chem. Soc. Jpn., 60, pp. 223-228, 1987.

Hideaki Hagihara et al., "Living Polymerization of Propene and 1-Hexene with the [$t$-BuNSiMe$_2$Flu]TiMe$_2$/ B(C$_6$F$_5$)3 Catalyst", Macromolecules, 31, pp. 3184-3188, 1998.

Stanley J. Cristol et al., "Bridged Polycyclic Compounds. LXXVIII. Reaction of Chromyl Chloride with Cyclopropanes", J. Org. Chem., vol. 39, No. 6, pp. 829-831, 1974.

Ronald N. Warrener et al., "The Photochemistry of Isobenzofuran. I Structure of the Dimers Resulting from Ultraviolet Irradiation of Isobenzofuran in Acetone and Ether Solution", Aust. J. Chem., 46, pp. 1515-1534, 1993.

R. W. Baker et al., "Enantiospecific synthesis of a planar chiral bidentate indenyl-alkoxide complex of zirconium using an axially chiral indene ligand", Chemical Communications, No. 15, pp. 1405-1406, 1999.

Dietmar Kuck et al., "*trifuso*-Centrotetraindan—Two Syntheses of a New Centropolyindan", Chem. Ber., 125, pp. 1461-1469, 1992.

Robert W. Baker et al., "Asymmetric Synthesis of Axially Chiral 1-(2'-Methyl-3'-indenyl)naphthalenes *via* Prototropic Rearrangements of Stable Rotamers of 1-(2'-Methyl-1'-indenyl)naphthalenes", Tetrahedron Letters, 39, pp. 6573-6576, 1998.

Thomas M. Bare et al., "Synthesis and Activity of Spiroisoindolines as Novel Noncompetitive NMDA Antagonists", Bioorg. Med. Chem. Lett., vol. 3, No. 1, pp. 55-60, 1993.

Ryo Saito et al., "Reactivities of Stable Rotamers. X. Reactions of 9-(2-Formyl-1-naphthyl)fluorene Rotamers and Related Compounds", Bull. Chem. Soc. Jpn., 55, pp. 3267-3272, 1982.

Yoriko Sonoda et al., "Reactivities of Stable Rotamers. XXVI. Some Bimolecular Elimination Reactions of 9-(2-Substituted 1-naphthyl)fluorene Rotamers", Bull. Chem. Soc. Jpn., 62, pp. 621-623, 1989.

Wang et al., "Cyclopentadienyl vs Indenyl Substituents. Organolanthanide Complexes and Biscarborane Compounds Derived from a Versatile Ligand, Me2Si(C9H7)(C2B10H11)", Organometallics, 18, 4478-4487, 1999.

Schock et al., "Organometallic Thermochemistry. Metal Hydrocarbyl, Hydride, Halide, Carbonyl, Amide, and Alkoxide Bond Enthalpy Relationships and Their Implications in Pentamethylcyclopentadienyl and Cyclopentadienyl Complexes of Zirconium and Hafnium", J. Am. Chem. Soc., 110, 7701-7715, 1998.

International Search Report issued in PCT/JP02/09314, mailed Nov. 26, 2002.

Translation of the International Preliminary Examination Report issued in PCT/JP02/09314, dated Oct. 20, 2003.

TRANSITION METAL COMPLEX, CATALYST FOR OLEFIN POLYMERIZATION, AND PROCESS FOR PRODUCING OLEFIN POLYMER WITH THE SAME

This application is a Divisional Application of U.S. Ser. No. 10/489,346, filed Mar. 12, 2004, now U.S. Pat. No. 7,439,379 which is a 371 Application of PCT/JP02/09314, filed Sep. 12, 2002.

TECHNICAL FIELD

The present invention relates to a transition metal complex and a catalyst for olefin polymerization comprising said complex, and to a process for production of olefin polymer using the same.

BACKGROUND ART

As a half-metallocene catalyst for olefin polymerization, dimethylsilyl(tetramethylcyclopentadienyl)(3-tert-butyl-5-methyl-2-phenoxy)titanium dichloride (JP-A 3-163088) and dimethylsilyl(tetramethylcyclopentadienyl)(tert-butylamido)titanium dichloride (JP-A 9-87313) have been respectively disclosed. However, production processes of these transition metal complexes require use of silicon compounds as a key intermediate, which is sensitive to moisture and difficult to be handled. Therefore, a catalyst that can be handled more easily and can afford various olefin polymers has been desired.

DISCLOSURE OF INVENTION

According to the present invention, a transition metal complex can be obtained using a ligand intermediate that can be produced and handled more easily, without using a silicon compound that is sensitive to moisture and difficult to be handled as a key intermediate, and a catalyst capable of producing various olefin polymers can be obtained using said transition metal complex as a catalyst component.

Namely, the present invention provides the following:

1. the formula (I):

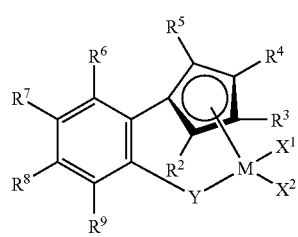

(I)

wherein M represents a Group 4 transition metal;
—Y— represents
(a): —C($R^1$)($R^{20}$)-A-,
(b): —C($R^1$)($R^{20}$)-$A^1$($R^{30}$)—,
(c): —C($R^1$)=$A^1$-, or
(d):

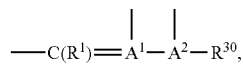

wherein $A^1$ and $A^2$ coordinate to M;
A represents a Group 16 element, $A^1$ and $A^2$ each represent a Group 15 element;
$R^1$ and $R^{20}$ are the same or different and each represents a hydrogen atom,
an optionally substituted $C_{1-10}$ alkyl group,
an optionally substituted $C_{6-20}$ aryl group or
an optionally substituted $C_{7-20}$ aralkyl group;
$R^{30}$ represents a hydrogen atom,
an optionally substituted $C_{1-10}$ alkyl group,
an optionally substituted $C_{6-20}$ aryl group,
an optionally substituted $C_{7-20}$ aralkyl group or
a silyl group optionally substituted with optionally substituted $C_{1-20}$ hydrocarbon(s);
$R^2$, $R^3$, $R^4$ and $R^5$ are the same or different and each represents a hydrogen atom,
an optionally substituted $C_{1-10}$ alkyl group,
an optionally substituted $C_{1-10}$ alkoxy group,
an optionally substituted $C_{6-20}$ aryl group,
an optionally substituted $C_{6-20}$ aryloxy group,
an optionally substituted $C_{7-20}$ aralkyl group,
an optionally substituted $C_{7-20}$ aralkyloxy group,
a silyl group substituted with optionally substituted $C_{1-20}$ hydrocarbon group(s), or
a $C_{1-20}$ hydrocarbon-substituted amino group;
$R^6$, $R^7$, $R^8$ and $R^9$ are the same or different and each represents a hydrogen atom, a halogen atom, an optionally substituted $C_{1-10}$ alkyl group,
an optionally substituted $C_{1-10}$ alkoxy group,
an optionally substituted $C_{6-20}$ aryl group,
an optionally substituted $C_{6-20}$ aryloxy group,
an optionally substituted $C_{7-20}$ aralkyl group,
an optionally substituted $C_{7-20}$ aralkyloxy group,
a silyl group substituted with optionally substituted $C_{1-20}$ hydrocarbon group(s), or
a $C_{1-20}$ hydrocarbon-substituted amino group; and
$X^1$ and $X^2$ are the same or different and each represents a hydrogen atom, a halogen atom,
an optionally substituted $Cl_{1-10}$ alkyl group,
an optionally substituted $C_{1-10}$ alkoxy group,
an optionally substituted $C_{6-20}$ aryl group,
an optionally substituted $C_{6-20}$ aryloxy group, an optionally substituted $C_{7-20}$ aralkyl group, an optionally substituted $C_{7-20}$ aralkyloxy group or a $C_{1-20}$ hydrocarbon-substituted amino group, or $X^1$ and $X^2$, $R^1$ and $R^{20}$, the adjacent $R^2$, $R^3$, $R^4$ and $R^5$ or the adjacent $R^6$, $R^7$, $R^8$ and $R^9$ may be linked to each other to form a ring;

provided that when —Y— represents (a), there is no case that both $R^1$ and $R^{20}$ represent hydrogen atoms and $R^2$, $R^3$, $R^4$ and $R^5$ are taken together with the cyclopentadiene ring to form a 2-methylinden-1-yl group;

2. a catalyst for olefin polymerization comprising the above-mentioned transition metal complex in combination with the following compound (A):

wherein (A) represents at least one compound selected from the following compounds (A1) to (A3):

(A1): an organic aluminum compound represented by the formula $E1_aAl(Z)_{(3-a)}$, (A2): cyclic aluminoxane having the structure represented by the formula $\{-Al(E2)-O-\}_b$, and (A3): linear aluminoxane having the structure represented by the formula $E3\{-Al(E3)-O-\}_cAl(E3)_2$, wherein E1 to E3 are the same or different and each represents a C1-8 hydrocarbon group;

Z are the same or different and each represents a hydrogen atom or a halogen atom; and a is 1, 2 or 3, b is an integer of not less than 2, and c is an integer of not less than 1;

3. a catalyst for olefin polymerization comprising the above transition metal complex in combination with the compound (A) and further (B), wherein (B) represents at least one compound selected from the following compounds (B1) to (B3):

(B1): a boron compound represented by the formula $BQ_1Q_2Q_3$, (B2): a boron compound represented by the formula $Z^+(BQ_1Q_2Q_3Q_4)^-$, and (B3): a boron compound represented by the formula $(L-H)^+(BQ_1Q_2Q_3Q_4)^-$, wherein B is a boron atom in a trivalent valence state;

$Q_1$ to $Q_4$ are the same or different and each represents a halogen atom, a $C_{1-20}$ hydrocarbon group, a $C_{1-20}$ halogenated hydrocarbon group, a silyl group substituted with $C_{1-20}$ hydrocarbon group(s), a $C_{1-20}$ alkoxy group, or an amino group substituted with two $C_{2-20}$ hydrocarbon groups;

L-H represents a Brønsted acid; and

Z are the same or different and each represents an inorganic or organic cation (for example, a hydrogen atom, a halogen atom or a trityl cation);

4. a process for producing an olefin polymer, comprising polymerizing olefin using the above-mentioned catalyst for olefin polymerization;

5. a substituted cyclopentadiene ligand represented by the formula (II):

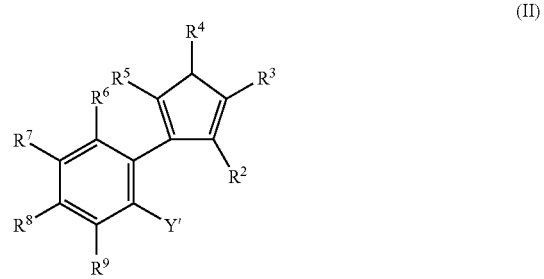

wherein —Y' represents (a'): $-C(R^1)(R^{20})-A-H$,
(b'): $-C(R^1)(R^{20})-A^1(R^{30})-H$,
(c'): $-C(R^1)=A^1-H$
(d'):

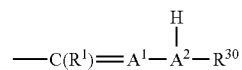

(e): $-C(R^1)=A^1-R^{30}$
(f): $-CH=A^1-OR^+$, or
(g): $-CN$; and
$R^1$, $R^2$, $R^3$, $R^4$, $R^5$, $R^6$, $R^7$, $R^8$, $R^9$, $R^{20}$, $R^{30}$, A, $A^1$ and $A^2$ have the same meanings as defined above;

provided that:

1) when —Y' represents (a'), neither $R^2$ and $R^3$ nor $R^4$ and $R^5$ are taken together with the cyclopentadiene ring to form a fluorene ring or an indenyl ring; and 2) when —Y' represents (g), neither $R^2$ and $R^3$ nor $R^4$ and $R^5$ are taken together with the cyclopentadiene ring to form a fluorene ring, and the compound represented by the formula (II) is not 2-(4-methoxyinden-1-yl)benzonitrile; furthermore, regarding the double bonds of the cyclopentadiene ring, their positions are not limited to the positions as depicted in the formula and are optional or the cyclopentadiene ring represents a mixture of isomers having the double bonds in any positions, or an intermediate product thereof;

6. a process for producing a transition metal complex represented by the formula (I), which comprises reacting a substituted cyclopentadiene represented by the formula (II), wherein —Y' represents any of (a') to (d') with a transition metal compound represented by the formula (III):

$$MX^1X^2X^3X^4 \qquad (III)$$

wherein M represents a Group 4 transition metal; and $X^1$, $X^2$, $X^3$ and $X^4$ are the same or different and each represents a hydrogen atom, a halogen atom, a $C_{1-10}$ alkyl group, a $C_{1-10}$ alkoxy group, a $C_{6-20}$ aryl group, a $C_{6-20}$ aryloxy group, a $C_{7-20}$ aralkyl group, a $C_{7-20}$ aralkyloxy group, or a $C_{1-20}$ hydrocarbon-substituted amino group;

7. a carbonyl compound represented by the formula (1):

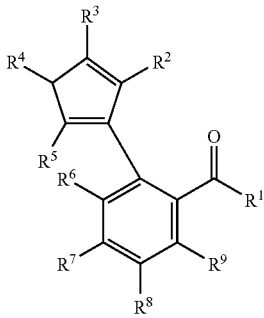

(1)

wherein $R^1$ represents a hydrogen atom, an optionally substituted $C_{1-10}$ alkyl group, an optionally substituted $C_{6-20}$ aryl group, or an optionally substituted $C_{7-20}$ aralkyl group;

$R^2$, $R^3$, $R^4$ and $R^5$ are the same or different and each independently represents a hydrogen atom, an optionally substituted $C_{1-10}$ alkyl group, an optionally substituted $C_{1-10}$ alkoxy group, an optionally substituted $C_{6-20}$ aryl group, an optionally substituted $C_{6-20}$ aryloxy group, an optionally substituted $C_{7-20}$ aralkyl group, an optionally substituted $C_{7-20}$ aralkyloxy group, a silyl group substituted with optionally substituted $C_{1-20}$ hydrocarbon group(s), or a $C_{1-20}$ hydrocarbon-substituted amino group; and $R^6$, $R^7$, $R^8$ and $R^9$ are the same or different and each independently represents a hydrogen atom, a halogen atom, an optionally substituted $C_{1-10}$ alkyl group, an optionally substituted $C_{1-10}$ alkoxy group, an optionally substituted $C_{6-20}$ aryl group, an optionally substituted $C_{6-20}$ aryloxy group, an optionally substituted $C_{7-20}$ aralkyl group, an optionally substituted $C_{7-20}$ aralkyloxy group, a silyl group substituted with optionally substituted $C_{1-20}$ hydrocarbon group(s) or a $C_{1-20}$ hydrocarbon-substituted amino group, or the adjacent $R^2$, $R^3$, $R^4$ and $R^5$ and the adjacent $R^6$, $R^7$, $R^8$ and $R^9$ link with each other to form a benzene ring or a cycloalkylene ring;

provided that 1) the positions of the double bonds in the cyclopentadiene ring are optional or the cyclopentadiene ring represents a mixture of compounds having double bonds at optional positions; and 2) neither $R^2$ and $R^3$ nor $R^4$ and $R^5$ are taken together with the cyclopentadiene ring to form a fluorene ring or an indenyl ring;

8. a process for producing a substituted cyclopentadiene compound represented by the formula (1), which comprises reacting a halogen compound represented by the formula (2):

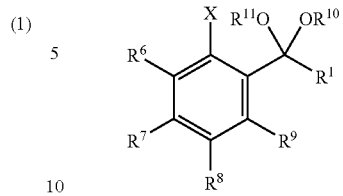

(2)

wherein $R^1$, $R^6$, $R^7$, $R^8$ and $R^9$ have the same meaning as defined below;

$R^{10}$ and $R^{11}$ are the same or different and each represents an optionally substituted $C_{1-10}$ alkyl group, or they are linked to each other at their ends and taken together with oxygen atoms and a carbon atom to which said oxygen atoms are attached to form a 5- or 6-membered ring; and X represents a chlorine, bromine or iodine atom, with cyclopentenone represented by the formula (3):

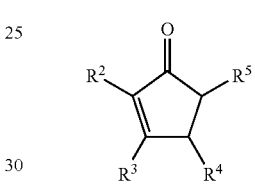

(3)

wherein $R^2$, $R^3$, $R^4$ and $R^5$ have the same meaning defined below, in the presence of a magnesium compound or an organic lithium compound to give cyclopentenol represented by the formula (4):

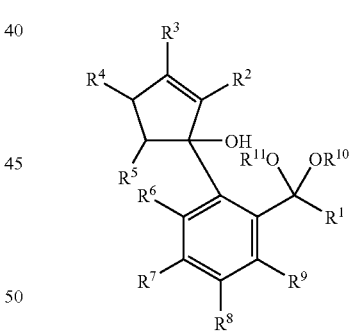

(4)

wherein $R^1$ represents a hydrogen atom, an optionally substituted $C_{1-10}$ alkyl group, an optionally substituted $C_{6-20}$ aryl group, or an optionally substituted $C_{7-20}$ aralkyl group;

$R^2$, $R^3$, $R^4$ and $R^5$ are the same or different and each represents a hydrogen atom, an optionally substituted $C_{1-10}$ alkyl group, an optionally substituted $C_{1-10}$ alkoxy group, an optionally substituted $C_{6-20}$ aryl group, an optionally substituted $C_{6-20}$ aryloxy group, an optionally substituted $C_{7-20}$ aralkyl group, an optionally substituted $C_{7-20}$ aralkyloxy group, a silyl group substituted with optionally substituted $C_{1-20}$ hydrocarbon group(s), or a $C_{1-20}$ hydrocarbon-substituted amino group;

$R^6$, $R^7$, $R^8$ and $R^9$ are the same or different and each independently represents a hydrogen atom, a halogen atom, an optionally substituted $C_{1-10}$ alkyl group, an optionally substituted $C_{1-10}$ alkoxy group, an optionally substituted $C_{6-20}$ aryl group, an optionally substituted $C_{6-20}$ aryloxy group, an optionally substituted $C_{7-20}$ aralkyl group, an optionally substituted $C_{7-20}$ aralkyloxy group, a silyl group substituted with optionally substituted $C_{1-20}$ hydrocarbon group(s) or a $C_{1-20}$ hydrocarbon-substituted amino group, or the adjacent $R^2$, $R^3$, $R^4$ and $R^5$ and the adjacent $R^6$, $R^7$, $R^8$ and $R^9$ are linked to each other to form a benzene ring or a cycloalkylene ring; and $R^{10}$ and $R^{11}$ have the same meanings as defined above, and treating said compound with an acid; and 9. the cyclopentenol represented by the formula (4).

MODE FOR CARRYING OUT THE INVENTION

Hereinafter the substituents $R^1$, $R^2$, $R^3$, $R^4$, $R^5$, $R^6$, $R^7$, $R^8$, $R^9$, $R^{20}$ and $R^{30}$ for the compounds of the above-mentioned formulas (I), (II), and (1) to (4) and for the following compounds (5) to (13) are explained.

Specific examples of the optionally-substituted $C_{1-10}$ alkyl group for the substituents $R^1$, $R^2$, $R^3$, $R^4$, $R^5$, $R^6$, $R^7$, $R^8$, $R^9$, $R^{20}$, $R^{30}$ and $X^1$ to $X^4$ include a methyl group, an ethyl group, a n-propyl group, an isopropyl group, a n-butyl group, a sec-butyl group, a tert-butyl group, a n-pentyl group, a neopentyl group, an amyl group, a n-hexyl group, a n-octyl group and a n-decyl group. Furthermore, the above substituents which are substituted with halogen atom(s) (especially fluorine atom(s)) are exemplified, and specific examples thereof include a fluoromethyl group, a difluoromethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluorohexyl group, a perfluorooctyl group, a perfluorodecyl group, a trichloromethyl group, and the like. Among these, a methyl group, an ethyl group, an isopropyl group, a tert-butyl group, an amyl group and the like are preferred.

The optionally substituted $C_{6-20}$ aryl group for $R^1$, $R^2$, $R^3$, $R^4$, $R^5$, $R^6$, $R^7$, $R^8$, $R^9$, $R^{20}$, $R^{30}$ and $X^1$ to $X^4$ includes a phenyl group, a naphthyl group, an anthracenyl group and the like, and specific examples thereof include, for example, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, a isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, and an anthracenyl group. Furthermore, the above substituents which are substituted, for example, with halogen atom(s), more specifically with fluorine atom(s), are exemplified. As preferable aryl group, a phenyl group is exemplified.

The optionally substituted $C_{7-20}$ aralkyl group includes a benzyl group, a naphthylmethyl group, an anthracenylmethyl group, a diphenylmethyl group and the like, and specific examples thereof include, for example, a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-dodecylphenyl)methyl group, a naphthylmethyl group, an anthracenylmethyl group, a diphenylmethyl group, and the above substituents substituted by halogen, more specifically, a fluorine-substituted aralkyl group. A benzyl group is exemplified as a preferable substituent.

Specific examples of the optionally substituted $C_{1-10}$ alkoxy group for the substituents $R^2$, $R^3$, $R^4$, $R^5$, $R^6$, $R^7$, $R^8$ and $R^9$ include a methoxy group, an ethoxy group, a n-propoxy group, an isopropoxy group; a n-butoxy group, a sec-butoxy group, a tert-butoxy group, a n-pentyloxy group, a neopentyloxy group, a n-hexyloxy group, a n-octyloxy group, a n-nonyloxy group, and a n-decyloxy group. Furthermore, the alkoxy groups substituted with halogen(s) are exemplified, and more specifically, a fluorine atom-substituted alkoxy group, in which the alkoxy group is substituted with fluorine atom(s), is exemplified. Preferably, a methoxy group, an ethoxy group, and a tert-butoxy group are exemplified.

The optionally substituted $C_{6-20}$ aryloxy group for the substituents $R^2$, $R^3$, $R^4$, $R^5$, $R^6$, $R^7$, $R^8$, $R^9$ and $X^1$ to $X^4$ includes a phenoxy group, a naphthoxy group, and an anthracenoxy group. Furthermore, specific examples thereof include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group, an anthracenoxy group, and the above substituents substituted with halogen atom(s), and more specifically, a fluorine-substituted aryloxy group is exemplified.

The optionally substituted $C_{7-20}$ aralkyloxy group for the substituents $R^2$, $R^3$, $R^4$, $R^5$, $R^6$, $R^7$, $R^8$, $R^9$ and $X^1$ to $X^4$ includes a benzyloxy group, a naphthylmethoxy group, an anthracenylmethoxy group, and a diphenylmethoxy group. Furthermore, specific examples thereof include, for example, a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (2,3,4-trimethylphenyl)methoxy group, a (2,3,5-trimethylphenyl)methoxy group, a (2,3,6-trimethylphenyl)methoxy group, a (3,4,5-trimethylphenyl)methoxy group, a (2,4,6-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-pentylphenyl)methoxy group, a (neopentylphenyl)methoxy group, a (n-hexylphenyl)methoxy group, a (n-octylphenyl)methoxy group, a (n-decylphenyl)methoxy group, a (n-dodecylphenyl)methoxy group, a naphthylmethoxy group, an anthracenylmethoxy group, a diphenylmethoxy group and the above substituents substituted with halogen(s), and more specifically, a fluorine atom-substituted aralkyloxy group is exemplified. A benzyloxy group is exemplified as a preferable substituent.

The $C_{1-20}$ hydrocarbon-substituted silyl group for the substituents $R^2$, $R^3$, $R^4$, $R^5$, $R^6$, $R^7$, $R^8$, $R^9$ and $R^{30}$ is a silyl group substituted with $C_{1-20}$ hydrocarbon group(s). The hydrocarbon group as used herein includes, for example, $C_{1-10}$ alkyl groups such as a methyl group, an ethyl group, a n-propyl group, an isopropyl group, a n-butyl group, a sec-butyl group, a tert-butyl group, a n-pentyl group, a neopentyl group, an amyl group, a n-hexyl group, a cyclohexyl group, a n-octyl group, a n-decyl group and the like, and $C_{6-20}$ aryl groups such as a phenyl group, a tolyl group, a xylyl group, a naphthyl group, an anthracenyl group and the like. Such $C_{1-20}$ hydrocarbon-substituted silyl group includes, for example, mono-substituted silyl groups such as a methylsilyl group, an ethylsilyl group, a phenylsilyl group and the like, di-substituted silyl groups such as a dimethylsilyl group, a diethylsilyl group, a diphenylsilyl group and the like, tri-substituted silyl groups such as a trimethylsilyl group, a triethylsilyl group, a tri-n-propylsilyl group, a tri-isopropylsilyl group, a tri-n-butylsilyl group, a tri-sec-butylsilyl group, a tri-tert-butylsilyl group, a tri-isobutylsilyl group, a tert-butyldimethylsilyl group, a tri-n-pentylsilyl group, a tri-n-hexylsilyl group, a tricyclohexylsilyl group, a triphenylsilyl group and the like, preferably a trimethylsilyl group, a tert-butyldimethylsilyl group, and a triphenylsilyl group. Furthermore, the above substituted silyl groups in which the hydrocarbon groups are substituted with halogen atom(s), e.g., fluorine atom(s), are exemplified.

The $C_{1-20}$ hydrocarbon-substituted amino group for the substituents $R^2$, $R^3$, $R^4$, $R^5$, $R^6$, $R^7$, $R^8$, $R^9$ and $X^1$ to $X^4$ is an amino group substituted with two hydrocarbon groups. The hydrocarbon group as used herein includes, for example, $C_{1-10}$ alkyl groups such as a methyl group, an ethyl group, a n-propyl group, an isopropyl group, a n-butyl group, a sec-butyl group, a tert-butyl group, a n-pentyl group, a neopentyl group, an amyl group, a n-hexyl group, a cyclohexyl group, a n-octyl group, a n-decyl group and the like, and $C_{6-20}$ aryl groups such as a phenyl group, a tolyl group, a xylyl group, a naphthyl group, an anthracenyl group and the like. Such $C_{1-20}$ hydrocarbon-substituted amino group includes, for example, a dimethylamino group, a diethylamino group, a di-n-propylamino group, a diisopropylamino group, a di-n-butylamino group, a di-sec-butylamino group, a di-tert-butylamino group, a di-isobutylamino group, a tert-butylisopropylamino group, a di-n-hexylamino group, a di-n-octylamino group, a di-n-decylamino group, a diphenylamino group and the like, preferably, a dimethylamino group and a diethylamino group.

The halogen atom for the substituents $R^6$, $R^7$, $R^8$, $R^9$ and $X^1$ to $X^4$ includes a fluorine atom, a chlorine atom, a bromine atom and an iodine atom, preferably a fluorine atom and a chlorine atom.

In the formula (I), $R^{20}$ represents the same substituents as $R^1$, and specific examples thereof include those exemplified for $R^1$. $R^{30}$ represents the same substituents as $R^1$, and specific examples thereof include those exemplified for $R^1$. Furthermore, $R^{30}$ includes the same groups as the silyl group substituted with optionally substituted $C_{1-20}$ hydrocarbon group(s) for $R^2$ to $R^5$.

Hereinafter the transition metal complex represented by the formula (I) is exemplified.

A Group 4 transition metal represented by M includes transition metals of Group 4 in the periodic table of elements (IUPAC inorganic chemistry nomenclature, revised version, 1989), and for example, a titanium atom, a zirconium atom, a hafnium atom and the like are exemplified, preferably a titanium atom and a zirconium atom.

A Group 16 element represented by A includes, for example, an oxygen atom, a sulfur atom, a selenium atom and the like are exemplified, and as a preferable element, a oxygen atom is exemplified.

Atoms of Group 15 in the periodic table of elements represented by $A^1$ and $A^2$ include, for example, a nitrogen atom, a phosphorus atom, an arsenic atom and the like, preferably a nitrogen atom.

In a transition metal complex according to the formula (I), $R^2$, $R^3$, $R^4$ and $R^5$ are preferably each a hydrogen atom or a $C_{1-5}$ alkyl group.

$X^1$ and $X^2$ preferably include a halogen atom, a $C_{1-10}$ alkyl group, a $C_{7-20}$ aralkyl group, a $C_{6-20}$ aryl group or a $C_{1-20}$ hydrocarbon-substituted amino group, and more preferably, a halogen atom and a $C_{1-10}$ hydrocarbon-substituted amino group are exemplified.

As a transition metal complex according to the formula (I), those in which $X^1$ and $X^2$ are each a halogen atom or a $C_{1-10}$ hydrocarbon-substituted amino group, $R^2$, $R^3$, $R^4$ and $R^5$ are each a methyl group, and $R^6$, $R^7$, $R^8$ and $R^9$ are each a hydrogen atom are preferred.

As a transition metal complex represented by the formula (I), transition metal complexes represented by the following formulas (I-1), (I-2), (I-3) and (I-4) are exemplified.

A transition metal complex represented by the formula (I) wherein —Y— is (a), the formula (I-1):

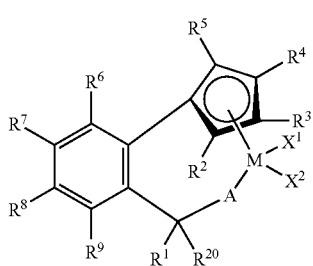

wherein $R^1$ to $R^9$, $R^{20}$, $X^1$, $X^2$, M and A have the same meaning as defined in the above-mentioned formula (I), is hereinafter explained.

In Chem. Commun., 1999, 1405-1406, 1-(2-methylinden-1-yl)-2-naphthylmethyloxyzirconiumbisdiethylamide is disclosed, however, its function as a polymerization catalyst is not disclosed and suggested at all.

In said transition metal complex, at least one of $R^1$ and $R^{20}$ preferably represents an optionally substituted $C_{1-10}$ alkyl group, an optionally substituted $C_{6-20}$ aryl group or an optionally substituted $C_{7-20}$ aralkyl group.

Specific compounds represented by the formula (I-1) include the following compounds: 2-(cyclopentadienyl)benzyloxytitanium dichloride, 2-(2-methylcyclopentadienyl)benzyloxytitanium dichloride, 2-(3-methylcyclopentadienyl)benzyloxytitanium dichloride, 2-(2,3-dimethylcyclopentadienyl)benzyloxytitanium dichloride, 2-(2,4-dimethylcyclopentadienyl)benzyloxytitanium dichloride, 2-(2,3,4-trimethylcyclopentadienyl)benzyloxytitanium dichloride, 2-(2,3,5-trimethylcyclopentadienyl)benzyloxytitanium dichloride, 2-(2,3,4,5-tetramethylcyclopentadienyl)benzyloxytitanium dichloride, 2-(2-dimethylaminomethylcyclopentadienyl)benzyloxytitanium dichloride, 2-(3-dimethylaminomethylcyclopentadienyl)benzyloxytitanium dichloride, 2-(inden-1-yl)benzyloxytitanium dichloride, 2-(2-phenylinden-1-yl)benzyloxytitanium dichloride, 2-(fluoren-9-yl)benzyloxytitanium dichloride, 2-(cyclopentadienyl)-1-naphthylmethyloxytitanium dichloride, 2-(2-methylcyclopentadienyl)-1-naphthylmethyloxytitanium dichloride, 2-(3-methylcyclopentadienyl)-1-naphthylmethyloxytitanium dichloride, 2-(2,3-dimethylcyclopentadienyl)-1-naphthylmethyloxytitanium dichloride, 2-(2,4-dimethylcyclopentadienyl)-1-naphthylmethyloxytitanium dichloride, 2-(2,3,4-trimethylcyclopentadienyl)-1-naphthylmethyloxytitanium dichloride, 2-(2,3,5-trimethylcyclopentadienyl)-1-naphthylmethyloxytitanium dichloride, 2-(2,3,4,5-tetramethylcyclopentadienyl)-1-naphthylmethyloxytitanium dichloride, 2-(2-dimethylaminomethylcyclopentadienyl)-1-naphthylmethyloxytitanium dichloride, 2-(3-dimethylaminomethylcyclopentadienyl)-1-naphthylmethyloxytitanium dichloride, 2-(inden-1-yl)-1-naphthylmethyloxytitanium dichloride, 2-(2-phenylinden-1-yl)-1-naphthylmethyloxytitanium dichloride, 2-(fluoren-9-yl)-1-naphthylmethyloxytitanium dichloride, 1-[2-(cyclopentadienyl)phenyl]ethyloxytitanium dichloride, 1-[2-(2-methylcyclopentadienyl)phenyl]ethyloxytitanium dichloride, 1-[2-(3-methylcyclopentadienyl)phenyl]ethyloxytitanium dichloride, 1-[2-(2,3-dimethylcyclopentadienyl)phenyl]ethyloxytitanium dichloride, 1-[2-(2,4-dimethylcyclopentadienyl)phenyl]ethyloxytitanium dichloride, 1-[2-(2,3,4-trimethylcyclopentadienyl)phenyl]ethyloxytitanium dichloride, 1-[2-(2,3,5-trimethylcyclopentadienyl)phenyl]ethyloxytitanium dichloride, 1-[2-(2,3,4,5-tetramethylcyclopentadienyl)phenyl]ethyloxytitanium dichloride, 1-[2-(2-dimethylaminomethylcyclopentadienyl)phenyl]ethyloxytitanium dichloride, 1-[2-(3-dimethylaminomethylcyclopentadienyl)phenyl]ethyloxytitanium dichloride, 1-[2-(inden-1-yl)phenyl]ethyloxytitanium dichloride, 1-[2-(2-phenylinden-1-yl)phenyl]ethyloxytitanium dichloride, 1-[2-(fluoren-9-yl)phenyl]ethyloxytitanium dichloride, 1-[2-(cyclopentadienyl)-1-naphthyl]ethyloxytitanium dichloride, 1-[2-(2-methylcyclopentadienyl)-1-naphthyl]ethyloxytitanium dichloride, 1-[2-(3-methylcyclopentadienyl)-1-naphthyl]ethyloxytitanium dichloride, 1-[2-(2,3-dimethylcyclopentadienyl)-1-naphthyl]ethyloxytitanium dichloride, 1-[2-(2,4-dimethylcyclopentadienyl)-1-naphthyl]ethyloxytitanium dichloride, 1-[2-(2,3,4-trimethylcyclopentadienyl)-1-naphthyl]ethyloxytitanium dichloride, 1-[2-(2,3,5-trimethylcyclopentadienyl)-1-naphthyl]ethyloxytitanium dichloride, 1-[2-(2,3,4,5-tetramethylcyclopentadienyl)-1-naphthyl]ethyloxytitanium dichloride, 1-[2-(2-dimethylaminomethylcyclopentadienyl)-1-naphthyl]ethyloxytitanium dichloride, 1-[2-(3-dimethylaminomethylcyclopentadienyl)-1-naphthyl]ethyloxytitanium dichloride, 1-[2-(inden-1-yl)-1-naphthyl]ethyloxytitanium dichloride, 1-[2-(2-phenylinden-1-yl)-1-naphthyl]ethyloxytitanium dichloride, 1-[2-(fluoren-9-yl)-1-naphthyl]ethyloxytitanium dichloride, 1-[2-(cyclopentadienyl)phenyl]-1-methyl-ethyloxytitanium dichloride, 1-[2-(2-methylcyclopentadienyl)phenyl]-1-methyl-ethyloxytitanium dichloride, 1-[2-(3-methylcyclopentadienyl)phenyl]-1-methyl-ethyloxytitanium dichloride, 1-[2-(2,3-dimethylcyclopentadienyl)phenyl]-1-methyl-ethyloxytitanium dichloride, 1-[2-(2,4-dimethylcyclopentadienyl)phenyl]-1-methyl-ethyloxytitanium dichloride, 1-[2-(2,3,4-trimethylcyclopentadienyl)phenyl]-1-methyl-ethyloxytitanium dichloride, 1-[2-(2,3,5-trimethylcyclopentadienyl)phenyl]-1-methyl-ethyloxytitanium dichloride, 1-[2-(2,3,4,5-tetramethylcyclopentadienyl)phenyl]-1-methyl-ethyloxytitanium dichloride, 1-[2-(2-dimethylaminomethylcyclopentadienyl)phenyl]-1-methyl-ethyloxytitanium dichloride, 1-[2-(3-dimethylaminomethylcyclopentadienyl)phenyl]-1-methyl-ethyloxytitanium dichloride, 1-[2-(inden-1-yl)phenyl]-1-methyl-ethyloxytitanium dichloride, 1-[2-(2-phenylinden-1-yl)phenyl]-1-methyl-ethyloxytitanium dichloride, 1-[2-(fluoren-9-yl)phenyl]-1-methyl-ethyloxytitanium dichloride, 1-[2-(cyclopentadienyl)-1-naphthyl]-1-methyl-ethyloxytitanium dichloride, 1-[2-(2-methylcyclopentadienyl)-1-naphthyl]-1-methyl-ethyloxytitanium dichloride, 1-[2-(3-methylcyclopentadienyl)-1-naphthyl]-1-methyl-ethyloxytitanium dichloride, 1-[2-(2,3-dimethylcyclopentadienyl)-1-naphthyl]-1-methyl-ethyloxytitanium dichloride, 1-[2-(2,4-dimethylcyclopentadienyl)-1-naphthyl]-1-methyl-ethyloxytitanium dichloride, 1-[2-(2,3,4-trimethylcyclopentadienyl)-1-naphthyl]-1-methyl-ethyloxytitanium dichloride, 1-[2-(2,3,5-trimethylcyclopentadienyl)-1-naphthyl]-1-methyl-ethyloxytitanium dichloride, 1-[2-(2,3,4,5-tetramethylcyclopentadienyl)-1-naphthyl]-1-methyl-ethyloxytitanium dichloride, 1-[2-(2-dimethylaminomethylcyclopentadienyl)-1-naphthyl]-1-methyl-ethyloxytitanium dichloride, 1-[2-(3-dimethylaminomethylcyclopentadienyl)-1-naphthyl]-1- methyl-ethyloxytitanium dichloride, 1-[2-(inden-1-yl)-1-naphthyl]-1-methyl-ethyloxytitanium dichloride, 1-[2-(2-phenylinden-1-yl)-1-naphthyl]-1-methyl-ethyloxytitanium dichloride, 1-[2-(fluoren-9-yl)-1-naphthyl]-1-methyl-ethyloxytitanium dichloride, [2-(cyclopentadienyl)phenyl]-t-butyl-methyloxytitanium dichloride, [2-(2-methylcyclopentadienyl)phenyl]-t-butyl-methyloxytitanium dichloride, [2-(3-methylcyclopentadienyl)phenyl]-t-butyl-methyloxytitanium dichloride, [2-(2,3-dimethylcyclopentadienyl)phenyl]-t-butyl-methyloxytitanium dichloride, [2-(2,4-dimethylcyclopentadienyl)phenyl]-t-butyl-methyloxytitanium dichloride, [2-(2,3,4-trimethylcyclopentadienyl)phenyl]-t-butyl-methyloxytitanium dichloride, [2-(2,3,5-trimethylcyclopentadienyl)phenyl]-t-butyl-methyloxytitanium dichloride, [2-(2,3,4,5-tetramethylcyclopentadienyl)phenyl]-t-butyl-methyloxytitanium dichloride, [2-(2-dimethylaminomethylcyclopentadienyl)phenyl]-t-butyl-methyloxyoxytitanium dichloride, [2-(3-dimethylaminomethylcyclopentadienyl)phenyl]-t-butyl-methyloxytitanium dichloride, [2-(inden-1-yl)phenyl]-t-butyl-methyloxytitanium dichloride, [2-(2-phenylinden-1-yl)phenyl]-t-butyl-methyloxytitanium dichloride, [2-(fluoren-9-yl)phenyl]-t-butyl-methyloxytitanium dichloride, [2-(cyclopentadienyl)-1-naphthyl]-t-butyl-methyloxytitanium dichloride, [2-(2-methylcyclopentadienyl)-1-naphthyl]-t-butyl-methyloxytitanium dichloride, [2-(3-methylcyclopentadienyl)-1-naphthyl]-t-butyl-methyloxytitanium dichloride, [2-(2,3-dimethylcyclopentadienyl)-1-naphthyl]-butyl-methyloxytitanium dichloride, [2-(2,4-dimethylcyclopentadienyl)-1-naphthyl]-t-butyl-methyloxytitanium dichloride, [2-(2,3,4-trimethylcyclopentadienyl)-1-naphthyl]-t-butyl-methyloxytitanium dichloride, [2-(2,3,5-trimethylcyclopentadienyl)-1-naphthyl]-t-butyl-methyloxytitanium dichloride, [2-(2,3,4,5-tetramethylcyclopentadienyl)-1-naphthyl]-t-butyl-methyloxytitanium dichloride, [2-(2-dimethylaminomethylcyclopentadienyl)-1-naphthyl]-t-butyl-methyloxytitanium dichloride, [2-(3-dimethylaminomethylcyclopentadienyl)-1-naphthyl]-t-butyl-methyloxytitanium dichloride, [2-(inden-1-yl)-1-naphthyl]-t-butyl-methyloxytitanium dichloride, [2-(2-phenylinden-1-yl)-1-naphthyl]-t-butyl-methyloxytitanium dichloride, [2-(fluoren-9-yl)-1-naphthyl]-t-butyl-methyloxytitanium dichloride, [2-(cyclopentadienyl)phenyl]phenylmethyloxytitanium dichloride, [2-(2-methylcyclopentadienyl)phenyl]phenylmethyloxytitanium dichloride, [2-(3-methylcyclopentadienyl)phenyl]phenylmethyloxytitanium dichloride, [2-(2,3-dimethylcyclopentadienyl)phenyl]phenylmethyloxytitanium dichloride, [2-(2,4-dimethylcyclopentadienyl)phenyl]phenylmethyloxytitanium dichloride, [2-(2,3,4-trimethylcyclopentadienyl)phenyl]phenylmethyloxytitanium dichloride, [2-(2,3,5-trimethylcyclopentadienyl)phenyl]phenylmethyloxytitanium dichloride, [2-(2,3,4,5-tetramethylcyclopentadienyl)phenyl]phenylmethyloxytitanium dichloride, [2-(2-dimethylaminomethylcyclopentadienyl)phenyl]phenylmethyloxytitanium dichloride, [2-(3-dimethylaminomethylcyclopentadienyl)phenyl]phenylmethyloxytitanium dichloride, [2-(inden-1-yl)phenyl]phenylmethyloxytitanium dichloride, [2-(2-phenylinden-1-yl)phenyl]phenylmethyloxytitanium dichloride, [2-(fluoren-9-yl)phenyl]phenylmethyloxytitanium dichloride, [2-(cyclopentadienyl)-1-naphthyl]phenylmethyloxytitanium dichloride, [2-(2-methylcyclopentadienyl)-1-naphthyl]phenylmethyloxytitanium dichloride, [2-(3-methylcyclopentadienyl)-1-naphthyl]phenylmethyloxytitanium dichloride, [2-(2,3-dimethylcyclopentadienyl)-1-naphthyl] phenyloxytitanium dichloride, [2-(2,4-dimethylcyclopentadienyl)-1-naphthyl]phenylmethyloxytitanium dichloride, [2-(2,3,4-trimethylcyclopentadienyl)-1-naphthyl]phenylmethyloxytitanium dichloride, [2-(2,3,5-trimethylcyclopentadienyl)-1-naphthyl]phenylmethyloxytitanium dichloride, [2-(2,3,4,5-tetramethylcyclopentadienyl)-1-naphthyl]phenylmethyloxytitanium dichloride, [2-(2-dimethylaminomethylcyclopentadienyl)-1-naphthyl]phenylmethyloxytitanium dichloride, [2-(3-dimethylaminomethylcyclopentadienyl)-1-naphthyl]phenylmethyloxytitanium dichloride, [2-(inden-1-yl)-1-naphthyl]phenylmethyloxytitanium dichloride, [2-(2-phenylinden-1-yl)-1-naphthyl]phenylmethyloxytitanium dichloride, [2-(fluoren-9-yl)-1-naphthyl]phenylmethyloxytitanium dichloride, [2-(cyclopentadienyl)phenyl]diphenylmethyloxytitanium dichloride, [2-(2-methylcyclopentadienyl)phenyl]diphenylmethyloxytitanium dichloride, [2-(3-methylcyclopentadienyl)phenyl]diphenylmethyloxytitanium dichloride, [2-(2,3-dimethylcyclopentadienyl)phenyl]diphenylmethyloxytitanium dichloride, [2-(2,4-dimethylcyclopentadienyl)phenyl]diphenylmethyloxytitanium dichloride, [2-(2,3,4-dimethylcyclopentadienyl)phenyl]diphenylmethyloxytitanium dichloride, [2-(2,3,5-trimethylcyclopentadienyl)phenyl]diphenylmethyloxytitanium dichloride, [2-(2,3,4,5-tetramethylcyclopentadienyl)phenyl]diphenylmethyloxytitanium dichloride, [2-(2-dimethylaminomethylcyclopentadienyl)phenyl]diphenylmethyloxyoxytitanium dichloride, [2-(3-dimethylaminomethylcyclopentadienyl)phenyl]diphenylmethyloxytitanium dichloride, [2-(inden-1-yl)phenyl]diphenylmethyloxytitanium dichloride, [2-(2-phenylinden-1-yl)phenyl]diphenylmethyloxytitanium dichloride, [2-(fluoren-9-yl)phenyl]diphenylmethyloxytitanium dichloride, [2-(cyclopentadienyl)-1-naphthyl]diphenylmethyloxytitanium dichloride, [2-(2-methylcyclopentadienyl)-1-naphthyl]diphenylmethyloxytitanium dichloride, [2-(3-methylcyclopentadienyl)-1-naphthyl]diphenylmethyloxytitanium dichloride, [2-(2,3-dimethylcyclopentadienyl)-1-naphthyl]diphenylmethyloxytitanium dichloride, [2-(2,4-dimethylcyclopentadienyl)-1-naphthyl]diphenylmethyloxytitanium dichloride, [2-(2,3,4-trimethylcyclopentadienyl)-1-naphthyl]diphenylmethyloxytitanium dichloride, [2-(2,3,5-trimethylcyclopentadienyl)-1-naphthyl]diphenylmethyloxytitanium dichloride, [2-(2,3,4,5-tetramethylcyclopentadienyl)-1-naphthyl]diphenylmethyloxytitanium dichloride, [2-(2-dimethylaminomethylcyclopentadienyl)-1-naphthyl]diphenylmethyloxytitanium dichloride, [2-(3-dimethylaminomethylcyclopentadienyl)-1-naphthyl]diphenylmethyloxytitanium dichloride, [2-(inden-1-yl)-1-naphthyl]diphenylmethyloxytitanium dichloride, [2-(2-phenylinden-1-yl)-1-naphthyl]diphenylmethyloxytitanium dichloride, [2-(fluoren-9-yl)-1-naphthyl]diphenylmethyloxytitanium dichloride and the like. Similarly, the above-mentioned compounds in which (2-cyclopentadienyl-1-naphthyl) is changed to (2-cyclopentadienyl-3-naphthyl), in which (inden-1-yl) is changed to (inden-2-yl), in which titanium is changed to zirconium or hafnium, or in which dichloride is changed to dibromide, diiodide, dimethoxide, diisopropoxide, dibutoxide, bisdimethylamide, bisdiethylamide, dimethyl or bistrimethylsilylmethyl, and the like are also exemplified.

The transition metal complex represented by the formula (I) wherein —Y— is (b), the formula (I-2):

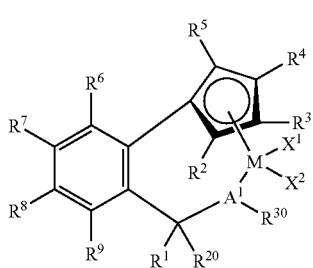

(I-2)

is hereinafter explained.

In the formula (I-2), $A^1$ is preferably a nitrogen atom.

$R^2$, $R^3$, $R^4$ and $R^5$ are preferably each a hydrogen atom or a $C_{1-5}$ alkyl group.

Specific examples of the transition metal complex represented by the formula (I-2) include the following compounds: N-[(2-(cyclopentadienyl)phenyl)methyl]-N-phenylamidotitanium dichloride, N-[(2-(2-methylcyclopentadienyl)phenyl)methyl]-N-phenylamidotitanium dichloride, N-[(2-(3-methylcyclopentadienyl)phenyl)methyl]-N-phenylamidotitanium dichloride, N-[(2-(2,3-dimethylcyclopentadienyl)phenyl)methyl]-N-phenylamidotitanium dichloride, N-[(2-(2,4-dimethylcyclopentadienyl)phenyl)methyl]-N-phenylamidotitanium dichloride, N-[(2-(2,3,4-trimethylcyclopentadienyl)phenyl)methyl]-N-phenylamidotitanium dichloride, N-[(2-(2,3,5-trimethylcyclopentadienyl)phenyl)methyl]-N-phenylamine, N-[(2-(2,3,4,5-tetramethylcyclopentadienyl)phenyl)methyl]-N-phenylamidotitanium dichloride, N-[(2-(2-dimethylaminomethylcyclopentadienyl)phenyl)methyl]-N-phenylamidotitanium dichloride, N-[(2-(3-dimethylaminomethylcyclopentadienyl)phenyl)methyl]-N-phenylamidotitanium dichloride, N-[(2-(inden-1-yl)phenyl)methyl]-N-phenylamidotitanium dichloride, N-[(2-(2-methylinden-1-yl)phenyl)methyl]-N-phenylamidotitanium dichloride, N-[(2-(2-phenylinden-1-yl)phenyl)methyl]-N-phenylamidotitanium dichloride, N-[(2-(fluoren-9-yl)phenyl)methyl]-N-phenylamidotitanium dichloride, N-[(2-(cyclopentadienyl)phenyl)methyl]-N-(2,4,6-trimethylphenyl)amidotitanium dichloride, N-[(2-(2-methylcyclopentadienyl)phenyl)methyl]-N-(2,4,6-trimethylphenyl)titanium dichloride, N-[(2-(3-methylcyclopentadienyl)phenyl)methyl]-N-(2,4,6-trimethylphenyl)amidotitanium dichloride, N-[(2-(2,3-dimethylcyclopentadienyl)phenyl)methyl]-N-(2,4,6-trimethylphenyl)amidotitanium dichloride, N-[(2-(2,4-dimethylcyclopentadienyl)phenyl)methyl]-N-(2,4,6-trimethylphenyl)amidotitanium dichloride, N-[(2-(2,3,4-trimethylcyclopentadienyl)phenyl)methyl]-N-(2,4,6-trimethylphenyl)amidotitanium dichloride, N-[(2-(2,3,5-trimethylcyclopentadienyl)phenyl)methyl]-N-(2,4,6-trimethylphenyl)amidotitanium dichloride, N-[(2-(2,3,4,5-tetramethylcyclopentadienyl)phenyl)methyl]-N-(2,4,6-trimethylphenyl)amidotitanium dichloride, N-[(2-(2-dimethylaminomethylcyclopentadienyl)phenyl)methyl]-N-(2,4,6-trimethylphenyl)amidotitanium dichloride, N-[(2-(3-dimethylaminomethylcyclopentadienyl)phenyl)methyl]-N-(2,4,6-trimethylphenyl)amidotitanium dichloride, N-[(2-(inden-1-yl)phenyl)methyl]-N-(2,4,6-trimethylphenyl)amidotitanium dichloride, N-[(2-(2-methylinden-1-yl)phenyl)methyl]-N-(2,4,6-trimethylphenyl)amidotitanium dichloride, N-[(2-(2-phenylinden-1-yl)phenyl)methyl]-N-(2,4,6-trimethylphenyl)amidotitanium dichloride, N-[(2-(fluoren-9-yl)phenyl)methyl]-N-(2,4,6-trimethylphenyl)amidotitanium dichloride, N-[(2-(cyclopentadienyl)phenyl)methyl]-N-tert-butylamidotitanium dichloride, N-[(2-(2-methylcyclopentadienyl)phenyl)methyl]-N-tert-butylamidotitanium dichloride, N-[(2-(3-methylcyclopentadienyl)phenyl)methyl]-N-tert-butylamidotitanium dichloride, N-[2-(2,3-dimethylcyclopentadienyl)phenyl)methyl]-N-tert-butylamidotitanium dichloride, N-[(2-(2,4-dimethylcyclopentadienyl)phenyl)methyl]-N-tert-butylamidotitanium dichloride, N-[(2-(2,3,4-trimethylcyclopentadienyl)phenyl)methyl]-N-tert-butylamidotitanium dichloride, N-[(2-(2,3,5-trimethylcyclopentadienyl)phenyl)methyl]-N-tert-butylamidotitanium dichloride, N-[(2-(2,3,4,5-tetramethylcyclopentadienyl)phenyl)methyl]-N-tert-butylamidotitanium dichloride, N-[(2-(2-dimethylaminomethylcyclopentadienyl)phenyl)methyl]-N-tert-butylamidotitanium dichloride, N-[(2-(3-dimethylaminomethylcyclopentadienyl)phenyl)methyl]-N-tert-butylamidotitanium dichloride, N-[(2-(inden-1-yl)phenyl)methyl]-N-tert-butylamidotitanium dichloride, N-[(2-(2-methylinden-1-yl)phenyl)methyl]-N-tert-butylamidotitanium dichloride, N-[(2-(2-phenylinden-1-yl)phenyl)methyl]-N-tert-butylamidotitanium dichloride, N-[(2-(fluoren-9-yl)phenyl)methyl]-N-tert-butylamidotitanium dichloride, N-[(2-(cyclopentadienyl)phenyl)methyl]-N-n-butylamidotitanium dichloride, N-[(2-(2-methylcyclopentadienyl)phenyl)methyl]-N-n-butylamidotitanium dichloride, N-[(2-(3-methylcyclopentadienyl)phenyl)methyl]-N-n-butylamidotitanium dichloride, N-[(2-(2,3-dimethylcyclopentadienyl)phenyl)methyl]-N-n-butylamidotitanium dichloride, N-[(2-(2,4-dimethylcyclopentadienyl)phenyl)methyl]-N-n-butylamidotitanium dichloride, N-[(2-(2,3,4-trimethylcyclopentadienyl)phenyl)methyl]-N-n-butylamidotitanium dichloride, N-[(2-(2,3,5-trimethylcyclopentadienyl)phenyl)methyl]-N-n-butylamidotitanium dichloride, N-[(2-(2,3,4,5-tetramethylcyclopentadienyl)phenyl)methyl]-N-n-butylamidotitanium dichloride, N-[(2-(2-dimethylaminomethylcyclopentadienyl)phenyl)methyl]-N-n-butylamidotitanium dichloride, N-[(2-(3-dimethylaminomethylcyclopentadienyl)phenyl)methyl]-N-n-butylamidotitanium dichloride, N-[(2-(inden-1-yl)phenyl)methyl]-N-n-butylamidotitanium dichloride, N-[(2-(2-methylinden-1-yl)phenyl)methyl]-N-n-butylamidotitanium dichloride, N-[(2-(2-phenylinden-1-yl)phenyl)methyl]-N-n-butylamidotitanium dichloride, N-[(2-(fluoren-9-yl)phenyl)methyl]-N-n-butylamidotitanium dichloride, N-[1-(2-(cyclopentadienyl)phenyl)ethyl]-N-phenylamidotitanium dichloride, N-[1-(2-(2-methylcyclopentadienyl)phenyl)ethyl]-N-phenylamidotitanium dichloride, N-[1-(2-(3-methylcyclopentadienyl)phenyl)ethyl]-N-phenylamidotitanium dichloride, N-[1-(2-(2,3-dimethylcyclopentadienyl)phenyl)ethyl]-N-phenylamidotitanium dichloride, N-[1-(2-(2,4-dimethylcyclopentadienyl)phenyl)ethyl]-N-phenylamidotitanium dichloride, N-[1-(2-(2,3,4-trimethylcyclopentadienyl)phenyl)ethyl]-N-phenylamidotitanium dichloride, N-[1-(2-(2,3,5-trimethylcyclopentadienyl)phenyl)ethyl]-N-phenylamidotitanium dichloride, N-[1-(2-(2,3,4,5-tetramethylcyclopentadienyl)phenyl)ethyl]-N-phenylamidotitanium dichloride, N-[1-(2-(2- dimethylaminomethylcyclopentadienyl)phenyl)ethyl]-N-phenylamidotitanium dichloride, N-[1-(2-(3-dimethylaminomethylcyclopentadienyl)phenyl)ethyl]-N-phenylamidotitanium dichloride, N-[1-(2-(inden-1-yl)phenyl)ethyl]-N-phenylamidotitanium dichloride, N-[1-(2-(2-methylinden-1-yl)phenyl)ethyl]-N-phenylamidotitanium dichloride, N-[1-(2-(2-phenylinden-1-yl)phenyl)ethyl]-N-phenylamidotitanium dichloride, N-[1-(2-(fluoren-9-yl)phenyl)ethyl]-N-phenylamidotitanium dichloride, N-[1-(2-(cyclopentadienyl)phenyl)ethyl]-N-(2,4,6-trimethylphenyl)amidotitanium dichloride, N-[1-(2-(2-methylcyclopentadienyl)phenyl)ethyl]-N-(2,4,6-trimethylphenyl)amidotitanium dichloride, N-[1-(2-(3-methylcyclopentadienyl)phenyl)ethyl]-N-(2,4,6-trimethylphenyl)amidotitanium dichloride, N-[1-(2-(2,3-dimethylcyclopentadienyl)phenyl)ethyl]-N-(2,4,6-trimethylphenyl)amidotitanium dichloride, N-[1-(2-(2,4-dimethylcyclopentadienyl)phenyl)ethyl]-N-(2,4,6-trimethylphenyl)amidotitanium dichloride, N-[1-(2-(2,3,4-trimethylcyclopentadienyl)phenyl)ethyl]-N-(2,4,6-trimethylphenyl)amidotitanium dichloride, N-[1-(2-(2,3,5-trimethylcyclopentadienyl)phenyl)ethyl]-N-(2,4,6-trimethylphenyl)amidotitanium dichloride, N-[1-(2-(2,3,4,5-tetramethylcyclopentadienyl)phenyl)ethyl]-N-(2,4,6-trimethylphenyl)amidotitanium dichloride, N-[1-(2-(2-dimethylaminomethylcyclopentadienyl)phenyl)ethyl]-N-(2,4,6-trimethylphenyl)amidotitanium dichloride, N-[1-(2-(3-dimethylaminomethylcyclopentadienyl)phenyl)ethyl]-N-(2,4,6-trimethylphenyl)amidotitanium dichloride, N-[1-(2-(inden-1-yl)phenyl)ethyl]-N-(2,4,6-trimethylphenyl)amidotitanium dichloride, N-[1-(2-(2-methylinden-1-yl)phenyl)ethyl]-N-(2,4,6-trimethylphenyl)amidotitanium dichloride, N-[1-(2-(2-phenylinden-1-yl)phenyl)ethyl]-N-(2,4,6-trimethylphenyl)amidotitanium dichloride, N-[1-(2-(fluoren-9-yl)phenyl)ethyl]-N-(2,4,6-trimethylphenyl)amidotitanium dichloride, N-[1-(2-(cyclopentadienyl)phenyl)ethyl]-N-tert-butylamidotitanium dichloride, N-[1-(2-(2-methylcyclopentadienyl)phenyl)ethyl]-N-tert-butylamidotitanium dichloride, N-[1-(2-(3-methylcyclopentadienyl)phenyl)ethyl]-N-tert-butylamidotitanium dichloride, N-[1-(2-(2,3-dimethylcyclopentadienyl)phenyl)ethyl]-N-tert-butylamidotitanium dichloride, N-[1-(2-(2,4-dimethylcyclopentadienyl)phenyl)ethyl]-N-tert-butylamidotitanium dichloride, N-[1-(2-(2,3,4-trimethylcyclopentadienyl)phenyl)ethyl]-N-tert-butylamidotitanium dichloride, N-[1-(2-(2,3,5-trimethylcyclopentadienyl)phenyl)ethyl]-N-tert-butylamidotitanium dichloride, N-[1-(2-(2,3,4,5-tetramethylcyclopentadienyl)phenyl)ethyl]-N-tert-butylamidotitanium dichloride, N-[1-(2-(2-dimethylaminomethylcyclopentadienyl)phenyl)ethyl]-N-tert-butylamidotitanium dichloride, N-[1-(2-(3-dimethylaminomethylcyclopentadienyl)phenyl)ethyl]-N-tert-butylamidotitanium dichloride, N-[1-(2-(inden-1-yl)phenyl)ethyl]-N-tert-butylamidotitanium dichloride, N-[1-(2-(2-methylinden-1-yl)phenyl)ethyl]-N-tert-butylamidotitanium dichloride, N-[1-(2-(2-phenylinden-1-yl)phenyl)ethyl]-N-tert-butylamidotitanium dichloride, N-[1-(2-(fluoren-9-yl)phenyl)ethyl]-N-tert-butylamidotitanium dichloride, N-[1-(2-(cyclopentadienyl)phenyl)ethyl]-N-n-butylamidotitanium dichloride, N-[1-(2-(2-methylcyclopentadienyl)phenyl)ethyl]-N-n-butylamidotitanium dichloride, N-[1-(2-(3-methylcyclopentadienyl)phenyl)ethyl]-N-n-butylamidotitanium dichloride, N-[1-(2-(2,3-dimethylcyclopentadienyl)phenyl)ethyl]-N-n-butylamidotitanium dichloride, N-[1-(2-(2,4-dimethylcyclopentadienyl)phenyl)ethyl]-N-n-butylamidotitanium dichloride, N-[1-(2-(2,3,4-trimethylcyclopentadienyl)phenyl)ethyl]-N-n-butylamidotitanium dichloride, N-[1-(2-(2,3,5-trimethylcyclopentadienyl)phenyl)ethyl]-N-n-butylamidotitanium dichloride, N-[1-(2-(2,3,4,5-tetramethylcyclopentadienyl)phenyl)ethyl]-N-n-butylamidotitanium dichloride, N-[1-(2-(2-dimethylaminomethylcyclopentadienyl)phenyl)ethyl]N-n-butylamidotitanium dichloride, N-[1-(2-(3-dimethylaminomethylcyclopentadienyl)phenyl)ethyl]-N-n-butylamidotitanium dichloride, N-[1-(2-(inden-1-yl)phenyl)ethyl]-N-n-butylamidotitanium dichloride, N-[1-(2-(2-methylinden-1-yl)phenyl)ethyl]-N-n-butylamidotitanium dichloride, N-[1-(2-(2-phenylinden-1-yl)phenyl)ethyl]-N-n-butylamidotitanium dichloride, N-[1-(2-(fluoren-9-yl)phenyl)ethyl]-N-n-butylamidotitanium dichloride, N-[1-(2-(cyclopentadienyl)phenyl)-1-methylethyl]-N-phenylamidotitanium dichloride, N-[1-(2-(2-methylcyclopentadienyl)phenyl)-1-methylethyl]-N-phenylamidotitanium dichloride, N-[1-(2-(3-methylcyclopentadienyl)phenyl)-1-methylethyl]-N-phenylamidotitanium dichloride, N-[1-(2-(2,3-dimethylcyclopentadienyl)phenyl)-1-methylethyl]-N-phenylamidotitanium dichloride, N-[1-(2-(2,4-dimethylcyclopentadienyl)phenyl)-1-methylethyl]-N-phenylamidotitanium dichloride, N-[1-(2-(2,3,4-trimethylcyclopentadienyl)phenyl)-1-methylethyl]-N-phenylamidotitanium dichloride, N-[1-(2-(2,3,5-trimethylcyclopentadienyl)phenyl)-1-methylethyl]-N-phenylamidotitanium dichloride, N-[1-(2-(2,3,4,5-tetramethylcyclopentadienyl)phenyl)-1-methylethyl]-N-phenylamidotitanium dichloride, N-[1-(2-(2-dimethylaminomethylcyclopentadienyl)phenyl)-1-methylethyl]-N-phenylamidotitanium dichloride, N-[1-(2-(3-dimethylaminomethyl cyclopentadienyl)phenyl)-1-methylethyl]-N-phenylamidotitanium dichloride, N-[1-(2-(inden-1-yl)phenyl)-1-methylethyl]-N-phenylamidotitanium dichloride, N-[1-(2-(2-methylinden-1-yl)phenyl)-1-methylethyl]-N-phenylamidotitanium dichloride, N-[1-(2-(2-phenylinden-1-yl)phenyl)-1-methylethyl]-N-phenylamidotitanium dichloride, N-[1-(2-(fluoren-9-yl)phenyl)-1-methylethyl]-N-phenylamidotitanium dichloride, N-[1-(2-(cyclopentadienyl)phenyl)-1-methylethyl]-N-(2,4,6-trimethylphenyl)amidotitanium dichloride, N-[1-(2-(2-methylcyclopentadienyl)phenyl)-1-methylethyl]-N-(2,4,6-trimethylphenyl)amidotitanium dichloride, N-[1-(2-(3-methylcyclopentadienyl)phenyl)-1-methylethyl]-N-(2,4,6-trimethylphenyl)amidotitanium dichloride, N-[1-(2-(2,3-dimethylcyclopentadienyl)phenyl)-1-methylethyl]-N-(2,4,6-trimethylphenyl)amidotitanium dichloride, N-[1-(2-(2,4-dimethylcyclopentadienyl)phenyl)-1-methylethyl]-N-(2,4,6-trimethylphenyl)amidotitanium dichloride, N-[1-(2-(2,3,4-trimethylcyclopentadienyl)phenyl)-1-methylethyl]-N-(2,4,6-trimethylphenyl)amidotitanium dichloride, N-[1-(2-(2,3,5-trimethylcyclopentadienyl)phenyl)-1-methylethyl]-N-(2,4,6-trimethylphenyl)amidotitanium dichloride, N-[1-(2-(2,3,4,5-tetramethylcyclopentadienyl)phenyl)-1-methylethyl]-N-(2,4,6-trimethylphenyl)amidotitanium dichloride, N-[1-(2-(2-dimethylaminomethylcyclopentadienyl)phenyl)-1-methylethyl]-N-(2,4,6-trimethylphenyl)amidotitanium dichloride, N-[1-(2-(3-dimethylaminomethylcyclopentadienyl)phenyl)-1-methylethyl]-N-(2,4,6-trimethylphenyl)amidotitanium dichloride, N-[1-(2-(inden-1-yl)phenyl)-1-methylethyl]-N-(2,4,6-trimethylphenyl)amidotitanium dichloride, N-[1-(2-(2-methylinden-1-yl)phenyl)-1-methylethyl]-N-(2,4,6-trimethylphenyl)amidotitanium dichloride, N-[1-(2-(2-phenylinden-1-yl)phenyl)-1-methylethyl]-N-(2,4,6-trimethylphenyl)amidotitanium dichloride, N-[1-(2-(fluoren-9-yl)phenyl)-1-methylethyl]-N-(2,4,6-trimethylphenyl)amidotitanium dichloride, N-[1-(2-(cyclopentadienyl)phenyl)-1-methylethyl]-N-tert-butylamidotitanium dichloride, N-[1-(2-(2-methylcyclopentadienyl)phenyl)-1-methylethyl]-N-tert-butylamidotitanium dichloride, N-[1-(2-(3-methylcyclopentadienyl)phenyl)-1-methylethyl]-N-tert-butylamidotitanium dichloride, N-[1-(2-(2,3-dimethylcyclopentadienyl)phenyl)-1-methylethyl]-N-tert-butylamidotitanium dichloride, N-[1-(2-(2,4-dimethylcyclopentadienyl)phenyl)-1-methylethyl]-N-tert-butylamidotitanium dichloride, N-[1-(2-(2,3,4-trimethylcyclopentadienyl)phenyl)-1-methylethyl]-N-tert-butylamidotitanium dichloride, N-[1-(2-(2,3,5-trimethylcyclopentadienyl)phenyl)-1-methylethyl]-N-tert-butylamidotitanium dichloride, N-[1-(2-(2,3,4,5-tetramethylcyclopentadienyl)phenyl)-1-methylethyl]-N-tert-butylamidotitanium dichloride, N-[1-(2-(2-dimethylaminomethylcyclopentadienyl)phenyl)-1-methylethyl]-N-tert-butylamidotitanium dichloride, N-[1-(2-(3-dimethylaminomethylcyclopentadienyl)phenyl)-1-methylethyl]-N-tert-butylamidotitanium dichloride, N-[1-(2-(inden-1-yl)phenyl)-1-methylethyl]-N-tert-butylamidotitanium dichloride, N-[1-(2-(2-methylinden-1-yl)phenyl)-1-methylethyl]-N-tert-butylamidotitanium dichloride, N-[1-(2-(2-phenylinden-1-yl)phenyl)-1-methylethyl]-N-tert-butylamidotitanium dichloride, N-[1-(2-(fluoren-9-yl)phenyl)-1-methylethyl]-N-tert-butylamidotitanium dichloride, N-[1-(2-(cyclopentadienyl)phenyl)-1-methylethyl]-N-n-butylamidotitanium dichloride, N-[1-(2-(2-methylcyclopentadienyl)phenyl)-1-methylethyl]-N-n-butylamidotitanium dichloride, N-[1-(2-(3-methylcyclopentadienyl)phenyl)-1-methylethyl]-N-n-butylamidotitanium dichloride, N-[1-(2-(2,3-dimethylcyclopentadienyl)phenyl)-1-methylethyl]-N-n-butylamidotitanium dichloride, N-[1-(2-(2,4-dimethylcyclopentadienyl)phenyl)-1-methylethyl]-N-n-butylamidotitanium dichloride, N-[1-(2-(2,3,4-trimethylcyclopentadienyl)phenyl)-1-methylethyl]-N-n-butylamidotitanium dichloride, N-[1-(2-(2,3,5-trimethylcyclopentadienyl)phenyl)-1-methylethyl]-N-n-butylamidotitanium dichloride, N-[1-(2-(2,3,4,5-tetramethylcyclopentadienyl)phenyl)-1-methylethyl]-N-n-butylamidotitanium dichloride, N-[1-(2-(2-dimethylaminomethylcyclopentadienyl)phenyl)-1-methylethyl]-N-n-butylamidotitanium dichloride, N-[1-(2-(3-dimethylaminomethylcyclopentadienyl)phenyl)-1-methylethyl]-N-n-butylamidotitanium dichloride, N-[1-(2-(inden-1-yl)phenyl)-1-methylethyl]-N-n-butylamidotitanium dichloride, N-[1-(2-(2-methylinden-1-yl)phenyl)-1-methylethyl]-N-n-butylamidotitanium dichloride, N-[1-(2-(2-phenylinden-1-yl)phenyl)-1-methylethyl]-N-n-butylamidotitanium dichloride, N-[1-(2-(fluoren-9-yl)phenyl)-1-methylethyl]-N-n-butylamidotitanium dichloride, N-[(2-(cyclopentadienyl)-1-naphthyl)methyl]-N-phenylamidotitanium dichloride, N-[(2-(2-methylcyclopentadienyl)-1-naphthyl)methyl]-N-phenylamidotitanium dichloride, N-[(2-(3-methylcyclopentadienyl)-1-naphthyl)methyl]-N-phenylamidotitanium dichloride, N-[(2-(2,3-dimethylcyclopentadienyl)-1-naphthyl)methyl]-N-phenylamidotitanium dichloride, N-[(2-(2,4-dimethylcyclopentadienyl)-1-naphthyl)methyl]-N-phenylamidotitanium dichloride, N-[(2-(2,3,4-trimethylcyclopentadienyl)-1-naphthyl)methyl]-N-phenylamidotitanium dichloride, N-[(2-(2,3,5-trimethylcyclopentadienyl)-1-naphthyl)methyl]-N-phenylamidotitanium dichloride, N-[(2-(2,3,4,5-tetramethylcyclopentadienyl)-1-naphthyl)methyl]-N-phenylamidotitanium dichloride, N-[(2-(2-dimethylaminomethylcyclopentadienyl)-1-naphthyl)methyl]-N-phenylamidotitanium dichloride, N-[(2-(3-dimethylaminomethylcyclopentadienyl)-1-naphthyl)methyl]-N-phenylamidotitanium dichloride, N-[(2-(inden-1-yl)-1-naphthyl)methyl]-N-phenylamidotitanium dichloride, N-[(2-(2-methylinden-1-yl)-1-naphthyl)methyl]-N-phenylamidotitanium dichloride, N-[(2-(2-phenylinden-1-yl)-1-naphthyl)methyl]-N-phenylamidotitanium dichloride, N-[(2-(fluoren-9-yl)-1-naphthyl)methyl]-N-phenylamidotitanium dichloride, N-[(2-(cyclopentadienyl)-1-naphthyl)methyl]-N-(2,4,6-trimethylphenyl)amidotitanium dichloride, N-[(2-(2-methylcyclopentadienyl)-1-naphthyl)methyl]-N-(2,4,6-trimethylphenyl)amidotitanium dichloride, N-[(2-(3-methylcyclopentadienyl)-1-naphthyl)methyl]-N-(2,4,6-trimethylphenyl)amidotitanium dichloride, N-[(2-(2,3-dimethylcyclopentadienyl)-1-naphthyl)methyl]-N-(2,4,6-trimethylphenyl)amidotitanium dichloride, N-[(2-(2,4-dimethylcyclopentadienyl)-1-naphthyl)methyl]-N-(2,4,6-trimethylphenyl)amidotitanium dichloride, N-[(2-(2,3,4-trimethylcyclopentadienyl)-1-naphthyl)methyl]-N-(2,4,6-trimethylphenyl)amidotitanium dichloride, N-[(2-(2,3,5-trimethylcyclopentadienyl)-1-naphthyl)methyl]-N-(2,4,6-trimethylphenyl)amidotitanium dichloride, N-[(2-(2,3,4,5-tetramethylcyclopentadienyl)-1-naphthyl)methyl]-N-(2,4,6-trimethylphenyl)amidotitanium dichloride, N-[(2-(2-dimethylaminomethylcyclopentadienyl)-1-naphthyl)methyl]-N-(2,4,6-trimethylphenyl)amidotitanium dichloride, N-[(2-(3-dimethylaminomethylcyclopentadienyl)-1-naphthyl)methyl]-N-(2,4,6-trimethylphenyl)amidotitanium dichloride, N-[(2-(inden-1-yl)-1-naphthyl)methyl]-N-(2,4,6-trimethylphenyl)amidotitanium dichloride, N-[(2-(2-methylinden-1-yl)-1-naphthyl)methyl]-N-(2,4,6-trimethylphenyl)amidotitanium dichloride, N-[(2-(2-phenylinden-1-yl)-1-naphthyl)methyl]-N-(2,4,6-trimethylphenyl)amidotitanium dichloride, N-[(2-(fluoren-9-yl)-1-naphthyl)methyl]-N-(2,4,6-trimethylphenyl)amidotitanium dichloride, N-[(2-(cyclopentadienyl)-1-naphthyl)methyl]-N-tert-butylamidotitanium dichloride, N-[(2-(2-methylcyclopentadienyl)-1-naphthyl)methyl]-N-tert-butylamidotitanium dichloride, N-[(2-(3-methylcyclopentadienyl)-1-naphthyl)methyl]-N-tert-butylamidotitanium dichloride, N-[(2-(2,3-dimethylcyclopentadienyl)-1-naphthyl)methyl]-N-tert-butylamidotitanium dichloride, N-[(2-(2,4-dimethylcyclopentadienyl)-1-naphthyl)methyl]-N-tert-butylamidotitanium dichloride, N-[(2-(2,3,4-trimethylcyclopentadienyl)-1-naphthyl)methyl]-N-tert-butylamidotitanium dichloride, N-[(2-(2,3,5-trimethylcyclopentadienyl)-1-naphthyl)methyl]-N-tert-butylamidotitanium dichloride, N-[(2-(2,3,4,5-tetramethylcyclopentadienyl)-1-naphthyl)methyl]-N-tert-butylamidotitanium dichloride, N-[(2-(2-dimethylaminomethylcyclopentadienyl)-1-naphthyl)methyl]-N-tert-butylamidotitanium dichloride, N-[(2-(3-dimethylaminomethylcyclopentadienyl)-1-naphthyl)methyl]-N-tert-butylamidotitanium dichloride, N-[(2-(inden-1-yl)-1-naphthyl)methyl]-N-tert-butylamidotitanium dichloride, N-[(2-(2-methylinden-1-yl)-1-naphthyl)methyl]-N-tert-butylamidotitanium dichloride, N-[(2-(2-phenylinden-1-yl)-1-naphthyl)methyl]-N-tert-butylamidotitanium dichloride, N-[(2-(fluoren-9-yl)-1-naphthyl)methyl]-N-tert-butylamidotitanium dichloride, N-[(2-(cyclopentadienyl)-1-naphthyl)methyl]-N-n-butylamidotitanium dichloride, N-[(2-(2-methylcyclopentadienyl)-1-naphthyl)methyl]-N-n-butylamidotitanium dichloride, N-[(2-(3-methylcyclopentadienyl)-1-naphthyl)methyl]-N-n-butylamidotitanium dichloride, N-[(2-(2,3-dimethylcyclopentadienyl)-1-naphthyl)methyl]-N-n-butylamidotitanium dichloride, N-[(2-(2,4-dimethylcyclopentadienyl)-1-naphthyl)methyl]-N-n-butylamidotitanium dichloride, N-[(2-(2,3,4-trimethylcyclopentadienyl)-1-naphthyl)methyl]-N-n-butylamidotitanium dichloride, N-[(2-(2,3,5-trimethylcyclopentadienyl)-1-naphthyl)methyl]-N-n-butylamidotitanium dichloride, N-[(2-(2,3,4,5-tetramethylcyclopentadienyl)-1-naphthyl)methyl]-N-n-butylamidotitanium dichloride, N-[(2-(2-dimethylaminomethylcyclopentadienyl)-1-naphthyl)methyl]-N-n-butylamidotitanium dichloride, N-[(2-(3-dimethylaminomethylcyclopentadienyl)-1-naphthyl)methyl]-N-n-butylamidotitanium dichloride, N-[(2-(inden-1-yl)-1-naphthyl)methyl]-N-n-butylamidotitanium dichloride, N-[(2-(2-methylinden-1-yl)-1-naphthyl)methyl]-N-n-butylamidotitanium dichloride, N-[(2-(2-phenylinden-1-yl)-1-naphthyl)methyl]-N-n-butylamidotitanium dichloride, N-[(2-(fluoren-9-yl)-1-naphthyl)methyl]-N-n-butylamidotitanium dichloride and the like.

Similarly, the above-mentioned compounds in which (2-cyclopentadienyl-1-naphthyl) is changed to (2-cyclopentadienyl-3-naphthyl), in which (inden-1-yl) is changed to (inden-2-yl), in which titanium is changed to zirconium or hafnium, or in which dichloride is changed to dibromide, diiodide, dimethoxide, diisopropoxide, dibutoxide, bisdimethylamide, bisdiethylamide, dimethyl or bistrimethylsilylmethyl, and the like are also exemplified.

The transition metal complex represented by the formula (I) wherein —Y— is (d), the formula (I-3):

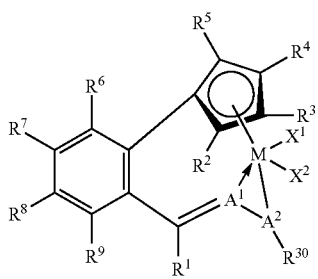

is hereinafter explained.

In the formula (I-3), $A^1$ and $A^2$ are preferably both nitrogen atoms.

Specific examples of the transition metal complex represented by the formula (I-3) include compounds obtained by reacting compounds exemplified as hydrazone compounds of the formula (7) described below with transition metal compounds represented by the formula (III).

The transition metal complex represented by the formula (I) wherein —Y— is (c), the formula (I-4):

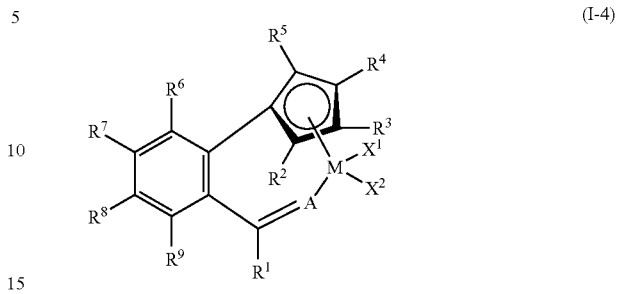

is hereinafter explained.

In the formula (I-4), A is preferably a nitrogen atom.

Specific examples of the transition metal complex represented by the formula (I-4) include the following compounds: 2-(cyclopentadienyl)-α-tert-butyl-benzenemethanimidotitanium dichloride, 2-(2-methylcyclopentadienyl)-α-tert-butyl-benzenemethanimidotitanium dichloride, 2-(3-methylcyclopentadienyl)-α-tert-butyl-benzenemethanimidotitanium dichloride, 2-(2,3-dimethylcyclopentadienyl)-α-tert-butyl-benzenemethanimidotitanium dichloride, 2-(2,4-dimethylcyclopentadienyl)-α-tert-butyl-benzenemethanimidotitanium dichloride, 2-(2,3,4-trimethylcyclopentadienyl)-α-tert-butyl-benzenemethanimidotitanium dichloride, 2-(2,3,5-trimethylcyclopentadienyl)-α-tert-butyl-benzenemethanimidotitanium dichloride, 2-(2,3,4,5-tetramethylcyclopentadienyl)-α-tert-butyl-benzenemethanimidotitanium dichloride, 2-(2-dimethylaminomethylcyclopentadienyl)-α-tert-butyl-benzenemethanimidotitanium dichloride, 2-(3-dimethylaminomethylcyclopentadienyl)-α-tert-butyl-benzenemethanimidotitanium dichloride, 2-(inden-1-yl)-α-tert-butyl-benzenemethanimidotitanium dichloride, 2-(2-methylinden-1-yl)-α-tert-butyl-benzenemethanimidotitanium dichloride, 2-(2-phenylinden-1-yl)-α-tert-butyl-benzenemethanimidotitanium dichloride, 2-(fluoren-9-yl)-α-tert-butyl-benzenemethanimidotitanium dichloride, 2-(cyclopentadienyl)-α-n-butyl-benzenemethanimidotitanium dichloride, 2-(2-methylcyclopentadienyl)-α-n-butyl-benzenemethanimidotitanium dichloride, 2-(3-methylcyclopentadienyl)-α-n-butyl-benzenemethanimidotitanium dichloride, 2-(2,3-dimethylcyclopentadienyl)-α-n-butyl-benzenemethanimidotitanium dichloride, 2-(2,4-dimethylcyclopentadienyl)-α-n-butyl-benzenemethanimidotitanium dichloride, 2-(2,3,4-trimethylcyclopentadienyl)-α-n-butyl-benzenemethanimidotitanium dichloride, 2-(2,3,5-trimethylcyclopentadienyl)-α-n-butyl-benzenemethanimidotitanium dichloride, 2-(2,3,4,5-tetramethylcyclopentadienyl)-α-n-butyl-benzenemethanimidotitanium dichloride, 2-(2-dimethylaminomethylcyclopentadienyl)-α-n-butyl-benzenemethanimidotitanium dichloride, 2-(3-dimethylaminomethylcyclopentadienyl)-α-n-butyl-benzenemethanimidotitanium dichloride, 2-(inden-1-yl)-α-n-butyl-benzenemethanimidotitanium dichloride, 2-(2-methylinden-1-yl)-α-n-butyl-benzenemethanimidotitanium dichloride, 2-(2-phenylinden-1-yl)-α-n-butyl-benzenemethanimidotitanium dichloride, 2-(fluoren-9-yl)-α-n-butyl-benzenemethanimidotitanium dichloride, 2-(cyclopentadienyl)-α-phenyl-benzenemethanimidotitanium dichloride, 2-(2-methylcyclopentadienyl)-α-phenyl-benzenemethanimidotitanium dichloride, 2-(3-methylcyclopentadienyl)-α-phenyl-benzenemethanimidotitanium dichloride, 2-(2,3-dimethylcyclopentadienyl)-α-phenyl-benzenemethanimidotitanium dichloride, 2-(2,4-dimethylcyclopentadienyl)-α-phenyl-benzenemethanimidotitanium dichloride, 2-(2,3,4-trimethylcyclopentadienyl)-α-phenyl-benzenemethanimidotitanium dichloride, 2-(2,3,5-trimethylcyclopentadienyl)-α-phenyl-benzenemethanimidotitanium dichloride, 2-(2,3,4,5-tetramethylcyclopentadienyl)-α-phenyl-benzenemethanimidotitanium dichloride, 2-(2-dimethylaminomethylcyclopentadienyl)-α-phenyl-benzenemethanimidotitanium dichloride, 2-(3-dimethylaminomethylcyclopentadienyl)-α-phenyl-benzenemethanimidotitanium dichloride, 2-(inden-1-yl)-α-phenyl-benzenemethanimidotitanium dichloride, 2-(2-methylinden-1-yl)-α-phenyl-benzenemethanimidotitanium dichloride, 2-(2-phenylinden-1-yl)-α-phenyl-benzenemethanimidotitanium dichloride, 2-(fluoren-9-yl)-α-phenyl-benzenemethanimidotitanium dichloride, 2-(cyclopentadienyl)-α-(2,3,4-trimethylphenyl)-benzenemethanimidotitanium dichloride, 2-(2-methylcyclopentadienyl)-α-(2,3,4-trimethylphenyl)-benzenemethanimidotitanium dichloride, 2-(3-methylcyclopentadienyl)-α-(2,3,4-trimethylphenyl)-benzenemethanimidotitanium dichloride, 2-(2,3-dimethylcyclopentadienyl)-α-(2,3,4-trimethylphenyl)-benzenemethanimidotitanium dichloride, 2-(2,4-dimethylcyclopentadienyl)-α-(2,3,4-trimethylphenyl)-benzenemethanimidotitanium dichloride, 2-(2,3,4-trimethylcyclopentadienyl)-α-(2,3,4-trimethylphenyl)-benzenemethanimidotitanium dichloride, 2-(2,3,5-trimethylcyclopentadienyl)-α-(2,3,4-trimethylphenyl)-benzenemethanimidotitanium dichloride, 2-(2,3,4,5-tetramethylcyclopentadienyl)-α-(2,3,4-trimethylphenyl)-benzenemethanimidotitanium dichloride, 2-(2-dimethylaminomethylcyclopentadienyl)-α-(2,3,4-trimethylphenyl)-benzenemethanimidotitanium dichloride, 2-(3-dimethylaminomethylcyclopentadienyl)-α-(2,3,4-trimethylphenyl)-benzenemethanimidotitanium dichloride, 2-(inden-1-yl)-α-(2,3,4-trimethylphenyl)-benzenemethanimidotitanium dichloride, 2-(2-methylinden-1-yl)-α-(2,3,4-trimethylphenyl)-benzenemethanimidotitanium dichloride, 2-(2-phenylinden-1-yl)-α-(2,3,4-trimethylphenyl)-benzenemethanimidotitanium dichloride, 2-(fluoren-9-α-(2,3,4-trimethylphenyl)-benzenemethanimidotitanium dichloride, 2-(cyclopentadienyl)-α-cyclohexyl-benzenemethanimidotitanium dichloride, 2-(2-methylcyclopentadienyl)-α-cyclohexyl-benzenemethanimidotitanium dichloride, 2-(3-methylcyclopentadienyl)-α-cyclohexyl-benzenemethanimidotitanium dichloride, 2-(2,3-dimethylcyclopentadienyl)-α-cyclohexyl-benzenemethanimidotitanium dichloride, 2-(2,4-dimethylcyclopentadienyl)-α-cyclohexyl-benzenemethanimidotitanium dichloride, 2-(2,3,4-trimethylcyclopentadienyl)-α-cyclohexyl-benzenemethanimidotitanium dichloride, 2-(2,3,5-trimethylcyclopentadienyl)-α-cyclohexyl-benzenemethanimidotitanium dichloride, 2-(2,3,4,5-tetramethylcyclopentadienyl)-α-cyclohexyl-benzenemethanimidotitanium dichloride, 2-(2-dimethylaminomethylcyclopentadienyl)-α-cyclohexyl-benzenemethanimidotitanium dichloride, 2-(3-dimethylaminomethylcyclopentadienyl)-α-cyclohexyl-benzenemethanimidotitanium dichloride, 2-(inden-1-yl)-α-cyclohexyl-benzenemethanimidotitanium dichloride, 2-(2-methylinden-1-yl)-α-cyclohexyl-benzenemethanimidotitanium dichloride, 2-(2-phenylinden-1-yl)-α-cyclohexyl-benzenemethanimidotitanium dichloride, 2-(fluoren-9-yl)-α-cyclohexyl-benzenemethanimidotitanium dichloride, 2-(cyclopentadienyl)-α-tert-butyl-1-naphthalenemethanimidotitanium dichloride, 2-(2-methylcyclopentadienyl)-α-tert-butyl-1-naphthalenemethanimidotitanium dichloride, 2-(3-methylcyclopentadienyl)-α-tert-butyl-1-naphthalenemethanimidotitanium dichloride, 2-(2,3-dimethylcyclopentadienyl)-α-tert-butyl-1-naphthalenemethanimidotitanium dichloride, 2-(2,4-dimethylcyclopentadienyl)-α-tert-butyl-1-naphthalenemethanimidotitanium dichloride, 2-(2,3,4-trimethylcyclopentadienyl)-α-tert-butyl-1-naphthalenemethanimidotitanium dichloride, 2-(2,3,5-trimethylcyclopentadienyl)-α-tert-butyl-1-naphthalenemethanimidotitanium dichloride, 2-(2,3,4,5-tetramethylcyclopentadienyl)-α-tert-butyl-1-naphthalenemethanimidotitanium dichloride, 2-(2-dimethylaminomethylcyclopentadienyl)-α-tert-butyl-1-naphthalenemethanimidotitanium dichloride, 2-(3-dimethylaminomethylcyclopentadienyl)-α-tert-butyl-1-naphthalenemethanimidotitanium dichloride, 2-(inden-1-yl)-α-tert-butyl-1-naphthalenemethanimidotitanium dichloride, 2-(2-methylinden-1-yl)-α-tert-butyl-1-naphthalenemethanimidotitanium dichloride, 2-(2-phenylinden-1-yl)-α-tert-butyl-1-naphthalenemethanimidotitanium dichloride, 2-(fluoren-9-yl)-α-tert-butyl-1-naphthalenemethanimidotitanium dichloride, 2-(cyclopentadienyl)-α-n-butyl-1-naphthalenemethanimidotitanium dichloride, 2-(2-methylcyclopentadienyl)-α-n-butyl-1-naphthalenemethanimidotitanium dichloride, 2-(3-methylcyclopentadienyl) α-n-butyl-1-naphthalenemethanimidotitanium dichloride, 2-(2,3-dimethylcyclopentadienyl)-α-n-butyl-1-naphthalenemethanimidotitanium dichloride, 2-(2,4-dimethylcyclopentadienyl)-α-n-butyl-1-naphthalenemethanimidotitanium dichloride, 2-(2,3,4-trimethylcyclopentadienyl)-α-n-butyl-1-naphthalenemethanimidotitanium dichloride, 2-(2,3,5-trimethylcyclopentadienyl)-α-n-butyl-1-naphthalenemethanimidotitanium dichloride, 2-(2,3,4,5-tetramethylcyclopentadienyl)-α-n-butyl-1-naphthalenemethanimidotitanium dichloride, 2-(2-dimethylaminomethylcyclopentadienyl)-α-n-butyl-1-naphthalenemethanimidotitanium dichloride, 2-(3-dimethylaminomethylcyclopentadienyl)-α-n-butyl-1-naphthalenemethanimidotitanium dichloride, 2-(inden-1-yl)-α-n-butyl-1-naphthalenemethanimidotitanium dichloride, 2-(2-methylinden-1-yl)-α-n-butyl-1-naphthalenemethanimidotitanium dichloride, 2-(2-phenylinden-1-yl)-α-n-butyl-1-naphthalenemethanimidotitanium dichloride, 2-(fluoren-9-yl)-α-n-butyl-1-naphthalenemethanimidotitanium dichloride, 2-(cyclopentadienyl)-α-phenyl-1-naphthalenemethanimidotitanium dichloride, 2-(2-methylcyclopentadienyl)-α-phenyl-1-naphthalenemethanimidotitanium dichloride, 2-(3-methylcyclopentadienyl)-α-phenyl-1-naphthalenemethanimidotitanium dichloride, 2-(2,3-dimethylcyclopentadienyl)-α-phenyl-1-naphthalenemethanimidotitanium dichloride, 2-(2,4-dimethylcyclopentadienyl)-α-phenyl-1-naphthalenemethanimidotitanium dichloride, 2-(2,3,4-trimethylcyclopentadienyl)-α-phenyl-1-naphthalenemethanimidotitanium dichloride, 2-(2,3,5-trimethylcyclopentadienyl)-α-phenyl-1- naphthalenemethanimidotitanium dichloride, 2-(2,3,4,5-tetramethylcyclopentadienyl)-α-phenyl-1-naphthalenemethanimidotitanium dichloride, 2-(2-dimethylaminomethylcyclopentadienyl)-α-phenyl-1-naphthalenemethanimidotitanium dichloride, 2-(3-dimethylaminomethylcyclopentadienyl)-α-phenyl-1-naphthalenemethanimidotitanium dichloride, 2-(inden-1-yl)-α-phenyl-1-naphthalenemethanimidotitanium dichloride, 2-(2-methylinden-1-yl)-α-phenyl-1-naphthalenemethanimidotitanium dichloride, 2-(2-phenylinden-1-yl)-α-phenyl-1-naphthalenemethanimidotitanium dichloride, 2-(fluoren-9-yl)-α-phenyl-1-naphthalenemethanimidotitanium dichloride, 2-(cyclopentadienyl)-α-(2,3,4-trimethylphenyl)-1-naphthalenemethanimidotitanium dichloride, 2-(2-methylcyclopentadienyl)-α-(2,3,4-trimethylphenyl)-1-naphthalenemethanimidotitanium dichloride, 2-(3-methylcyclopentadienyl)-α-(2,3,4-trimethylphenyl)-1-naphthalenemethanimidotitanium dichloride, 2-(2,3-dimethylcyclopentadienyl)-α-(2,3,4-trimethylphenyl)-1-naphthalenemethanimidotitanium dichloride, 2-(2,4-dimethylcyclopentadienyl)-α-(2,3,4-trimethylphenyl)-1-naphthalenemethanimidotitanium dichloride, 2-(2,3,4-trimethylcyclopentadienyl)-α-(2,3,4-trimethylphenyl)-1-naphthalenemethanimidotitanium dichloride, 2-(2,3,5-trimethylcyclopentadienyl)-α-(2,3,4-trimethylphenyl)-1-naphthalenemethanimidotitanium dichloride, 2-(2,3,4,5-tetramethylcyclopentadienyl)-α-(2,3,4-trimethylphenyl)-1-naphthalenemethanimidotitanium dichloride, 2-(2-dimethylaminomethylcyclopentadienyl)-α-(2,3,4-trimethylphenyl)-1-naphthalenemethanimidotitanium dichloride, 2-(3-dimethylaminomethylcyclopentadienyl)-α-(2,3,4-trimethylphenyl)-1-naphthalenemethanimidotitanium dichloride, 2-(inden-1-yl)-α-(2,3,4-trimethylphenyl)-1-naphthalenemethanimidotitanium dichloride, 2-(2-methylinden-1-yl)-α-(2,3,4-trimethylphenyl)-1-naphthalenemethanimidotitanium dichloride, 2-(2-phenylinden-1-yl)-α-(2,3,4-trimethylphenyl)-1-naphthalenemethanimidotitanium dichloride, 2-(fluoren-9-yl)-α-(2,3,4-trimethylphenyl)-1-naphthalenemethanimidotitanium dichloride, 2-(cyclopentadienyl)-α-cyclohexyl-1-naphthalenemethanimidotitanium dichloride, 2-(2-methylcyclopentadienyl)-α-cyclohexyl-1-naphthalenemethanimidotitanium dichloride, 2-(3-methylcyclopentadienyl)-α-cyclohexyl-1-naphthalenemethanimidotitanium dichloride, 2-(2,3-dimethylcyclopentadienyl)-α-cyclohexyl-1-naphthalenemethanimidotitanium dichloride, 2-(2,4-dimethylcyclopentadienyl)-α-cyclohexyl-1-naphthalenemethanimidotitanium dichloride, 2-(2,3,4-trimethylcyclopentadienyl)-α-cyclohexyl-1-naphthalenemethanimidotitanium dichloride, 2-(2,3,5-trimethylcyclopentadienyl)-α-cyclohexyl-1-naphthalenemethanimidotitanium dichloride, 2-(2,3,4,5-tetramethylcyclopentadienyl)-α-cyclohexyl-1-naphthalenemethanimidotitanium dichloride, 2-(2-dimethylaminomethylcyclopentadienyl)-α-cyclohexyl-1-naphthalenemethanimidotitanium dichloride, 2-(3-dimethylaminomethylcyclopentadienyl)-α-cyclohexyl-1-naphthalenemethanimidotitanium dichloride, 2-(inden-1-yl)-α-cyclohexyl-1-naphthalenemethanimidotitanium dichloride, 2-(2-methylinden-1-yl)-α-cyclohexyl-1-naphthalenemethanimidotitanium dichloride, 2-(2-phenylinden-1-yl)-α-cyclohexyl-1-naphthalenemethanimidotitanium dichloride, 2-(fluoren-9-yl)-α-cyclohexyl-1-naphthalenemethanimidotitanium dichloride, 3-(cyclopentadienyl)-α-tert-butyl-2-naphthalenemethanimidotitanium dichloride, 3-(2-methylcyclopentadienyl)-α-tert-butyl-2-naphthalenemethanimidotitanium dichloride, 3-(3-methylcyclopentadienyl)-α-tert-butyl-2-naphthalenemethanimidotitanium dichloride, 3-(2,3-dimethylcyclopentadienyl)-α-tert-butyl-2-naphthalenemethanimidotitanium dichloride, 3-(2,4-dimethylcyclopentadienyl)-α-tert-butyl-2-naphthalenemethanimidotitanium dichloride, 3-(2,3,4-trimethylcyclopentadienyl)-α-tert-butyl-2-naphthalenemethanimidotitanium dichloride, 3-(2,3,5-trimethylcyclopentadienyl)-α-tert-butyl-2-naphthalenemethanimidotitanium dichloride, 3-(2,3,4,5-tetramethylcyclopentadienyl)-α-tert-butyl-2-naphthalenemethanimidotitanium dichloride, 3-(2-dimethylaminomethylcyclopentadienyl)-α-tert-butyl-2-naphthalenemethanimidotitanium dichloride, 3-(3-dimethylaminomethylcyclopentadienyl)-α-tert-butyl-2-naphthalenemethanimidotitanium dichloride, 3-(inden-1-yl)-α-tert-butyl-2-naphthalenemethanimidotitanium dichloride, 3-(2-methylinden-1-yl)-α-tert-butyl-2-naphthalenemethanimidotitanium dichloride, 3-(2-phenylinden-1-yl)-α-tert-butyl-2-naphthalenemethanimidotitanium dichloride, 3-(fluoren-9-yl)-α-tert-butyl-2-naphthalenemethanimidotitanium dichloride, 3-(cyclopentadienyl)-α-n-butyl-2-naphthalenemethanimidotitanium dichloride, 3-(2-methylcyclopentadienyl)-α-n-butyl-2-naphthalenemethanimidotitanium dichloride, 3-(3-methylcyclopentadienyl)-α-n-butyl-2-naphthalenemethanimidotitanium dichloride, 3-(2,3-dimethylcyclopentadienyl)-α-n-butyl-2-naphthalenemethanimidotitanium dichloride, 3-(2,4-dimethylcyclopentadienyl)-α-n-butyl-2-naphthalenemethanimidotitanium dichloride, 3-(2,3,4-trimethylcyclopentadienyl)-α-n-butyl-2-naphthalenemethanimidotitanium dichloride, 3-(2,3,5-trimethylcyclopentadienyl)-α-n-butyl-2-naphthalenemethanimidotitanium dichloride, 3-(2,3,4,5-tetramethylcyclopentadienyl)-α-n-butyl-2-naphthalenemethanimidotitanium dichloride, 3-(2-dimethylaminomethylcyclopentadienyl)-α-n-butyl-2-naphthalenemethanimidotitanium dichloride, 3-(3-dimethylaminomethylcyclopentadienyl)-α-n-butyl-2-naphthalenemethanimidotitanium dichloride, 3-(inden-1-yl)-α-n-butyl-2-naphthalenemethanimidotitanium dichloride, 3-(2-methylinden-1-yl)-α-n-butyl-2-naphthalenemethanimidotitanium dichloride, 3-(2-phenylinden-1-yl)-α-n-butyl-2-naphthalenemethanimidotitanium dichloride, 3-(fluoren-9-yl)-α-n-butyl-2-naphthalenemethanimidotitanium dichloride, 3-(cyclopentadienyl)-α-phenyl-2-naphthalenemethanimidotitanium dichloride, 3-(2-methylcyclopentadienyl)-α-phenyl-2-naphthalenemethanimidotitanium dichloride, 3-(3-methylcyclopentadienyl)-α-phenyl-2-naphthalenemethanimidotitanium dichloride, 3-(2,3-dimethylcyclopentadienyl)-α-phenyl-2-naphthalenemethanimidotitanium dichloride, 3-(2,4-dimethylcyclopentadienyl)-α-phenyl-2-naphthalenemethanimidotitanium dichloride, 3-(2,3,4-trimethylcyclopentadienyl)-α-phenyl-2-naphthalenemethanimidotitanium dichloride, 3-(2,3,5-trimethylcyclopentadienyl)-α-phenyl-2-naphthalenemethanimidotitanium dichloride, 3-(2,3,4,5-tetramethylcyclopentadienyl)-α-phenyl-2-naphthalenemethanimidotitanium dichloride, 3-(2-dimethylaminomethylcyclopentadienyl)-α-phenyl-2-naphthalenemethanimidotitanium dichloride, 3-(3-dimethylaminomethylcyclopentadienyl)-α-phenyl-2-naphthalenemethanimidotitanium dichloride, 3-(inden-1-yl)-α-phenyl-2-naphthalenemethanimidotitanium dichloride, 3-(2-methylinden-1-yl)-α-phenyl-2-naphthalenemethanimidotitanium dichloride, 3-(2-phenylinden-1-yl)-α-phenyl-2-naphthalenemethanimidotitanium dichloride, 3-(fluoren-9-yl)-α-phenyl-2-naphthalenemethanimidotitanium dichloride, 3-(cyclopentadienyl)-α-(2,3,4-trimethylphenyl)-2-naphthalenemethanimidotitanium dichloride, 3-(2-methylcyclopentadienyl)-α-(2,3,4-trimethylphenyl)-2-naphthalenemethanimidotitanium dichloride, 3-(3-methylcyclopentadienyl)-α-(2,3,4-trimethylphenyl)-2-naphthalenemethanimidotitanium dichloride, 3-(2,3-dimethylcyclopentadienyl)-α-(2,3,4-trimethylphenyl)-2-naphthalenemethanimidotitanium dichloride, 3-(2,4-dimethylcyclopentadienyl)-α-(2,3,4-trimethylphenyl)-2-naphthalenemethanimidotitanium dichloride, 3-(2,3,4-trimethylcyclopentadienyl)-α-(2,3,4-trimethylphenyl)-2-naphthalenemethanimidotitanium dichloride, 3-(2,3,5-trimethylcyclopentadienyl)-α-(2,3,4-trimethylphenyl)-2-naphthalenemethanimidotitanium dichloride, 3-(2,3,4,5-tetramethylcyclopentadienyl)-α-(2,3,4-trimethylphenyl)-2-naphthalenemethanimidotitanium dichloride, 3-(2-dimethylaminomethylcyclopentadienyl)-α-(2,3,4-trimethylphenyl)-2-naphthalenemethanimidotitanium dichloride, 3-(3-dimethylaminomethylcyclopentadienyl)-α-(2,3,4-trimethylphenyl)-2-naphthalenemethanimidotitanium dichloride, 3-(inden-1-yl)-α-(2,3,4-trimethylphenyl)-2-naphthalenemethanimidotitanium dichloride, 3-(2-methylinden-L-yl)-α-(2,3,4-trimethylphenyl)-2-naphthalenemethanimidotitanium dichloride, 3-(2-phenylinden-1-yl)-α-(2,3,4-trimethylphenyl)-2-naphthalenemethanimidotitanium dichloride, 3-(fluoren-9-yl)-α-(2,3,4-trimethylphenyl)-2-naphthalenemethanimidotitanium dichloride, 3-(cyclopentadienyl)-α-cyclohexyl-2-naphthalenemethanimidotitanium dichloride, 3-(2-methylcyclopentadienyl)-α-cyclohexyl-2-naphthalenemethanimidotitanium dichloride, 3-(3-methylcyclopentadienyl)-α-cyclohexyl-2-naphthalenemethanimidotitanium dichloride, 3-(2,3-dimethylcyclopentadienyl)-α-cyclohexyl-2-naphthalenemethanimidotitanium dichloride, 3-(2,4-dimethylcyclopentadienyl)-α-cyclohexyl-2-naphthalenemethanimidotitanium dichloride, 3-(2,3,4-trimethylcyclopentadienyl)-α-cyclohexyl-2-naphthalenemethanimidotitanium dichloride, 3-(2,3,5-trimethylcyclopentadienyl)-α-cyclohexyl-2-naphthalenemethanimidotitanium dichloride, 3-(2,3,4,5-tetramethylcyclopentadienyl)-α-cyclohexyl-2-naphthalenemethanimidotitanium dichloride, 3-(2-dimethylaminomethylcyclopentadienyl)-α-cyclohexyl-2-naphthalenemethanimidotitanium dichloride, 3-(3-dimethylaminomethylcyclopentadienyl)-α-cyclohexyl-2-naphthalenemethanimidotitanium dichloride, 3-(inden-1-yl)-α-cyclohexyl-2-naphthalenemethanimidotitanium dichloride, 3-(2-methylinden-1-yl)-α-cyclohexyl-2-naphthalenemethanimidotitanium dichloride, 3-(2-phenylinden-1-yl)-α-cyclohexyl-2-naphthalenemethanimidotitanium dichloride, 3-(fluoren-9-yl)-α-cyclohexyl-2-naphthalenemethanimidotitanium dichloride, 3-dimethylamino-6-(cyclopentadienyl)-α-tert-butyl-benzenemethanimidotitanium dichloride, 3-dimethylamino-6-(2-methylcyclopentadienyl)-α-tert-butyl-benzenemethanimidotitanium dichloride, 3-dimethylamino-6-(3-methylcyclopentadienyl)-α-tert-butyl-benzenemethanimidotitanium dichloride, 3-dimethylamino-6-(2,3-dimethylcyclopentadienyl)-α-tert-butyl-benzenemethanimidotitanium dichloride, 3-dimethylamino-6-(2,4-dimethylcyclopentadienyl)-α-tert-butyl-benzenemethanimidotitanium dichloride, 3-dimethylamino-6-(2,3,4-trimethylcyclopentadienyl)-α-tert-butyl-benzenemethanimidotitanium dichloride, 3-dimethylamino-6-(2,3,5-trimethylcyclopentadienyl)-α-tert-butyl-benzenemethanimidotitanium dichloride, 3-dimethylamino-6-(2,3,4,5-tetramethylcyclopentadienyl)-α-tert-butyl-benzenemethanimidotitanium dichloride, 3-dimethylamino-6-(2-dimethylaminomethylcyclopentadienyl)-α-tert-butyl-benzenemethanimidotitanium dichloride, 3-dimethylamino-6-(3-dimethylaminomethylcyclopentadienyl)-α-tert-butyl-benzenemethanimidotitanium dichloride, 3-dimethylamino-6-(inden-1-yl)-α-tert-butyl-benzenemethanimidotitanium dichloride, 3-dimethylamino-6-(2-methylinden-1-yl)-α-tert-butyl-benzenemethanimidotitanium dichloride, 3-dimethylamino-6-(2-phenylinden-1-yl)-α-tert-butyl-benzenemethanimidotitanium dichloride, 3-dimethylamino-6-(fluoren-9-yl)-α-tert-butyl-benzenemethanimidotitanium dichloride, 3-dimethylamino-6-(cyclopentadienyl)-α-n-butyl-benzenemethanimidotitanium dichloride, 3-dimethylamino-6-(2-methylcyclopentadienyl)-α-n-butyl-benzenemethanimidotitanium dichloride, 3-dimethylamino-6-(3-methylcyclopentadienyl)-α-n-butyl-benzenemethanimidotitanium dichloride, 3-dimethylamino-6-(2,3-dimethylcyclopentadienyl)-α-n-butyl-benzenemethanimidotitanium dichloride, 3-dimethylamino-6-(2,4-dimethylcyclopentadienyl)-α-n-butyl-benzenemethanimidotitanium dichloride, 3-dimethylamino-6-(2,3,4-trimethylcyclopentadienyl)-α-n-butyl-benzenemethanimidotitanium dichloride, 3-dimethylamino-6-(2,3,5-trimethylcyclopentadienyl)-α-n-butyl-benzenemethanimidotitanium dichloride, 3-dimethylamino-6-(2,3,4,5-tetramethylcyclopentadienyl)-α-n-butyl-benzenemethanimidotitanium dichloride, 3-dimethylamino-6-(2-dimethylaminomethylcyclopentadienyl)-α-n-butyl-benzenemethanimidotitanium dichloride, 3-dimethylamino-6-(3-dimethylaminomethylcyclopentadienyl)-α-n-butyl-benzenemethanimidotitanium dichloride, 3-dimethylamino-6-(inden-1-yl)-α-n-butyl-benzenemethanimidotitanium dichloride, 3-dimethylamino-6-(2-methylinden-1-yl)-α-n-butyl-benzenemethanimidotitanium dichloride, 3-dimethylamino-6-(2-phenylinden-1-yl)-α-n-butyl-benzenemethanimidotitanium dichloride, 3-dimethylamino-6-(fluoren-9-yl)-α-n-butyl-benzenemethanimidotitanium dichloride, 3-dimethylamino-6-(cyclopentadienyl)-α-phenyl-benzenemethanimidotitanium dichloride, 3-dimethylamino-6-(2-methylcyclopentadienyl)-α-phenyl-benzenemethanimidotitanium dichloride, 3-dimethylamino-6-(3-methylcyclopentadienyl)-α-phenyl-benzenemethanimidotitanium dichloride, 3-dimethylamino-6-(2,3-dimethylcyclopentadienyl)-α-phenyl-benzenemethanimidotitanium dichloride, 3-dimethylamino-6-(2,4-dimethylcyclopentadienyl)-α-phenyl-benzenemethanimidotitanium dichloride, 3-dimethylamino-6-(2,3,4-trimethylcyclopentadienyl)-α-phenyl-benzenemethanimidotitanium dichloride, 3-dimethylamino-6-(2,3,5-trimethylcyclopentadienyl)-α-phenyl-benzenemethanimidotitanium dichloride, 3-dimethylamino-6-(2,3,4,5-tetramethylcyclopentadienyl)-α-phenyl-benzenemethanimidotitanium dichloride, 3-dimethylamino-6-(2-dimethylaminomethylcyclopentadienyl)-α-phenyl-benzenemethanimidotitanium dichloride, 3-dimethylamino-6-(3-dimethylaminomethylcyclopentadienyl)-α-phenyl-benzenemethanimidotitanium dichloride, 3-dimethylamino-6-(inden-1-yl)-α-phenyl-benzenemethanimidotitanium dichloride, 3-dimethylamino-6-(2-methylinden-1-yl)-α-phenyl-benzenemethanimidotitanium dichloride, 3-dimethylamino-6-(2-phenylinden-1-yl)-α-phenyl-benzenemethanimidotitanium dichloride, 3-dimethylamino-6-(fluoren-9-yl)-α-phenyl-benzenemethanimidotitanium dichloride, 3-dimethylamino-6-(cyclopentadienyl)-α-(2,3,4-trimethylphenyl)-benzenemethanimidotitanium dichloride, 3-dimethylamino-6-(2-methylcyclopentadienyl)-α-(2,3,4-trimethylphenyl)-benzenemethanimidotitanium dichloride, 3-dimethylamino-6-(3-methylcyclopentadienyl)-α-(2,3,4-trimethylphenyl)-benzenemethanimidotitanium dichloride, 3-dimethylamino-6-(2,3-dimethylcyclopentadienyl)-α-(2,3, 4-trimethylphenyl)-benzenemethanimidotitanium dichloride, 3-dimethylamino-6-(2,4-dimethylcyclopentadienyl)-α-(2,3,4-trimethylphenyl)-benzenemethanimidotitanium dichloride, 3-dimethylamino-6-(2,3,4-trimethylcyclopentadienyl)-α-(2,3,4-trimethylphenyl)-benzenemethanimidotitanium dichloride, 3-dimethylamino-6-(2,3,5-trimethylcyclopentadienyl)-α-(2,3,4-trimethylphenyl)-benzenemethanimidotitanium dichloride, 3-dimethylamino-6-(2,3,4,5-tetramethylcyclopentadienyl)-α-(2,3,4-trimethylphenyl)-benzenemethanimidotitanium dichloride, 3-dimethylamino-6-(2-dimethylaminomethylcyclopentadienyl)-α-(2,3,4-trimethylphenyl)-benzenemethanimidotitanium dichloride, 3-dimethylamino-6-(3-dimethylaminomethylcyclopentadienyl)-α-(2,3,4-trimethylphenyl)-benzenemethanimidotitanium dichloride, 6-(inden-1-yl)-α-(2,3,4-trimethylphenyl)benzenemethanimidotitanium dichloride, 3-dimethylamino-6-(2-methylinden-1-yl)-α-(2,3,4-trimethylphenyl)-benzenemethanimidotitanium dichloride, 3-dimethylamino-6-(2-phenylinden-1-yl)-α-(2,3,4-trimethylphenyl)-benzenemethanimidotitanium dichloride, 3-dimethylamino-6-(fluoren-9-yl)-α-(2,3,4-trimethylphenyl)-benzenemethanimidotitanium dichloride, 3-dimethylamino-6-(cyclopentadienyl)-α-cyclohexyl-benzenemethanimidotitanium dichloride, 3-dimethylamino-6-(2-methylcyclopentadienyl)-α-cyclohexyl-benzenemethanimidotitanium dichloride, 3-dimethylamino-6-(3-methylcyclopentadienyl)-α-cyclohexyl-benzenemethanimidotitanium dichloride, 3-dimethylamino-6-(2,3-dimethylcyclopentadienyl)-α-cyclohexyl-benzenemethanimidotitanium dichloride, 3-dimethylamino-6-(2,4-dimethylcyclopentadienyl)-α-cyclohexyl-benzenemethanimidotitanium dichloride, 3-dimethylamino-6-(2,3,4-trimethylcyclopentadienyl)-α-cyclohexyl-benzenemethanimidotitanium dichloride, 3-dimethylamino-6-(2,3,5-trimethylcyclopentadienyl)-α-cyclohexyl-benzenemethanimidotitanium dichloride, 3-dimethylamino-6-(2,3,4,5-tetramethylcyclopentadienyl)-α-cyclohexyl-benzenemethanimidotitanium dichloride, 3-dimethylamino-6-(2-dimethylaminomethylcyclopentadienyl)-α-cyclohexyl-benzenemethanimidotitanium dichloride, 3-dimethylamino-6-(3-dimethylaminomethylcyclopentadienyl)-α-cyclohexyl-benzenemethanimidotitanium dichloride, 3-dimethylamino-6-(inden-1-yl)-α-cyclohexyl-benzenemethanimidotitanium dichloride, 3-dimethylamino-6-(2-methylinden-1-yl)-α-cyclohexyl-benzenemethanimidotitanium dichloride, 3-dimethylamino-6-(2-phenylinden-1-yl)-α-cyclohexyl-benzenemethanimidotitanium dichloride, 3-dimethylamino-6-(fluoren-9-yl)-α-cyclohexyl-benzenemethanimidotitanium dichloride and the like. Similarly, the above-mentioned compounds in which (2-cyclopentadienyl-1-naphthyl) is changed to (2-cyclopentadienyl-3-naphthyl), in which (inden-1-yl) is changed to (inden-2-yl), in which titanium is changed to zirconium or hafnium, or in which dichloride is changed to dibromide, diiodide, dimethoxide, diisopropoxide, dibutoxide, bisdimethylamide, bisdiethylamide, dimethyl or bistrimethylsilylmethyl, and the like are also exemplified.

The transition metal complex (I) of the present invention is generally used as a polymerization catalyst in combination with the compound selected from the above-mentioned A1 to A3.

Hereinafter A1 to A3 are explained.

Specific examples of the organic aluminum compound (A1) represented by the formula $E1_aAl(Z)_{(3-a)}$ include, for example, trialkylaluminum such as trimethylaluminum, triethylaluminum, tripropylaluminum, triisobutylaluminum, trihexylaluminum and the like; dialkylaluminum chloride such as dimethylaluminum chloride, diethylaluminum chloride, dipropylaluminum chloride, diisobutylaluminum chloride, dihexylaluminum chloride and the like; alkylaluminum dichloride such as methylaluminum dichloride, ethylaluminum dichloride, propylaluminum dichloride, isobutylaluminum dichloride, hexylaluminum dichloride and the like; and dialkylaluminum hydride such as dimethylaluminum hydride, diethylaluminum hydride, dipropylaluminum hydride, diisobutylaluminum hydride, dihexylaluminum hydride and the like. Preferably trialkylaluminum is exemplified, and more preferably, triethylaluminum and triisobutylaluminum are exemplified.

Specific examples of E2 and E3 for the cyclic aluminoxane (A2) having the structure represented by the formula $\{-Al(E2)-O-\}_b$ and the linear aluminoxane (A3) having the structure represented by the formula $E3\{-Al(E3)-O-\}_cAl(E3)_2$ include alkyl groups (preferably C1-C5 alkyl groups) such as a methyl group, an ethyl group, a normal propyl group, an isopropyl group, a normal butyl group, an isobutyl group, a normal pentyl group, a neopentyl group and the like b is an integer of not less than 2, and c is an integer of not less than 1. Preferably, E2 and E3 are each a methyl group or an isobutyl group, b is 2 to 40, and c is 1 to 40.

The above-mentioned aluminoxanes are prepared by various methods, which methods are not specifically limited, and may be prepared according to known methods. For example, trialkylaluminum (e.g., trimethylaluminum and the like) is dissolved in a suitable organic solvent (e.g., benzene, aliphatic hydrocarbon and the like) and then the solution is contacted with water to prepare aluminoxane. A method for preparation of aluminoxane comprising contacting trialkylaluminum (e.g., trimethylaluminum and the like) to a metal salt containing crystal water (e.g., copper sulfate hydrate and the like) can be also exemplified.

Specifically, methylaluminoxane (MAO) and the like are exemplified. Furthermore, MMAO (Modified methyl aluminoxane) obtained by modifying methylaluminoxane by addition of triisobutylaluminum is exemplified. The amount of triisobutylaluminum to be used for obtaining MMAO may be an effective amount in modifying methylaluminoxane and is not specifically limited. Alternatively, aluminoxane to be used in the present invention may be a commercial available product.

The combination of the transition metal complex of the present invention and a compound selected from A1 to A3 can be used further in combination with a compound (B) as a polymerization catalyst.

Hereinafter the compounds (B1), (B2) and (B3) used in the present invention are explained.

In the boron compound (B1) represented by the formula $BQ_1Q_2Q_3$, B is a boron atom in a trivalent valence state, and $Q_1$ to $Q_3$ may be the same or different and each is a halogen atom, a hydrocarbon group containing 1 to 20 carbon atoms, a halogenated hydrocarbon group containing 1 to 20 carbon atoms, a substituted silyl group containing 1 to 20 carbon atoms, an alkoxy group containing 1 to 20 carbon atoms or a di-substituted amino group containing 2 to 20 carbon atoms. Specifically, $Q_1$ to $Q_3$ include the same substituents as those exemplified for $R^1$ to $R^9$. Preferably, $Q_1$ to $Q_3$ are each a halogen atom, a hydrocarbon group containing 1 to 20 carbon atoms, or a halogenated hydrocarbon group containing 1 to 20 carbon atoms.

Specific examples of (B1) include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane and the like, more preferably tris(pentafluorophenyl)borane.

In the boron compound (B2) represented by the formula $Z^+(BQ_1Q_2Q_3Q_4)^-$, $Z^+$ is an inorganic or organic cation, B is a boron atom in a trivalent valence state, and $Q_1$ to $Q_4$ have the same meaning as the $Q_1$ to $Q_3$ in the above-mentioned (B1).

For specific examples of the compound represented by the formula $Z^+(BQ_1Q_2Q_3Q_4)$, $Z^+$ includes a ferrocenium cation, an alkyl-substituted ferrocenium cation, a silver cation and the like as an inorganic cation, and a triphenylmethyl cation and the like as an organic cation. As the $(BQ_1Q_2Q_3Q_4)^-$, tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenylbis(pentafluorophenyl)borate, tetrakis(3,5-bistrifluoromethylphenyl)borate and the like are exemplified.

Specific combinations of the $Z^+$ and the $(BQ_1Q_2Q_3Q_4)^-$ include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis(3,5-bistrifluoromethylphenyl)borate and the like, and more preferably triphenylmethyl tetrakis(pentafluorophenyl)borate.

Furthermore, in the boron compound represented by the formula $(L-H)^+(BQ_1Q_2Q_3Q_4)^-$, L is a neutral Lewis base, $(L-H)^+$ is a Brønsted acid, B is a boron atom in a trivalent valence state, and $Q_1$ to $Q_4$ are the same as the $Q_1$ to $Q_3$ in the above-mentioned (B1).

For specific examples of the compound represented by the formula $(L-H)^+(BQ_1Q_2Q_3Q_4)^-$, the Brønsted acid $(L-H)^+$ includes trialkyl-substituted ammonium, N,N-dialkylanilinium, dialkylammonium, triarylphosphonium and the like, and the $(BQ_1Q_2Q_3Q_4)^-$ includes those as described above.

Specific combinations of the $(L-H)^+$ and the $(BQ_1Q_2Q_3Q_4)^-$ include triethylammonium tetrakis(pentafluorophenyl)borate, tripropylammonium tetrakis(pentafluorophenyl)borate, tri(normal butyl)ammonium tetrakis(pentafluorophenyl)borate, tri(normal butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, tri(dimethylphenyl)phosphonium tetrakis(pentafluorophenyl)borate and the like, and most preferably, tri(normal butyl)ammonium tetrakis(pentafluorophenyl)borate, N,N-dimethylanilinium tetrakis(pentafluorophenyl)borate and the like.

In addition to the transition metal complex represented by the formula (I) and the compound (A), or a combination thereof, the compound (B) can be used as a catalyst component to carry out polymerization reaction. Into the polymerization reaction, these catalyst components may be added in any order. Alternatively, components optionally selected from the catalyst components used in a combination as described above are previously contacted with each other and the reaction product thus obtained can also be used in the polymerization reaction.

The amount of each catalyst component to be used is preferably 0.1 to 10,000, more preferably 5 to 2000 in the mole ratio of compound (A)/transition metal complex, and preferably 0.01 to 100, more preferably 0.5 to 10 in the mole ratio of compound (B)/transition metal complex. The concentration of each catalyst component, if it is used in a solution state, is preferably 0.0001 to 5 mmol/L, more preferably 0.001 to 1 mmol/L for the transition metal complex represented by the formula (I); preferably 0.01 to 500 mmol/L, more preferably 0.1 to 100 mmol/L (as converted to Al atom) for the compound (A); and preferably 0.0001 to 5 mmol/L, more preferably 0.001 to 1 mmol/L for the compound (B).

In the present invention, as a monomer used for polymerization, olefins, diolefins and the like consisting of 2 to 20 carbon atoms can be used, and two or more monomers can be used simultaneously. Such monomers are exemplified hereinafter, but the present invention is not limited to the following compounds. Specific examples of such olefin include ethylene, propylene, butene-1, pentene-1, hexene-1, heptene-1, octene-1, nonene-1, decene-1,5-methyl-2-pentene-1, vinylcyclohexene and the like. The diolefin compound includes conjugated dienes of hydrocarbon compounds and non-conjugated dienes. Specific examples of such diene compounds include, as specific examples of the non-conjugated diene compound, 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornene, 5-methyl-2-norbornene, norbornadiene, 5-methylene-2-norbornene, 1,5-cyclooctadiene, 5,8-endomethylenehexahydronaphthalene and the like, and as specific examples of the conjugated diene compound, 1,3-butadiene, isoprene, 1,3-hexadiene, 1,3-octadiene, 1,3-cyclooctadiene, 1,3-cyclohexadiene and the like.

Specific examples of monomers constituting a copolymer include, but not limited to, ethylene and propylene, ethylene and butene-1, ethylene and hexene-1, propylene and butene-1, and a combination of the above any combination and 5-ethylidene-2-norbornene.

In the present invention, aromatic vinyl compounds can be also used as a monomer. Specific examples of the aromatic vinyl compound include styrene, o-methylstyrene, m-methylstyrene, p-methylstyrene, o,p-dimethylstyrene, o-ethylstyrene, m-ethylstyrene, p-ethylstyrene, o-chlorostyrene, p-chlorostyrene, α-methylstyrene, divinylbenzene and the like.

The method for polymerization is not specifically limited, and for example, may be solvent polymerization or slurry polymerization, in which aliphatic hydrocarbon such as butane, pentane, hexane, heptane or octane, aromatic hydrocarbon such as benzene or toluene, or halogenated hydrocarbon such as methylene dichloride is used as a solvent, or gas phase polymerization in a gaseous monomer, which may be either successive polymerization or batch polymerization.

The polymerization temperature can be generally in the range of −50° C. to 200° C., specifically preferably in the range of −20° C. to 100° C. The polymerization pressure is preferably ordinary pressure to 60 kg/cm$^2$G (6 MPa). The polymerization period is generally suitably determined depending on the kind of an objective polymer and reaction apparatus and can be in the range of 1 min to 20 hrs. In the present invention, a chain transfer agent such as hydrogen can be also added to the polymerization reaction in order to adjust the molecular weight of a copolymer.

Next, the substituted cyclopentadiene ligand represented by the formula (II) is explained.

As the compounds represented by the formula (II), the compounds represented by the following formulas (5), (6) and (7) are exemplified.

A substituted cyclopentadiene compound represented by the formula (5):

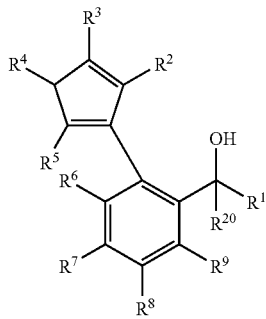

(5)

wherein $R^1$ to $R^9$ and $R^{20}$ have the same meanings as above; provided that neither $R^2$ and $R^3$ nor $R^4$ and $R^5$ are linked to each other and taken together with the cyclopentadiene ring to form a fluorene ring or an indenyl ring, is explained below.

In Tetrahedron Letters, 39 (1998), 6537-6576, 1-(2'-methyl-3'-indenyl)-2-naphthalenemethanol and 1-(3'-indenyl)-2-naphthalenemethanol are disclosed, but polymerization catalysts comprising these compounds as a ligand are not disclosed and suggested at all. Furthermore, 9-(2-hydroxymethyl-1-naphthyl)fluorene, 9-[2-α-hydroxybenzyl)-1-naphthyl]fluorene and 9-[2-(α-hydroxyethyl)-1-naphthyl]fluorene are disclosed in Bull. Chem. Soc. Jpn., 55, 3267-3272 (1982) and 9-[2-(1-hydroxy-2-trimethylsilylethyl)-1-naphthyl]fluorene is disclosed in Bull. Chem. Soc. Jpn., 62, 621-623 (1989). However, each of these articles fails to disclose or suggest polymerization catalysts comprising these compounds as a ligand.

The compound of the formula (5) can be produced by reacting the carbonyl compound of formula (1) with a nucleophilic agent.

A nucleophilic agent used in such reaction includes, for example, hydride compounds and carbanion compounds ($R^{20}$Li or $R^{20}$MgX or metal hydride compounds). Such a nucleophilic agent includes sodium hydride, lithium aluminum hydride, methylmagnesium bromide, ethylmagnesium bromide, phenylmagnesium bromide, n-butylmagnesium bromide, t-butylmagnesium bromide, methyllithium, phenyllithium, t-butyllithium and the like. Similarly, the above-mentioned compounds in which magnesium bromide is changed to magnesium chloride or magnesium iodide are also exemplified.

The reaction is generally carried out in an inert solvent to reaction. Such a solvent includes, for example, aprotic solvents such as aromatic hydrocarbon solvents such as benzene and toluene and the like; aliphatic hydrocarbon solvents such as hexane, heptane and the like; ether solvents such as diethyl ether, tetrahydrofuran, 1,4-dioxane and the like; amide solvents such as hexamethylphosphoric amide, dimethylformamide and the like; polar solvents such as acetonitrile, propionitrile, acetone, diethyl ketone, methyl isobutyl ketone, cyclohexanone and the like; and halogenated solvents such as dichloromethane, dichloroethane, chlorobenzene, dichlorobenzene and the like. One or a mixture of two or more of the solvents is used. The amount of a solvent to be used is usually in the range of 1 to 200 times, preferably 3 to 50 times the weight of the carbonyl compound represented by the formula (1).

The reaction temperature is usually in the range of −100° C. to the boiling point of a solvent, preferably −80 to 120° C.

After the reaction, if needed, water is added to the resulting reaction mixture. The mixture is then separated into an organic layer and an aqueous layer to give a solution of the objective compound as the organic layer. When the organic layer and the aqueous layer cannot be easily separated due to use of a solvent compatible with water or use of a small amount of a solvent in said reaction, the separation may be carried out after addition of a water-insoluble organic solvent such as toluene, ethyl acetate or chlorobenzene to the reaction mixture. The cyclopentadiene represented by the formula (5) can be purified, for example, by washing said solution of the compound with water, drying said solution, and then distilling off the solvent and further by methods such as recrystallization, distillation, column chromatography treatment and the like.

Specific examples of the compound of the formula (5) thus obtained include the following compounds: 2-(cyclopentadienyl)benzylalcohol, 2-(2-methylcyclopentadienyl)benzylalcohol, 2-(3-methylcyclopentadienyl)benzylalcohol, 2-(2,3-dimethylcyclopentadienyl)benzylalcohol, 2-(2,4-dimethylcyclopentadienyl)benzylalcohol, 2-(2,3,4-trimethylcyclopentadienyl)benzylalcohol, 2-(2,3,5-trimethylcyclopentadienyl)benzylalcohol, 2-(2,3,4,5-tetramethylcyclopentadienyl)benzylalcohol, 2-(2-dimethylaminomethylcyclopentadienyl)benzylalcohol, 2-(3-dimethylaminomethylcyclopentadienyl)benzylalcohol, 2-(cyclopentadienyl)-1-naphthylmethylalcohol, 2-(2-methylcyclopentadienyl)-1-naphthylmethylalcohol, 2-(3-methylcyclopentadienyl)-1-naphthylmethylalcohol, 2-(2,3-dimethylcyclopentadienyl)-1-naphthylmethylalcohol, 2-(2,4-dimethylcyclopentadienyl)-1-naphthylmethylalcohol, 2-(2,3,4-trimethylcyclopentadienyl)-1-naphthylmethylalcohol, 2-(2,3,5-trimethylcyclopentadienyl)-1-naphthylmethylalcohol, 2-(2,3,4,5-tetramethylcyclopentadienyl)-1-naphthylmethylalcohol, 2-(2-dimethylaminomethylcyclopentadienyl)-1-naphthylmethylalcohol, 2-(3-dimethylaminomethylcyclopentadienyl)-1-naphthylmethylalcohol, 2-(fluoren-9-yl)-1-naphthylmethylalcohol, 1-[2-(cyclopentadienyl)phenyl]ethylalcohol, 1-[2-(2-methylcyclopentadienyl)phenyl]ethylalcohol, 1-[2-(3-methylcyclopentadienyl)phenyl]ethylalcohol, 1-[2-(2,3-dimethylcyclopentadienyl)phenyl]ethylalcohol, 1-[2-(2,4-dimethylcyclopentadienyl)phenyl]ethylalcohol, 1-[2-(2,3,4-trimethylcyclopentadienyl)phenyl]ethylalcohol, 1-[2-(2,3,5-trimethylcyclopentadienyl)phenyl]ethylalcohol, 1-[2-(2,3,4,5-tetramethylcyclopentadienyl)phenyl]ethylalcohol, 1-[2-(2-dimethylaminomethylcyclopentadienyl)phenyl]ethylalcohol, 1-[2-(3-dimethylaminomethylcyclopentadienyl)phenyl]ethylalcohol, 1-[2-(cyclopentadienyl)-1-naphthyl]ethylalcohol, 1-[2-(2-methylcyclopentadienyl)-1-naphthyl]ethylalcohol, 1-[2-(3-methylcyclopentadienyl)-1-naphthyl]ethylalcohol, 1-[2-(2,3-dimethylcyclopentadienyl)-1-naphthyl]ethylalcohol, 1-[2-(2,4-dimethylcyclopentadienyl)-1-naphthyl]ethylalcohol, 1-[2-(2,3,4-trimethylcyclopentadienyl)-1-naphthyl]ethylalcohol, 1-[2-(2,3,5-trimethylcyclopentadienyl)-1-naphthyl]ethylalcohol, 1-[2-(2,3,4,5-tetramethylcyclopentadienyl)-1-naphthyl]ethylalcohol, 1-[2-(2-dimethylaminomethylcyclopentadienyl)-1-naphthyl]ethylalcohol, 1-[2-(3-dimethylaminomethylcyclopentadienyl)-1-naphthyl]ethylalcohol, 1-[2-(cyclopentadienyl)phenyl]-1-methyl-ethylalcohol, 1-[2-(2-methylcyclopentadienyl)phenyl]-1-methyl-ethylalcohol, 1-[2-(3-methylcyclopentadienyl)

phenyl]-1-methyl-ethylalcohol, 1-[2-(2,3-dimethylcyclopentadienyl)phenyl]-1-methyl-ethylalcohol, 1-[2-(2,4-dimethylcyclopentadienyl)phenyl]-1-methyl-ethylalcohol, 1-[2-(2,3,4-trimethylcyclopentadienyl)phenyl]-1-methyl-ethylalcohol, 1-[2-(2,3,5-trimethylcyclopentadienyl)phenyl]-1-methyl-ethylalcohol, 1-[2-(2,3,4,5-tetramethylcyclopentadienyl)phenyl]-1-methyl-ethylalcohol, 1-[2-(2-dimethylaminomethylcyclopentadienyl)phenyl]-1-methyl-ethylalcohol, 1-[2-(3-dimethylaminomethylcyclopentadienyl)phenyl]-1-methyl-ethylalcohol, 1-[2-(cyclopentadienyl)-1-naphthyl]-1-methyl-ethylalcohol, 1-[2-(2-methylcyclopentadienyl)-1-naphthyl]-1-methyl-ethylalcohol, 1-[2-(3-methylcyclopentadienyl)-1-naphthyl]-1-methyl-ethylalcohol, 1-[2-(2,3-dimethylcyclopentadienyl)-1-naphthyl]-1-methyl-ethylalcohol, 1-[2-(2,4-dimethylcyclopentadienyl)-1-naphthyl]-1-methyl-ethylalcohol, 1-[2-(2,3,4-trimethylcyclopentadienyl)-1-naphthyl]-1-methyl-ethylalcohol, 1-[2-(2,3,5-trimethylcyclopentadienyl)-1-naphthyl]-1-methyl-ethylalcohol, 1-[2-(2,3,4,5-tetramethylcyclopentadienyl)-1-naphthyl]-1-methyl-ethylalcohol, 1-[2-(2-dimethylaminomethylcyclopentadienyl)-1-naphthyl]-1-methyl-ethylalcohol, 1-[2-(3-dimethylaminomethylcyclopentadienyl)-1-naphthyl]-1-methyl-ethylalcohol, [2-(cyclopentadienyl)phenyl]-t-butyl-methylalcohol, [2-(2-methylcyclopentadienyl)phenyl]-t-butyl-methylalcohol, [2-(3-methylcyclopentadienyl)phenyl]-t-butyl-methylalcohol, [2-(2,3-dimethylcyclopentadienyl)phenyl]-t-butyl-methylalcohol, [2-(2,4-dimethylcyclopentadienyl)phenyl]-t-butyl-methylalcohol, [2-(2,3,4-trimethylcyclopentadienyl)phenyl]-t-butyl-methylalcohol, [2-(2,3,5-trimethylcyclopentadienyl)phenyl]-t-butyl-methylalcohol, [2-(2,3,4,5-tetramethylcyclopentadienyl)phenyl]-t-butyl-methylalcohol, [2-(2-dimethylaminomethylcyclopentadienyl)phenyl]-t-butyl-methyloxyalcohol, [2-(3-dimethylaminomethylcyclopentadienyl)phenyl]-t-butyl-methylalcohol, [2-(cyclopentadienyl)-1-naphthyl]-t-butyl-methylalcohol, [2-(2-methylcyclopentadienyl)-1-naphthyl]-t-butyl-methylalcohol, [2-(3-methylcyclopentadienyl)-1-naphthyl]-t-butyl-methylalcohol, [2-(2,3-dimethylcyclopentadienyl)-1-naphthyl]-t-butyl-methylalcohol, [2-(2,4-dimethylcyclopentadienyl)-1-naphthyl]-t-butyl-methylalcohol, [2-(2,3,4-trimethylcyclopentadienyl)-1-naphthyl]-t-butyl-methylalcohol, [2-(2,3,5-trimethylcyclopentadienyl)-1-naphthyl]-t-butyl-methylalcohol, [2-(2,3,4,5-tetramethylcyclopentadienyl)-1-naphthyl]-t-butyl-methylalcohol, [2-(2-dimethylaminomethylcyclopentadienyl)-1-naphthyl]-t-butyl-methylalcohol, [2-(3-dimethylaminomethylcyclopentadienyl)-1-naphthyl]-t-butyl-methylalcohol, [2-(cyclopentadienyl)phenyl]phenylmethylalcohol, [2-(2-methylcyclopentadienyl)phenyl]phenylmethylalcohol, [2-(3-methylcyclopentadienyl)phenyl]phenylmethylalcohol, [2-(2,3-dimethylcyclopentadienyl)phenyl]phenylmethylalcohol, [2-(2,4-dimethylcyclopentadienyl)phenyl]phenylmethylalcohol, [2-(2,3,4-trimethylcyclopentadienyl)phenyl]phenylmethylalcohol, [2-(2,3,5-trimethylcyclopentadienyl)phenyl]phenylmethylalcohol, [2-(2,3,4,5-tetramethylcyclopentadienyl)phenyl]phenylmethylalcohol, [2-(2-dimethylaminomethylcyclopentadienyl)phenyl]phenylmethyloxyalcohol, [2-(3-dimethylaminomethylcyclopentadienyl)phenyl]phenylmethylalcohol, [2-(cyclopentadienyl)-1-naphthyl]phenylmethylalcohol, [2-(2-methylcyclopentadienyl)-1-naphthyl]phenylmethylalcohol, [2-(3-methylcyclopentadienyl)-1-naphthyl]phenylmethylalcohol, [2-(2,3-dimethylcyclopentadienyl)-1-naphthyl]phenylalcohol, [2-(2,4-dimethylcyclopentadienyl)-1-naphthyl]phenylmethylalcohol, [2-(2,3,4-trimethylcyclopentadienyl)-1-naphthyl]phenylmethylalcohol, [2-(2,3,5-trimethylcyclopentadienyl)-1-naphthyl]phenylmethylalcohol, [2-(2,3,4,5-tetramethylcyclopentadienyl)-1-naphthyl]phenylmethylalcohol, [2-(2-dimethylaminomethylcyclopentadienyl)-1-naphthyl]phenylmethylalcohol, [2-(3-dimethylaminomethylcyclopentadienyl)-1-naphthyl]phenylmethylalcohol, [2-(cyclopentadienyl)phenyl]diphenylmethylalcohol, [2-(2-methylcyclopentadienyl)phenyl]diphenylmethylalcohol, [2-(3-methylcyclopentadienyl)phenyl]diphenylmethylalcohol, [2-(2,3-dimethylcyclopentadienyl)phenyl]diphenylmethylalcohol, [2-(2,4-dimethylcyclopentadienyl)phenyl]diphenylmethylalcohol, [2-(2,3,4-trimethylcyclopentadienyl)phenyl]diphenylmethylalcohol, [2-(2,3,5-trimethylcyclopentadienyl)phenyl]diphenylmethylalcohol, [2-(2,3,4,5-tetramethylcyclopentadienyl)phenyl]diphenylmethylalcohol, [2-(2-dimethylaminomethylcyclopentadienyl)phenyl]diphenylmethyloxyalcohol, [2-(3-dimethylaminomethylcyclopentadienyl)phenyl]diphenylmethylalcohol, [2-(cyclopentadienyl)-1-naphthyl]diphenylmethylalcohol, [2-(2-methylcyclopentadienyl)-1-naphthyl]diphenylmethylalcohol, [2-(3-methylcyclopentadienyl)-1-naphthyl]diphenylmethylalcohol, [2-(2,3-dimethylcyclopentadienyl)-1-naphthyl]diphenylalcohol, [2-(2,4-dimethylcyclopentadienyl)-1-naphthyl]diphenylmethylalcohol, [2-(2,3,4-trimethylcyclopentadienyl)-1-naphthyl]diphenylmethylalcohol, [2-(2,3,5-trimethylcyclopentadienyl)-1-naphthyl]diphenylmethylalcohol, [2-(2,3,4,5-tetramethylcyclopentadienyl)-1-naphthyl]diphenylmethylalcohol, [2-(2-dimethylaminomethylcyclopentadienyl)-1-naphthyl]diphenylmethylalcohol, [2-(3-dimethylaminomethylcyclopentadienyl)-1-naphthyl]diphenylmethylalcohol and the like.

The amine compound represented by the formula (6):

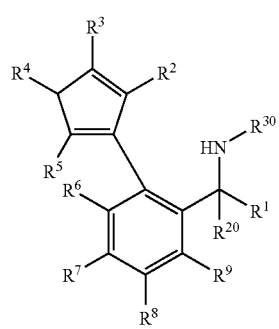

(6)

wherein $R^1$, $R^2$, $R^3$, $R^4$, $R^5$, $R^6$, $R^7$, $R^8$, $R^9$, $R^{20}$ and $R^{30}$ the same meanings as defined for the above-mentioned formula (I-2), is hereinafter explained.

The amine compound of the formula (6) can be obtained by reducing an imine compound represented by the formula (9):

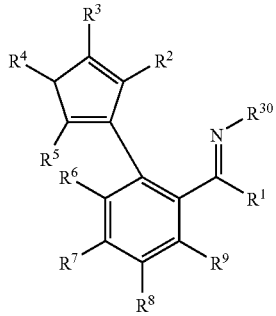

(9)

wherein $R^1$, $R^2$, $R^3$, $R^4$, $R^5$, $R^6$, $R^7$, $R^8$; $R^9$ and $R^{30}$ have the same meanings as defined for the formula (I-2); provided that $R^{30}$ is not a hydrogen atom, or reacting said compound with a nucleophilic agent.

A nucleophilic agent used in the reaction includes metal hydride compounds, organic lithium compounds, organic magnesium compounds and the like ($R^{20}$Li or $R^{20}$MgX; provided that $R^{20}$ is not a hydrogen atom).

Such a nucleophilic agent includes metal hydride compounds such as lithium aluminum hydride, sodium borohydride, sodium cyanoborohydride and the like; methylmagnesium bromide, ethylmagnesium bromide, phenylmagnesium bromide, n-butylmagnesium bromide, t-butylmagnesium bromide, methyllithium, phenyllithium, t-butyllithium and the like. Similarly, the above-mentioned compounds in which magnesium bromide is changed to magnesium chloride or magnesium iodide are also exemplified. The amount of the nucleophilic agent to be used is usually about 0.25 to 5 moles relative to 1 mole of the imine.

The above reaction is usually carried out in a solvent. Such a solvent includes, for example, alcohol solvents such as methanol, ethanol, isopropanol and the like; aprotic solvents such as aromatic hydrocarbon solvents such as benzene, toluene and the like; aliphatic hydrocarbon solvents such as hexane, heptane and the like; ether solvents such as diethyl ether, tetrahydrofuran, 1,4-dioxane and the like; amide solvents such as hexamethylphosphoric amide, dimethylformamide and the like; polar solvents such as acetonitrile, propionitrile, acetone, diethyl ketone, methyl isobutyl ketone, cyclohexanone and the like; and halogenated solvents such as dichloromethane, dichloroethane, chlorobenzene, dichlorobenzene and the like. One or a mixture of two or more of the solvents is used. The amount of a solvent to be used is usually in the range of 1 to 200 times, preferably 3 to 50 times the weight of the imine represented by the formula (9).

The reaction temperature is usually in the range of –100° C. to the boiling point of a solvent, preferably –80 to 120° C.

After the reaction, if needed, water is added to the resulting reaction mixture. The mixture is then separated into an organic layer and an aqueous layer to give a solution of the objective compound as the organic layer. When the organic layer and the aqueous layer can not be easily separated due to use of a solvent compatible with water or use of a small amount of a solvent in said reaction, the separation may be carried out after addition of a water-insoluble organic solvent such as toluene, ethyl acetate or chlorobenzene to the reaction mixture. The amine represented by the formula (6) can be purified, for example, by washing said solution of the compound with water, drying said solution, and then distilling off the solvent, and further by methods such as recrystallization, distillation, column chromatography treatment and the like.

The imine compound of the formula (9) can be produced by reacting the carbonyl compound of the formula (1) with an amine compound ($R^{30}$—NH$_2$).

Specific examples of the imine compound of the formula (9) include the following compounds: N-(2-(cyclopentadienyl)phenyl)methylene-N-phenylamine, N-(2-(2-methylcyclopentadienyl)phenyl)methylene-N-phenylamine, N-(2-(3-methylcyclopentadienyl)phenyl)methylene-N-phenylamine, N-(2-(2,3-dimethylcyclopentadienyl)phenyl)methylene-N-phenylamine, N-(2-(2,4-dimethylcyclopentadienyl)phenyl)methylene-N-phenylamine, N-(2-(2,3,4-trimethylcyclopentadienyl)phenyl)methylene-N-phenylamine, N-(2-(2,3,5-trimethylcyclopentadienyl)phenyl)methylene-N-phenylamine, N-(2-(2,3,4,5-tetramethylcyclopentadienyl)phenyl)methylene-N-phenylamine, N-(2-(2-dimethylaminocyclopentadienyl)phenyl)methylene-N-phenylamine, N-(2-(3-dimethylaminocyclopentadienyl)phenyl)methylene-N-phenylamine, N-(2-(inden-1-yl)phenyl)methylene-N-phenylamine, N-(2-(2-methylinden-1-yl)phenyl)methylene-N-phenylamine, N-(2-(2-phenylinden-1-yl)phenyl)methylene-N-phenylamine, N-(2-(cyclopentadienyl)phenyl)methylene-N-(2,4,6-trimethylphenyl)amine, N-(2-(2-methylcyclopentadienyl)phenyl)methylene-N-(2,4,6-trimethylphenyl)amine, N-(2-(3-methylcyclopentadienyl)phenyl)methylene-N-(2,4,6-trimethylphenyl)amine, N-(2-(2,3-dimethylcyclopentadienyl)phenyl)methylene-N-(2,4,6-trimethylphenyl)amine, N-(2-(2,4-dimethylcyclopentadienyl)phenyl)methylene-N-(2,4,6-trimethylphenyl)amine, N-(2-(2,3,4-trimethylcyclopentadienyl)phenyl)methylene-N-(2,4,6-trimethylphenyl)amine, N-(2-(2,3,5-trimethylcyclopentadienyl)phenyl)methylene-N-(2,4,6-trimethylphenyl)amine, N-(2-(2,3,4,5-tetramethylcyclopentadienyl)phenyl)methylene-N-(2,4,6-trimethylphenyl)amine, N-(2-(2-dimethylaminocyclopentadienyl)phenyl)methylene-N-(2,4,6-trimethylphenyl)amine, N-(2-(3-dimethylaminocyclopentadienyl)phenyl)methylene-N-(2,4,6-trimethylphenyl)amine, N-(2-(inden-1-yl)phenyl)methylene-N-(2,4,6-trimethylphenyl)amine, N-(2-(2-methylinden-1-yl)phenyl)methylene-N-(2,4,6-trimethylphenyl)amine, N-(2-(2-phenylinden-1-yl)phenyl)methylene-N-(2,4,6-trimethylphenyl)amine, N-(2-(cyclopentadienyl)phenyl)methylene-N-tert-butylamine, N-(2-(2-methylcyclopentadienyl)phenyl)methylene-N-tert-butylamine, N-(2-(3-methylcyclopentadienyl)-phenyl)methylene-N-tert-butylamine, N-(2-(2,3-dimethylcyclopentadienyl)phenyl)methylene-N-tert-butylamine, N-(2-(2,4-dimethylcyclopentadienyl)phenyl)methylene-N-tert-butylamine, N-(2-(2,3,4-trimethylcyclopentadienyl)phenyl)methylene-N-tert-butylamine, N-(2-(2,3,5-trimethylcyclopentadienyl)phenyl)methylene-N-tert-butylamine, N-(2-(2,3,4,5-tetramethylcyclopentadienyl)phenyl)methylene-N-tert-butylamine, N-(2-(2-dimethylaminocyclopentadienyl)phenyl)methylene-N-tert-butylamine, N-(2-(3-dimethylaminocyclopentadienyl)phenyl)methylene-N-tert-butylamine, N-(2-(inden-1-yl)phenyl)methylene-N-tert-butylamine, N-(2-(2-methylinden-1-yl)phenyl)methylene-N-tert-butylamine, N-(2-(2-phenylinden-1-yl)phenyl)methylene-N-tert-butylamine, N-(2-(cyclopentadienyl)phenyl)methylene-N-n-butylamine, N-(2-(2-methylcyclopentadienyl)phenyl)methylene-N-n-butylamine, N-(2-(3-methylcyclopentadienyl)phenyl)methylene-N-n-butylamine, N-(2-(2,3-dimethylcyclopentadienyl)phenyl)methylene-N-n-butylamine, N-(2-(2,4-dimethylcyclopentadienyl)phenyl)methylene-N-n-butylamine, N-(2-(2,3,4-trimethylcyclopentadienyl)phenyl)methylene-N-n-butylamine, N-(2-(2,3,5-trimethylcyclopentadienyl)phenyl)methylene-N-n-butylamine, N-(2-(2,3,4,5-tetramethylcyclopentadienyl)phenyl)methylene-N-n-butylamine, N-(2-(2-dimethylaminocyclopentadienyl)phenyl)methylene-N-n-butylamine, N-(2-(3-dimethylaminocyclopentadienyl)phenyl)methylene-N-n-butylamine, N-(2-(inden-1-yl)phenyl)methylene-N-n-butylamine, N-(2-(2-methylinden-1-yl)phenyl)methylene-N-n-butylamine, N-(2-(2-phenylinden-1-yl)phenyl)methylene-N-n-butylamine, N-(2-(cyclopentadienyl)phenyl)ethylidene-N-phenylamine, N-(2-(2-methylcyclopentadienyl)phenyl)ethylidene-N-phenylamine, N-(2-(3-methylcyclopentadienyl)phenyl)ethylidene-N-phenylamine, N-(2-(2,3-dimethylcyclopentadienyl)phenyl)ethylidene-N-phenylamine, N-(2-(2,4-dimethylcyclopentadienyl)phenyl)ethylidene-N-phenylamine, N-(2-(2,3,4-trimethylcyclopentadienyl)phenyl)ethylidene-N-phenylamine, N-(2-(2,3,5-trimethylcyclopentadienyl)phenyl)ethylidene-N-phenylamine, N-(2-(2,3,4,5-tetramethylcyclopentadienyl)phenyl)ethylidene-N-phenylamine, N-(2-(2-dimethylaminocyclopentadienyl)phenyl)ethylidene-N-phenylamine, N-(2-(3-dimethylaminocyclopentadienyl)phenyl)ethylidene-N-phenylamine, N-(2-(inden-1-yl)phenyl)ethylidene-N-phenylamine, N-(2-(2-methylinden-1-yl)phenyl)ethylidene-N-phenylamine, N-(2-(2-phenylinden-1-yl)phenyl)ethylidene-N-phenylamine, N-(2-(cyclopentadienyl)phenyl)ethylidene-N-(2,4,6-trimethylphenyl)amine, N-(2-(2-methylcyclopentadienyl)phenyl)ethylidene-N-(2,4,6-trimethylphenyl)amine, N-(2-(3-methylcyclopentadienyl)phenyl)ethylidene-N-(2,4,6-trimethylphenyl)amine, N-(2-(2,3-dimethylcyclopentadienyl)phenyl)ethylidene-N-(2,4,6-trimethylphenyl)amine, N-(2-(2,4-dimethylcyclopentadienyl)phenyl)ethylidene-N-(2,4,6-trimethylphenyl)amine, N-(2-(2,3,4-trimethylcyclopentadienyl)phenyl)ethylidene-N-(2,4,6-trimethylphenyl)amine, N-(2-(2,3,5-trimethylcyclopentadienyl)phenyl)ethylidene-N-(2,4,6-trimethylphenyl)amine, N-(2-(2,3,4,5-tetramethylcyclopentadienyl)phenyl)ethylidene-N-(2,4,6-trimethylphenyl)amine, N-(2-(2-dimethylaminocyclopentadienyl)phenyl)ethylidene-N-(2,4,6-trimethylphenyl)amine, N-(2-(3-dimethylaminocyclopentadienyl)phenyl)ethylidene-N-(2,4,6-trimethylphenyl)amine, N-(2-(inden-1-yl)phenyl)ethylidene-N-(2,4,6-trimethylphenyl)amine, N-(2-(2-methylinden-1-yl)phenyl)ethylidene-N-(2,4,6-trimethylphenyl)amine, N-(2-(2-phenylinden-1-yl)phenyl)ethylidene-N-(2,4,6-trimethylphenyl)amine, N-(2-(cyclopentadienyl)phenyl)ethylidene-N-tert-butylamine, N-(2-(2-methylcyclopentadienyl)phenyl)ethylidene-N-tert-butylamine, N-(2-(3-methylcyclopentadienyl)phenyl)ethylidene-N-tert-butylamine, N-(2-(2,3-dimethylcyclopentadienyl)phenyl)ethylidene-N-tert-butylamine, N-(2-(2,4-dimethylcyclopentadienyl)phenyl)ethylidene-N-tert-butylamine, N-(2-(2,3,4-trimethylcyclopentadienyl)phenyl)ethylidene-N-tert-butylamine, N-(2-(2,3,5-trimethylcyclopentadienyl)phenyl)ethylidene-N-tert-butylamine, N-(2-(2,3,4,5-tetramethylcyclopentadienyl)phenyl)ethylidene-N-tert-butylamine, N-(2-(2-dimethylaminocyclopentadienyl)phenyl)ethylidene-N-tert-butylamine, N-(2-(3-dimethylaminocyclopentadienyl)phenyl)ethylidene-N-tert-butylamine, N-(2-(inden-1-yl)phenyl)ethylidene-N-tert-butylamine, N-(2-(2-methylinden-1-yl)phenyl)ethylidene-N-tert-butylamine, N-(2-(2-phenylinden-1-yl)phenyl)ethylidene-N-tert-butylamine, N-(2-(cyclopentadienyl)phenyl)ethylidene-N-n-butylamine, N-(2-(2-methylcyclopentadienyl)phenyl)ethylidene-N-n-butylamine, N-(2-(3-methylcyclopentadienyl)phenyl)ethylidene-N-n-butylamine, N-(2-(2,3-dimethylcyclopentadienyl)phenyl)ethylidene-N-n-butylamine, N-(2-(2,4-dimethylcyclopentadienyl)phenyl)ethylidene-N-n-butylamine, N-(2-(2,3,4-trimethylcyclopentadienyl)phenyl)ethylidene-N-n-butylamine, N-(2-(2,3,5-trimethylcyclopentadienyl)phenyl)ethylidene-N-n-butylamine, N-(2-(2,3,4,5-tetramethylcyclopentadienyl)phenyl)ethylidene-N-n-butylamine, N-(2-(2-dimethylaminocyclopentadienyl)phenyl)ethylidene-N-n-butylamine, N-(2-(3-dimethylaminocyclopentadienyl)phenyl)ethylidene-N-n-butylamine, N-(2-(inden-1-yl)phenyl)ethylidene-N-n-butylamine, N-(2-(2-methylinden-1-yl)phenyl)ethylidene-N-n-butylamine, N-(2-(2-phenylinden-1-yl)phenyl)ethylidene-N-n-butylamine, N-(2-(cyclopentadienyl)-1-naphthyl)methylene-N-phenylamine, N-(2-(2-methylcyclopentadienyl)-1-naphthyl)methylene-N-phenylamine, N-(2-(3-methylcyclopentadienyl)-1-naphthyl)methylene-N-phenylamine, N-(2-(2,3-dimethylcyclopentadienyl)-1-naphthyl)methylene-N-phenylamine, N-(2-(2,4-dimethylcyclopentadienyl)-1-naphthyl)methylene-N-phenylamine, N-(2-(2,3,4-trimethylcyclopentadienyl)-1-naphthyl)methylene-N-phenylamine, N-(2-(2,3,5-trimethylcyclopentadienyl)-1-naphthyl)methylene-N-phenylamine, N-(2-(2,3,4,5-tetramethylcyclopentadienyl)-1-naphthyl)methylene-N-phenylamine, N-(2-(2-dimethylaminocyclopentadienyl)-1-naphthyl)methylene-N-phenylamine, N-(2-(3-dimethylaminocyclopentadienyl)-1-naphthyl)methylene-N-phenylamine, N-(2-(inden-1-yl)-1-naphthyl)methylene-N-phenylamine, N-(2-(2-methylinden-1-yl)-1-naphthyl)methylene-N-phenylamine, N-(2-(2-phenylinden-1-yl)-1-naphthyl)methylene-N-phenylamine, N-(2-(cyclopentadienyl)-1-naphthyl)methylene-N-(2,4,6-trimethylphenyl)amine, N-(2-(2-methylcyclopentadienyl)-1-naphthyl)methylene-N-(2,4,6-trimethylphenyl)amine, N-(2-(3-methylcyclopentadienyl)-1-naphthyl)methylene-N-(2,4,6-trimethylphenyl)amine, N-(2-(2,3-dimethylcyclopentadienyl)-1-naphthyl)methylene-N-(2,4,6-trimethylphenyl)amine, N-(2-(2,4-dimethylcyclopentadienyl)-1-naphthyl)methylene-N-(2,4,6-trimethylphenyl)amine, N-(2-(2,3,4-trimethylcyclopentadienyl)-1-naphthyl)methylene-N-(2,4,6-trimethylphenyl)amine, N-(2-(2,3,5-trimethylcyclopentadienyl)-1-naphthyl)methylene-N-(2,4,6-trimethylphenyl)amine, N-(2-(2,3,4,5-tetramethylcyclopentadienyl)-1-naphthyl)methylene-N-(2,4,6-trimethylphenyl)amine, N-(2-(2-dimethylaminocyclopentadienyl)-1-naphthyl)methylene-N-(2,4,6-trimethylphenyl)amine, N-(2-(3-dimethylaminocyclopentadienyl)-1-naphthyl)methylene-N-(2,4,6-trimethylphenyl)amine, N-(2-(inden-1-yl)-1-naphthyl)methylene-N-(2,4,6-trimethylphenyl)amine, N-(2-(2-methylinden-1-yl)-1-naphthyl)methylene-N-(2,4,6-trimethylphenyl)amine, N-(2-(2-phenylinden-1-yl)-1-naphthyl)methylene-N-(2,4,6-trimethylphenyl)amine, N-(2-(cyclopentadienyl)-1-naphthyl)methylene-N-tert-butylamine, N-(2-(2-methylcyclopentadienyl)-1-naphthyl)methylene-N-tert-butylamine, N-(2-(3-methylcyclopentadienyl)-1-naphthyl)methylene-N-tert-butylamine, N-(2-(2,3-dimethylcyclopentadienyl)-1-naphthyl)methylene-N-tert-butylamine, N-(2-(2,4- dimethylcyclopentadienyl)-1-naphthyl)methylene-N-tert-butylamine, N-(2-(2,3,4-trimethylcyclopentadienyl)-1-naphthyl)methylene-N-tert-butylamine, N-(2-(2,3,5-trimethylcyclopentadienyl)-1-naphthyl)methylene-N-tert-butylamine, N-(2-(2,3,4,5-tetramethylcyclopentadienyl)-1-naphthyl)methylene-N-tert-butylamine, N-(2-(2-dimethylaminocyclopentadienyl)-1-naphthyl)methylene-N-tert-butylamine, N-(2-(3-dimethylaminocyclopentadienyl)-1-naphthyl)methylene-N-tert-butylamine, N-(2-(inden-1-yl)-1-naphthyl)methylene-N-tert-butylamine, N-(2-(2-methylinden-1-yl)-1-naphthyl)methylene-N-tert-butylamine, N-(2-(2-phenylinden-1-yl)-1-naphthyl)methylene-N-tert-butylamine, N-(2-(cyclopentadienyl)-1-naphthyl)methylene-N-n-butylamine, N-(2-(2-methylcyclopentadienyl)-1-naphthyl)methylene-N-n-butylamine, N-(2-(3-methylcyclopentadienyl)-1-naphthyl)methylene-N-n-butylamine, N-(2-(2,3-dimethylcyclopentadienyl)-1-naphthyl)methylene-N-n-butylamine, N-(2-(2,4-dimethylcyclopentadienyl)-1-naphthyl)methylene-N-n-butylamine, N-(2-(2,3,4-trimethylcyclopentadienyl)-1-naphthyl)methylene-N-n-butylamine, N-(2-(2,3,5-trimethylcyclopentadienyl)-1-naphthyl)methylene-N-n-butylamine, N-(2-(2,3,4,5-tetramethylcyclopentadienyl)-1-naphthyl)methylene-N-n-butylamine, N-(2-(2-dimethylaminocyclopentadienyl)-1-naphthyl)methylene-N-n-butylamine, N-(2-(3-dimethylaminocyclopentadienyl)-1-naphthyl)methylene-N-n-butylamine, N-(2-(inden-1-yl)-1-naphthyl)methylene-N-n-butylamine, N-(2-(2-methylinden-1-yl)-1-naphthyl)methylene-N-n-butylamine, N-(2-(2-phenylinden-1-yl)-1-naphthyl)methylene-N-n-butylamine and the like.

Specific examples of the amine compound of the formula (6) thus obtained include the following compounds: N-[(2-(cyclopentadienyl)phenyl)methyl]-N-phenylamine, N-[(2-(2-methylcyclopentadienyl)phenyl)methyl]-N-phenylamine, N-[(2-(3-methylcyclopentadienyl)phenyl)methyl]-N-phenylamine, N-[(2-(2,3-dimethylcyclopentadienyl)phenyl)methyl]-N-phenylamine, N-[(2-(2,4-dimethylcyclopentadienyl)phenyl)methyl]-N-phenylamine, N-[(2-(2,3,4-trimethylcyclopentadienyl)phenyl)methyl]-N-phenylamine, N-[(2-(2,3,5-trimethylcyclopentadienyl)phenyl)methyl]-N-phenylamine, N-[(2-(2,3,4,5-tetramethylcyclopentadienyl)phenyl)methyl]-N-phenylamine, N-[(2-(2-dimethylaminomethylcyclopentadienyl)phenyl)methyl]-N-phenylamine, N-[(2-(3-dimethylaminomethylcyclopentadienyl)phenyl)methyl]-N-phenylamine, N-[(2-(inden-1-yl)phenyl)methyl]-N-phenylamine, N-[(2-(2-methylinden-1-yl)phenyl)methyl]-N-phenylamine, N-[(2-(2-phenylinden-1-yl)phenyl)methyl]-N-phenylamine, N-[(fluoren-9-yl)phenyl)methyl]-N-phenylamine, N-[(2-(cyclopentadienyl)phenyl)methyl]-N-(2,4,6-trimethylphenyl)amine, N-[(2-(2-methylcyclopentadienyl)phenyl)methyl]-N-(2,4,6-trimethylphenyl)titanium dichloride, N-[2-(3-methylcyclopentadienyl)phenyl)methyl]-N-(2,4,6-trimethylphenyl)amine, N-[(2-(2,3-dimethylcyclopentadienyl)phenyl)methyl]-N-(2,4,6-trimethylphenyl)amine, N-[(2-(2,4-dimethylcyclopentadienyl)phenyl)methyl]-N-(2,4,6-trimethylphenyl)amine, N-[(2-(2,3,4-trimethylcyclopentadienyl)phenyl)methyl]-N-(2,4,6-trimethylphenyl)amine, N-[(2-(2,3,5-trimethylcyclopentadienyl)phenyl)methyl]-N-(2,4,6-trimethylphenyl)amine, N-[(2-(2,3,4,5-tetramethylcyclopentadienyl)phenyl)methyl]-N-(2,4,6-trimethylphenyl)amine, N-[(2-(2-dimethylaminomethylcyclopentadienyl)phenyl)methyl]-N-(2,4,6-trimethylphenyl)amine, N-[(2-(3-dimethylaminomethylcyclopentadienyl)phenyl)methyl]-N-(2,4,6-trimethylphenyl)amine, N-[(2-(inden-1-yl)phenyl)methyl]-N-(2,4,6-trimethylphenyl)amine, N-[(2-(2-methylinden-1-yl)phenyl)methyl]-N-(2,4,6-trimethylphenyl)amine, N-[(2-(2-phenylinden-1-yl)phenyl)methyl]-N-(2,4,6-trimethylphenyl)amine, N-[(2-(fluoren-9-yl)phenyl)methyl]-N-(2,4,6-trimethylphenyl)amine, N-[(2-(cyclopentadienyl)phenyl)methyl]-N-tert-butylamine, N-[(2-(2-methylcyclopentadienyl)phenyl)methyl]-N-tert-butylamine, N-[(2-(3-methylcyclopentadienyl)phenyl)methyl]-N-tert-butylamine, N-[(2-(2,3-dimethylcyclopentadienyl)phenyl)methyl]-N-tert-butylamine, N-[(2-(2,4-dimethylcyclopentadienyl)phenyl)methyl]-N-tert-butylamine, N-[(2-(2,3,4-trimethylcyclopentadienyl)phenyl)methyl]-N-tert-butylamine, N-[(2-(2,3,5-trimethylcyclopentadienyl)phenyl)methyl]-N-tert-butylamine, N-[(2-(2,3,4,5-tetramethylcyclopentadienyl)phenyl)methyl]-N-tert-butylamine, N-[(2-(2-dimethylaminomethylcyclopentadienyl)phenyl)methyl]-N-tert-butylamino, N-[(2-(3-dimethylaminomethylcyclopentadienyl)phenyl)methyl]-N-tert-butylamine, N-[(2-(inden-1-yl)phenyl)methyl]-N-tert-butylamine, N-[(2-(2-methylinden-1-yl)phenyl)methyl]-N-tert-butylamine, N-[(2-(2-phenylinden-1-yl)phenyl)methyl]-N-tert-butylamine, N-[(fluoren-9-yl)phenyl)methyl]-N-tert-butylamine, N-[(2-(cyclopentadienyl)phenyl)methyl]-N-n-butylamine, N-[(2-(2-methylcyclopentadienyl)phenyl)methyl]-N-n-butylamine, N-[(2-(3-methylcyclopentadienyl)phenyl)methyl]-N-n-butylamine, N-[2-(2,3-dimethylcyclopentadienyl)phenyl)methyl]-N-n-butylamine, N-[(2-(2,4-dimethylcyclopentadienyl)phenyl)methyl]-N-n-butylamine, N-[(2-(2,3,4-trimethylcyclopentadienyl)phenyl)methyl]-N-n-butylamine, N-[(2-(2,3,5-trimethylcyclopentadienyl)phenyl)methyl]-N-n-butylamine, N-[(2-(2,3,4,5-tetramethylcyclopentadienyl)phenyl)methyl]-N-n-butylamine, N-[(2-(2-dimethylaminomethylcyclopentadienyl)phenyl)methyl]-N-n-butylamine, N-[(2-(3-dimethylaminomethylcyclopentadienyl)phenyl)methyl]-N-n-butylamine, N-[(2-(inden-1-yl)phenyl)methyl]-N-n-butylamine, N-[(2-(2-methylinden-1-yl)phenyl)methyl]-N-n-butylamine, N-[(2-(2-phenylinden-1-yl)phenyl)methyl]-N-n-butylamine, N-[(2-(fluoren-9-yl)phenyl)methyl]-N-n-butylamine, N-[1-(2-(cyclopentadienyl)phenyl)ethyl]-N-phenylamine, N-[1-(2-(2-methylcyclopentadienyl)phenyl)ethyl]-N-phenylamine, N-[1-(2-(3-methylcyclopentadienyl)phenyl)ethyl]-N-phenylamine, N-[1-(2-(2,3-dimethylcyclopentadienyl)phenyl)ethyl]-N-phenylamine, N-[1-(2-(2,4-dimethylcyclopentadienyl)phenyl)ethyl]-N-phenylamine, N-[1-(2-(2,3,4-trimethylcyclopentadienyl)phenyl)ethyl]-N-phenylamine, N-[1-(2-(2,3,5-trimethylcyclopentadienyl)phenyl)ethyl]-N-phenylamine, N-[1-(2-(2,3,4,5-tetramethylcyclopentadienyl)phenyl)ethyl]-N-phenylamine, N-[1-(2-(2-dimethylaminomethylcyclopentadienyl)phenyl)ethyl]-N-phenylamine, N-[1-(2-(3-dimethylaminomethylcyclopentadienyl)phenyl)ethyl]-N-phenylamine, N-[1-(2-(inden-1-yl)phenyl)ethyl]-N-phenylamine, N-[1-(2-(2-methylinden-1-yl)phenyl)ethyl]-N-phenylamine, N-[1-(2-(2-phenylinden-1-yl)phenyl)ethyl]-N-phenylamine, N-[1-(2-(fluoren-9-yl)phenyl)ethyl]-N-phenylamine, N-[1-(2-(cyclopentadienyl)phenyl)ethyl]-N-(2,4,6-trimethylphenyl)amine, N-[1-(2-(2-methylcyclopentadienyl)phenyl)ethyl]-N-(2,4,6-trimethylphenyl)amine, N-[1-(2-(3-methylcyclopentadienyl)phenyl)ethyl]-N-(2,4,6-trimethylphenyl)amine, N-[1-(2-(2, 3-dimethylcyclopentadienyl)phenyl)ethyl]-N-(2,4,6-trimethylphenyl)amine, N-[1-(2-(2,4-dimethylcyclopentadienyl)phenyl)ethyl]-N-(2,4,6-trimethylphenyl)amine, N-[1-(2-(2,3,4-trimethylcyclopentadienyl)phenyl)ethyl]-N-(2,4,6-trimethylphenyl)amine, N-[1-(2-(2,3,5-trimethylcyclopentadienyl)phenyl)ethyl]-N-(2,4,6-trimethylphenyl)amine, N-[1-(2-(2,3,4,5-tetramethylcyclopentadienyl)phenyl)ethyl]-N-(2,4,6-trimethylphenyl)amine, N-[1-(2-(2-dimethylaminomethylcyclopentadienyl)phenyl)ethyl]-N-(2,4,6-trimethylphenyl)amine, N-[1-(2-(3-dimethylaminomethylcyclopentadienyl)phenyl)ethyl]-N-(2,4,6-trimethylphenyl)amine, N-[1-(2-(inden-1-yl)phenyl)ethyl]-N-(2,4,6-trimethylphenyl)amine, N-[1-(2-(2-methylinden-1-yl)phenyl)ethyl]-N-(2,4,6-trimethylphenyl)amine, N-[1-(2-(2-phenylinden-1-yl)phenyl)ethyl]-N-(2,4,6-trimethylphenyl)amine, N-[1-(2-(fluoren-9-yl)phenyl)ethyl]-N-(2,4,6-trimethylphenyl)amine, N-[1-(2-(cyclopentadienyl)phenyl)ethyl]-N-tert-butylamine, N-[1-(2-(2-methylcyclopentadienyl)phenyl)ethyl]-N-tert-butylamine, N-[1-(2-(3-methylcyclopentadienyl)phenyl)ethyl]-N-tert-butylamine, N-[1-(2-(2,3-dimethylcyclopentadienyl)phenyl)ethyl]-N-tert-butylamine, N-[1-(2-(2,4-dimethylcyclopentadienyl)phenyl)ethyl]-N-tert-butylamine, N-[1-(2-(2,3,4-trimethylcyclopentadienyl)phenyl)ethyl]-N-tert-butylamine, N-[1-(2-(2,3,5-trimethylcyclopentadienyl)phenyl)ethyl]-N-tert-butylamine, N-[1-(2-(2,3,4,5-tetramethylcyclopentadienyl)phenyl)ethyl]-N-tert-butylamine, N-[1-(2-(2-dimethylaminomethylcyclopentadienyl)phenyl)ethyl]-N-tert-butylamine, N-[1-(2-(3-dimethylaminomethylcyclopentadienyl)phenyl)ethyl]-N-tert-butylamine, N-[1-(2-(inden-1-yl)phenyl)ethyl]-N-tert-butylamine, N-[1-(2-(2-methylinden-1-yl)phenyl)ethyl]-N-tert-butylamine, N-[1-(2-(2-phenylinden-1-yl)phenyl)ethyl]-N-tert-butylamine, N-[1-(2-(fluoren-9-yl)phenyl)ethyl]-N-tert-butylamine, N-[1-(2-(cyclopentadienyl)phenyl)ethyl]-N-n-butylamine, N-[1-(2-(2-methylcyclopentadienyl)phenyl)ethyl]-N-n-butylamine, N-[1-(2-(3-methylcyclopentadienyl)phenyl)ethyl]-N-n-butylamine, N-[1-(2-(2,3-dimethylcyclopentadienyl)phenyl)ethyl]-N-n-butylamine, N-[1-(2-(2,4-dimethylcyclopentadienyl)phenyl)ethyl]-N-n-butylamine, N-[1-(2-(2,3,4-trimethylcyclopentadienyl)phenyl)ethyl]-N-n-butylamine, N-[1-(2-(2,3,5-trimethylcyclopentadienyl)phenyl)ethyl]-N-n-butylamine, N-[1-(2-(2,3,4,5-tetramethylcyclopentadienyl)phenyl)ethyl]-N-n-butylamine, N-[1-(2-(2-dimethylaminomethylcyclopentadienyl)phenyl)ethyl]-N-n-butylamine, N-[1-(2-(3-dimethylaminomethylcyclopentadienyl)phenyl)ethyl]-N-n-butylamine, N-[1-(2-(inden-1-yl)phenyl)ethyl]-N-n-butylamine, N-[1-(2-(2-methylinden-1-yl)phenyl)ethyl]-N-n-butylamine, N-[1-(2-(2-phenylinden-1-yl)phenyl)ethyl]-N-n-butylamine, N-[1-(2-(fluoren-9-yl)phenyl)ethyl]-N-n-butylamine, N-[1-(2-(cyclopentadienyl)phenyl)-1-methylethyl]-N-phenylamine, N-[1-(2-(2-methylcyclopentadienyl)phenyl)-1-methylethyl]-N-phenylamine, N-[1-(2-(3-methylcyclopentadienyl)phenyl)-1-methylethyl]-N-phenylamine, N-[1-(2-(2,3-dimethylcyclopentadienyl)phenyl)-1-methylethyl]-N-phenylamine, N-[1-(2-(2,4-dimethylcyclopentadienyl)phenyl)-1-methylethyl]-N-phenylamine, N-[1-(2-(2,3,4-trimethylcyclopentadienyl)phenyl)-1-methylethyl]-N-phenylamine, N-[1-(2-(2,3,5-trimethylcyclopentadienyl)phenyl)-1-methylethyl]-N-phenylamine, N-[1-(2-(2,3,4,5-tetramethylcyclopentadienyl)phenyl)-1-methylethyl]-N-phenylamine, N-[1-(2-(2-dimethylaminomethylcyclopentadienyl)phenyl)-1-methylethyl]-N-phenylamine, N-[1-(2-(3-dimethylaminomethylcyclopentadienyl)phenyl)-1-methylethyl]-N-phenylamine, N-[1-(2-(inden-1-yl)phenyl)-1-methylethyl]-N-phenylamine, N-[1-(2-(2-methylinden-1-yl)phenyl)-1-methylethyl]-N-phenylamine, N-[1-(2-(2-phenylinden-1-yl)phenyl)-1-methylethyl]-N-phenylamine, N-[1-(2-(fluoren-9-yl)phenyl)-1-methylethyl]-N-phenylamine, N-[1-(2-(cyclopentadienyl)phenyl)-1-methylethyl]-N-(2,4,6-trimethylphenyl)amine, N-[1-(2-(2-methylcyclopentadienyl)phenyl)-1-methylethyl]-N-(2,4,6-trimethylphenyl)amine, N-[1-(2-(3-methylcyclopentadienyl)phenyl)-1-methylethyl]-N-(2,4,6-trimethylphenyl)amine, N-[1-(2-(2,3-dimethylcyclopentadienyl)phenyl)-1-methylethyl]-N-(2,4,6-trimethylphenyl)amine, N-[1-(2-(2,4-dimethylcyclopentadienyl)phenyl)-1-methylethyl]-N-(2,4,6-trimethylphenyl)amine, N-[1-(2-(2,3,4-trimethylcyclopentadienyl)phenyl)-1-methylethyl]-N-(2,4,6-trimethylphenyl)amine, N-[1-(2-(2,3,5-trimethylcyclopentadienyl)phenyl)-1-methylethyl]-N-(2,4,6-trimethylphenyl)amine, N-[1-(2-(2,3,4,5-tetramethylcyclopentadienyl)phenyl)-1-methylethyl]-N-(2,4,6-trimethylphenyl)amine, N-[1-(2-(2-dimethylaminomethylcyclopentadienyl)phenyl)-1-methylethyl]-N-(2,4,6-trimethylphenyl)amine, N-[1-(2-(3-dimethylaminomethylcyclopentadienyl)phenyl)-1-methylethyl]-N-(2,4,6-trimethylphenyl)amine, N-[1-(2-(inden-1-yl)phenyl)-1-methylethyl]-N-(2,4,6-trimethylphenyl)amine, N-[1-(2-(2-methylinden-1-yl)phenyl)-1-methylethyl]-N-(2,4,6-trimethylphenyl)amine, N-[1-(2-(2-phenylinden-1-yl)phenyl)-1-methylethyl]-N-(2,4,6-trimethylphenyl)amine, N-[1-(2-(fluoren-9-yl)phenyl)-1-methylethyl]-N-(2,4,6-trimethylphenyl)amine, N-[1-(2-(cyclopentadienyl)phenyl)-1-methylethyl]-N-tert-butylamine, N-[1-(2-(2-methylcyclopentadienyl)phenyl)-1-methylethyl]-N-ten-butylamine, N-[1-(2-(3-methylcyclopentadienyl)phenyl)-1-methylethyl]-N-tert-butylamine, N-[1-(2-(2,3-dimethylcyclopentadienyl)phenyl)-1-methylethyl]-N-tert-butylamine, N-[1-(2-(2,4-dimethylcyclopentadienyl)phenyl)-1-methylethyl]-N-tert-butylamine, N-[1-(2-(2,3,4-trimethylcyclopentadienyl)phenyl)-1-methylethyl]-N-tert-butylamine, N-[1-(2-(2,3,5-trimethylcyclopentadienyl)phenyl)-1-methylethyl]-N-tert-butylamine. N-[1-(2-(2,3,4,5-tetramethylcyclopentadienyl)phenyl)-1-methylethyl]-N-tert-butylamine, N-[1-(2-(2-dimethylaminomethylcyclopentadienyl)phenyl)-1-methylethyl]-N-tert-butylamine, N-[1-(2-(3-dimethylaminomethylcyclopentadienyl)phenyl)-1-methylethyl]-N-tert-butylamine, N-[1-(2-(inden-1-yl)phenyl)-1-methylethyl]-N-tert-butylamine, N-[1-(2-(2-methylinden-1-yl)phenyl)-1-methylethyl]-N-tert-butylamine, N-[1-(2-(2-phenylinden-1-yl)phenyl)-1-methylethyl]-N-tert-butylamine, N-[1-(2-(fluoren-9-yl)phenyl)-1-methylethyl]-N-tert-butylamine, N-[1-(2-(cyclopentadienyl)phenyl)-1-methylethyl]-N-n-butylamine, N-[1-(2-(2-methylcyclopentadienyl)phenyl)-1-methylethyl]-N-n-butylamine, N-[1-(2-(3-methylcyclopentadienyl)phenyl)-1-methylethyl]-N-n-butylamine, N-[1-(2-(2,3-dimethylcyclopentadienyl)phenyl)-1-methylethyl]-N-n-butylamine, N-[1-(2-(2,4-dimethylcyclopentadienyl)phenyl)-1-methylethyl]-N-n-butylamine, N-[1-(2-(2,3,4-trimethylcyclopentadienyl)phenyl)-1-methylethyl]-N-n-butylamine, N-[1-(2-(2,3,5-trimethylcyclopentadienyl)phenyl)-1-methylethyl]-N-n-butylamine, N-[1-(2-(2,3,4,5-tetramethylcyclopentadienyl)phenyl)-1-methylethyl]-N-n-butylamine, N-[1-(2-(2-dimethylaminomethylcyclopentadienyl)phenyl)-1-methylethyl]-N-n-butylamine, N-[1-(2-(3- dimethylaminomethylcyclopentadienyl)phenyl)-1-methylethyl]-N-n-butylamine, N-[1-(2-(inden-1-yl)phenyl)-1-methylethyl]-N-n-butylamine, N-[1-(2-(2-methylinden-1-yl)phenyl)-1-methylethyl]-N-n-butylamine, N-[1-(2-(2-phenylinden-1-yl)phenyl)-1-methylethyl]-N-n-butylamine, N-[1-(2-(fluoren-9-yl)phenyl)-1-methylethyl]-N-n-butylamine, N-[(2-(cyclopentadienyl)-1-naphthyl)methyl]-N-phenylamine, N-[(2-(2-methylcyclopentadienyl)-1-naphthyl)methyl]-N-phenylamine, N-[(2-(3-methylcyclopentadienyl)-1-naphthyl)methyl]-N-phenylamine, N-[(2-(2,3-dimethylcyclopentadienyl)-1-naphthyl)methyl]-N-phenylamine, N-[(2-(2,4-dimethylcyclopentadienyl)-1-naphthyl)methyl]-N-phenylamine, N-[(2-(2,3,4-trimethylcyclopentadienyl)-1-naphthyl)methyl]-N-phenylamine, N-[(2-(2,3,5-trimethylcyclopentadienyl)-1-naphthyl)methyl]-N-phenylamine, N-[(2-(2,3,4,5-tetramethylcyclopentadienyl)-1-naphthyl)methyl]-N-phenylamine, N-[(2-(2-dimethylaminomethylcyclopentadienyl)-1-naphthyl)methyl]-N-phenylamine, N-[(2-(3-dimethylaminomethylcyclopentadienyl)-1-naphthyl)methyl]-N-phenylamine, N-[(2-(inden-1-yl)-1-naphthyl)methyl]-N-phenylamine, N-[(2-(2-methylinden-1-yl)-1-naphthyl)methyl]-N-phenylamine, N-[(2-(2-phenylinden-1-yl)-1-naphthyl)methyl]-N-phenylamine, N-[(2-(fluoren-9-yl)-1-naphthyl)methyl]-N-phenylamine, N-[(2-(cyclopentadienyl)-1-naphthyl)methyl]-N-(2,4,6-trimethylphenyl)amine, N-[(2-(2-methylcyclopentadienyl)-1-naphthyl)methyl]-N-(2,4,6-trimethylphenyl)amine, N-[(2-(3-methylcyclopentadienyl)-1-naphthyl)methyl]-N-(2,4,6-trimethylphenyl)amine, N-[(2-(2,3-dimethylcyclopentadienyl)-1-naphthyl)methyl]-N-(2,4,6-trimethylphenyl)amine, N-[(2-(2,4-dimethylcyclopentadienyl)-1-naphthyl)methyl]-N-(2,4,6-trimethylphenyl)amine, N-[(2-(2,3,4-trimethylcyclopentadienyl)-1-naphthyl)methyl]-N-(2,4,6-trimethylphenyl)amine, N-[(2-(2,3,5-trimethylcyclopentadienyl)-1-naphthyl)methyl]-N-(2,4,6-trimethylphenyl)amine, N-[(2-(2,3,4,5-tetramethylcyclopentadienyl)-1-naphthyl)methyl]-N-(2,4,6-trimethylphenyl)amine, N-[(2-(2-dimethylaminomethylcyclopentadienyl)-1-naphthyl)methyl]-N-(2,4,6-trimethylphenyl)amine, N-[(2-(3-dimethylaminomethylcyclopentadienyl)-1-naphthyl)methyl]-N-(2,4,6-trimethylphenyl)amine, N-[(2-(inden-1-yl)-1-naphthyl)methyl]-N-(2,4,6-trimethylphenyl)amine, N-[(2-(2-methylinden-1-yl)-1-naphthyl)methyl]-N-(2,4,6-trimethylphenyl)amine, N-[(2-(2-phenylinden-1-yl)-1-naphthyl)methyl]-N-(2,4,6-trimethylphenyl)amine, N-[(2-(fluoren-9-yl)-1-naphthyl)methyl]-N-(2,4,6-trimethylphenyl)amine, N-[(2-(cyclopentadienyl)-1-naphthyl)methyl]-N-tert-butylamine, N-[(2-(2-methylcyclopentadienyl)-1-naphthyl)methyl]-N-tert-butylamine, N-[(2-(3-methylcyclopentadienyl)-1-naphthyl)methyl]-N-tert-butylamine, N-[(2-(2,3-dimethylcyclopentadienyl)-1-naphthyl)methyl]-N-tert-butylamine, N-[(2-(2,4-dimethylcyclopentadienyl)-1-naphthyl)methyl]-N-tert-butylamine, N-[(2-(2,3,4-trimethylcyclopentadienyl)-1-naphthyl)methyl]-N-tert-butylamine, N-[(2-(2,3,5-trimethylcyclopentadienyl)-1-naphthyl)methyl]-N-tert-butylamine, N-[(2-(2,3,4,5-tetramethylcyclopentadienyl)-1-naphthyl)methyl]-N-tert-butylamine, N-[(2-(2-dimethylaminomethylcyclopentadienyl)-1-naphthyl)methyl]-N-tert-butylamine, N-[(2-(3-dimethylaminomethylcyclopentadienyl)-1-naphthyl)methyl]-N-tert-butylamine, N-[(2-(inden-1-yl)-1-naphthyl)methyl]-N-tert-butylamine, N-[(2-(2-methylinden-1-yl)-1-naphthyl)methyl]-N-tert-butylamine, N-[(2-(2-phenylinden-1-yl)-1-naphthyl)methyl]-N-tert-butylamine, N-[(2-(fluoren-9-yl)-1-naphthyl)methyl]-N-tert-butylamine, N-[(2-(cyclopentadienyl)-1-naphthyl)methyl]-N-n-butylamine, N-[(2-(2-methylcyclopentadienyl)-1-naphthyl)methyl]-N-n-butylamine, N-[(2-(3-methylcyclopentadienyl)-1-naphthyl)methyl]-N-n-butylamine, N-[(2-(2,3-dimethylcyclopentadienyl)-1-naphthyl)methyl]-N-n-butylamine, N-[(2-(2,4-dimethylcyclopentadienyl)-1-naphthyl)methyl]-N-n-butylamine, N-[(2-(2,3,4-trimethylcyclopentadienyl)-1-naphthyl)methyl]-N-n-butylamine, N-[(2-(2,3,5-trimethylcyclopentadienyl)-1-naphthyl)methyl]-N-n-butylamine, N-[2-(2,3,4,5-tetramethylcyclopentadienyl)-1-naphthyl)methyl]-N-n-butylamine, N-[(2-(2-dimethylaminomethylcyclopentadienyl)-1-naphthyl)methyl]-N-n-butylamine, N-[(2-(3-dimethylaminomethylcyclopentadienyl)-1-naphthyl)methyl]-N-n-butylamine, N-[(2-(inden-1-yl)-1-naphthyl)methyl]-N-n-butylamine, N-[(2-(2-methylinden-1-yl)-1-naphthyl)methyl]-N-n-butylamine, N-[(2-(2-phenylinden-1-yl)-1-naphthyl)methyl]-N-n-butylamine, N-[(2-(fluoren-9-yl)-1-naphthyl)methyl]-N-n-butylamine and the like.

The hydrazone compound represented by the formula (7):

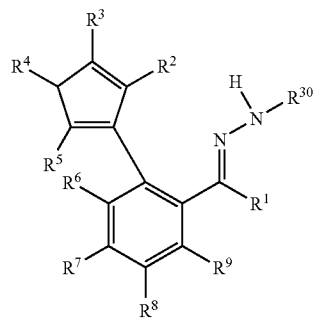

(7)

wherein $R^1$, $R^2$, $R^3$, $R^4$, $R^5$, $R^6$, $R^7$, $R^8$, $R^9$ and $R^{30}$ have the same meanings as defined for the above-mentioned formula (II), is hereinafter explained.

The compound of the formula (7) can be produced by reacting the carbonyl compound of the formula (I) with a hydrazine compound ($R^{30}$—NHNH$_2$).

As the hydrazine compound, the following compounds are exemplified.

The hydrazine to be used in the reaction includes aromatic hydrazines such as phenylhydrazine, 2-methylphenylhydrazine, 3-methylphenylhydrazine, 4-methylphenylhydrazine, 2,4-dimethylphenylhydrazine, 2,6-dimethylphenylhydrazine, 3,5-dimethylphenylhydrazine, 2,4,6-trimethylphenylhydrazine, 2-isopropylphenylhydrazine, 3-isopropylphenylhydrazine, 4-isopropylphenylhydrazine, 2,6-diisopropylphenylhydrazine, 2-tert-butylphenylhydrazine, 4-tert-butylphenylhydrazine, 2,4-di-tert-butylphenylhydrazine, 2,6-di-tert-butylphenylhydrazine, 2-phenylphenylhydrazine, 4-phenylphenylhydrazine, 2,4-diphenylphenylhydrazine, 2,6-diphenylphenylhydrazine, pentafluorophenylhydrazine, 3,5-bis(trifluoromethyl)phenylhydrazine, naphthylhydrazine and the like; and aliphatic hydrazines such as methylhydrazine, ethylhydrazine, isopropylhydrazine, tert-butylhydrazine, n-butylhydrazine, isobutylhydrazine, n-pentylhydrazine, n-hexylhydrazine, cyclohexylhydrazine, n-decylhydrazine, benzylhydrazine and the like. The amount of hydrazine to be used is usually about 0.5 to 1.5 moles relative to 1 mole of the carbonyl compound.

The above reaction is usually carried out in a solvent. Such a solvent includes, for example, alcohol solvents such as methanol, ethanol, isopropanol and the like; aprotic solvents such as aromatic hydrocarbon solvents such as benzene, toluene and the like; aliphatic hydrocarbon solvents such as hexane, heptane and the like; ether solvents such as diethyl ether, tetrahydrofuran, 1,4-dioxane and the like; amide solvents such as hexamethylphosphoric amide, dimethylformamide and the like; polar solvents such as acetonitrile, propionitrile, acetone, diethyl ketone, methyl isobutyl ketone, cyclohexanone and the like; halogenated solvents such as dichloromethane, dichloroethane, chlorobenzene, dichlorobenzene and the like. One or a mixture of two or more of the solvents is used. The amount of a solvent to be used is usually in the range of 1 to 200 parts by weight, preferably 3 to 50 parts by weight relative to 1 part by weight of the carbonyl compound of the formula (1).

The reaction temperature is usually in the range of −100° C. to the boiling point of a solvent, preferably −80 to 120° C.

After the reaction, if needed, water is added to the resulting reaction mixture. The mixture is then separated into an organic layer and an aqueous layer to give a solution of the objective compound as the organic layer. When the organic layer and the aqueous layer can not be easily separated due to use of a solvent compatible with water or use of a small amount of solvent in said reaction, the separation may be carried out after addition of a water-insoluble organic solvent such as toluene, ethyl acetate or chlorobenzene to the reaction mixture. The hydrazone compound represented by the formula (7) can be purified, for example, by washing said solution of the compound with water, drying said solution, and then distilling off the solvent, and further by methods such as recrystallization, distillation, column chromatography treatment and the like.

Specific examples of the hydrazone compound represented by the formula (7) include the following compound: 2-(cyclopentadienyl)benzaldehyde phenylhydrazone, 2-(2-methylcyclopentadienyl)benzaldehyde phenylhydrazone, 2-(3-methylcyclopentadienyl)benzaldehyde phenylhydrazone, 2-(2,3-dimethylcyclopentadienyl)benzaldehyde phenylhydrazone, 2-(2,4-dimethylcyclopentadienyl)benzaldehyde phenylhydrazone, 2-(3,4-dimethylcyclopentadienyl)benzaldehyde phenylhydrazone, 2-(2,3,4-trimethylcyclopentadienyl)benzaldehyde phenylhydrazone, 2-(2,4,5-trimethylcyclopentadienyl)benzaldehyde phenylhydrazone, 2-(2,3,4,5-tetramethylcyclopentadienyl)benzaldehyde phenylhydrazone, 2-(2-tert-butylcyclopentadienyl)benzaldehyde phenylhydrazone, 2-(3-tert-butylcyclopentadienyl)benzaldehyde phenylhydrazone, 2-(2-dimethylaminocyclopentadienyl)benzaldehyde phenylhydrazone, 2-(3-dimethylaminocyclopentadienyl)benzaldehyde phenylhydrazone, 2-(inden-1-yl)benzaldehyde phenylhydrazone, 2-(2-methylinden-1-yl)benzaldehyde phenyl hydrazone, 2-(2-phenylinden-1-yl)benzaldehyde phenylhydrazone, 2-(fluoren-9-yl)benzaldehyde phenylhydrazone, 2-(cyclopentadienyl)benzaldehyde 2-methylphenylhydrazone, 2-(2-methylcyclopentadienyl)benzaldehyde 2-methylphenylhydrazone, 2-(3-methylcyclopentadienyl)benzaldehyde 2-methylphenylhydrazone, 2-(2,3-dimethylcyclopentadienyl)benzaldehyde 2-methylphenylhydrazone, 2-(2,4-dimethylcyclopentadienyl)benzaldehyde 2-methylphenylhydrazone, 2-(3,4-dimethylcyclopentadienyl)benzaldehyde 2-methylphenylhydrazone, 2-(2,3,4-trimethylcyclopentadienyl)benzaldehyde 2-methylphenylhydrazone, 2-(2,4,5-trimethylcyclopentadienyl)benzaldehyde 2-methylphenylhydrazone, 2-(2,3,4,5-tetramethylcyclopentadienyl)benzaldehyde 2-methylphenylhydrazone, 2-(2-tert-butylcyclopentadienyl)benzaldehyde 2-methylphenylhydrazone, 2-(3-tert-butylcyclopentadienyl) benzaldehyde 2-methylphenylhydrazone, 2-(2-dimethylaminocyclopentadienyl)benzaldehyde 2-methylphenylhydrazone, 2-(3-dimethylaminocyclopentadienyl)benzaldehyde 2-methylphenylhydrazone, 2-(inden-1-yl)benzaldehyde 2-methylphenylhydrazone, 2-(2-methylinden-1-yl)benzaldehyde 2-methylphenylhydrazone, 2-(2-phenylinden-1-yl) benzaldehyde 2-methylphenylhydrazone, 2-(fluoren-9-yl)benzaldehyde 2-methylphenylhydrazone, 2-(cyclopentadienyl)benzaldehyde 2,4,6-trimethylphenylhydrazone, 2-(2-methylcyclopentadienyl)benzaldehyde 2,4,6-trimethylphenylhydrazone, 2-(3-methylcyclopentadienyl)benzaldehyde 2,4,6-trimethylphenylhydrazone, 2-(2,3-dimethylcyclopentadienyl)benzaldehyde 2,4,6-trimethylphenylhydrazone, 2-(2,4-dimethylcyclopentadienyl)benzaldehyde 2,4,6-trimethylphenylhydrazone, 2-(3,4-dimethylcyclopentadienyl)benzaldehyde 2,4,6-trimethylphenylhydrazone, 2-(2,3,4-trimethylcyclopentadienyl)benzaldehyde 2,4,6-trimethylphenylhydrazone, 2-(2,4,5-trimethylcyclopentadienyl)benzaldehyde 2,4,6-trimethylphenylhydrazone, 2-(2,3,4,5-tetramethylcyclopentadienyl)benzaldehyde 2,4,6-trimethylphenylhydrazone, 2-(2-tert-butylcyclopentadienyl)benzaldehyde 2,4,6-trimethylphenylhydrazone, 2-(3-tert-butylcyclopentadienyl)benzaldehyde 2,4,6-trimethylphenylhydrazone, 2-(2-dimethylaminocyclopentadienyl)benzaldehyde 2,4,6-trimethylphenylhydrazone, 2-(3-dimethylaminocyclopentadienyl)benzaldehyde 2,4,6-trimethylphenylhydrazone, 2-(inden-1-yl)benzaldehyde 2,4,6-trimethylphenylhydrazone, 2-(2-methylinden-1-yl)benzaldehyde 2,4,6-trimethylphenylhydrazone, 2-(2-phenylinden-1-yl)benzaldehyde 2,4,6-trimethylphenylhydrazone, 2-(fluoren-9-yl)benzaldehyde 2,4,6-trimethylphenylhydrazone, 2-(cyclopentadienyl)benzaldehyde 2,6-diisopropylphenylhydrazone, 2-(2-methylcyclopentadienyl)benzaldehyde 2,6-diisopropylphenylhydrazone, 2-(3-methylcyclopentadienyl)benzaldehyde 2,6-diisopropylphenylhydrazone, 2-(2,3-dimethylcyclopentadienyl)benzaldehyde 2,6-diisopropylphenylhydrazone, 2-(2,4-dimethylcyclopentadienyl)benzaldehyde 2,6-diisopropylphenylhydrazone, 2-(3,4-dimethylcyclopentadienyl)benzaldehyde 2,6-diisopropylphenylhydrazone, 2-(2,3,4-trimethylcyclopentadienyl)benzaldehyde 2,6-diisopropylphenylhydrazone, 2-(2,4,5-trimethylcyclopentadienyl)benzaldehyde 2,6-diisopropylphenylhydrazone, 2-(2,3,4,5-tetramethylcyclopentadienyl)benzaldehyde 2,6-diisopropylphenylhydrazone, 2-(2-tert-butylcyclopentadienyl)benzaldehyde 2,6-diisopropylphenylhydrazone, 2-(3-tert-butylcyclopentadienyl)benzaldehyde 2,6-diisopropylphenylhydrazone, 2-(2-dimethylaminocyclopentadienyl)benzaldehyde 2,6-diisopropylphenylhydrazone, 2-(3-dimethylaminocyclopentadienyl)benzaldehyde 2,6-diisopropylphenylhydrazone, 2-(inden-1-yl)benzaldehyde 2,6-diisopropylphenylhydrazone, 2-(2-methylinden-1-yl) benzaldehyde 2,6-diisopropylphenylhydrazone, 2-(2-phenylinden-1-yl)benzaldehyde 2,6-diisopropylphenylhydrazone, 2-(fluoren-9-yl)benzaldehyde 2,6-diisopropylphenylhydrazone, 2-(cyclopentadienyl)benzaldehyde 2-naphthylhydrazone, 2-(2-methylcyclopentadienyl)benzaldehyde 2-naphthylhydrazone, 2-(3-methylcyclopentadienyl)benzaldehyde 2-naphthylhydrazone, 2-(2,3-dimethylcyclopentadienyl)benzaldehyde 2-naphthylhydrazone, 2-(2,4-dimethylcyclopentadienyl)benzaldehyde 2-naphthylhydrazone, 2-(3,4-dimethylcyclopentadienyl)benzaldehyde 2-naphthylhydrazone, 2-(2,3,4-trimethylcyclopentadienyl)benzaldehyde 2-naphthylhydrazone, 2-(2,4,5-trimethylcyclopentadienyl)benzaldehyde 2-naphthylhydrazone, 2-(2,3,4,5-tetramethylcyclopentadienyl)benzaldehyde 2-naphthylhydrazone, 2-(2-tert butylcyclopentadienyl)benzaldehyde 2-naphthylhydrazone, 2-(3-tert-butylcyclopentadienyl)benzaldehyde 2-naphthylhydrazone, 2-(2-dimethylaminocyclopentadienyl)benzaldehyde 2-naphthylhydrazone, 2-(3-dimethylaminocyclopentadienyl)benzaldehyde 2-naphthylhydrazone, 2-(inden-1-yl)benzaldehyde 2-naphthylhydrazone, 2-(2-methylinden-1-yl)benzaldehyde 2-naphthylhydrazone, 2-(2-phenylinden-1-yl)benzaldehyde 2-naphthylhydrazone, 2-(fluoren-9-yl)benzaldehyde 2-naphthylhydrazone, 2-(cyclopentadienyl)benzaldehyde cyclohexylhydrazone, 2-(2-methylcyclopentadienyl)benzaldehyde cyclohexylhydrazone, 2-(3-methylcyclopentadienyl)benzaldehyde cyclohexylhydrazone, 2-(2,3-dimethylcyclopentadienyl)benzaldehyde cyclohexylhydrazone, 2-(2,4-dimethylcyclopentadienyl)benzaldehyde cyclohexylhydrazone, 2-(3,4-dimethylcyclopentadienyl)benzaldehyde cyclohexylhydrazone, 2-(2,3,4-trimethylcyclopentadienyl)benzaldehyde cyclohexylhydrazone, 2-(2,4,5-trimethylcyclopentadienyl)benzaldehyde cyclohexylhydrazone, 2-(2,3,4,5-tetramethylcyclopentadienyl)benzaldehyde cyclohexylhydrazone, 2-(2-tert-butylcyclopentadienyl)benzaldehyde cyclohexylhydrazone, 2-(3-tert-butylcyclopentadienyl)benzaldehyde cyclohexylhydrazone, 2-(2-dimethylaminocyclopentadienyl)benzaldehyde cyclohexylhydrazone, 2-(3-dimethylaminocyclopentadienyl)benzaldehyde cyclohexylhydrazone, 2-(inden-1-yl)benzaldehyde cyclohexylhydrazone, 2-(2-methylinden-1-yl)benzaldehyde cyclohexylhydrazone, 2-(2-phenylinden-1-yl)benzaldehyde cyclohexylhydrazone, 2-(fluoren-9-yl)benzaldehyde cyclohexylhydrazone, 2-(cyclopentadienyl)benzaldehyde tert-butylhydrazone, 2-(2-methylcyclopentadienyl)benzaldehyde tert-butylhydrazone, 2-(3-methylcyclopentadienyl)benzaldehyde tert-butylhydrazone, 2-(2,3-dimethylcyclopentadienyl)benzaldehyde tert-butylhydrazone, 2-(2,4-dimethylcyclopentadienyl)benzaldehyde tert-butylhydrazone, 2-(3,4-dimethylcyclopentadienyl)benzaldehyde tert-butylhydrazone, 2-(2,3,4-trimethylcyclopentadienyl)benzaldehyde tert-butylhydrazone, 2-(2,4,5-trimethylcyclopentadienyl)benzaldehyde tert-butylhydrazone, 2-(2,3,4,5-tetramethylcyclopentadienyl)benzaldehyde tert-butylhydrazone, 2-(2-tert-butylcyclopentadienyl)benzaldehyde tert-butylhydrazone, 2-(3-tert-butylcyclopentadienyl)benzaldehyde tert-butylhydrazone, 2-(2-dimethylaminocyclopentadienyl)benzaldehyde tert-butylhydrazone, 2-(3-dimethylaminocyclopentadienyl)benzaldehyde tert-butylhydrazone, 2-(inden-1-yl)benzaldehyde tert-butylhydrazone, 2-(2-methylinden-1-yl)benzaldehyde tert-butylhydrazone, 2-(2-phenylinden-1-yl)benzaldehyde tert-butylhydrazone, 2-(fluoren-9-yl)benzaldehyde tert-butylhydrazone, 2-(cyclopentadienyl)-1-naphthaldehyde phenylhydrazone, 2-(2-methylcyclopentadienyl)-1-naphthaldehyde phenylhydrazone, 2-(3-methylcyclopentadienyl)-1-naphthaldehyde phenylhydrazone, 2-(2,3-dimethylcyclopentadienyl)-1-naphthaldehyde phenylhydrazone, 2-(2,4-dimethylcyclopentadienyl)-1-naphthaldehyde phenylhydrazone, 2-(3,4-dimethylcyclopentadienyl)-1-naphthaldehyde phenylhydrazone, 2-(2,3,4-trimethylcyclopentadienyl)-1-naphthaldehyde phenylhydrazone, 2-(2,4,5-trimethylcyclopentadienyl)-1-naphthaldehyde phenylhydrazone, 2-(2,3,4,5-tetramethylcyclopentadienyl)-1-naphthaldehyde phenylhydrazone, 2-(2-tert-butylcyclopentadienyl)-1-naphthaldehyde phenylhydrazone, 2-(3-tert-butylcyclopentadienyl)-1-naphthaldehyde phenylhydrazone, 2-(2-dimethylaminocyclopentadienyl)-1-naphthaldehyde phenylhydrazone, 2-(3-dimethylaminocyclopentadienyl)-1-naphthaldehyde phenylhydrazone, 2-(inden-1-yl)-1-naphthaldehyde phenylhydrazone, 2-(2-methylinden-1-yl)-1-naphthaldehyde phenylhydrazone, 2-(2-phenylinden-1-yl)-1-naphthaldehyde phenylhydrazone, 2-(fluoren-9-yl)-1-naphthaldehyde phenylhydrazone, 2-(cyclopentadienyl)acetophenone phenylhydrazone, 2-(2-methylcyclopentadienyl)acetophenone phenylhydrazone, 2-(3-methylcyclopentadienyl)acetophenone phenylhydrazone, 2-(2,3-dimethylcyclopentadienyl)acetophenone phenylhydrazone, 2-(2,4-dimethylcyclopentadienyl)acetophenone phenylhydrazone, 2-(3,4-dimethylcyclopentadienyl)acetophenone phenylhydrazone, 2-(2,3,4-trimethylcyclopentadienyl)acetophenone phenylhydrazone, 2-(2,4,5-trimethylcyclopentadienyl)acetophenone phenylhydrazone, 2-(2,3,4,5-tetramethylcyclopentadienyl)acetophenone phenylhydrazone, 2-(2-tert-butylcyclopentadienyl)acetophenone phenylhydrazone, 2-(3-tert-butylcyclopentadienyl)acetophenone phenylhydrazone, 2-(2-dimethylaminocyclopentadienyl)acetophenone phenylhydrazone, 2-(3-dimethylaminocyclopentadienyl)acetophenone phenylhydrazone, 2-(inden-1-yl)acetophenone phenylhydrazone, 2-(2-methylinden-1-yl)acetophenone phenylhydrazone, 2-(2-phenylinden-1-yl)acetophenone phenylhydrazone, 2-(fluoren-9-yl)acetophenone phenylhydrazone, 2-(cyclopentadienyl)acetophenone 2-methylphenylhydrazone, 2-(2-methylcyclopentadienyl)acetophenone 2-methylphenylhydrazone, 2-(3-methylcyclopentadienyl)acetophenone 2-methylphenylhydrazone, 2-(2,3-dimethylcyclopentadienyl)acetophenone 2-methylphenylhydrazone, 2-(2,4-dimethylcyclopentadienyl)acetophenone 2-methylphenylhydrazone, 2-(3,4-dimethylcyclopentadienyl)acetophenone 2-methylphenylhydrazone, 2-(2,3,4-trimethylcyclopentadienyl)acetophenone 2-methylphenylhydrazone, 2-(2,4,5-trimethylcyclopentadienyl)acetophenone 2-methylphenylhydrazone, 2-(2,3,4,5-tetramethylcyclopentadienyl)acetophenone 2-methylphenylhydrazone, 2-(2-tert-butylcyclopentadienyl)acetophenone 2-methylphenylhydrazone, 2-(3-tert-butylcyclopentadienyl)acetophenone 2-methylphenylhydrazone, 2-(2-dimethylaminocyclopentadienyl)acetophenone 2-methylphenylhydrazone, 2-(3-dimethylaminocyclopentadienyl)acetophenone 2-methylphenylhydrazone, 2-(inden-1-yl)acetophenone 2-methylphenylhydrazone, 2-(2-methylinden-1-yl)acetophenone 2-methylphenylhydrazone, 2-(2-phenylinden-1-yl)acetophenone 2-methylphenylhydrazone, 2-(fluoren-9-yl)acetophenone 2-methylphenylhydrazone, 2-(cyclopentadienyl)acetophenone 2,4,6-trimethylphenylhydrazone, 2-(2-methylcyclopentadienyl)acetophenone 2,4,6-trimethylphenylhydrazone, 2-(3-methylcyclopentadienyl)acetophenone 2,4,6-trimethylphenylhydrazone, 2-(2,3-dimethylcyclopentadienyl)acetophenone 2,4,6-trimethylphenylhydrazone, 2-(2,4-dimethylcyclopentadienyl)acetophenone 2,4,6-trimethylphenylhydrazone, 2-(3,4- dimethylcyclopentadienyl)acetophenone 2,4,6-trimethylphenylhydrazone, 2-(2,3,4-trimethylcyclopentadienyl)acetophenone 2,4,6-trimethylphenylhydrazone, 2-(2,4,5-trimethylcyclopentadienyl)acetophenone 2,4,6-trimethylphenylhydrazone, 2-(2,3,4,5-tetramethylcyclopentadienyl)acetophenone 2,4,6-trimethylphenylhydrazone, 2-(2-tert-butylcyclopentadienyl)acetophenone 2,4,6-trimethylphenylhydrazone, 2-(3-tert-butylcyclopentadienyl)acetophenone 2,4,6-trimethylphenylhydrazone, 2-(2-dimethylaminocyclopentadienyl)acetophenone 2,4,6-trimethylphenylhydrazone, 2-(3-dimethylaminocyclopentadienyl)acetophenone 2,4,6-trimethylphenylhydrazone, 2-(inden-1-yl)acetophenone 2,4,6-trimethylphenylhydrazone, 2-(2-methylinden-1-yl)acetophenone 2,4,6-trimethylphenylhydrazone, 2-(2-phenylinden-1-yl)acetophenone 2,4,6-trimethylphenylhydrazone, 2-(fluoren-9-yl)acetophenone 2,4,6-trimethylphenylhydrazone, 2-(cyclopentadienyl)acetophenone 2,6-diisopropylphenylhydrazone, 2-(2-methylcyclopentadienyl)acetophenone 2,6-diisopropylphenylhydrazone, 2-(3-methylcyclopentadienyl)acetophenone 2,6-diisopropylphenylhydrazone, 2-(2,3-dimethylcyclopentadienyl)acetophenone 2,6-diisopropylphenylhydrazone, 2-(2,4-dimethylcyclopentadienyl)acetophenone 2,6-diisopropylphenylhydrazone, 2-(3,4-dimethylcyclopentadienyl)acetophenone 2,6-diisopropylphenylhydrazone, 2-(2,3,4-trimethylcyclopentadienyl)acetophenone 2,6-diisopropylphenyl hydrazone, 2-(2,4,5-trimethylcyclopentadienyl)acetophenone 2,6-diisopropylphenylhydrazone, 2-(2,3,4,5-tetramethylcyclopentadienyl)acetophenone 2,6-diisopropylphenylhydrazone, 2-(2-tert-butylcyclopentadienyl)acetophenone 2,6-diisopropylphenylhydrazone, 2-(3-tert-butylcyclopentadienyl)acetophenone 2,6-diisopropylphenylhydrazone, 2-(2-dimethylaminocyclopentadienyl)acetophenone 2,6-diisopropylphenylhydrazone, 2-(3-dimethylaminocyclopentadienyl)acetophenone 2,6-diisopropylphenylhydrazone, 2-(inden-1-yl)acetophenone 2,6-diisopropylphenylhydrazone, 2-(2-methylinden-1-yl)acetophenone 2,6-diisopropylphenylhydrazone, 2-(2-phenylinden-1-yl)acetophenone 2,6-diisopropylphenylhydrazone, 2-(fluoren-9-yl)acetophenone 2,6-diisopropylphenylhydrazone, 2-(cyclopentadienyl)acetophenone 2-naphthylhydrazone, 2-(2-methylcyclopentadienyl)acetophenone 2-naphthylhydrazone, 2-(3-methylcyclopentadienyl)acetophenone 2-naphthylhydrazone, 2-(2,3-dimethylcyclopentadienyl)acetophenone 2-naphthylhydrazone, 2-(2,4-dimethylcyclopentadienyl)acetophenone 2-naphthylhydrazone, 2-(3,4-dimethylcyclopentadienyl)acetophenone 2-naphthylhydrazone, 2-(2,3,4-trimethylcyclopentadienyl)acetophenone 2-naphthylhydrazone, 2-(2,4,5-trimethylcyclopentadienyl)acetophenone 2-naphthylhydrazone, 2-(2,3,4,5-tetramethylcyclopentadienyl)acetophenone 2-naphthylhydrazone, 2-(2-tert-butylcyclopentadienyl)acetophenone 2-naphthylhydrazone, 2-(3-tert-butylcyclopentadienyl)acetophenone 2-naphthylhydrazone, 2-(2-dimethylaminocyclopentadienyl)acetophenone 2-naphthylhydrazone, 2-(3-dimethylaminocyclopentadienyl)acetophenone 2-naphthylhydrazone, 2-(inden-1-yl)acetophenone 2-naphthylhydrazone, 2-(2-methylinden-1-yl)acetophenone 2-naphthylhydrazone, 2-(2-phenylinden-1-yl)acetophenone 2-naphthylhydrazone, 2-(fluoren-9-yl)acetophenone 2-naphthylhydrazone, 2-(cyclopentadienyl)acetophenone cyclohexylhydrazone, 2-(2-methylcyclopentadienyl)acetophenone cyclohexylhydrazone, 2-(3-trimethylcyclopentadienyl)acetophenone cyclohexyl hydrazone, 2-(2,3-dimethylcyclopentadienyl)acetophenone cyclohexylhydrazone, 2-(2,4-dimethylcyclopentadienyl)acetophenone cyclohexylhydrazone, 2-(3,4-dimethylcyclopentadienyl)acetophenone cyclohexylhydrazone, 2-(2,3,4-trimethylcyclopentadienyl)acetophenone cyclohexylhydrazone, 2-(2,4,5-trimethylcyclopentadienyl)acetophenone cyclohexylhydrazone, 2-(2,3,4,5-tetramethylcyclopentadienyl)acetophenone cyclohexylhydrazone, 2-(2-tert-butylcyclopentadienyl)acetophenone cyclohexylhydrazone, 2-(3-tert-butylcyclopentadienyl)acetophenone cyclohexylhydrazone, 2-(2-dimethylaminocyclopentadienyl)acetophenone cyclohexylhydrazone, 2-(3-dimethylaminocyclopentadienyl)acetophenone cyclohexylhydrazone, 2-(inden-1-yl)acetophenone cyclohexylhydrazone, 2-(2-methylinden-1-yl)acetophenone cyclohexylhydrazone, 2-(2-phenylinden-1-yl)acetophenone cyclohexylhydrazone, 2-(fluoren-9-yl)acetophenone cyclohexylhydrazone, 2-(cyclopentadienyl)acetophenone tert-butylhydrazone, 2-(2-methylcyclopentadienyl)acetophenone tert-butylhydrazone, 2-(3-methylcyclopentadienyl)acetophenone tert-butylhydrazone, 2-(2,3-dimethylcyclopentadienyl)acetophenone tert-butylhydrazone, 2-(2,4-dimethylcyclopentadienyl)acetophenone tert-butylhydrazone, 2-(3,4-dimethylcyclopentadienyl)acetophenone tert-butylhydrazone, 2-(2,3,4-trimethylcyclopentadienyl)acetophenone tert-butylhydrazone, 2-(2,4,5-trimethylcyclopentadienyl)acetophenone tert-butylhydrazone, 2-(2,3,4,5-tetramethylcyclopentadienyl)acetophenone tert-butylhydrazone, 2-(2-tert-butylcyclopentadienyl)acetophenone tert-butylhydrazone, 2-(3-tert-butylcyclopentadienyl)acetophenone tert-butylhydrazone, 2-(2-dimethylaminocyclopentadienyl)acetophenone tert-butylhydrazone, 2-(3-dimethylaminocyclopentadienyl)acetophenone tert-butylhydrazone, 2-(inden-1-yl)acetophenone tert-butylhydrazone, 2-(2-methylinden-1-yl)acetophenone tert-butylhydrazone, 2-(2-phenylinden-1-yl)acetophenone tert-butylhydrazone, 2-(fluoren-9-yl)acetophenone tert-butylhydrazone and the like.

The substituted cyclopentadiene compound represented by the formula (8):

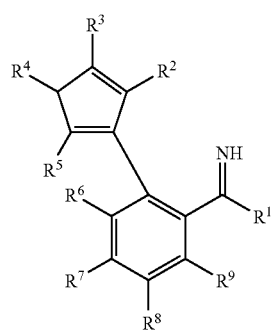

(8)

wherein $R^1$, $R^2$, $R^3$, $R^4$, $R^5$, $R^6$, $R^7$, $R^8$ and $R^9$ have the same meanings as defined in the formula (I), is hereinafter explained.

The compound of the formula (8) can be produced by reacting a nitrile compound represented by the formula (10):

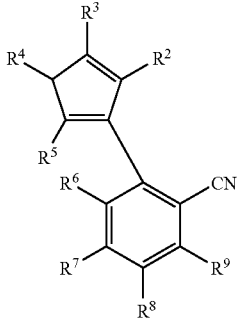

wherein $R^1$, $R^2$, $R^3$, $R^4$, $R^5$, $R^6$, $R^7$, $R^8$ and $R^9$ have the same meanings as defined in the formula (II), or a compound represented by the formula (11):

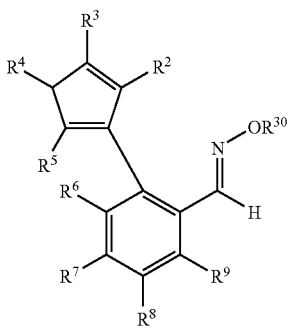

wherein $R^1$, $R^2$, $R^3$, $R^4$, $R^5$, $R^6$, $R^7$, $R^8$, $R^9$ and $R^{30}$ have the same meanings as defined in the formula (II), with a nucleophilic agent (an organic lithium compound or an organic magnesium compound).

A nucleophilic agent used in the reaction includes the above-mentioned organic lithium compounds or organic magnesium compounds and the like ($R^1Li$ or $R^1MgX$; wherein X is a halogen atom; provided that $R^1$ is not a hydrogen atom).

Such a nucleophilic agent includes methylmagnesium bromide, ethylmagnesium bromide, phenylmagnesium bromide, n-butylmagnesium bromide, t-butylmagnesium bromide, methyllithium, phenyllithium, t-butyllithium and the like. Similarly, the above-mentioned compounds in which magnesium bromide is changed to magnesium chloride or magnesium iodide are also exemplified.

Although 2-(4-methoxy-inden-1-yl)benzonitrile (Bioorg. Med. Chem. Lett., 1993, 3, 55) has been known to be obtained by reacting methylchloroaluminum amide, which is derived from hard-to-handle trimethylaluminum, with the precursor spirolactone, said method is not necessarily a general synthesis method and is not satisfactory because amide and carboxylic acid are simultaneously produced as by-products. However, according to the method of the present invention, the nitrile compound of the present invention including the above-mentioned nitrile compound can be easily obtained.

Specific examples of the nitrile compound represented by the formula (10) include the following compounds: 2-(cyclopentadienyl)benzonitrile, 2-(2-methylcyclopentadienyl)benzonitrile, 2-(3-methylcyclopentadienyl)benzonitrile, 2-(2,3-dimethylcyclopentadienyl)benzonitrile, 2-(2,4-dimethylcyclopentadienyl)benzonitrile, 2-(2,3,4-trimethylcyclopentadienyl)benzonitrile, 2-(2,3,5-trimethylcyclopentadienyl)benzonitrile, 2-(2,3,4,5-tetramethylcyclopentadienyl)benzonitrile, 2-(2-dimethylaminocyclopentadienyl)benzonitrile, 2-(3-dimethylaminocyclopentadienyl)benzonitrile, 2-(inden-1-yl)benzonitrile, 2-(2-methylinden-1-yl)benzonitrile, 2-(2-phenylinden-1-yl)benzonitrile, 2-(cyclopentadienyl)-1-cyanonaphthalene, 2-(2-methylcyclopentadienyl)-1-cyanonaphthalene, 2-(3-methylcyclopentadienyl)-1-cyanonaphthalene, 2-(2,3-dimethylcyclopentadienyl)-1-cyanonaphthalene, 2-(2,4-dimethylcyclopentadienyl)-1-cyanonaphthalene, 2-(2,3,4-trimethylcyclopentadienyl)-1-cyanonaphthalene, 2-(2,3,5-trimethylcyclopentadienyl)-1-cyanonaphthalene, 2-(2,3,4,5-tetramethylcyclopentadienyl)-1-cyanonaphthalene, 2-(2-dimethylaminocyclopentadienyl)-1-cyanonaphthalene, 2-(3-dimethylaminocyclopentadienyl)-1-cyanonaphthalene, 2-(inden-1-yl)-1-cyanonaphthalene, 2-(2-methylinden-1-yl)-1-cyanonaphthalene, 2-(2-phenylinden-1-yl)-1-cyanonaphthalene, 3-(cyclopentadienyl)-2-cyanonaphthalene, 3-(2-methylcyclopentadienyl)-2-cyanonaphthalene, 3-(3-methylcyclopentadienyl)-2-cyanonaphthalene, 3-(2,3-dimethylcyclopentadienyl)-2-cyanonaphthalene, 3-(2,4-dimethylcyclopentadienyl)-2-cyanonaphthalene, 3-(2,3,4-trimethylcyclopentadienyl)-2-cyanonaphthalene, 3-(2,3,5-trimethylcyclopentadienyl)-2-cyanonaphthalene, 3-(2,3,4,5-tetramethylcyclopentadienyl)-2-cyanonaphthalene, 3-(2-dimethylaminocyclopentadienyl)-2-cyanonaphthalene, 3-(3-dimethylaminocyclopentadienyl)-2-cyanonaphthalene, 3-(inden-1-yl)-2-cyanonaphthalene, 3-(2-methylinden-1-yl)-2-cyanonaphthalene, 3-(2-phenylinden-1-yl)-2-cyanonaphthalene, 3-dimethylamino-6-(cyclopentadienyl)benzonitrile, 3-dimethylamino-6-(2-methylcyclopentadienyl)benzonitrile, 3-dimethylamino-6-(3-methylcyclopentadienyl)benzonitrile, 3-dimethylamino-6-(2,3-dimethylcyclopentadienyl)benzonitrile, 3-dimethylamino-6-(2,4-dimethylcyclopentadienyl)benzonitrile, 3-dimethylamino-6-(2,3,4-trimethylcyclopentadienyl)benzonitrile, 3-dimethylamino-6-(2,3,5-trimethylcyclopentadienyl)benzonitrile, 3-dimethylamino-6-(2,3,4,5-tetramethylcyclopentadienyl)benzonitrile, 3-dimethylamino-6-(2-dimethylaminocyclopentadienyl)benzonitrile, 3-dimethylamino-6-(3-dimethylaminocyclopentadienyl)benzonitrile, 3-dimethylamino-6-(inden-1-yl)benzonitrile, 3-dimethylamino-6-(2-methylinden-1-yl)benzonitrile, 3-dimethylamino-6-(2-phenylinden-1-yl)benzonitrile and the like.

Specific examples of the oxime ether compound represented by the formula (11) include the following compounds: O-Methyl-2-(cyclopentadienyl)benzaldehyde oxime, O-methyl-2-(2-methylcyclopentadienyl)benzaldehyde oxime, O-methyl-2-(3-methylcyclopentadienyl)benzaldehyde oxime, O-methyl-2-(2,3-dimethylcyclopentadienyl)benzaldehyde oxime, O-methyl-2-(2,4-dimethylcyclopentadienyl)benzaldehyde oxime, O-methyl-2-(2,3,4-trimethylcyclopentadienyl)benzaldehyde oxime, O-methyl-2-(2,3,5-trimethylcyclopentadienyl)benzaldehyde oxime, O-methyl-2-(2,3,4,5-tetramethylcyclopentadienyl)benzaldehyde oxime, O-methyl-2-(2-dimethylaminocyclopentadienyl)benzaldehyde oxime, O-methyl-2-(3-dimethylaminocyclopentadienyl)benzaldehyde oxime, O-methyl-2-(inden-1-yl)benzaldehyde oxime, O-methyl-2-(2-methylinden-1-yl)benzaldehyde oxime, O-methyl-2-(2-phenylinden-1-yl)benzaldehyde oxime, O-methyl-2-(cyclopentadienyl)-1- naphthaldehyde oxime, O-methyl-2-(2-methylcyclopentadienyl)-1-naphthaldehyde oxime, O-methyl-(3-methylcyclopentadienyl)-1-naphthaldehyde oxime, O-methyl-2-(2,3-dimethylcyclopentadienyl)-1-naphthaldehyde oxime, O-methyl-2-(2,4-dimethylcyclopentadienyl)-1-naphthaldehyde oxime, O-methyl-2-(2,3,4-trimethylcyclopentadienyl)-1-naphthaldehyde oxime, O-methyl-2-(2,3,5-trimethylcyclopentadienyl)-1-naphthaldehyde oxime, O-methyl-2-(2,3,4,5-tetramethylcyclopentadienyl)-1-naphthaldehyde oxime, O-methyl-2-(2-dimethylaminocyclopentadienyl)-1-naphthaldehyde oxime, O-methyl-2-(3-dimethylaminocyclopentadienyl)-1-naphthaldehyde oxime, O-methyl-2-(inden-1-yl)-1-naphthaldehyde oxime, O-methyl-2-(2-methylinden-1-yl)-1-naphthaldehyde oxime, O-methyl-2-(2-phenylinden-1-yl)-1-naphthaldehyde oxime, O-methyl-3-(cyclopentadienyl)-2-naphtaldehyde oxime, O-methyl-3-(2-methylcyclopentadienyl)-2-naphtaldehyde oxime, O-methyl-3-(3-methylcyclopentadienyl)-2-naphtaldehyde oxime, O-methyl-3-(2,3-dimethylcyclopentadienyl)-2-naphtaldehyde oxime, O-methyl-3-(2,4-dimethylcyclopentadienyl)-2-naphtaldehyde oxime, O-methyl-3-(2,3,4-trimethylcyclopentadienyl)-2-naphtaldehyde oxime, O-methyl-3-(2,3,4,5-trimethylcyclopentadienyl)-2-naphtaldehyde oxime, O-methyl-3-(2,3,4,5-tetramethylcyclopentadienyl)-2-naphtaldehyde oxime, O-methyl-3-(2-dimethylaminocyclopentadienyl)-2-naphtaldehyde oxime, O-methyl-3-(3-dimethylaminocyclopentadienyl)-2-naphtaldehyde oxime, O-methyl-3-(inden-1-yl)-2-naphtaldehyde oxime, O-methyl-3-(2-methylinden-1-yl)-2-naphtaldehyde oxime, O-methyl-3-(2-phenylinden-1-yl)-2-naphtaldehyde oxime, O-methyl-3-dimethylamino-6-(cyclopentadienyl)benzaldehyde oxime, O-methyl-3-dimethylamino-6-(2-methylcyclopentadienyl)benzaldehyde oxime, O-methyl-3-dimethylamino-6-(3-methylcyclopentadienyl)benzaldehyde oxime, O-methyl-3-dimethylamino-6-(2,3-dimethylcyclopentadienyl)benzaldehyde oxime, O-methyl-3-dimethylamino-6-(2,4-dimethylcyclopentadienyl)benzaldehyde oxime, O-methyl-3-dimethylamino-6-(2,3,4-trimethylcyclopentadienyl)benzaldehyde oxime, O-methyl-3-dimethylamino-6-(2,3,5-trimethylcyclopentadienyl)benzaldehyde oxime, O-methyl-3-dimethylamino-6-(2,3,4,5-tetramethylcyclopentadienyl)benzaldehyde oxime, O-methyl-3-dimethylamino-6-(2-dimethylaminocyclopentadienyl)benzaldehyde oxime, O-methyl-3-dimethylamino-6-(3-dimethylaminocyclopentadienyl)benzaldehyde-oxime, O-methyl-3-dimethylamino-6-(inden-1-yl)benzaldehyde oxime, O-methyl-3-dimethylamino-6-(2-methylinden-1-yl)benzaldehyde oxime, O-methyl-3-dimethylamino-6-(2-phenylinden-1-yl)benzaldehyde oxime and the like. Similarly, the above-mentioned compounds in which O-methyl is changed to O-ethyl or O-benzyl are also exemplified.

There are isomers based on the nitrogen-oxygen bond of oxime ether. The present invention also encompasses the isomers and a mixture thereof.

The reaction of a nucleophilic agent and the compound of the formula (10) or (11) is usually carried out in an inert solvent to the reaction. Such a solvent includes, for example, aprotic solvents such as aromatic hydrocarbon solvents such as benzene, toluene and the like; aliphatic hydrocarbon solvents such as hexane, heptane and the like; ether solvents such as diethyl ether, tetrahydrofuran, 1,4-dioxane and the like; amide solvents such as hexamethylphosphoric amide, dimethylformamide and the like; polar solvents such as acetonitrile, propionitrile, acetone, diethyl ketone, methyl isobutyl ketone, cyclohexanone and the like; halogenated solvents such as dichloromethane, dichloroethane, chlorobenzene, dichlorobenzene and the like. One or a mixture of two or more of the solvents is used. The amount of a solvent to be used is usually in the range of 1 to 200 times, preferably 3 to 50 times the weight of the substituted cyclopentadiene of the formula (10) or (11).

The reaction temperature is usually in the range of −100° C. to the boiling point of a solvent, preferably −80 to 120° C.

After the reaction, if needed, water is added to the resulting reaction mixture. The mixture is then separated into an organic layer and an aqueous layer to give a solution of the objective compound as the organic layer. When the organic layer and the aqueous layer can not be easily separated due to use of a solvent compatible with water or use of a small amount of solvent in said reaction, the separation may be carried out after addition of a water-insoluble organic solvent such as toluene, ethyl acetate, chlorobenzene and the like to the reaction mixture. The imine compound represented by the formula (8) can be purified, for example, by washing said solution of the compound with water, drying said solution, and then distilling off the solvent, and further by methods such as recrystallization, distillation, column chromatography treatment and the like.

Specific examples of the imine compound of the formula (8) thus obtained include the following compounds: 2-(cyclopentadienyl)-α-tert-butyl-benzenemethanimine, 2-(2-methylcyclopentadienyl)-α-tert-butyl-benzenemethanimine, 2-(3-methylcyclopentadienyl)-α-tert-butyl-benzenemethanimine, 2-(2,3-dimethylcyclopentadienyl)-α-tert-butyl-benzenemethanimine, 2-(2,4-dimethylcyclopentadienyl)-α-tert-butyl-benzenemethanimine, 2-(2,3,4-trimethylcyclopentadienyl)-α-tert-butyl-benzenemethanimine, 2-(2,3,5-trimethylcyclopentadienyl)-α-tert-butyl-benzenemethanimine, 2-(2,3,4,5-tetramethylcyclopentadienyl)-α-tert-butyl-benzenemethanimine, 2-(2-dimethylaminomethylcyclopentadienyl)-α-tert-butyl-benzenemethanimine, 2-(3-dimethylaminomethylcyclopentadienyl)-α-tert-butyl-benzenemethanimine, 2-(inden-1-yl)-α-tert-butyl-benzenemethanimine, 2-(2-methylinden-1-yl)-α-tert-butyl-benzenemethanimine, 2-(2-phenylinden-1-yl)-α-tert-butyl-benzenemethanimine, 2-(fluoren-9-yl)-α-tert-butyl-benzenemethanimine, 2-(cyclopentadienyl)-α-n-butyl-benzenemethanimine, 2-(2-methylcyclopentadienyl)-α-n-butyl-benzenemethanimine, 2-(3-methylcyclopentadienyl)-α-n-butyl-benzenemethanimine, 2-(2,3-dimethylcyclopentadienyl)-α-n-butyl-benzenemethanimine, 2-(2,4-dimethylcyclopentadienyl)-α-n-butyl-benzenemethanimine, 2-(2,3,4-trimethylcyclopentadienyl)-α-n-butyl-benzenemethanimine, 2-(2,3,5-trimethylcyclopentadienyl)-α-n-butyl-benzenemethanimine, 2-(2,3,4,5-tetramethylcyclopentadienyl)-α-n-butyl-benzenemethanimine, 2-(2-dimethylaminomethylcyclopentadienyl)-α-n-butyl-benzenemethanimine, 2-(3-dimethylaminomethylcyclopentadienyl)-α-n-butyl-benzenemethanimine, 2-(inden-1-yl)-α-butyl-benzenemethanimine, 2-(2-methylinden-1-yl)-α-n-butyl-benzenemethanimine, 2-(2-phenylinden-1-yl)-α-n-butyl-benzenemethanimine, 2-(fluoren-9-yl)-α-n-butyl-benzenemethanimine, 2-(cyclopentadienyl)-α-phenyl-benzenemethanimine, 2-(2-methylcyclopentadienyl)-α-phenyl-benzenemethanimine, 2-(3-methylcyclopentadienyl)-α-phenyl-benzenemethanimine, 2-(2,3-dimethylcyclopentadienyl)-α-phenyl-benzenemethanimine, 2-(2,4-dimethylcyclopentadienyl)-α-phenyl-benzenemethanimine, 2-(2,3,4-trimethylcyclopentadienyl)-α-phenyl-benzenemethanimine, 2-(2,3,5- trimethylcyclopentadienyl)-α-phenyl-benzenemethanimine, 2-(2,3,4,5-tetramethylcyclopentadienyl)-α-phenyl-benzenemethanimine, 2-(2-dimethylaminomethylcyclopentadienyl)-α-phenyl-benzenemethanimine, 2-(3-dimethylaminomethylcyclopentadienyl)-α-phenyl-benzenemethanimine, 2-(inden-1-yl)-α-phenyl-benzenemethanimine, 2-(2-methylinden-1-yl)-α-phenyl-benzenemethanimine, 2-(2-phenylinden-1-yl)-α-phenyl-benzenemethanimine, 2-(fluoren-9-yl)-α-phenyl-benzenemethanimine, 2-(cyclopentadienyl)-α-(2,3,4-trimethylphenyl)-benzenemethanimine, 2-(2-methylcyclopentadienyl)-α-(2,3,4-trimethylphenyl)-benzenemethanimine, 2-(3-methylcyclopentadienyl)-α-(2,3,4-trimethylphenyl)-benzenemethanimine, 2-(2,3-dimethylcyclopentadienyl)-α-(2,3,4-trimethylphenyl)-benzenemethanimine, 2-(2,4-dimethylcyclopentadienyl)-α-(2,3,4-trimethylphenyl)-benzenemethanimine, 2-(2,3,4-trimethylcyclopentadienyl)-α-(2,3,4-trimethylphenyl)-benzenemethanimine, 2-(2,3,5-trimethylcyclopentadienyl)-α-(2,3,4-trimethylphenyl)-benzenemethanimine, 2-(2,3,4,5-tetramethylcyclopentadienyl)-α-(2,3,4-trimethylphenyl)-benzenemethanimine, 2-(2-dimethylaminomethylcyclopentadienyl)-α-(2,3,4-trimethylphenyl)-benzenemethanimine, 2-(3-dimethylaminomethylcyclopentadienyl)-α-(2,3,4-trimethylphenyl)-benzenemethanimine, 2-(inden-1-yl)-α-(2,3,4-trimethylphenyl)-benzenemethanimine, 2-(2-methylinden-1-yl)-α-(2,3,4-trimethylphenyl)-benzenemethanimine, 2-(2-phenylinden-1-yl)-α-(2,3,4-trimethylphenyl)-benzenemethanimine, 2-(fluoren-9-yl)-α-(2,3,4-trimethylphenyl)-benzenemethanimine, 2-(cyclopentadienyl)-α-cyclohexyl-benzenemethanimine, 2-(2-methylcyclopentadienyl)-α-cyclohexyl-benzenemethanimine, 2-(3-methylcyclopentadienyl)-α-cyclohexyl-benzenemethanimine, 2-(2,3-dimethylcyclopentadienyl)-α-cyclohexyl-benzenemethanimine, 2-(2,4-dimethylcyclopentadienyl)-α-cyclohexyl-benzenemethanimine, 2-(2,3,4-trimethylcyclopentadienyl)-α-cyclohexyl-benzenemethanimine, 2-(2,3,5-trimethylcyclopentadienyl)-α-cyclohexyl-benzenemethanimine, 2-(2,3,4,5-tetramethylcyclopentadienyl)-α-cyclohexyl-benzenemethanimine, 2-(2-dimethylaminomethylcyclopentadienyl)-α-cyclohexyl-benzenemethanimine, 2-(3-dimethylaminomethylcyclopentadienyl)-α-cyclohexyl-benzenemethanimine, 2-(inden-1-yl)-α-cyclohexyl-benzenemethanimine, 2-(2-methylinden-1-yl)-α-cyclohexyl-benzenemethanimine, 2-(2-phenylinden-1-yl)-α-cyclohexyl-benzenemethanimine, 2-(fluoren-9-yl)-α-cyclohexyl-benzenemethanimine, 2-(cyclopentadienyl)-α-tert-butyl-1-naphthalenemethanimine, 2-(2-methylcyclopentadienyl)-α-tert-butyl-1-naphthalenemethanimine, 2-(3-methylcyclopentadienyl)-α-tert-butyl-1-naphthalenemethanimine, 2-(2,3-dimethylcyclopentadienyl)-α-tert-butyl-1-naphthalenemethanimine, 2-(2,4-dimethylcyclopentadienyl)-α-tert-butyl-1-naphthalenemethanimine, 2-(2,3,4-trimethylcyclopentadienyl)-α-tert-butyl-1-naphthalenemethanimine, 2-(2,3,5-trimethylcyclopentadienyl)-α-tert-butyl-1-naphthalenemethanimine, 2-(2,3,4,5-tetramethylcyclopentadienyl)-α-tert-butyl-1-naphthalenemethanimine, 2-(2-dimethylaminomethylcyclopentadienyl)-α-tert-butyl-1-naphthalenemethanimine, 2-(3-dimethylaminomethylcyclopentadienyl)-α-tert-butyl-1-naphthalenemethanimine, 2-(inden-1-yl)-α-tert-butyl-1-naphthalenemethanimine, 2-(2-methylinden-1-yl)-α-tert-butyl-1-naphthalenemethanimine, 2-(2-phenylinden-1-yl)-α-tert-butyl-1-naphthalenemethanimine, 2-(fluoren-9-yl)-α-tert-butyl-1-naphthalenemethanimine, 2-(cyclopentadienyl)-α-n-butyl-1-naphthalenemethanimine, 2-(2-methylcyclopentadienyl)-α-n-butyl-1-naphthalenemethanimine, 2-(3-methylcyclopentadienyl)-α-n-butyl-1-naphthalenemethanimine, 2-(2,3-dimethylcyclopentadienyl)-α-n-butyl-1-naphthalenemethanimine, 2-(2,4-dimethylcyclopentadienyl)-α-n-butyl-1-naphthalenemethanimine, 2-(2,3,4-trimethylcyclopentadienyl)-α-n-butyl-1-naphthalenemethanimine, 2-(2,3,5-trimethylcyclopentadienyl)-α-n-butyl-1-naphthalenemethanimine, 2-(2,3,4,5-tetramethylcyclopentadienyl)-α-n-butyl-1-naphthalenemethanimine, 2-(2-dimethylaminomethylcyclopentadienyl)-α-n-butyl-1-naphthalenemethanimine, 2-(3-dimethylaminomethylcyclopentadienyl)-α-n-butyl-1-naphthalenemethanimine, 2-(inden-1-yl)-α-n-butyl-1-naphthalenemethanimine, 2-(2-methylinden-1-yl)-α-n-butyl-1-naphthalenemethanimine, 2-(2-phenylinden-1-yl)-α-n-butyl-1-naphthalenemethanimine, 2-(fluoren-9-yl)-α-n-butyl-1-naphthalenemethanimine, 2-(cyclopentadienyl)-α-phenyl-1-naphthalenemethanimine, 2-(2-methylcyclopentadienyl)-α-phenyl-1-naphthalenemethanimine, 2-(3-methylcyclopentadienyl)-α-phenyl-1-naphthalenemethanimine, 2-(2,3-dimethylcyclopentadienyl)-α-phenyl-1-naphthalenemethanimine, 2-(2,4-dimethylcyclopentadienyl)-α-phenyl-1-naphthalenemethanimine, 2-(2,3,4-trimethylcyclopentadienyl)-α-phenyl-1-naphthalenemethanimine, 2-(2,3,5-trimethylcyclopentadienyl)-α-phenyl-1-naphthalenemethanimine, 2-(2,3,4,5-tetramethylcyclopentadienyl)-α-phenyl-1-naphthalenemethanimine, 2-(2-dimethylaminomethylcyclopentadienyl)-α-phenyl-1-naphthalenemethanimine, 2-(3-dimethylaminomethylcyclopentadienyl)-α-phenyl-1-naphthalenemethanimine, 2-(inden-1-yl)-α-phenyl-1-naphthalenemethanimine, 2-(2-methylinden-1-yl)-α-phenyl-1-naphthalenemethanimine, 2-(2-phenylinden-1-yl)-α-phenyl-1-naphthalenemethanimine, 2-(fluoren-9-yl)-α-phenyl-1-naphthalenemethanimine, 2-(cyclopentadienyl)-α-(2,3,4-trimethylphenyl)-1-naphthalenemethanimine, 2-(2-methylcyclopentadienyl)-α-(2,3,4-trimethylphenyl)-1-naphthalenemethanimine, 2-(2,3-methylcyclopentadienyl)-α-(2,3,4-trimethylphenyl)-1-naphthalenemethanimine, 2-(2,3-dimethylcyclopentadienyl)-α-(2,3,4-trimethylphenyl)-1-naphthalenemethanimine, 2-(2,4-dimethylcyclopentadienyl)-α-(2,3,4-trimethylphenyl)-1-naphthalenemethanimine, 2-(2,3,4-trimethylcyclopentadienyl)-α-(2,3,4-trimethylphenyl)-1-naphthalenemethanimine, 2-(2,3,5-trimethylcyclopentadienyl)-α-(2,3,4-trimethylphenyl)-1-naphthalenemethanimine, 2-(2,3,4,5-tetramethylcyclopentadienyl)-α-(2,3,4-trimethylphenyl)-1-naphthalenemethanimine, 2-(2-dimethylaminomethylcyclopentadienyl)-α-(2,3,4-trimethylphenyl)-1-naphthalenemethanimine, 2-(3-dimethylaminomethylcyclopentadienyl)-α-(2,3,4- trimethylphenyl)-1-naphthalenemethanimine, 2-(inden-1-yl)-α-(2,3,4-trimethylphenyl)-1-naphthalenemethanimine, 2-(2-methylinden-1-yl)-α-(2,3,4-trimethylphenyl)-1-naphthalenemethanimine, 2-(2-phenylinden-1-yl)-α-(2,3,4-trimethylphenyl)-1-naphthalenemethanimine, 2-(fluoren-9-yl)-α-(2,3,4-trimethylphenyl)-1-naphthalenemethanimine, 2-(cyclopentadienyl)-α-cyclohexyl-1-naphthalenemethanimine, 2-(2-methylcyclopentadienyl)-α-cyclohexyl-1-naphthalenemethanimine, 2-(3-methylcyclopentadienyl)-α-cyclohexyl-1-naphthalenemethanimine, 2-(2,3-dimethylcyclopentadienyl)-α-cyclohexyl-1-naphthalenemethanimine, 2-(2,4-dimethylcyclopentadienyl)-α-cyclohexyl-1-naphthalenemethanimine, 2-(2,3,4-trimethylcyclopentadienyl)-α-cyclohexyl-1-naphthalenemethanimine, 2-(2,3,5-trimethylcyclopentadienyl)-α-cyclohexyl-1-naphthalenemethanimine, 2-(2,3,4,5-tetramethylcyclopentadienyl)-α-cyclohexyl-1-naphthalenemethanimine, 2-(2-dimethylaminomethylcyclopentadienyl)-α-cyclohexyl-1-naphthalenemethanimine, 2-(3-dimethylaminomethylcyclopentadienyl)-α-cyclohexyl-1-naphthalenemethanimine, 2-(inden-1-yl)-α-cyclohexyl-1-naphthalenemethanimine, 2-(2-methylinden-1-yl)-α-cyclohexyl-1-naphthalenemethanimine, 2-(2-phenylinden-1-yl)-α-cyclohexyl-1-naphthalenemethanimine, 2-(fluoren-9-yl)-α-cyclohexyl-1-naphthalenemethanimine, 3-(cyclopentadienyl)-α-tert-butyl-2-naphthalenemethanimine, 3-(2-methylcyclopentadienyl)-α-tert-butyl-2-naphthalenemethanimine, 3-(3-methylcyclopentadienyl)-α-tert-butyl-2-naphthalenemethanimine, 3-(2,3-dimethylcyclopentadienyl)-α-tert-butyl-2-naphthalenemethanimine, 3-(2,4-dimethylcyclopentadienyl)-α-tert-butyl-2-naphthalenemethanimine, 3-(2,3,4-trimethylcyclopentadienyl)-α-tert-butyl-2-naphthalenemethanimine, 3-(2,3,5-trimethylcyclopentadienyl)-α-tert-butyl-2-naphthalenemethanimine, 3-(2,3,4,5-tetramethylcyclopentadienyl)-α-tert-butyl-2-naphthalenemethanimine, 3-(2-dimethylaminomethylcyclopentadienyl)-α-tert-butyl-2-naphthalenemethanimine, 3-(3-dimethylaminomethylcyclopentadienyl)-α-tert-butyl-2-naphthalenemethanimine, 3-(inden-1-yl)-α-tert-butyl-2-naphthalenemethanimine, 3-(2-methylinden-1-yl)-α-tert-butyl-2-naphthalenemethanimine, 3-(2-phenylinden-1-yl)-α-tert-butyl-2-naphthalenemethanimine, 3-(fluoren-9-yl)-α-tert-butyl-2-naphthalenemethanimine, 3-(cyclopentadienyl)-α-n-butyl-2-naphthalenemethanimine, 3-(2-methylcyclopentadienyl)-α-n-butyl-2-naphthalenemethanimine, 3-(3-methylcyclopentadienyl)-α-n-butyl-2-naphthalenemethanimine, 3-(2,3-dimethylcyclopentadienyl)-α-n-butyl-2-naphthalenemethanimine, 3-(2,4-dimethylcyclopentadienyl)-α-n-butyl-2-naphthalenemethanimine, 3-(2,3,4-trimethylcyclopentadienyl)-α-n-butyl-2-naphthalenemethanimine, 3-(2,3,5-trimethylcyclopentadienyl)-α-n-butyl-2-naphthalenemethanimine, 3-(2,3,4,5-tetramethylcyclopentadienyl)-α-n-butyl-2-naphthalenemethanimine, 3-(2-dimethylaminomethylcyclopentadienyl)-α-n-butyl-2-naphthalenemethanimine, 3-(3-dimethylaminomethylcyclopentadienyl)-α-n-butyl-2-naphthalenemethanimine, 3-(inden-1-yl)-α-n-butyl-2-naphthalenemethanimine, 3-(2-methylinden-1-yl)-α-n-butyl-2-naphthalenemethanimine, 3-(2-phenylinden-1-yl)-α-n-butyl-2-naphthalenemethanimine, 3-(fluoren-9-yl)-α-n-butyl-2-naphthalenemethanimine, 3-(cyclopentadienyl)-α-phenyl-2-naphthalenemethanimine, 3-(2-methylcyclopentadienyl)-α-phenyl-2-naphthalenemethanimine, 3-(3-methylcyclopentadienyl)-α-phenyl-2-naphthalenemethanimine, 3-(2,3-dimethylcyclopentadienyl)-α-phenyl-2-naphthalenemethanimine, 3-(2,4-dimethylcyclopentadienyl)-α-phenyl-2-naphthalenemethanimine, 3-(2,3,4-trimethylcyclopentadienyl)-α-phenyl-2-naphthalenemethanimine, 3-(2,3,5-trimethylcyclopentadienyl)-α-phenyl-2-naphthalenemethanimine, 3-(2,3,4,5-tetramethylcyclopentadienyl)-α-phenyl-2-naphthalenemethanimine, 3-(2-dimethylaminomethylcyclopentadienyl)-α-phenyl-2-naphthalenemethanimine, 3-(3-dimethylaminomethylcyclopentadienyl)-α-phenyl-2-naphthalenemethanimine, 3-(inden-1-yl)-α-phenyl-2-naphthalenemethanimine, 3-(2-methylinden-1-yl)-α-phenyl-2-naphthalenemethanimine, 3-(2-phenylinden-1-yl)-α-phenyl-2-naphthalenemethanimine, 3-(fluoren-9-yl)-α-phenyl-2-naphthalenemethanimine, 3-(cyclopentadienyl)-α-(2,3,4-trimethylphenyl)-2-naphthalenemethanimine, 3-(2-methylcyclopentadienyl)-α-(2,3,4-trimethylphenyl)-2-naphthalenemethanimine, 3-(3-methylcyclopentadienyl)-α-(2,3,4-trimethylphenyl)-2-naphthalenemethanimine, 3-(2,3-dimethylcyclopentadienyl)-α-(2,3,4-trimethylphenyl)-2-naphthalenemethanimine, 3-(2,4-dimethylcyclopentadienyl)-α-(2,3,4-trimethylphenyl)-2-naphthalenemethanimine, 3-(2,3,4-trimethylcyclopentadienyl)-α-(2,3,4-trimethylphenyl)-2-naphthalenemethanimine, 3-(2,3,5-trimethylcyclopentadienyl)-α-(2,3,4-trimethylphenyl)-2-naphthalenemethanimine, 3-(2,3,4,5-tetramethylcyclopentadienyl)-α-(2,3,4-trimethylphenyl)-2-naphthalenemethanimine, 3-(2-dimethylaminomethylcyclopentadienyl)-α-(2,3,4-trimethylphenyl)-2-naphthalenemethanimine, 3-(3-dimethylaminomethylcyclopentadienyl)-α-(2,3,4-trimethylphenyl)-2-naphthalenemethanimine, 3-(inden-1-yl)-α-(2,3,4-trimethylphenyl)-2-naphthalenemethanimine, 3-(2-methylinden-1-yl)-α-(2,3,4-trimethylphenyl)-2-naphthalenemethanimine, 3-(2-phenylinden-1-yl)-α-(2,3,4-trimethylphenyl)-2-naphthalenemethanimine, 3-(fluoren-9-yl)-α-(2,3,4-trimethylphenyl)-2-naphthalenemethanimine, 3-(cyclopentadienyl)-α-cyclohexyl-2-naphthalenemethanimine, 3-(2-methylcyclopentadienyl)-α-cyclohexyl-2-naphthalenemethanimine, 3-(3-methylcyclopentadienyl)-α-cyclohexyl-2-naphthalenemethanimine, 3-(2,3-dimethylcyclopentadienyl)-α-cyclohexyl-2-naphthalenemethanimine, 3-(2,4-dimethylcyclopentadienyl)-α-cyclohexyl-2-naphthalenemethanimine, 3-(2,3,4-trimethylcyclopentadienyl)-α-cyclohexyl-2-naphthalenemethanimine, 3-(2,3,5-trimethylcyclopentadienyl)-α-cyclohexyl-2-naphthalenemethanimine, 3-(2,3,4,5-tetramethylcyclopentadienyl)-α-cyclohexyl-2-naphthalenemethanimine, 3-(2-dimethylaminomethylcyclopentadienyl)-α-cyclohexyl-2-naphthalenemethanimine, 3-(3-dimethylaminomethylcyclopentadienyl)-α-cyclohexyl-2- naphthalenemethanimine, 3-(inden-1-yl)-α-cyclohexyl-2-naphthalenemethanimine, 3-(2-methylinden-1-yl)-α-cyclohexyl-2-naphthalenemethanimine, 3-(2-phenylinden-1-yl)-α-cyclohexyl-2-naphthalenemethanimine, 3-(fluoren-9-yl)-α-cyclohexyl-2-naphthalenemethanimine, 3-dimethylamino-6-(cyclopentadienyl)-α-tert-butyl-benzenemethanimine, 3-dimethylamino-6-(2-methylcyclopentadienyl)-α-tert-butyl-benzenemethanimine, 3-dimethylamino-6-(3-methylcyclopentadienyl)-α-tert-butyl-benzenemethanimine, 3-dimethylamino-6-(2,3-dimethylcyclopentadienyl)-α-tert-butyl-benzenemethanimine, 3-dimethylamino-6-(2,4-dimethylcyclopentadienyl)-α-tert-butyl-benzenemethanimine, 3-dimethylamino-6-(2,3,4-trimethylcyclopentadienyl)-α-tert-butyl-benzenemethanimine, 3-dimethylamino-6-(2,3,5-trimethylcyclopentadienyl)-α-tert-butyl-benzenemethanimine, 3-dimethylamino-6-(2,3,4,5-tetramethylcyclopentadienyl)-α-tert-butyl-benzenemethanimine, 3-dimethylamino-6-(2-dimethylaminomethylcyclopentadienyl)-α-tert-butyl-benzenemethanimine, 3-dimethylamino-6-(3-dimethylaminomethylcyclopentadienyl)-α-tert-butyl-benzenemethanimine, 3-dimethylamino-6-(inden-1-yl)-α-tert-butyl-benzenemethanimine, 3-dimethylamino-6-(2-methylinden-1-yl)-α-tert-butyl-benzenemethanimine, 3-dimethylamino-6-(2-phenylinden-1-yl)-α-tert-butyl-benzenemethanimine, 3-dimethylamino-6-(fluoren-9-yl)-α-tert-butyl-benzenemethanimine, 3-dimechylamino-6-(cyclopentadienyl)-α-n-butyl-benzenemethanimine, 3-dimethylamino-6-(2-methylcyclopentadienyl)-α-n-butyl-benzenemethanimine, 3-dimethylamino-6-(3-methylcyclopentadienyl)-α-n-butyl-benzenemethanimine, 3-dimethylamino-6-(2,3-dimethylcyclopentadienyl)-α-n-butyl-benzenemethanimine, 3-dimethylamino-6-(2,4-dimethylcyclopentadienyl)-α-n-butyl-benzenemethanimine, 3-dimethylamino-6-(2,3,4-trimethylcyclopentadienyl)-α-n-butyl-benzenemethanimine, 3-dimethylamino-6-(2,3,5-trimethylcyclopentadienyl)-α-n-butyl-benzenemethanimine, 3-dimethylamino-6-(2,3,4,5-tetramethylcyclopentadienyl)-α-n-butyl-benzenemethanimine, 3-dimethylamino-6-(2-dimethylaminomethylcyclopentadienyl)-α-n-butyl-benzenemethanimine, 3-dimethylamino-6-(3-dimethylaminomethylcyclopentadienyl)-α-n-butyl-benzenemethanimine, 3-dimethylamino-6-(inden-1-yl)-α-n-butyl-benzenemethanimine, 3-dimethylamino-6-(2-methylinden-1-yl)-α-n-butyl-benzenemethanimine, 3-dimethylamino-6-(2-phenylinden-1-yl)-α-n-butyl-benzenemethanimine, 3-dimethylamino-6-(fluoren-9-yl)-α-n-butyl-benzenemethanimine, 3-dimethylamino-6-(cyclopentadienyl)-α-phenyl-benzenemethanimine, 3-dimethylamino-6-(2-methylcyclopentadienyl)-α-phenyl-benzenemethanimine, 3-dimethylamino-6-(3-methylcyclopentadienyl)-α-phenyl-benzenemethanimine, 3-dimethylamino-6-(2,3-dimethylcyclopentadienyl)-α-phenyl-benzenemethanimine, 3-dimethylamino-6-(2,4-dimethylcyclopentadienyl)-α-phenyl-benzenemethanimine, 3-dimethylamino-6-(2,3,4-trimethylcyclopentadienyl)-α-phenyl-benzenemethanimine, 3-dimethylamino-6-(2,3,5-trimethylcyclopentadienyl)-α-phenyl-benzenemethanimine, 3-dimethylamino-6-(2,3,4,5-tetramethylcyclopentadienyl)-α-phenyl-benzenemethanimine, 3-dimethylamino-6-(2-dimethylaminomethylcyclopentadienyl)-α-phenyl-benzenemethanimine, 3-dimethylamino-6-(3-dimethylaminomethylcyclopentadienyl)-α-phenyl-benzenemethanimine, 3-dimethylamino-6-(inden-1-yl)-α-phenyl-benzenemethanimine, 3-dimethylamino-6-(2-methylinden-1-yl)-α-phenyl-benzenemethanimine, 3-dimethylamino-6-(2-phenylinden-1-yl)-α-phenyl-benzenemethanimine, 3-dimethylamino-6-(fluoren-9-yl)-α-phenyl-benzenemethanimine, 3-dimethylamino-6-(cyclopentadienyl)-α-(2,3,4-trimethylphenyl)-benzenemethanimine, 3-dimethylamino-6-(2-methylcyclopentadienyl)-α-(2,3,4-trimethylphenyl)-benzenemethanimine, 3-dimethylamino-6-(3-methylcyclopentadienyl)-α-(2,3,4-trimethylphenyl)-benzenemethanimine, 3-dimethylamino-6-(2,3-dimethylcyclopentadienyl)-α-(2,3,4-trimethylphenyl)-benzenemethanimine, 3-dimethylamino-6-(2,4-dimethylcyclopentadienyl)-α-(2,3,4-trimethylphenyl)-benzenemethanimine, 3-dimethylamino-6-(2,3,4-trimethylcyclopentadienyl)-α-(2,3,4-trimethylphenyl)-benzenemethanimine, 3-dimethylamino-6-(2,3,5-trimethylcyclopentadienyl)-α-(2,3,4-trimethylphenyl)-benzenemethanimine, 3-dimethylamino-6-(2,3,4,5-tetramethylcyclopentadienyl)-α-(2,3,4-trimethylphenyl)-benzenemethanimine, 3-dimethylamino-6-(2-dimethylaminomethylcyclopentadienyl)-α-(2,3,4-trimethylphenyl)-benzenemethanimine, 3-dimethylamino-6-(3-dimethylaminomethylcyclopentadienyl)-α-(2,3,4-trimethylphenyl)-benzenemethanimine, 3-dimethylamino-6-(inden-1-yl)-α-(2,3,4-trimethylphenyl)-benzenemethanimine, 3-dimethylamino-6-(2-methylinden-1-yl)-α-(2,3,4-trimethylphenyl)-benzenemethanimine, 3-dimethylamino-6-(2-phenylinden-1-yl)-α-(2,3,4-trimethylphenyl)-benzenemethanimine, 3-dimethylamino-6-(fluoren-9-yl)-α-(2,3,4-trimethylphenyl)-benzenemethanimine, 3-dimethylamino-6-(cyclopentadienyl)-α-cyclohexyl-benzenemethanimine, 3-dimethylamino-6-(2-methylcyclopentadienyl)-α-cyclohexyl-benzenemethanimine, 3-dimethylamino-6-(3-methylcyclopentadienyl)-α-cyclohexyl-benzenemethanimine, 3-dimethylamino-6-(2,3-dimethylcyclopentadienyl)-α-cyclohexyl-benzenemethanimine, 3-dimethylamino-6-(2,4-dimethylcyclopentadienyl)-α-cyclohexyl-benzenemethanimine, 3-dimethylamino-6-(2,3,4-trimethylcyclopentadienyl)-α-cyclohexyl-benzenemethanimine, 3-dimethylamino-6-(2,3,5-trimethylcyclopentadienyl)-α-cyclohexyl-benzenemethanimine, 3-dimethylamino-6-(2,3,4,5-tetramethylcyclopentadienyl)-α-cyclohexyl-benzenemethanimine, 3-dimethylamino-6-(2-dimethylaminomethylcyclopentadienyl)-α-cyclohexyl-benzenemethanimine, 3-dimethylamino-6-(3-dimethylaminomethylcyclopentadienyl)-α-cyclohexyl-benzenemethanimine, 3-dimethylamino-6-(inden-1-yl)-α-cyclohexyl-benzenemethanimine, 3-dimethylamino-6-(2-methylinden-1-yl)-α-cyclohexyl-benzenemethanimine, 3-dimethylamino-6-(2-phenylinden-1-yl)-α-cyclohexyl-benzenemethanimine, 3-dimethylamino-6-(fluoren-9-yl)-α-cyclohexyl-benzenemethanimine and the like.

The nitrile compound of the formula (10) can be produced by reacting the oxime ether compound of formula (11) with a base.

A base to be reacted with the compound of the formula (11) includes methyllithium, ethyllithium, n-butyllithium, sec-butyllithium, lithium trimethylsilyl acetylide, trimethylsilylmethyllithium, vinyllithium, phenyllithium, lithium methoxide, lithium ethoxide, lithium tert-butoxide, sodium methoxide, sodium ethoxide, sodium tert-butoxide, potassium methoxide, potassium ethoxide, potassium tert-butoxide, lithium amide, lithium dimethylamide, lithium diisopropylamide, lithium bis(trimethylsilyl)amide, sodium amide, sodium diisopropylamide, sodium bis(trimethylsilyl)amide and the like, preferably alkali metal amides such as lithium amide, lithium dimethylamide, lithium diisopropylamide, lithium bis(trimethylsilyl)amide, sodium amide, sodium diisopropylamide, sodium bis(trimethylsilyl)amide and the like.

The amount of a base to be used is usually in the range of about 0.5 to 3 moles, preferably about 1.9 to 2.5 moles relative to 1 mole of the oxime ether compound represented by the formula (11).

A method for the reaction is not specifically limited, but usually the method can comprise addition in dropwise of a base to the oxime ether compound represented by the formula (11) in the presence of a solvent or addition of the oxime ether compound represented by the formula (11) to a base. The reaction temperature is usually from −80° C. to the boiling point of a solvent, preferably −80 to 40° C.

A solvent used in the reaction is an inert solvent to the reaction. Such a solvent includes aromatic hydrocarbon solvents such as benzene, toluene, xylene and the like; aliphatic hydrocarbon solvents such as hexane, heptane and the like; ether solvents such as diethyl ether, tetrahydrofuran, 1,4-dioxane and the like; amide solvents such as hexamethylphosphoric triamide, dimethylformamide and the like. One or a mixture of two or more of the solvents is used. The amount of a solvent to be used is usually in the range of 1 to 200 parts by weight, preferably 3 to 50 parts by weight relative to 1 part by weight of the oxime ether compound represented by the formula (11).

After the reaction, if needed, water is added to the resulting reaction mixture. The mixture is then separated into an organic layer and an aqueous layer to give a solution of the objective compound as the organic layer. When the organic layer and the aqueous layer can not be easily separated due to use of a solvent compatible with water or use of a small amount of solvent in said reaction, the separation may be carried out after addition of a water-insoluble organic solvent such as toluene, ethyl acetate, chlorobenzene and the like to the reaction mixture.

In order to isolate the nitrile compound represented by the formula (10), for example, by washing said solution of the compound with water, drying said solution, and then distilling off the solvent, and further by methods such as recrystallization, distillation, column chromatography treatment and the like.

The oxime ether compound of the formula (11) can be produced by reacting the carbonyl compound of the formula (1) with oxime ether according to a conventional method.

By reacting the substituted cyclopentadiene ligand compound of the formula (II) thus obtained with the transition metal compound of the formula (III), the transition metal complex of the formula (I) can be produced.

The $X^1$ to $X^4$ for the transition metal compound of the formula (III) are already explained. Said transition metal compound in which each of $X^1$ to $X^4$ is a $C_{1-5}$ hydrocarbon-substituted amino group is preferably used for the production of the transition metal complex.

The transition metal compound represented by the formula (III) includes tetrakis(dimethylamino)titanium, tetrakis(diethylamino)titanium, tetrakis(dimethylamino)zirconium, tetrakis(diethylamino)zirconium, tetrakis(dimethylamino)hafnium, tetrakis(diethylamino)hafnium, tris(dimethylamino)titanium chloride, tris(diethylamino)titanium chloride, tris(dimethylamino)zirconium chloride, tris(diethylamino)zirconium chloride, tris(dimethylamino)hafnium chloride, tris(diethylamino)hafnium chloride, bis(dimethylamino)titanium dichloride, bis(diethylamino)titanium dichloride, bis(dimethylamino)zirconium dichloride, bis(diethylamino)zirconium dichloride, bis(dimethylamino)hafnium dichloride, bis(diethylamino)hafnium dichloride and the like.

The above reaction is usually carried out in an inert solvent to the reaction. Such a solvent includes, for example, aprotic solvents such as aromatic hydrocarbon solvents such as benzene, toluene and the like; aliphatic hydrocarbon solvents such as hexane, heptane and the like; ether solvents such as diethyl ether, tetrahydrofuran, 1,4-dioxane and the like; amide solvents such as hexamethylphosphoric amide, dimethylformamide and the like; polar solvents such as acetonitrile, propionitrile, acetone, diethyl ketone, methyl isobutyl ketone, cyclohexanone and the like; halogenated solvents such as dichloromethane, dichloroethane, chlorobenzene, dichlorobenzene and the like, preferably aromatic hydrocarbon solvents such as benzene, toluene and the like; aliphatic hydrocarbon solvents such as hexane, heptane and the like. One or a mixture of two or more of the solvents is used. The amount of a solvent to be used is usually in the range of 1 to 200 parts by weight, preferably 3 to 50 parts by weight relative to 1 part by weight of the substituted cyclopentadiene ligand compound represented by the formula (II).

This reaction can be usually carried out by adding the substituted cyclopentadiene represented by the formula (II) to a solvent and then adding the transition metal compound represented by the formula (III) thereto. Thus the transition metal complex represented by the formula (I) can be obtained.

The reaction temperature is usually in the range of −100° C. to the boiling point of a solvent, preferably −80 to 120° C.

The transition metal complex wherein $X^1$ and $X^2$ are each a substituted amino group is converted to a halide thereof by reacting with a halogen compound such as a chlorosilane compound or a hydrogen chloride. The transition metal complex thus obtained includes the compounds described in the explanation for the formulas (I-1), (I-2), (I-3) and (I-4).

Hereinafter the carbonyl compound of formula (I), which is a starting material for the substituted cyclopentadiene ligand compounds (5), (6), (7) and (8), and a production method thereof are explained.

The carbonyl compound of the formula (I) is produced by reacting the halogen compound of formula (2) and the cyclopentenone of the formula (3) in the presence of a magnesium compound or an organic lithium compound and then treating the resultant cyclopentenol represented by the formula (4) with an acid.

In the halogen compound represented by the formula (2), the substituent X represents a chlorine, bromine or iodine atom, preferably a bromine atom or an iodine atom.

The optionally substituted $C_{1-10}$ alkyl group for the substituents $R^{10}$ and $R^{11}$ includes a methyl group, an ethyl group, a n-propyl group, an isopropyl group, a n-butyl group, a sec-butyl group, a tert-butyl group, a n-pentyl group, a neopentyl group, an amyl group, a n-hexyl group, a n-octyl group, a n-decyl group, a fluoromethyl group, a difluoromethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluorohexyl group, a perfluorooctyl group, a perfluorodecyl group and the like, and preferably a methyl group, an ethyl group, an isopropyl group, a tert-butyl group, an amyl group and the like are exemplified. Alternatively, $R^{10}$ and $R^{11}$ may be linked to each other to form a 5- or 6-membered ring, and preferably an ethylene group and a propylene group are exemplified.

Specific examples of such a halogen compound include 1-chloro-2-(1,3-dioxolan-2-yl)-benzene, 1-chloro-2-(2-methyl-1,3-dioxolan-oxolan-2-yl)-benzene, 1-chloro-2-(2-ethyl-1,3-oxolan-2-yl)-benzene, 1-chloro-2-(2-phenyl-1,3-oxolan-2-yl)-benzene, 1-chloro-2-(dimethoxymethyl)-benzene, 1-chloro-2-(1,1-dimethoxyethyl)-benzene, 1-chloro-2-(1,1-dimethoxy-1-phenylmethyl)-benzene, 1-bromo-2-(1,3-dioxolan-2-yl)-benzene, 1-bromo-2-(2-methyl-1,3-dioxolan-2-yl)-benzene, 1-bromo-2-(2-ethyl-1,3-dioxolan-2-yl)-benzene, 1-bromo-2-(2-phenyl-1,3-dioxolan-2-yl)-benzene, 1-bromo-2-(dimethoxymethyl)-benzene, 1-bromo-2-(1,1-dimethoxyethyl)-benzene, 1-bromo-2-(1,1-dimethoxy-1-phenylmethyl)-benzene, 1-iodo-2-(1,3-dioxolan-2-yl)-benzene, 1-iodo-2-(2-methyl-1,3-dioxolan-2-yl)-benzene, 1-iodo-2-(2-ethyl-1,3-dioxolan-2-yl)-benzene, 1-iodo-2-(2-phenyl-1,3-dioxolan-2-yl)-benzene, 1-iodo-2-(dimethoxymethyl)-benzene, 1-iodo-2-(1,1-dimethoxyethyl)-benzene, 1-iodo-2-(1,1-dimethoxy-1-phenylmethyl)-benzene, 1-chloro-2-(1,3-dioxolan-2-yl)-naphthalene, 1-chloro-2-(2-methyl-1,3-dioxolan-2-yl)-naphthalene, 1-chloro-2-(2-ethyl-1,3-dioxolan-2-yl)-naphthalene, 1-chloro-2-(2-phenyl-1,3-dioxolan-2-yl)-naphthalene, 1-chloro-2-(dimethoxymethyl)-naphthalene, 1-chloro-2-(1,1-dimethoxyethyl)-naphthalene, 1-chloro-2-(1,1-dimethoxy-1-phenylmethyl)-naphthalene, 1-bromo-2-(1,3-dioxolan-2-yl)-naphthalene, 1-bromo-2-(2-methyl-1,3-dioxolan-2-yl)-naphthalene, 1-bromo-2-(2-ethyl-1,3-dioxolan-2-yl)-naphthalene, 1-bromo-2-(2-phenyl-1,3-dioxolan-2-yl)-naphthalene, 1-bromo-2-(dimethoxymethyl)-naphthalene, 1-bromo-2-(1,1-dimethoxyethyl)-naphthalene, 1-bromo-2-(1,1-dimethoxy-1-phenylmethyl)-naphthalene, 1-iodo-2-(1,3-dioxolan-2-yl)-naphthalene, 1-iodo-2-(2-methyl-1,3-dioxolan-2-yl)-naphthalene, 1-iodo-2-(2-ethyl-1,3-dioxolan-2-yl)-naphthalene, 1-iodo-2-(2-phenyl-1,3-dioxolan-2-yl)-naphthalene, 1-iodo-2-(dimethoxymethyl)-naphthalene, 1-iodo-2-(1,1-dimethoxyethyl)-naphthalene, 1-iodo-2-(1,1-dimethoxy-1-phenylmethyl)-naphthalene, 1-chloro-2-(1,3-dioxolan-2-yl)-4-tert-butylbenzene, 1-chloro-2-(2-methyl-1,3-dioxolan-2-yl)-4-tert-butylbenzene, 1-chloro-2-(2-ethyl-1,3-oxolan-2-yl)-4-tert-butylbenzene, 1-chloro-2-(2-phenyl-1,3-dioxolan-2-yl)-4-tert-butylbenzene, 1-chloro-2-(dimethoxymethyl)-4-tert-butylbenzene, 1-chloro-2-(1,1-dimethoxyethyl)-4-tert-butylbenzene, 1-chloro-2-(1,1-dimethoxy-1-phenylmethyl)-4-tert-butylbenzene, 1-bromo-2-(1,3-dioxolan-2-yl)-4-tert-butylbenzene, 1-bromo-2-(2-methyl-1,3-dioxolan-2-yl)-4-tert-butylbenzene, 1-bromo-2-(2-ethyl-1,3-dioxolan-2-yl)-4-tert-butylbenzene, 1-bromo-2-(2-phenyl-1,3-dioxolan-2-yl)-4-tert-butylbenzene, 1-bromo-2-(dimethoxymethyl)-4-tert-butylbenzene, 1-bromo-2-(1,1-dimethoxyethyl)-4-tert-butylbenzene, 1-bromo-2-(1,1-dimethoxy-1-phenylmethyl)-4-tert-butylbenzene, 1-iodo-2-(1,3-dioxolan-2-yl)-4-tert-butylbenzene, 1-iodo-2-(2-methyl-1,3-dioxolan-2-yl)-4-tert-butylbenzene, 1-iodo-2-(2-ethyl-1,3-dioxolan-2-yl)-4-tert-butylbenzene, 1-iodo-2-(2-phenyl-1,3-dioxolan-2-yl)-4-tert-butylbenzene, 1-iodo-2-(dimethoxymethyl)-4-tert-butylbenzene, 1-iodo-2-(1,1-dimethoxyethyl)-4-tert-butylbenzene, 1-iodo-2-(1,1-dimethoxy-1-phenylmethyl)-4-tert-butylbenzene and the like.

The first step of production process of the carbonyl compound of the formula (1) is a step of reacting the halogen compound represented by the formula (2) and the cyclopentenone represented by the formula (3) in the presence of a magnesium compound or an organic lithium compound to give the cyclopentenol represented by the formula (4).

An organic lithium compound used in the above reaction includes methyllithium, ethyllithium, n-butyllithium, sec-butyllithium, tert-butyllithium, phenyllithium and the like. The amount of an organic lithium compound to be used is usually in the range of 0.5 to 3 moles, preferably 0.9 to 2.5 moles relative to 1 mole of the halogen compound represented by the formula (2).

The cyclopentenone represented by the formula (3) includes 2-cyclopentenone, 2-methylcyclopentenone, 3-methylcyclopentenone, 2,3-dimethylcyclopentenone, 2,4-dimethylcyclopentenone, 3,4-dimethylcyclopentenone, 2,3,4-trimethylcyclopentenone, 2,3,5-trimethylcyclopentenone, 2,3,4,5-tetramethylcyclopentenone, 2-tert-butylcyclopentenone, 3-tert-butylcyclopentenone, 4-tert-butylcyclopentenone, 5-tert-butylcyclopentenone, 2-dimethylaminocyclopentenone, 3-dimethylaminocyclopentenone, 4-dimethylaminocyclopentenone, 5-dimethylaminocyclopentenone, 2-methylindanone, 2-phenylindanone, 2-trimethylsilylcyclopentenone, 3-trimethylsilylcyclopentenone, 4-trimethylsilylcyclopentenone, and 5-trimethylsilylcyclopentenone.

The above reaction is usually carried out by reacting the halogen compound represented by the formula (2) with a magnesium compound or an organic lithium compound in the presence of a solvent and then adding the cyclopentenone represented by the formula (3) thereto. The temperature for reacting the halogen compound represented by the formula (2) with a magnesium compound or an organic lithium compound is usually from −80° C. to the boiling point of a solvent. When the halogen compound represented by the formula (2) is reacted with an organic lithium compound, the range of −80 to 40° C. is preferred, and when used magnesium, the range of 10 to 100° C. is preferred.

The reaction temperature for adding the cyclopentenone represented by the formula (3) after the reaction with a magnesium compound or an organic lithium compound is usually in the range of −80° C. to the boiling point of a solvent, preferably −50 to 60° C.

A solvent used in the reaction is inert to the reaction is used. Such a solvent includes, for example, aromatic hydrocarbon solvents such as benzene, toluene, xylene and the like; aliphatic hydrocarbon solvents such as hexane, heptane and the like; ether solvents such as diethyl ether, tetrahydrofuran, 1,4-dioxane and the like; amide solvents such as hexamethylphosphoric triamide, dimethylformamide and the like. One or a mixture of two or more of the solvents is used. The amount of a solvent to be used is usually in the range of 1 to 200 times, preferably 3 to 50 times the weight of the halogen compound represented by the formula (2).

After the reaction, water is added to the resulting reaction mixture, and the mixture is then separated into an organic layer and an aqueous layer to give a solution of the objective compound as the organic layer. When the organic layer and the aqueous layer can not be easily separated due to use of a solvent compatible with water or use of a small amount of a solvent in said reaction, the separation may be carried out after addition of a water-insoluble organic solvent such as toluene, ethyl acetate, chlorobenzene and the like to the reaction mixture. A solution of the cyclopentenols of the formula (4) thus-obtained may be used in the next step as it is, or the cyclopentenols may be purified from said solution and then used in the next step. The cyclopentenols represented by the formula (4) can be purified, for example, by washing said solution with water, drying said solution, and then distilling off the solvent, and further by methods such as recrystallization, distillation, column chromatography treatment and the like.

The cyclopentenols represented by the formula (4) thus-obtained include 1-(1,3-dioxolan-2-yl)-2-(1-hydroxy-2-cyclopentenyl)benzene, 1-(1,3-dioxolan-2-yl)-2-(1-hydroxy-2-methyl-2-cyclopentenyl)benzene, 1-(1,3-dioxolan-2-yl)-

2-(1-hydroxy-3-methyl-2-cyclopentenyl)benzene, 1-(1,3-dioxolan-2-yl)-2-(1-hydroxy-2,3-dimethyl-2-cyclopentenyl)benzene, 1-(1,3-dioxolan-2-yl)-2-(1-hydroxy-2,4-dimethyl-2-cyclopentenyl)benzene, 1-(1,3-dioxolan-2-yl)-2-(1-hydroxy-3,4-dimethyl-2-cyclopentenyl)benzene, 1-(1,3-dioxolan-2-yl)-2-(1-hydroxy-2,3,4-trimethyl-2-cyclopentenyl)benzene, 1-(1,3-dioxolan-2-yl)-2-(2-hydroxy-2,4,5-trimethyl-2-cyclopentenyl)benzene, 1-(1,3-dioxolan-2-yl)-2-(1-hydroxy-2,3,4,5-tetramethyl-2-cyclopentenyl)benzene, 1-(1,3-dioxolan-2-yl)-2-(1-hydroxy-2-tert-butyl-2-cyclopentenyl)benzene, 1-(1,3-dioxolan-2-yl)-2-(1-hydroxy-3-tert-butyl-2-cyclopentenyl)benzene, 1-(1,3-dioxolan-2-yl)-2-(1-hydroxy-2-dimethylamino-2-cyclopentenyl)benzene, 1-(1,3-dioxolan-2-yl)-2-(1-hydroxy-3-dimethylamino-2-cyclopentenyl)benzene, 1-(1,3-dioxolan-2-yl)-2-(1-hydroxy-2-methylindan-1-yl)benzene, 1-(1,3-dioxolan-2-yl)-2-(1-hydroxy-2-phenylindan-1-yl)benzene, 1-(2-methyl-1,3-dioxolan-2-yl)-2-(1-hydroxy-2-cyclopentenyl)benzene, 1-(2-methyl-1,3-dioxolan-2-yl)-2-(1-hydroxy-2-methyl-2-cyclopentenyl)benzene, 1-(2-methyl-1,3-dioxolan-2-yl)-2-(1-hydroxy-3-methyl-2-cyclopentenyl)benzene, 1-(2-methyl-1,3-dioxolan-2-yl)-2-(1-hydroxy-2,3-dimethyl-2-cyclopentenyl)benzene, 1-(2-methyl-1,3-dioxolan-2-yl)-2-(1-hydroxy-2,4-dimethyl-2-cyclopentenyl)benzene, 1-(2-methyl-1,3-dioxolan-2-yl)-2-(1-hydroxy-3,4-dimethyl-2-cyclopentenyl)benzene, 1-(2-methyl-1,3-dioxolan-2-yl)-2-(1-hydroxy-2,3,4-trimethyl-2-cyclopentenyl)benzene, 1-(2-methyl-1,3-dioxolan-2-yl)-2-(2-hydroxy-2,4,5-trimethyl-2-cyclopentenyl)benzene, 1-(2-methyl-1,3-dioxolan-2-yl)-2-(1-hydroxy-2,3,4,5-tetramethyl-2-cyclopentenyl)benzene, 1-(2-methyl-1,3-dioxolan-2-yl)-2-(1-hydroxy-2-tert-butyl-2-cyclopentenyl)benzene, 1-(2-methyl-1,3-dioxolan-2-yl)-2-(1-hydroxy-3-tert-butyl-2-cyclopentenyl)benzene, 1-(2-methyl-1,3-dioxolan-2-yl)-2-(1-hydroxy-2-dimethylamino-2-cyclopentenyl)benzene, 1-(2-methyl-1,3-dioxolan-2-yl)-2-(1-hydroxy-3-dimethylamino-2-cyclopentenyl)benzene, 1-(2-methyl-1,3-dioxolan-2-yl)-2-(1-hydroxy-2-methylindan-1-yl)benzene, 1-(2-methyl-1,3-dioxolan-2-yl)-2-(1-hydroxy-2-phenylindan-1-yl)benzene, 1-(2-ethyl-1,3-dioxolan-2-yl)-2-(1-hydroxy-2-cyclopentenyl)benzene, 1-(2-ethyl-1,3-dioxolan-2-yl)-2-(1-hydroxy-2-methyl-2-cyclopentenyl)benzene, 1-(2-ethyl-1,3-dioxolan-2-yl)-2-(1-hydroxy-3-methyl-2-cyclopentenyl)benzene, 1-(2-ethyl-1,3-dioxolan-2-yl)-2-(1-hydroxy-2,3-dimethyl-2-cyclopentenyl)benzene, 1-(2-ethyl-1,3-dioxolan-2-yl)-2-(1-hydroxy-2,4-dimethyl-2-cyclopentenyl)benzene, 1-(2-ethyl-1,3-dioxolan-2-yl)-2-(1-hydroxy-3,4-dimethyl-2-cyclopentenyl)benzene, 1-(2-ethyl-1,3-dioxolan-2-yl)-2-(1-hydroxy-2,3,4-trimethyl-2-cyclopentenyl)benzene, 1-(2-ethyl-1,3-dioxolan-2-yl)-2-(2-hydroxy-2,4,5-trimethyl-2-cyclopentenyl)benzene, 1-(2-ethyl-1,3-dioxolan-2-yl)-2-(1-hydroxy-2,3,4,5-tetramethyl-2-cyclopentenyl)benzene, 1-(2-ethyl-1,3-dioxolan-2-yl)-2-(1-hydroxy-2-tert-butyl-2-cyclopentenyl)benzene, 1-(2-ethyl-1,3-dioxolan-2-yl)-2-(1-hydroxy-3-tert-butyl-2-cyclopentenyl)benzene, 1-(2-ethyl-1,3-dioxolan-2-yl)-2-(1-hydroxy-2-dimethylamino-2-cyclopentenyl)benzene, 1-(2-ethyl-1,3-dioxolan-2-yl)-2-(1-hydroxy-3-dimethylamino-2-cyclopentenyl)benzene, 1-(2-ethyl-1,3-dioxolan-2-yl)-2-(1-hydroxy-2-methylindan-1-yl)benzene, 1-(2-ethyl-1,3-dioxolan-2-yl)-2-(1-hydroxy-2-phenylindan-1-yl)benzene, 1-(2-phenyl-1,3-dioxolan-2-yl)-2-(1-hydroxy-2-cyclopentenyl)benzene, 1-(2-phenyl-1,3-dioxolan-2-yl)-2-(1-hydroxy-2-methyl-2-cyclopentenyl)benzene, 1-(2-phenyl-1,3-dioxolan-2-yl)-2-(1-hydroxy-3-methyl-2-cyclopentenyl)benzene, 1-(2-phenyl-1,3-dioxolan-2-yl)-2-(1-hydroxy-2,3-dimethyl-2-cyclopentenyl)benzene, 1-(2-phenyl-1,3-dioxolan-2-yl)-2-(1-hydroxy-2,4-dimethyl-2-cyclopentenyl)benzene, 1-(2-phenyl-1,3-dioxolan-2-yl)-2-(1-hydroxy-3,4-dimethyl-2-cyclopentenyl)benzene, 1-(2-phenyl-1,3-dioxolan-2-yl)-2-(1-hydroxy-2,3,4-trimethyl-2-cyclopentenyl)benzene, 1-(2-phenyl-1,3-dioxolan-2-yl)-2-(2-hydroxy-2,4,5-trimethyl-2-cyclopentenyl)benzene, 1-(2-phenyl-1,3-dioxolan-2-yl)-2-(1-hydroxy-2,3,4,5-tetramethyl-2-cyclopentenyl)benzene, 1-(2-phenyl-1,3-dioxolan-2-yl)-2-(1-hydroxy-2-tert-butyl-2-cyclopentenyl)benzene, 1-(2-phenyl-1,3-dioxolan-2-yl)-2-(1-hydroxy-3-tert-butyl-2-cyclopentenyl)benzene, 1-(2-phenyl-1,3-dioxolan-2-yl)-2-(1-hydroxy-2-dimethylamino-2-cyclopentenyl)benzene, 1-(2-phenyl-1,3-dioxolan-2-yl)-2-(1-hydroxy-3-dimethylamino-2-cyclopentenyl)benzene, 1-(2-phenyl-1,3-dioxolan-2-yl)-2-(1-hydroxy-2-methylindan-1-yl)benzene, 1-(2-phenyl-1,3-dioxolan-2-yl)-2-(1-hydroxy-2-phenylindan-1-yl)benzene, 1-(dimethoxymethyl)-2-(1-hydroxy-2-cyclopentenyl)benzene, 1-(dimethoxymethyl)-2-(1-hydroxy-2-methyl-2-cyclopentenyl)benzene, 1-(dimethoxymethyl)-2-(1-hydroxy-3-methyl-2-cyclopentenyl)benzene, 1-(dimethoxymethyl)-2-(1-hydroxy-2,3-dimethyl-2-cyclopentenyl)benzene, 1-(dimethoxymethyl)-2-(1-hydroxy-2,4-dimethyl-2-cyclopentenyl)benzene, 1-(dimethoxymethyl)-2-(1-hydroxy-3,4-dimethyl-2-cyclopentenyl)benzene, 1-(dimethoxymethyl)-2-(1-hydroxy-2,3,4-trimethyl-2-cyclopentenyl)benzene, 1-(dimethoxymethyl)-2-(2-hydroxy-2,4,5-trimethyl-2-cyclopentenyl)benzene, 1-(dimethoxymethyl)-2-(1-hydroxy-2,3,4,5-tetramethyl-2-cyclopentenyl)benzene, 1-(dimethoxymethyl)-2-(1-hydroxy-2-tert-butyl-2-cyclopentenyl)benzene, 1-(dimethoxymethyl)-2-(1-hydroxy-3-tert-butyl-2-cyclopentenyl)benzene, 1-(dimethoxymethyl)-2-(1-hydroxy-2-dimethylamino-2-cyclopentenyl)benzene, 1-(dimethoxymethyl)-2-(1-hydroxy-3-dimethylamino-2-cyclopentenyl)benzene, 1-(dimethoxymethyl)-2-(1-hydroxy-2-methylindan-1-yl)benzene, 1-(dimethoxymethyl)-2-(1-hydroxy-2-phenylindan-1-yl)benzene, 1-(1,1-dimethoxyethyl)-2-(1-hydroxy-2-cyclopentenyl)benzene, 1-(1,1-dimethoxyethyl)-2-(1-hydroxy-2-methyl-2-cyclopentenyl)benzene, 1-(1,1-dimethoxyethyl)-2-(1-hydroxy-3-methyl-2-cyclopentenyl)benzene, 1-(1,1-dimethoxyethyl)-2-(1-hydroxy-2,3-dimethyl-2-cyclopentenyl)benzene, 1-(1,1-dimethoxyethyl)-2-(1-hydroxy-2,4-dimethyl-2-cyclopentenyl)benzene, 1-(1,1-dimethoxyethyl)-2-(1-hydroxy-3,4-dimethyl-2-cyclopentenyl)benzene, 1-(1,1-dimethoxyethyl)-2-(1-hydroxy-2,3,4-trimethyl-2-cyclopentenyl)benzene, 1-(1,1-dimethoxyethyl)-2-(2-hydroxy-2,4,5-trimethyl-2-cyclopentenyl)benzene, 1-(1,1-dimethoxyethyl)-2-(1-hydroxy-2,3,4,5-tetramethyl-2-cyclopentenyl)benzene, 1-(1,1-dimethoxyethyl)-2-(1-hydroxy-2-tert-butyl-2-cyclopentenyl)benzene, 1-(1,1-dimethoxyethyl)-2-(1-hydroxy-3-tert-butyl-2-cyclopentenyl)benzene, 1-(1,1-dimethoxyethyl)-2-(1-hydroxy-2-dimethylamino-2-cyclopentenyl)benzene, 1-(1,1-dimethoxyethyl)-2-(1-hydroxy-3-dimethylamino-2-cyclopentenyl)benzene, 1-(1,1-dimethoxyethyl)-2-(1-hydroxy-2-methylindan-1-yl)benzene, 1-(1,1-dimethoxyethyl)-2-(1-hydroxy-2-phenylindan-1-yl)benzene, 1-(1,1-dimethoxypropyl)-2-(1-hydroxy-2-cyclopentenyl)benzene, 1-(1,1-dimethoxypropyl)-2-(1-hydroxy-2-methyl-2-cyclopentenyl)benzene, 1-(1,1-dimethoxypropyl)-2-(1-hydroxy-3-methyl-2-cyclopentenyl)benzene, 1-(1,1-dimethoxypropyl)-2-(1-hydroxy-2,3-dimethyl-2-cyclopentenyl)benzene, 1-(1,1-dimethoxypropyl)-2-(1-hydroxy-2,4-dimethyl-2-cyclopentenyl)benzene, 1-(1,1-dimethoxypropyl)-2-(1-hydroxy-3,4-dimethyl-2-cyclopentenyl)benzene, 1-(1,1- dimethoxypropyl)-2-(1-hydroxy-2,3,4-trimethyl-2-cyclopentenyl)benzene, 1-(1,1-dimethoxypropyl)-2-(2-hydroxy-2,4,5-trimethyl-2-cyclopentenyl)benzene, 1-(1,1-dimethoxypropyl)-2-(1-hydroxy-2,3,4,5-tetramethyl-2-cyclopentenyl)benzene, 1-(1,1-dimethoxypropyl)-2-(1-hydroxy-2-tert-butyl-2-cyclopentenyl)benzene, 1-(1,1-dimethoxypropyl)-2-(1-hydroxy-3-tert-butyl-2-cyclopentenyl)benzene, 1-(1,1-dimethoxypropyl)-2-(1-hydroxy-2-dimethylamino-2-cyclopentenyl)benzene, 1-(1,1-dimethoxypropyl)-2-(1-hydroxy-3-dimethylamino-2-cyclopentenyl)benzene, 1-(1,1-dimethoxypropyl)-2-(1-hydroxy-2-methylindan-1-yl)benzene, 1-(1,1-dimethoxypropyl)-2-(1-hydroxy-2-phenylindan-1-yl)benzene, 1-(1,1-dimethoxy-1-phenylmethyl)-2-(1-hydroxy-2-cyclopentenyl)benzene, 1-(1,1-dimethoxy-1-phenylmethyl)-2-(1-hydroxy-2-methyl-2-cyclopentenyl)benzene, 1-(1,1-dimethoxy-1-phenylmethyl)-2-(1-hydroxy-3-methyl-2-cyclopentenyl)benzene, 1-(1,1-dimethoxy-1-phenylmethyl)-2-(1-hydroxy-2,3-dimethyl-2-cyclopentenyl)benzene, 1-(1,1-dimethoxy-1-phenylmethyl)-2-(1-hydroxy-2,4-dimethyl-2-cyclopentenyl)benzene, 1-(1,1-dimethoxy-1-phenylmethyl)-2-(1-hydroxy-3,4-dimethyl-2-cyclopentenyl)benzene, 1-(1,1-dimethoxy-1-phenylmethyl)-2-(1-hydroxy-2,3,4-trimethyl-2-cyclopentenyl)benzene, 1-(1,1-dimethoxy-1-phenylmethyl)-2-(2-hydroxy-2,4,5-trimethyl-2-cyclopentenyl)benzene, 1-(1,1-dimethoxy-1-phenylmethyl)-2-(1-hydroxy-2,3,4,5-tetramethyl-2-cyclopentenyl)benzene, 1-(1,1-dimethoxy-1-phenylmethyl)-2-(1-hydroxy-2-tert-butyl-2-cyclopentenyl)benzene, 1-(1,1-dimethoxy-1-phenylmethyl)-2-(1-hydroxy-3-tert-butyl-2-cyclopentenyl)benzene, 1-(1,1-dimethoxy-1-phenylmethyl)-2-(1-hydroxy-2-dimethylamino-2-cyclopentenyl)benzene, 1-(1,1-dimethoxy-1-phenylmethyl)-2-(1-hydroxy-3-dimethylamino-2-cyclopentenyl)benzene, 1-(1,1-dimethoxy-1-phenylmethyl)-2-(1-hydroxy-2-methylindan-1-yl)benzene, 1-(1,1-dimethoxy-1-phenylmethyl)-2-(1-hydroxy-2-phenylindan-1-yl)benzene and the like. Similarly the above-mentioned compounds in which benzene is changed to substituted benzene or substituted naphthalene and the like are also exemplified.

The second step is a step of reacting the cyclopentenols of the formula (4) with an acid to give the carbonyl compound (a substituted cyclopentadiene ligand) represented by the formula (1).

An acid to be used in the above reaction includes inorganic acids such as hydrochloric acid, sulfuric acid, nitric acid, phosphoric acid and the like; carboxylic acids such as formic acid, acetic acid, chloroacetic acid, trifluoroacetic acid, propionic acid, valeric acid, benzoic acid and the like; sulfonic acids such as methanesulfonic acid, trifluoromethanesulfonic acid, benzenesulfonic acid, toluenesulfonic acid and the like. These acids can be used alone or as a mixture or a diluted solution such as an aqueous solution. The amount of an acid to be used is not specifically limited.

The above reaction is usually carried out in the presence of a solvent and produces the carbonyl compound represented by the formula (1) having cyclopentadiene structure by addition of an acid to the cyclopentenol represented by the formula (4). The reaction is carried out in the range of −20° C. to the boiling point of a solvent, preferably 0 to 80° C.

A solvent used in the reaction includes aromatic hydrocarbon solvents such as benzene, toluene, xylene and the like; aliphatic hydrocarbon solvents such as hexane, heptane and the like; ether solvents such as diethyl ether, tetrahydrofuran, 1,4-dioxane and the like; amide solvents such as hexamethylphosphoric triamide, dimethylformamide and the like; alcohol solvents such as methanol, ethanol, propanol, butanol and the like; ketone solvents such as acetone, cyclopentanone, methyl isobutyl ketone and the like; and water. One or a mixture of two or more of these solvents is used. The solvents may be homogeneous system or two-phase system. The amount of a solvent to be used is usually in the range of 1 to 200 parts by weight, preferably 5 to 30 parts by weight relative to the 1 part by weight of the halogen compound represented by the formula (2).

After the reaction, if needed, water is added to the resulting reaction mixture. The mixture is then separated into an organic layer and an aqueous layer to give a solution of the objective compound as the organic layer. When the organic layer and the aqueous layer can not be easily separated due to use of a solvent compatible with water or use of a small amount of a solvent in said reaction, the separation may be carried out after addition of a water-insoluble organic solvent such as toluene, ethyl acetate, chlorobenzene and the like to the reaction mixture. The carbonyl compound represented by the formula (1) is purified, for example, by washing said solution with water, drying said solution, and then distilling off the solvent, and further by methods such as recrystallization, distillation, column chromatography treatment and the like.

In J. Org. Chem., 1974, 39, 829 and Aust. J. Chem., 1993, 46, 1515, 2-(inden-1-yl)benzaldehyde is disclosed. However, said compound is synthesized by oxidation of 3,6-dibenzotricyclo[3,3,0,0]octadiene with chromic acid and as a result, there is a problem of difficulty in obtaining the starting material 3,6-dibenzotricyclo[3,3,0,0]octadiene. In Chem. Ber., 1992, 125, 1461-1469, 2-(2-benzyl-3-phenyl-1H-inden-1-yl)benzaldehyde is described as a by-product in synthesis of a polyindane compound.

Specific examples of the carbonyl compound represented by the formula (1) include the following compounds: 2-(cyclopentadienyl)benzaldehyde, 2-(2-methylcyclopentadienyl)benzaldehyde, 2-(3-methylcyclopentadienyl)benzaldehyde, 2-(2,3-dimethylcyclopentadienyl)benzaldehyde, 2-(2,4-dimethylcyclopentadienyl)benzaldehyde, 2-(3,4-dimethylcyclopentadienyl)benzaldehyde, 2-(2,3,4-trimethylcyclopentadienyl)benzaldehyde, 2-(2,4,5-trimethylcyclopentadienyl)benzaldehyde, 2-(2,3,4,5-tetramethylcyclopentadienyl)benzaldehyde, 2-(2-tert-butylcyclopentadienyl)benzaldehyde, 2-(3-tert-butylcyclopentadienyl)benzaldehyde, 2-(2-dimethylaminocyclopentadienyl)benzaldehyde, 2-(3-dimethylaminocyclopentadienyl)benzaldehyde, 2-(cyclopentadienyl)acetophenone, 2-(2-methylcyclopentadienyl)acetophenone, 2-(3-methylcyclopentadienyl)acetophenone, 2-(2,3-dimethylcyclopentadienyl)acetophenone, 2-(2,4-dimethylcyclopentadienyl)acetophenone, 2-(3,4-dimethylcyclopentadienyl)acetophenone, 2-(2,3,4-trimethylcyclopentadienyl)acetophenone, 2-(2,4,5-trimethylcyclopentadienyl)acetophenone, 2-(2,3,4,5-tetramethylcyclopentadienyl)acetophenone, 2-(2-tert-butylcyclopentadienyl)acetophenone, 2-(3-tert-butylcyclopentadienyl)acetophenone, 2-(2-dimethylaminocyclopentadienyl)acetophenone, 2-(3-dimethylaminocyclopentadienyl)acetophenone, 2-(cyclopentadienyl)propiophenone, 2-(2-methylcyclopentadienyl)propiophenone, 2-(3-methylcyclopentadienyl)propiophenone, 2-(2,3-dimethylcyclopentadienyl)propiophenone, 2-(2,4-dimethylcyclopentadienyl)propiophenone, 2-(3,4-dimethylcyclopentadienyl)propiophenone, 2-(2,3,4-trimethylcyclopentadienyl)propiophenone, 2-(2,4,5-trimethylcyclopentadienyl)propiophenone, 2-(2,3,4,5-tetramethylcyclopentadienyl)propiophenone, 2-(2-tert-butylcyclopentadienyl)propiophenone, 2-(3-tertbutylcyclopentadienyl)propiophenone, 2-(2-dimethylaminocyclopentadienyl)propiophenone, 2-(3-dimethylaminocyclopentadienyl)propiophenone, 2-(cyclopentadienyl)benzophenone, 2-(2-methylcyclopentadienyl)benzophenone, 2-(3-methylcyclopentadienyl)benzophenone, 2-(2,3-dimethylcyclopentadienyl)benzophenone, 2-(2,4-dimethylcyclopentadienyl)benzophenone, 2-(3,4-dimethylcyclopentadienyl)benzophenone, 2-(2,3,4-trimethylcyclopentadienyl)benzophenone, 2-(2,4,5-trimethylcyclopentadienyl)benzophenone, 2-(2,3,4,5-tetramethylcyclopentadienyl)benzophenone, 2-(2-tert-butylcyclopentadienyl)benzophenone, 2-(3-tert-butylcyclopentadienyl)benzophenone, 2-(2-dimethylaminocyclopentadienyl)benzophenone, 2-(3-dimethylaminocyclopentadienyl)benzophenone, 3-(cyclopentadienyl)-2-naphtaldehyde, 3-(2-methylcyclopentadienyl)-2-naphtaldehyde, 3-(3-methylcyclopentadienyl)-2-naphtaldehyde, 3-(2,3-dimethylcyclopentadienyl)-2-naphtaldehyde, 3-(2,4-dimethylcyclopentadienyl)-2-naphtaldehyde, 3-(3,4-dimethylcyclopentadienyl)-2-naphtaldehyde, 3-(2,3,4-trimethylcyclopentadienyl)-2-naphtaldehyde, 3-(2,4,5-trimethylcyclopentadienyl)-2-naphtaldehyde, 3-(2,3,4,5-tetramethylcyclopentadienyl)-2-naphtaldehyde, 3-(2-tert-butylcyclopentadienyl)-2-naphtaldehyde, 3-(3-tert-butylcyclopentadienyl)-2-naphtaldehyde, 3-(2-dimethylaminocyclopentadienyl)-2-naphtaldehyde, 3-(3-dimethylaminocyclopentadienyl)-2-naphtaldehyde, 3-(cyclopentadienyl)-2-acetylnaphthalene, 3-(2-methylcyclopentadienyl)-2-acetylnaphthalene, 3-(3-methylcyclopentadienyl)-2-acetylnaphthalene, 3-(2,3-dimethylcyclopentadienyl)-2-acetylnaphthalene, 3-(2,4-dimethylcyclopentadienyl)-2-acetylnaphthalene, 3-(3,4-dimethylcyclopentadienyl)-2-acetylnaphthalene, 3-(2,3,4-trimethylcyclopentadienyl)-2-acetylnaphthalene, 3-(2,4,5-trimethylcyclopentadienyl)-2-acetylnaphthalene, 3-(2,3,4,5-tetramethylcyclopentadienyl)-2-acetylnaphthalene, 3-(2-tert-butylcyclopentadienyl)-2-acetylnaphthalene, 3-(3-tert-butylcyclopentadienyl)-2-acetylnaphthalene, 3-(2-dimethylaminocyclopentadienyl)-2-acetylnaphthalene, 3-(3-dimethylaminocyclopentadienyl)-2-acetylnaphthalene, 3-(cyclopentadienyl)-2-propionylnaphthalene, 3-(2-methylcyclopentadienyl)-2-propionylnaphthalene, 3-(3-methylcyclopentadienyl)-2-propionylnaphthalene, 3-(2,3-dimethylcyclopentadienyl)-2-propionylnaphthalene, 3-(2,4-dimethylcyclopentadienyl)-2-propionylnaphthalene, 3-(3,4-dimethylcyclopentadienyl)-2-propionylnaphthalene, 3-(2,3,4-trimethylcyclopentadienyl)-2-propionylnaphthalene, 3-(2,4,5-trimethylcyclopentadienyl)-2-propionylnaphthalene, 3-(2,3,4,5-tetramethylcyclopentadienyl)-2-propionylnaphthalene, 3-(2-tert-butylcyclopentadienyl)-2-propionylnaphthalene, 3-(3-tert-butylcyclopentadienyl)-2-propionylnaphthalene, 3-(2-dimethylaminocyclopentadienyl)-2-propionylnaphthalene, 3-(3-dimethylaminocyclopentadienyl)-2-propionylnaphthalene, 3-(cyclopentadienyl)-2-benzoylnaphthalene, 3-(2-methylcyclopentadienyl)-2-benzoylnaphthalene, 3-(3-methylcyclopentadienyl)-2-benzoylnaphthalene, 3-(2,3-dimethylcyclopentadienyl)-2-benzoylnaphthalene, 3-(2,4-dimethylcyclopentadienyl)-2-benzoylnaphthalene, 3-(3,4-dimethylcyclopentadienyl)-2-benzoylnaphthalene, 3-(2,3,4-trimethylcyclopentadienyl)-2-benzoylnaphthalene, 3-(2,4,5-trimethylcyclopentadienyl)-2-benzoylnaphthalene, 3-(2,3,4,5-tetramethylcyclopentadienyl)-2-benzoylnaphthalene, 3-(2-tert-butylcyclopentadienyl)-2-benzoylnaphthalene, 3-(3-tert-butylcyclopentadienyl)-2-benzoylnaphthalene, 3-(2-dimethylaminocyclopentadienyl)-2-benzoylnaphthalene, 3-(3-dimethylaminocyclopentadienyl)-2-benzoylnaphthalene, 2-(cyclopentadienyl)-1-naphthaldehyde, 2-(2-methylcyclopentadienyl)-1-naphthaldehyde, 2-(3-methylcyclopentadienyl)-1-naphthaldehyde, 2-(2,3-dimethylcyclopentadienyl)-1-naphthaldehyde, 2-(2,4-dimethylcyclopentadienyl)-1-naphthaldehyde, 2-(3,4-dimethylcyclopentadienyl)-1-naphthaldehyde, 2-(2,3,4-trimethylcyclopentadienyl)-1-naphthaldehyde, 2-(2,4,5-trimethylcyclopentadienyl)-1-naphthaldehyde, 2-(2,3,4,5-tetramethylcyclopentadienyl)-1-naphthaldehyde, 2-(2-tert-butylcyclopentadienyl)-1-naphthaldehyde, 2-(3-tert-butylcyclopentadienyl)-1-naphthaldehyde, 2-(2-dimethylaminocyclopentadienyl)-1-naphthaldehyde, 2-(3-dimethylaminocyclopentadienyl)-1-naphthaldehyde, 2-(cyclopentadienyl)-1-acetylnaphthalene, 2-(2-methylcyclopentadienyl)-1-acetylnaphthalene, 2-(3-methylcyclopentadienyl)-1-acetylnaphthalene, 2-(2,3-dimethylcyclopentadienyl)-1-acetylnaphthalene, 2-(2,4-dimethylcyclopentadienyl)-1-acetylnaphthalene, 2-(3,4-dimethylcyclopentadienyl)-1-acetylnaphthalene, 2-(2,3,4-trimethylcyclopentadienyl)-1-acetylnaphthalene, 2-(2,4,5-trimethylcyclopentadienyl)-1-acetylnaphthalene, 2-(2,3,4,5-tetramethylcyclopentadienyl)-1-acetylnaphthalene, 2-(2-tert-butylcyclopentadienyl)-1-acetylnaphthalene, 2-(3-tert-butylcyclopentadienyl)-1-acetylnaphthalene, 2-(2-dimethylaminocyclopentadienyl)-1-acetylnaphthalene, 2-(3-dimethylaminocyclopentadienyl)-1-acetylnaphthalene, 2-(cyclopentadienyl)-1-propionylnaphthalene, 2-(2-methylcyclopentadienyl)-1-propionylnaphthalene, 2-(3-methylcyclopentadienyl)-1-propionylnaphthalene, 2-(2,3-dimethylcyclopentadienyl)-1-propionylnaphthalene, 2-(2,4-dimethylcyclopentadienyl)-1-propionylnaphthalene, 2-(3,4-dimethylcyclopentadienyl)-1-propionylnaphthalene, 2-(2,3,4-trimethylcyclopentadienyl)-1-propionylnaphthalene, 2-(2,4,5-trimethylcyclopentadienyl)-1-propionylnaphthalene, 2-(2,3,4,5-tetramethylcyclopentadienyl)-1-propionylnaphthalene, 2-(2-tert-butylcyclopentadienyl)-1-propionylnaphthalene, 2-(3-tert-butylcyclopentadienyl)-1-propionylnaphthalene, 2-(2-dimethylaminocyclopentadienyl)-1-propionylnaphthalene, 2-(3-dimethylaminocyclopentadienyl)-1-propionylnaphthalene, 2-(cyclopentadienyl)-1-benzoylnaphthalene, 2-(2-methylcyclopentadienyl)-1-benzoylnaphthalene, 2-(3-methylcyclopentadienyl)-1-benzoylnaphthalene, 2-(2,3-dimethylcyclopentadienyl)-1-benzoylnaphthalene, 2-(2,4-dimethylcyclopentadienyl)-1-benzoylnaphthalene, 2-(3,4-dimethylcyclopentadienyl)-1-benzoylnaphthalene, 2-(2,3,4-trimethylcyclopentadienyl)-1-benzoylnaphthalene, 2-(2,4,5-trimethylcyclopentadienyl)-1-benzoylnaphthalene, 2-(2,3,4,5-tetramethylcyclopentadienyl)-1-benzoylnaphthalene, 2-(2-tert-butylcyclopentadienyl)-1-benzoylnaphthalene, 2-(3-tert-butylcyclopentadienyl)-1-benzoylnaphthalene, 2-(2-dimethylaminocyclopentadienyl)-1-benzoylnaphthalene, 2-(3-dimethylaminocyclopentadienyl)-1-benzoylnaphthalene, 2-(cyclopentadienyl)-5-tert-butylbenzaldehyde, 2-(2-methylcyclopentadienyl)-5-tert-butylbenzaldehyde, 2-(3-methylcyclopentadienyl)-5-tert-butylbenzaldehyde, 2-(2,3-dimethylcyclopentadienyl)-5-tert-butylbenzaldehyde, 2-(2,4-dimethylcyclopentadienyl)-5-tert-butylbenzaldehyde, 2-(3,4-dimethylcyclopentadienyl)-5-tert-butylbenzaldehyde, 2-(2,3,4-trimethylcyclopentadienyl)-5-tert-butylbenzaldehyde, 2-(2,4,5-trimethylcyclopentadienyl)-5-tert-butylbenzaldehyde, 2-(2,3,4,5-tetramethylcyclopentadienyl)-5-tert-butylbenzaldehyde, 2-(2-tert-butylcyclopentadienyl)-5-tert-butylbenzaldehyde, 2-(3-tert-butylcyclopentadienyl)-5-tert-butylbenzaldehyde, 2-(2-dimethylaminocyclopentadienyl)-5-tert-butylbenzaldehyde, 2-(3-dimethylaminocyclopentadienyl)-5-tert-butylbenzaldehyde, 2-(cyclopentadienyl)-5-tert-butylacetophenone, 2-(2-methylcyclopentadienyl)-5-tert-butylacetophenone, 2-(3-methylcyclopentadienyl)-5-tert-butylacetophenone, 2-(2,3-dimethylcyclopentadienyl)-5-tert-butylacetophenone, 2-(2,4-dimethylcyclopentadienyl)-5-tert-butylacetophenone, 2-(3,4-dimethylcyclopentadienyl)-5-tert-butylacetophenone, 2-(2,3,4-trimethylcyclopentadienyl)-5-tert-butylacetophenone, 2-(2,4,5-trimethylcyclopentadienyl)-5-tert-butylacetophenone, 2-(2,3,4,5-tetramethylcyclopentadienyl)-5-tert-butylacetophenone, 2-(2-tert-butylcyclopentadienyl)-5-tert-butylacetophenone, 2-(3-tert-butylcyclopentadienyl)-5-tert-butylacetophenone, 2-(2-dimethylaminocyclopentadienyl)-5-tert-butylacetophenone, 2-(3-dimethylaminocyclopentadienyl)-5-tert-butylacetophenone, 2-(cyclopentadienyl)-5-tert-butylpropiophenone, 2-(2-methylcyclopentadienyl)-5-tert-butylpropiophenone, 2-(3-methylcyclopentadienyl)-5-tert-butylpropiophenone, 2-(2,3-dimethylcyclopentadienyl)-5-tert-butylpropiophenone, 2-(2,4-dimethylcyclopentadienyl)-5-tert-butylpropiophenone, 2-(3,4-dimethylcyclopentadienyl)-5-tert-butylpropiophenone, 2-(2,3,4-trimethylcyclopentadienyl)-5-tert-butylpropiophenone, 2-(2,4,5-trimethylcyclopentadienyl)-5-tert-butylpropiophenone, 2-(2,3,4,5-tetramethylcyclopentadienyl)-5-tert-butylpropiophenone, 2-(2-tert-butylcyclopentadienyl)-5-tert-butylpropiophenone, 2-(3-tert-butylcyclopentadienyl)-5-tert-butylpropiophenone, 2-(2-dimethylaminocyclopentadienyl)-5-tert-butylpropiophenone, 2-(3-dimethylaminocyclopentadienyl)-5-tert-butylpropiophenone, 2-(cyclopentadienyl)-5-tert-butylbenzophenone, 2-(2-methylcyclopentadienyl)-5-tert-butylbenzophenone, 2-(3-methylcyclopentadienyl)-5-tert-butylbenzophenone, 2-(2,3-dimethylcyclopentadienyl)-5-tert-butylbenzophenone, 2-(2,4-dimethylcyclopentadienyl)-5-tert-butylbenzophenone, 2-(3,4-dimethylcyclopentadienyl)-5-tert-butylbenzophenone, 2-(2,3,4-trimethylcyclopentadienyl)-5-tert-butylbenzophenone, 2-(2,4,5-trimethylcyclopentadienyl)-5-tert-butylbenzophenone, 2-(2,3,4,5-tetramethylcyclopentadienyl)-5-tert-butylbenzophenone, 2-(2-tert-butylcyclopentadienyl)-5-tert-butylbenzophenone, 2-(3-tert-butylcyclopentadienyl)-5-tert-butylbenzophenone, 2-(2-dimethylaminocyclopentadienyl)-5-tert-butylbenzophenone, 2-(3-dimethylaminocyclopentadienyl)-5-tert-butylbenzophenone, 2-(cyclopentadienyl)-5-chlorobenzaldehyde, 2-(2-methylcyclopentadienyl)-5-chlorobenzaldehyde, 2-(3-methylcyclopentadienyl)-5-chlorobenzaldehyde, 2-(2,3-dimethylcyclopentadienyl)-5-chlorobenzaldehyde, 2-(2,4-dimethylcyclopentadienyl)-5-chlorobenzaldehyde, 2-(3,4-dimethylcyclopentadienyl)-5-chlorobenzaldehyde, 2-(2,3,4-trimethylcyclopentadienyl)-5-chlorobenzaldehyde, 2-(2,4,5-trimethylcyclopentadienyl)-5-chlorobenzaldehyde, 2-(2,3,4,5-tetramethylcyclopentadienyl)-5-chlorobenzaldehyde, 2-(2-tert-butylcyclopentadienyl)-5-chlorobenzaldehyde, 2-(3-tert-butylcyclopentadienyl)-5-chlorobenzaldehyde, 2-(2-dimethylaminocyclopentadienyl)-5-chlorobenzaldehyde, 2-(3-dimethylaminocyclopentadienyl)-5-chlorobenzaldehyde, 2-(cyclopentadienyl)-5-chloroacetophenone, 2-(2-methylcyclopentadienyl)-5-chloroacetophenone, 2-(3-methylcyclopentadienyl)-5-chloroacetophenone, 2-(2,3-dimethylcyclopentadienyl)-5-chloroacetophenone, 2-(2,4-dimethylcyclopentadienyl)-5-chloroacetophenone, 2-(3,4-dimethylcyclopentadienyl)-5-chloroacetophenone, 2-(2,3,4-trimethylcyclopentadienyl-5-chloroacetophenone, 2-(2,4,5-trimethylcyclopentadienyl)-5-chloroacetophenone, 2-(2,3,4,5-tetramethylcyclopentadienyl)-5-chloroacetophenone, 2-(2-tert-butylcyclopentadienyl)-5-chloroacetophenone, 2-(3-tert-butylcyclopentadienyl)-5-chloroacetophenone, 2-(2-dimethylaminocyclopentadienyl)-5-chloroacetophenone, 2-(3-dimethylaminocyclopentadienyl)-5-chloroacetophenone, 2-(cyclopentadienyl)-5-chloropropiophenone, 2-(2-methylcyclopentadienyl)-5-chloropropiophenone, 2-(3-methylcyclopentadienyl)-5-chloropropiophenone, 2-(2,3-dimethylcyclopentadienyl)-5-chloropropiophenone, 2-(2,4-dimethylcyclopentadienyl)-5-chloropropiophenone, 2-(3,4-dimethylcyclopentadienyl)-5-chloropropiophenone, 2-(2,3,4-trimethylcyclopentadienyl-5-chloropropiophenone, 2-(2,4,5-trimethylcyclopentadienyl)-5-chloropropiophenone, 2-(2,3,4,5-tetramethylcyclopentadienyl)-5-chloropropiophenone, 2-(2-tert-butylcyclopentadienyl)-5-chloropropiophenone, 2-(3-tert-butylcyclopentadienyl)-5-chloropropiophenone, 2-(2-dimethylaminocyclopentadienyl)-5-chloropropiophenone, 2-(3-dimethylaminocyclopentadienyl)-5-chloropropiophenone, 2-(cyclopentadienyl)-5-chlorobenzophenone, 2-(2-methylcyclopentadienyl)-5-chlorobenzophenone, 2-(3-methylcyclopentadienyl)-5-chlorobenzophenone, 2-(2,3-dimethylcyclopentadienyl)-5-chlorobenzophenone, 2-(2,4-dimethylcyclopentadienyl)-5-chlorobenzophenone, 2-(3,4-dimethylcyclopentadienyl)-5-chlorobenzophenone, 2-(2,3,4-trimethylcyclopentadienyl)-5-chlorobenzophenone, 2-(2,4,5-trimethylcyclopentadienyl)-5-chlorobenzophenone, 2-(2,3,4,5-tetramethylcyclopentadienyl)-5-chlorobenzophenone, 2-(2-tert-butylcyclopentadienyl)-5-chlorobenzophenone, 2-(3-tert-butylcyclopentadienyl)-5-chlorobenzophenone, 2-(2-dimethylaminocyclopentadienyl)-5-chlorobenzophenone, 2-(3-dimethylaminocyclopentadienyl)-5-chlorobenzophenone, 2-(cyclopentadienyl)-5-methoxybenzaldehyde, 2-(2-methylcyclopentadienyl)-5-methoxybenzaldehyde, 2-(3-methylcyclopentadienyl)-5-methoxybenzaldehyde, 2-(2,3-dimethylcyclopentadienyl)-5-methoxybenzaldehyde, 2-(2,4-dimethylcyclopentadienyl)-5-methoxybenzaldehyde, 2-(3,4-dimethylcyclopentadienyl)-5-methoxybenzaldehyde, 2-(2,3,4-trimethylcyclopentadienyl)-5-methoxybenzaldehyde, 2-(2,4,5-trimethylcyclopentadienyl)-5-methoxybenzaldehyde, 2-(2,3,4,5-tetramethylcyclopentadienyl)-5-methoxybenzaldehyde, 2-(2-tert-butylcyclopentadienyl)-5-methoxybenzaldehyde, 2-(3-tert-butylcyclopentadienyl)-5-methoxybenzaldehyde, 2-(2-dimethylaminocyclopentadienyl)-5-methoxybenzaldehyde, 2-(3-dimethylaminocyclopentadienyl)-5-methoxybenzaldehyde, 2-(cyclopentadienyl)-5-methoxyacetophenone, 2-(2-methylcyclopentadienyl)-5-methoxyacetophenone, 2-(3-methylcyclopentadienyl)-5-methoxyacetophenone, 2-(2,3-dimethylcyclopentadienyl)-5-methoxyacetophenone, 2-(2,4-dimethylcyclopentadienyl)-5-methoxyacetophenone, 2-(3,4-dimethylcyclopentadienyl)-5-methoxyacetophenone, 2-(2,3,4-trimethylcyclopentadienyl)-5-methoxyacetophenone, 2-(2,4,5-trimethylcyclopentadienyl)-5-methoxyacetophenone, 2-(2,3,4,5-tetramethylcyclopentadienyl)-5-methoxyacetophenone, 2-(2-tert-butylcyclopentadienyl)-5-methoxyacetophenone, 2-(3-tert-butylcyclopentadienyl)-5-methoxyacetophenone, 2-(2-dimethylaminocyclopentadienyl)-5-methoxyacetophenone, 2-(3-dimethylaminocyclopentadienyl)-5-methoxyacetophenone, 2-(cyclopentadienyl)-5-methoxypropiophenone, 2-(2-methylcyclopentadienyl)-5-methoxypropiophenone, 2-(3-methylcyclopentadienyl)-5-methoxypropiophenone, 2-(2,3-dimethylcyclopentadienyl)-5-methoxypropiophenone, 2-(2,4-dimethylcyclopentadienyl)-5-methoxypropiophenone, 2-(3,4-dimethylcyclopentadienyl)-5-methoxypropiophenone, 2-(2,3,4-trimethylcyclopentadienyl)-5-methoxypropiophenone, 2-(2,4,5-trimethylcyclopentadienyl)-5-methoxypropiophenone, 2-(2,3,4,5-tetramethylcyclopentadienyl)-5-methoxypropiophenone, 2-(2-tert-butylcyclopentadienyl)-5-methoxypropiophenone, 2-(3-tert-butylcyclopentadienyl)-5-methoxypropiophenone, 2-(2-dimethylaminocyclopentadienyl)-5-methoxypropiophenone, 2-(3-dimethylaminocyclopentadienyl)-5-methoxypropiophenone, 2-(cyclopentadienyl)-5-methoxybenzophenone, 2-(2-methylcyclopentadienyl)-5-methoxybenzophenone, 2-(3-methylcyclopentadienyl)-5-methoxybenzophenone, 2-(2,3-dimethylcyclopentadienyl)-5-methoxybenzophenone, 2-(2,4-dimethylcyclopentadienyl)-5-methoxybenzophenone, 2-(3,4-dimethylcyclopentadienyl)-5-methoxybenzophenone, 2-(2,3,4-trimethylcyclopentadienyl)-5-methoxybenzophenone, 2-(2,4,5-trimethylcyclopentadienyl)-5-methoxybenzophenone, 2-(2,3,4,5-tetramethylcyclopentadienyl)-5-methoxybenzophenone, 2-(2-tert-butylcyclopentadienyl)-5-methoxybenzophenone, 2-(3-tert-butylcyclopentadienyl)-5-methoxybenzophenone, 2-(2-dimethylaminocyclopentadienyl)-5-methoxybenzophenone, 2-(3-dimethylaminocyclopentadienyl)-5-methoxybenzophenone, 2-(cyclopentadienyl)-5-methoxybenzophenone, 2-(methylcyclopentadienyl)-5-methoxybenzophenone, 2-(dimethylcyclopentadienyl)-5-methoxybenzophenone, 2-(trimethylcyclopentadienyl)-5-methoxybenzophenone, 2-(tetramethylcyclopentadienyl)-5-methoxybenzophenone, 2-(tert-butylcyclopentadienyl)-5-methoxybenzophenone, 2-(dimethylaminocyclopentadienyl)-5-methoxybenzophenone and the like.

EXAMPLES

The following Examples illustrate the present invention specifically, but not limit the present invention.

In the Tables 1 to 5, the following abbreviations are used.

TIBA: triisobutylaluminum

MMAO: modified methyl aluminoxane (methyl aluminoxane modified by addition of triisobutylaluminum)

AB: dimethylanilinium tetrakis(pentafluorophenyl)borate

CB: triphenylmethyl tetrakis(pentafluorophenyl)borate

PE: polyethylene

Tm: the melting point of a polymer

Example 1

Synthesis of 1-(2-methyl-1,3-dioxolan-2-yl)-2-(1-hydroxy-2,3,4,5-tetramethyl-2-cyclopentenyl)benzene Under a nitrogen atmosphere, a solution of 2-(2-methyl-1,3-dioxolan-2-yl)-bromobenzene (1.22 g, 5.0 mmol) in tetrahydrofuran (7.3 g) was cooled to −10° C. and a solution of n-butyllithium in n-hexane (1.56 M, 3.4 mL) was added dropwise thereto. After keeping the temperature for 1 hr, a solution of 2,3,4,5-tetramethylcyclopentenone (0.73 g, 5.3 mmol) in tetrahydrofuran (4.9 g) was added dropwise to the mixture. After raising the temperature to 25° C., the mixture was stirred for 3 hrs. After quenching the reaction by addition of toluene and water, the aqueous layer was removed. The obtained organic layer was washed with saturated brine and then dried over sodium sulfate, and the solvent was removed. After concentration, the residue was washed with cooled hexane to give 1-(2-methyl-1,3-dioxolan-2-yl)-2-(1-hydroxy-2,3,4,5-tetramethyl-2-cyclopentenyl)benzene (0.53 g, yield 35.0%).

$^1$H-NMR (CDCl$_3$): δ 7.65 (1H), 7.15 (3H), 5.83 (1H), 4.08 (1H), 3.89 (2H), 2.34 (1H), 1.95 (3H), 1.82 (1H), 1.68 (3H), 1.36 (3H), 1.09 (3H), 1.03 (3H);

MS (EI) m/z 284 (M-H$_2$O), 269, 239, 222, 207, 192, 178, 165.

Example 2

Synthesis of 2-(2,3,4,5-tetramethylcyclopentadienyl)-acetophenone

Under a nitrogen atmosphere, a solution of 2-(2-methyl-1,3-dioxolan-2-yl)-bromobenzene (24.31 g, 100.0 mmol) in diethyl ether (146 g) was cooled to −70° C. and a solution of n-butyllithium in n-hexane (1.56 M, 67.3 mL) was added dropwise thereto. After keeping the temperature for 1 hr, a solution of 2,3,4,5-tetramethylcyclopentenone (14.51 g, 5.3 mmol) in diethyl ether (97 g) was added dropwise to the mixture. After raising the temperature to 25° C., the mixture was stirred for 3 hrs. After quenching the reaction by addition of toluene and water, the aqueous layer was removed. The obtained organic layer was washed with saturated brine and then dried over sodium sulfate. The solvent was removed to give a crude product of 1-(2-methyl-1,3-dioxolan-2-yl)-2-(1-hydroxy-2,3,4,5-tetramethyl-2-cyclopentenyl)benzene. To the obtained crude product were added tetrahydrofuran (320 g), 3% aqueous hydrochloric acid solution (80 g) and acetone (32 g) and the mixture was stirred at 25° C. for 24 hrs. After the reaction, toluene was added to the reaction mixture. The organic layer was washed with water and saturated brine and dried over sodium sulfate, and the solvent was removed. The residue was purified by silica gel column chromatography to give 2-(2,3,4,5-tetramethylcyclopentadienyl)acetophenone (10.00 g, yield 41.6%).

$^1$H-NMR (CDCl$_3$): δ 7.51 (1H), 7.43 (1H), 7.28 (1H), 7.15 (1H), 3.08-2.57 (1H), 2.26 (3H), 1.92 (3H), 1.85 (3H), 1.81-1.63 (3H), 1.11 (3H);

MS (EI) m/z 284 (M$^+$), 269, 239, 222, 207, 192, 178, 165.

Example 3

Synthesis of 2-(2,3,4,5-tetramethylcyclopentadienyl)-benzaldehyde

Under a nitrogen atmosphere, a solution of 2-(1,3-dioxolan-2-yl)-bromobenzene (34.36 g, 150.0 mmol) in diethyl ether (206 g) was cooled to −70° C. and a solution of n-butyllithium in n-hexane (1.56 M, 100.96 mL) was added dropwise thereto. After keeping the temperature for 1 hr, a solution of 2,3,4,5-tetramethylcyclopentenone (21.77 g, 157.5 mmol) in diethyl ether (137 g) was added dropwise to the mixture. After raising the temperature to 25° C., the mixture was stirred for 3 hrs. After quenching the reaction by addition of toluene and water, the aqueous layer was removed. The obtained organic layer was washed with saturated brine and then dried over sodium sulfate. The solvent was removed to give a crude product of 1-(1,3-dioxolan-2-yl)-2-(1-hydroxy-2,3,4,5-tetramethyl-2-cyclopentenyl)benzene. To the obtained crude product were added tetrahydrofuran (770 g), 3% aqueous hydrochloric acid solution (385.2 g) and acetone (77 g) and the mixture was stirred at 25° C. for 24 hrs. After the reaction, toluene was added the reaction mixture. The organic layer was washed with water and saturated brine and then dried over sodium sulfate, and the solvent was removed.

The residue was purified by silica gel column chromatography to give 2-(2,3,4,5-tetramethylcyclopentadienyl)benzaldehyde (15.78 g, yield 46.5%).

$^1$H-NMR (CDCl$_3$): δ 9.91 (1H), 7.97 (1H), 7.56 (1H), 7-37 (1H), 7.22 (1H), 3.22-2.75 (1H), 1.94 (3H), 1.87 (3H), 1.74 (3H), 0.95 (3H);

MS (EI) m/z 226 (M$^+$), 221, 193, 178, 165.

Example 4

Synthesis of 2-(2,3,4,5-tetramethylcyclopentadienyl)benzylalcohol

To a solution of 2-(2,3,4,5-tetramethylcyclopentadienyl)benzaldehyde (2.26 g, 10.0 mmol) in ethanol (29.0 mL) was added sodium borohydride (0.42 g, 11.0 mmol) at room temperature and the mixture was stirred for 3 hrs. To the reaction mixture solution were added toluene (20.0 mL) and deionized water (20.0 mL) to separate an organic layer and an aqueous layer. The organic layer was dried over sodium sulfate and the solvent was then distilled off to give 2-(2,3,4,5-tetramethylcyclopentadienyl)benzylalcohol (2.23 g, yield 96.0%) as a pale oily substance.

$^1$H-NMR (CDCl$_3$): δ 7.47-6.82 (4H), 4.48 (2H), 3.05-2.70 (1H), 2.35 (1H), 1.97 (3H), 1.85 (3H), 1.68 (3H), 1.22-0.91 (3H);

MS (EI) m/z 228 (M$^+$), 213, 195, 180, 165, 128, 115.

Example 5

Synthesis of {2-(2,3,4,5-tetramethylcyclopentadienyl)phenyl}phenylmethylalcohol

To a solution of 2-(2,3,4,5-tetramethylcyclopentadienyl)benzaldehyde (2.0 g, 8.80 mmol) in tetrahydrofuran (34.0 mL) was added dropwise a 1.05 M solution of phenyllithium in cyclohexane and ether (17.7 mL) at −78° C. The temperature of the mixture was raised to room temperature and the mixture was stirred for 4 hrs. To the reaction mixture solution were added deionized water (20.0 mL) and toluene (20.0 mL) to separate an organic layer and an aqueous layer. The organic layer was dried over sodium sulfate, then distilled to remove the solvent, and purified by a silica gel column (hexane/ethyl acetate=9/1) to give {2-(2,3,4,5-tetramethylcyclopentadienyl)phenyl}phenylmethylalcohol (2.83 g, yield 87.0%) as a pale yellow oily substance. $^1$H-NMR (CDCl$_3$): δ 7.77-6.91 (4H), 6.45-5.55 (2H), 3.21-2.25 (1H), 1.88-1.45 (9H), 1.16-0.82 (3H);

MS (EI) m/z 304 (M$^+$), 286, 271, 256, 193, 165, 77.

Example 6

Synthesis of 2-(2,3,4,5-tetramethylcyclopentadienyl)benzyloxytitanium bis(dimethylamide) [Complex 1]

To a solution of 2-(2,3,4,5-tetramethylcyclopentadienyl)benzylalcohol (0.3 g, 1.3 mmol) in toluene (5.2 mL) was added dropwise a solution of tetrakis(dimethylamido)titanium (0.29 g, 1.3 mmol) in toluene (1.7 mL) at −30° C. The mixture was stirred for 30 min at room temperature and then at 110° C. for 5 hrs. The solvent was distilled off to give 2-(2,3,4,5-tetramethylcyclopentadienyl)benzyloxytitanium bis(dimethylamide) (0.30 g, yield 83.3%).

$^1$H-NMR (C$_6$D$_6$): δ 7.25-6.88 (4H), 5.46 (2H), 3.16 (12H), 1.97 (6H), 1.86 (6H).

Example 7

Synthesis of 2-(2,3,4,5-tetramethylcyclopentadienyl)benzyloxytitanium dichloride [Complex 2]

To a solution of 2-(2,3,4,5-tetramethylcyclopentadienyl)benzyloxytitanium bis(dimethylamide) (0.84 g, 3.1 mmol) in pentane (15.2 mL) was added dropwise a solution of trimethylchlorosilane (3.67 g, 33.8 mmol) in pentane (5.0 mL) at 0° C. The mixture was stirred at room temperature for 15 hrs. 2-(2,3,4,5-Tetramethylcyclopentadienyl)benzyloxytitanium dichloride (1.00 g, yield 94.3%) was obtained as an yellow solid.

$^1$H-NMR (C$_6$D$_6$): δ 7.06-6.64 (4H), 5.12 (2H), 2.16 (6H), 1.63 (6H).

Example 8

An autoclave was charged with toluene (5.0 mL) under nitrogen and the temperature was stabilized at 70° C. It was then charged with ethylene until it was pressurized to 0.60 MPa, and the pressure was stabilized. Thereto MMAO (100 μl, 1.0 M, Kanto Kagaku) and 2-(2,3,4,5-tetramethylcyclopentadienyl)benzyloxytitanium bis(dimethylamide) (0.25 μmol) were added and polymerization was carried out for 30 min. As a result of polymerization, a polymer having the molecular weight (Mw) of 2,360,000 and the molecular weight distribution (Mw/Mn) of 3.7 was produced in an amount of 7.36×10$^4$ g per 1 mol of titanium and per an hour.

Example 9

Polymerization was carried out in a similar manner as in Example 8, except that absolution of triisobutylaluminum in hexane (100 μL, 1.0 M, Kanto Kagaku) was used instead of MMAO and triphenylcarbenium tetrakispentafluorophenylborate (0.75 μmol) was used. As a result of polymerization, a polymer having the molecular weight (Mw) of 737,000 and the molecular weight distribution (Mw/Mn) of 2.6 was produced in an amount of 6.56×10$^4$ g per 1 mol of titanium and per an hour.

Example 10

Polymerization was carried out in a similar manner as in Example 8, except that 2-(2,3,4,5-tetramethylcyclopentadienyl)benzyloxytitanium dichloride was used as a catalyst component. As a result of polymerization, a polymer having the molecular weight (Mw) of 143,000 and the molecular weight distribution (Mw/Mn) of 1.6 was produced in an amount of 1.65×10$^5$ g per 1 mol of titanium and per an hour.

Example 11

Polymerization was carried out in a similar manner as in Example 8 except that 2-(2,3,4,5-tetramethylcyclopentadienyl)benzyloxytitanium dichloride was used as a catalyst component, a solution of triisobutylaluminum in hexane (100 μL, 1.0 M, Kanto Kagaku) was used instead of MMAO and triphenylcarbenium tetrakispentafluorophenylborate (0.75 μmol) was used. As a result of polymerization, a polymer having the molecular weight (Mw) of 786,000 and the molecular weight distribution (Mw/Mn) of 2.7 was produced in an amount of 2.69×10$^5$ g per 1 mol of titanium and per an hour.

Example 12

Polymerization was carried out in a similar manner as in Example 8, except that 2-(2,3,4,5-tetramethylcyclopentadienyl)benzyloxytitanium dichloride was used as a catalyst component, a solution of triisobutylaluminum in hexane (100 μL, 1.0 M, Kanto Kagaku) was used instead of MMAO and dimethylanilinium tetrakispentafluorophenylborate (0.75 μmol) was used. As a result of polymerization, a: polymer having the molecular weight (Mw) of 674,000 and the molecular weight distribution (Mw/Mn) of 2.4 was produced in an amount of 2.38×10$^5$ g per 1 mol of titanium and per an hour.

Example 13

Synthesis of N-[2-(2,3,4,5-tetramethylcyclopentadienyl)phenylmethylene]-N-phenylamine Under a nitrogen atmosphere, aniline (31.5 mmol) was added dropwise to a solution of 2-(2,3,4,5-tetramethylcyclopentadienyl)benzaldehyde (30.0 mmol) in ethanol (90.0 mL) and the mixture was stirred at room temperature. After disappearance of the aldehyde was confirmed by gas chromatography, the solvent was distilled off under reduced pressure to give N-[2-(2,3,4,5-tetramethylcyclopentadienyl)phenylmethylene]-N-phenylamine (9.00 g, yield 100%).

$^1$H-NMR (C$_6$D$_6$): δ 8.75-8.65 (1H), 7.42-6.96 (9H), 3.01-2.50 (1H), 1.73-0.76 (12H).

MS (EI) m/z 301, 286, 270, 254, 195, 145.

Example 14

Synthesis of N-[2-(2,3,4,5-tetramethylcyclopentadienyl)phenylmethyl]-N-phenylamine To a solution of N-[2-(2,3,4,5-tetramethylcyclopentadienyl)phenylmethylene]-N-phenylamine (3.0 mmol) in ethanol (9.0 ml) was added sodium borohydride (4.5 mmol) and the mixture was reacted at room temperature for 3 hrs. Water and toluene were then added to the mixture. The organic layer was dried and concentrated. The obtained oily substance was purified by silica gel column chromatography to give N-[2-(2,3,4,5-tetramethylcyclopentadienyl)phenylmethyl]-N-phenylamine (0.60 g, yield 66.0%) as a yellow oily substance.

$^1$H-NMR (CDCl$_3$): δ 7.42-7.36 (1H), 7.22-7.08 (5H), 6.73-6.68 (1H), 6.50-6.44 (2H), 4.06-4.01 (2H), 3.52-3.45 (1H), 3.01-2.53 (1H), 1.79-1.58 (9H), 0.96-0.86 (3H);

MS (EI) m/z 303, 286, 210, 195.

Example 15

Synthesis of N-[2-(2,3,4,5-tetramethylcyclopentadienyl)phenylmethyl]-N-phenylamido titanium bis(dimethylamide) Complex 3

To a solution N-[2-(2,3,4,5-tetramethylcyclopentadienyl)phenylmethyl]-N-phenylamine (1.0 mmol) in toluene (5.3 mL) was added dropwise a solution of tetrakis(dimethylamino)titanium (1.0 mmol) in toluene (1.9 mL) at −78° C. Thereafter, the mixture was stirred at room temperature for 1 hr and then at 100° C. for 5 hrs to give a red solution. The solvent was distilled off under reduced pressure to give N-[2-(2,3,4,5-tetramethylcyclopentadienyl)phenylmethyl]-N-phenylamido titanium bis(dimethylamide) (0.30 g, yield 100%) as a red solid.

$^1$H-NMR (C$_6$D$_6$): δ 7.24-6.83 (9H), 4.44 (2H), 3.00 (12H), 1.94 (6H), 1.71 (6H).

Example 16

Synthesis of N-[2-(2,3,4,5-tetramethylcyclopentadienyl)phenylmethyl]-N-phenylamido titanium dichloride [Complex 4]

To a solution of N-[2-(2,3,4,5-tetramethylcyclopentadienyl)phenylmethyl]-N-phenylamido titanium bis(dimethylamide) (5.0 mmol) in toluene (32.0 mL) was added a solution of trimethylsilyl chloride (55.0 mmol) in toluene (24.0 mL) at 0° C. and the mixture was then stirred at room temperature for 16 hrs. The solvent was distilled off under reduced pressure and hexane (25.0 mL) was added to the residue. A precipitated solid was filtered to give N-[2-(2,3,4,5-tetramethylcyclopentadienyl)phenylmethyl]-N-phenylamido titanium dichloride (2.18 g, yield 100%) as an orange solid. $^1$H-NMR (C$_6$D$_6$): δ 7.46-7.43 (2H), 7.20-6.85 (7H), 4.64 (2H), 2.07 (6H), 1.83 (6H).

Example 17

Synthesis of N-[2-(2,3,4,5-tetramethylcyclopentadienyl)phenylmethyl]-N-phenylamido zirconium bis(dimethylamide) [Complex 5]

To a solution of N-[2-(2,3,4,5-tetramethylcyclopentadienyl)phenylmethyl]-N-phenylamine (3.0 mmol) in toluene (15.0 mL) was added dropwise a solution of tetrakis(dimethylamino)zirconium (3.0 mmol) in toluene (10.0 mL) at −78° C. Thereafter, the mixture was stirred at room temperature for 1 hr and then at 100° C. for hrs to give a yellow solution. The solvent was distilled off under reduced pressure to give N-[2-(2,3,4,5-tetramethylcyclopentadienyl)phenylmethyl]-N-phenylamido zirconium bis(dimethylamide) (1.43 g, yield 100%) as a brown solid.

$^1$H-NMR (C$_6$D$_6$): δ 7.43-6.77 (9H), 4.26 (2H), 2.89 (12H), 1.95 (6H), 1.71 (6H).

Example 18

Synthesis of N-[2-(2,3,4,5-tetramethylcyclopentadienyl)phenylmethyl]-N-phenylamido zirconium dichloride [Complex 6]

To a solution of N-[2-(2,3,4,5-tetramethylcyclopentadienyl)phenylmethyl]-N-phenylamido zirconium bis(dimethylamide) (3.0 mmol) in hexane (24.0 mL) was added a solution of trimethylsilyl chloride (33.0 mmol) in hexane (6.0 mL) at 0° C. and the mixture was then stirred at room temperature for 16 hrs. A precipitated solid was filtered to give N-[2-(2,3,4,5-tetramethylcyclopentadienyl)phenylmethyl]-N-phenylamido zirconium dichloride (0.59 g, 47.0%) as a yellowish green powder.

$^1$H-NMR (C$_6$D$_6$): δ 7.48-7.44 (2H), 7.22-6.94 (7H), 4.64 (2H), 2.02 (6H), 1.79 (6H).

<<Homopolymerization of Ethylene>>

Example 19

An autoclave was charged with toluene (5.0 mL) under nitrogen and the temperature was stabilized at 70° C. It was then charged with ethylene until it was pressurized to 0.60 MPa, and the pressure was stabilized. Thereto MMAO (250 μmol, 5.8 wt % Al, Tosoh-Akzo Corporation) and N-[2-(2,3,4,5-tetramethylcyclopentadienyl)phenylmethyl]-N-phenylamido titanium dichloride (0.25 μmol) were added and polymerization was carried out for 30 min. As a result of polymerization, a polymer having the molecular weight (Mw) of 1,030,000 and the molecular weight distribution (Mw/Mn) of 2.1 was produced in an amount of $5.85 \times 10^5$ g per 1 mol of titanium and per an hour.

Example 20

An autoclave was charged with toluene (5.0 mL) under nitrogen and the temperature was stabilized at 70° C. It was then charged with ethylene until it was pressurized to 0.60 MPa, and the pressure was stabilized. Thereto a solution of triisobutylaluminum in hexane (100 μL, 1.0 M, Kanto Kagaku), N-[2-(2,3,4,5-tetramethylcyclopentadienyl)phenylmethyl]-N-phenylamido titanium dichloride (0.25 μmol) and triphenylcarbenium tetrakispentafluorophenylborate (0.75 μmol) were added and polymerization was carried out for 24 min. As a result of polymerization, a polymer having the molecular weight (Mw) of 1,070,000 and the molecular weight distribution (Mw/Mn) of 1.9 was produced in an amount of $1.70 \times 10^6$ g per 1 mol of titanium and per an hour.

Example 21

Polymerization was carried out in a similar manner as in Example 20, except that dimethylanilinium tetrakispentafluorophenylborate was used instead of triphenylcarbenium tetrakispentafluorophenylborate and that the polymerization period was changed from 24 min to 21 min. As a result of polymerization, a polymer having the molecular weight (Mw) of 1,040,000 and the molecular weight distribution (Mw/Mn) of 2.3 was produced in an amount of $1.91 \times 10^6$ g per 1 mol of titanium and per an hour.

Example 22

Polymerization was carried out in a similar manner as in Example 21, except that trispentafluorophenylborane was used instead of triphenylcarbenium tetrakispentafluorophenylborate and that the polymerization period was changed from 24 min to 30 min. As a result of polymerization, a polymer having the molecular weight (Mw) of 172,000 and the molecular weight distribution (Mw/Mn) of 2.1 was produced in an amount of $5.60 \times 10^4$ g per 1 mol of titanium and per an hour.

Example 23

Polymerization was carried out in a similar manner as in Example 19, except that N-[2-(2,3,4,5-tetramethylcyclopentadienyl)phenylmethyl]-N-phenylamido titanium bis(dimethylamide) was used instead of N-[2-(2,3,4,5-tetramethylcyclopentadienyl)phenylmethyl]-N-phenylamido titanium dichloride. As a result of polymerization, a polymer having the molecular weight (Mw) of 803,000 and the molecular weight distribution (Mw/Mn) of 1.8 was produced in an amount of $7.52 \times 10^4$ g per 1 mol of titanium and per an hour.

Example 24

Polymerization was carried out in a similar manner as in Example 20, except that N-[2-(2,3,4,5-tetramethylcyclopentadienyl)phenylmethyl]-N-phenylamido titanium bis(dimethylamide) was used instead of N-[2-(2,3,4,5-tetramethylcyclopentadienyl)phenylmethyl]-N-phenylamido titanium dichloride and the stirring period was changed from 24 min to 30 min. As a result of polymerization, a polymer having the molecular weight (Mw) of 766,000 and the molecular weight distribution (Mw/Mn) of 1.7 was produced in an amount of $4.48 \times 10^5$ g per 1 mol of titanium and per an hour.

Example 25

Polymerization was carried out in a similar manner as in Example 19, except that N-[2-(2,3,4,5-tetramethylcyclopentadienyl)phenylmethyl]-N-phenylamido zirconium bis(dimethylamide) was used instead of N-[2-(2,3,4,5-tetramethylcyclopentadienyl)phenylmethyl]-N-phenylamido titanium dichloride. As a result of polymerization, a polymer having the molecular weight (Mw) of 916,000 and the molecular weight distribution (Mw/Mn) of 37.1 was produced in an amount of $5.52 \times 10^4$ g per 1 mol of titanium and per an hour.

Example 26

Polymerization was carried out in a similar manner as in Example 19, except that N-[2-(2,3,4,5-tetramethylcyclopentadienyl)phenylmethyl]-N-phenylamido zirconium dichloride was used instead of N-[2-(2,3,4,5-tetramethylcyclopentadienyl)phenylmethyl]-N-phenylamido titanium dichloride. As a result of polymerization, a polymer having the molecular weight (Mw) of 78,700 and the molecular weight distribution (Mw/Mn) of 5.8 was produced in an amount of $4.51 \times 10^5$ g per 1 mol of titanium and per an hour.

Example 27

Polymerization was carried out in a similar manner as in Example 24, except that N-[2-(2,3,4,5-tetramethylcyclopentadienyl)phenylmethyl]-N-phenylamido zirconium dichloride was used instead of N-[2-(2,3,4,5-tetramethylcyclopentadienyl)phenylmethyl]-N-phenylamido titanium dichloride. As a result of polymerization, a polymer having the molecular weight (Mw) of 9,190 and the molecular weight distribution (Mw/Mn) of 2.3 was produced in an amount of $8.38 \times 10^5$ g per 1 mol of titanium and per an hour.

Example 28

Polymerization was carried out in a similar manner as in Example 21, except that N-[2-(2,3,4,5-tetramethylcyclopentadienyl)phenylmethyl]-N-phenylamido zirconium dichloride was used instead of N-[2-(2,3,4,5-tetramethylcyclopentadienyl)phenylmethyl]-N-phenylamidotitanium dichloride and that the stirring period was changed from 21 min to 30 min. As a result of polymerization, a polymer having the molecular weight (Mw) of 10,600 and the molecular weight distribution (Mw/Mn) of 3.3 was produced per 6.44×10 μg per 1 mol of titanium and per an hour.

<<Copolymerization of Ethylene-Hexene>>

Example 29

An autoclave was charged with toluene (5.0 mL) and hexene (5.00 μL) under nitrogen and the temperature was stabilized at 70° C. It was then charged with ethylene until it was pressurized to 0.60 MPa, and the pressure was stabilized. Thereto a solution of triisobutylaluminum in hexane (100 μL, 1.0 M, Kanto Kagaku), N-[2-(2,3,4,5-tetramethylcyclopentadienyl)phenylmethyl]-N-phenylamido titanium dichloride (0.25 μmol) and triphenylcarbenium tetrakispentafluorophenylborate (0.75 μmol) were added and polymerization was carried out for 30 min. As a result of polymerization, a polymer having the molecular weight (Mw) of 873,000 and the molecular weight distribution (Mw/Mn) of 2.5 was produced in an amount of $1.06 \times 10^6$ g per 1 mol of titanium and per an hour.

Example 30

Polymerization was carried out in a similar manner as in Example 29, except that dimethylanilinium tetrakispentafluorophenylborate was used instead of triphenylcarbenium tetrakispentafluorophenylborate. As a result of polymerization, a polymer having the molecular weight (Mw) of 492,000 and the molecular weight distribution (Mw/Mn) of 5.3 was produced in an amount of $1.07 \times 10^6$ g per 1 mol of titanium and per an hour.

Example 31

Synthesis of 2-(2,3,4,5-tetramethylcyclopentadienyl) benzaldehyde phenylhydrazone Under a nitrogen atmosphere, to a solution of 2-(2,3,4,5-tetramethylcyclopentadienyl)benzaldehyde (20.0 mmol) in ethanol (60.0 mL) was added dropwise phenylhydrazine (22.0 mmol) and the mixture was stirred at room temperature for 2-hrs. The solvent was distilled off under reduced pressure and the residue was recrystallized from hexane to give 2-(2,3,4,5-tetramethylcyclopentadienyl)benzaldehyde phenylhydrazone (4.8 g, yield 76.3%).

$^1$H-NMR ($C_6D_6$): δ 8.13-8.08 (1H), 7.62-7.53 (2H), 7.30-7.23 (4H), 7.10-7.06 (3H), 6.86-6.82 (1H), 3.13-2.73 (1H), 1.93-1.88 (5H), 1.71-1.58 (4H), 1.20-0.91 (3H).

Example 32

Synthesis of Complex 7

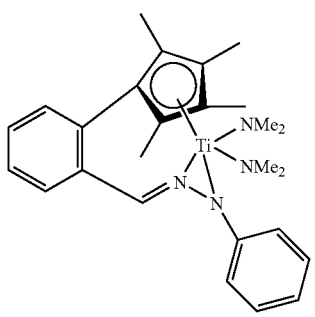

Complex 7

To a solution of 2-(2,3,4,5-tetramethylcyclopentadienyl) benzaldehyde phenylhydrazone (1.0 mmol) in toluene (5.3 mL) was added dropwise a solution of tetrakis(dimethylamino)titanium (1.0 mmol) in toluene (1.9 mL) at −78° C. The mixture was stirred at room temperature for 1 hr and then at 100° C. for 0.5 hrs to give a red solution. The solvent was distilled off under reduced pressure to give Complex 7 as a red solid (2.23 g, yield 100%).

$^1$H-NMR ($C_6D_6$): δ 8.55 (1H), 7.31-6.88 (9H), 3.18 (12H), 2.09 (6H), 1.50 (6H).

Example 33

Synthesis of Complex 8

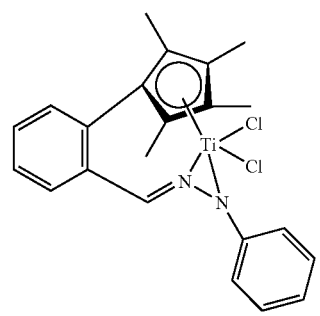

Complex 8

To a solution of Complex 7 (5.0 mmol) in toluene (32.0 mL) was added dropwise a solution of trimethylsilyl-chloride (55.0 mmol) in toluene (24.0 mL) at 0° C. and the mixture was then stirred at room temperature for 16 hrs. The solvent was distilled off under reduced pressure and hexane (25.0 mL) was added to the residue. A precipitated solid was filtered to give Complex 8 as an orange solid (2.20 g, 99.5%).

$^1$H-NMR ($C_6D_6$): δ 8.05 (1H), 7.63-7.61 (2H), 7.13-6.84 (7H), 2.11 (6H), 1.59 (6H).

Example 34

Synthesis of Complex 9

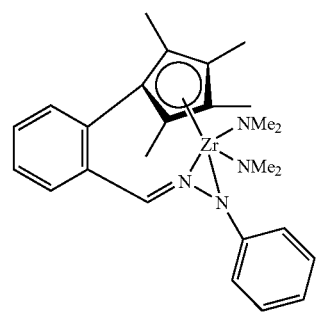

Complex 9

To a solution of 2-(2,3,4,5-tetramethylcyclopentadienyl) benzaldehyde phenylhydrazone (3.0 mmol) in toluene (15.0 mL) was added dropwise a solution of tetrakis(dimethylamino)zirconium (3.0 mmol) in toluene (10.0 mL) at −78° C. and the mixture was stirred at room temperature for 1 hr and then at 100° C. for 5 hrs to give a yellow solution. The solvent was distilled off under reduced pressure to give Complex 9 as a brown solid (1.47 g, yield 100%).

$^1$H-NMR (C$_6$D$_6$): δ 8.15 (1H), 7.28-6.90 (9H), 3.00 (12H), 2.09 (6H), 1.79 (6H).

Example 35

Synthesis of Complex 10

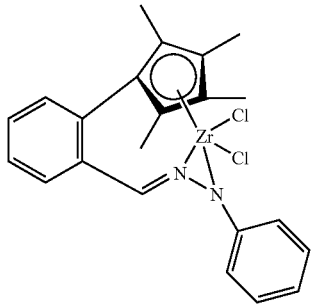

Complex 10

To a solution of Complex 9 (3.0 mmol) in hexane (24.0 mL) was added dropwise a solution of trimethylsilyl chloride (33.0 mmol) in hexane (6.0 mL) at 0° C. and the mixture was then stirred at room temperature for 20 hrs. A precipitated solid was filtered to give Complex 10 as a yellowish green powder (0.83 g, yield 58.1%).

$^1$H-NMR (C$_6$D$_6$): δ 7.94 (1H), 7.44-7.42 (2H), 7.16-6.86 (7H), 2.10 (6H), 1.64 (6H).

Polymerization

Example 36

An autoclave was charged with toluene (5.0 mL) under nitrogen and the temperature was stabilized at 70° C. It was then charged with ethylene until it was pressurized to 0.60 MPa, and the pressure was stabilized. Thereto MMAO (250 μmol, 5.8 wt % Al, Tosoh-Akzo Corporation) and Complex 2 (0.25 μmol) were added and polymerization was carried out for 30 min. As a result of polymerization, a polymer having the molecular weight (Mw) of 453,000 and the molecular weight distribution (Mw/Mn) of 2.1 was produced in an amount of 1.07×10$^6$ g per 1 mol of titanium and per an hour.

Example 37

An autoclave was charged with toluene (5.0 mL) under nitrogen and the temperature was stabilized at 70° C. It was then charged with ethylene until it was pressurized to 0.60 MPa, and the pressure was stabilized. Thereto a solution of triisobutylaluminum in hexane (100 μL, 1.0 M, Kanto Kagaku), Complex 2 (0.25 μmol) and triphenylcarbenium tetrakispentafluorophenylborate (0.75 μmol) were added and polymerization was carried out for 30 min. As a result of polymerization, a polymer having the molecular weight (Mw) of 658,000 and the molecular weight distribution (Mw/Mn) of 2.2 was produced in an amount of 1.11×10$^6$ g per 1 mol of titanium and per an hour.

Example 38

Polymerization was carried out in a similar manner as in Example 37, except that dimethylanilinium tetrakispentafluorophenylborate was used instead of triphenylcarbenium tetrakispentafluorophenylborate. As a result of polymerization, a polymer having the molecular weight (Mw) of 611,000 and the molecular weight distribution (Mw/Mn) of 2.2 was produced in an amount of 1.07×10$^6$ g per 1 mol of titanium and per an hour.

Example 39

Polymerization was carried out in a similar manner as in Example 36, except that Complex 1 was used instead of Complex 2. As a result of polymerization, a polymer having the molecular weight (Mw) of 416,000 and the molecular weight distribution (Mw/Mn) of 2.1 was produced in an amount of 2.42×10$^5$ g per 1 mol of titanium and per an hour.

Example 40

Polymerization was carried out in a similar manner as in Example 37, except that Complex 4 was used instead of Complex 2. As a result of polymerization, a polymer having the molecular weight (Mw) of 587,000 and the molecular weight distribution (Mw/Mn) of 13.0 was produced in an amount of 5.26×10$^5$ g per 1 mol of titanium and per an hour.

Example 41

Polymerization was carried out in a similar manner as in Example 38, except that Complex 4 was used instead of Complex 2. As a result of polymerization, a polymer having the molecular weight (Mw) of 94,000 and the molecular weight distribution (Mw/Mn) of 17.3 was produced in an amount of 4.91×10$^5$ g per 1 mol of titanium and per an hour.

Example 42

Synthesis of 2-(2,3,4,5-tetramethylcyclopentadienyl)-α-phenyl-benzenemethanimine To a solution of 2-(2,3,4,5-tetramethylcyclopentadienyl) benzaldehyde (8.86 g, 39.2 mmol) in tetrahydrofuran (150.0 mL) were added methoxyamine hydrochloride (4.25 g, 50.9 mmol), sodium acetate (4.18 g, 50.9 mmol) and water, and the mixture was stirred at room temperature for 2 hrs.

To the reaction mixture solution were added ethyl acetate (20.0 mL) and water (20.0 mL) to separate an organic layer and an aqueous layer. The organic layer was dried over sodium sulfate and the solvent was then distilled off to give O-methyl-2-(2,3,4,5-tetramethylcyclopentadienyl)benzaldehyde oxime (8.85 g, yield 88.5%) as a yellow oily substance.

To a solution of the obtained O-methyl-2-(2,3,4,5-tetramethylcyclopentadienyl)benzaldehyde oxime (4.00 g, 15.7 mmol) in tetrahydrofuran (68.0 mL) was added dropwise a 1.5 M solution of phenyllithium in cyclohexane/ether (60.0 mL) at −78° C. The temperature of the mixture was raised to room temperature and the mixture was stirred for 5 hrs.

To the reaction mixture solution were added toluene (30.0 mL) and water (30.0 mL) to separate an organic layer and an aqueous layer. The organic layer was dried over sodium sulfate and the solvent was then distilled off to give 2-(2,3,4,5-tetramethylcyclopentadienyl)-α-phenyl-benzenemethanimine (4.40 g, yield 93.2%) as a brown oily substance.

$^1$H-NMR (CDCl$_3$): δ 9.53 (1H), 7.59-7.47 (9H), 2.83-2.12 (1H), 1.72 (3H), 1.65 (3H), 1.59 (3H), 0.99-0.64 (3H);

MS (EI) m/z 301 (M$^+$), 286, 270, 256, 165, 77.

Example 43

Synthesis of 2-(2,3,4,5-tetramethylcyclopentadienyl)-α-tert-butyl-benzenemethanimine According to a similar manner as in Example 42, O-methyl-2-(2,3,4,5-tetramethylcyclopentadienyl)benzaldehyde oxime was synthesized. To a solution of O-methyl-2-(2,3,4,5-tetramethylcyclopentadienyl)benzaldehyde oxime (1.28 g, 5.0 mmol) in tetrahydrofuran (68.0 mL) was added dropwise a 1.02 M solution of tert-butyllithium in ether (60.0 mL) at −78° C. The temperature of the mixture was raised to room temperature and the mixture was stirred for 5 hrs.

To the reaction mixture solution were added toluene (30.0 mL) and deionized water (30.0 mL) to separate an organic layer and an aqueous layer. The organic layer was dried over sodium sulfate and the solvent was then distilled off to give 2-(2,3,4,5-tetramethylcyclopentadienyl)-α-tert-butyl-benzenemethanimine (1.34 g, yield 95.0%).

$^1$H-NMR (CDCl$_3$): δ 9.53 (1H), 7.36-7.02 (4H), 3.00-2.58 (1H), 1.85-1.83 (3H), 1.70 (3H), 1.67 (3H), 1.10 (9H), 0.83-0.80 (3H); MS (EI) m/z 281 (M$^+$), 266, 252, 208, 194, 165.

Example 44

Synthesis of 2-(2,3,4,5-tetramethylcyclopentadienyl)-α-phenyl-benzenemethanimidotitanium bis(dimethylamide) [Complex 11]

To a solution of 2-(2,3,4,5-tetramethylcyclopentadienyl)-α-phenyl-benzenemethanimine (0.45 g, 1.5 mmol) in toluene was added dropwise a solution of tetrakis(dimethylamido)titanium (0.34 g, 1.5 mmol) in toluene (10.5 mL) at −30° C. The mixture was stirred at room temperature for 30 min and then at 110° C. for 5 hrs. the solvent was then distilled off to give 2-(2,3,4,5-tetramethylcyclopentadienyl)-α-phenyl-benzenemethanimidotitanium bis(dimethylamide) (0.50 g, yield 76.9%).

$^1$H-NMR (C$_6$D$_6$): δ 7.88-6.98 (9H), 3.12 (6H), 3.10 (6H), 2.01 (6H), 1.92 (6H).

Example 45

Synthesis of 2-(2,3,4,5-tetramethylcyclopentadienyl)-α-phenyl-benzenemethanimidotitanium dichloride [Complex 12]

To a solution of 2-(2,3,4,5-tetramethylcyclopentadienyl)-α-phenyl-benzenemethanimidotitanium bis(dimethylamide) (0.65 g, 1.5 mmol) in hexane (15.9 mL) was added dropwise a solution of trimethylchlorosilane (1.63 g, 15.0 mmol) in hexane (3.9 mL) at 0° C. and the mixture was stirred at room temperature for 15 hrs. A precipitate was formed and then filtered to give 2-(2,3,4,5-tetramethylcyclopentadienyl)-α-phenyl-benzenemethanimidotitanium dichloride (0.50 g, yield 79.4%). $^1$H-NMR (C$_6$D$_6$): δ 7.64-6.86 (9H), 2.18 (6H), 1.72 (6H).

Example 46

Synthesis of 2-(2,3,4,5-tetramethylcyclopentadienyl)-α-phenyl-benzenemethanimidozirconium bis(dimethylamide) [Complex 13]

To a solution of 2-(2,3,4,5-tetramethylcyclopentadienyl)-α-phenyl-benzenemethanimine (1.50 g, 5.3 mmol) in toluene (13.9 mL) was added dropwise a solution of tetrakis(dimethylamido)zirconium (1.43 g, 5.3 mmol) in toluene (3.5 mL) at −30° C. The mixture was stirred at room temperature for 30 min and then at 110° C. for 5 hrs. The solvent was then distilled off to give 2-(2,3,4,5-tetramethylcyclopentadienyl)-α-phenyl-benzenemethanimidozirconium bis(dimethylamide) (2.31 g, yield 91.3%).

$^1$H-NMR (C$_6$D$_6$): δ 7.96-6.98 (9H), 2.92 (12H), 2.01 (6H), 1.91 (6H).

Example 47

Synthesis of 2-(2,3,4,5-tetramethylcyclopentadienyl)-α-tert-butyl-benzenemethanimidotitanium bis(dimethylamide) [Complex 14]

To a solution of 2-(2,3,4,5-tetramethylcyclopentadienyl)-α-tert-butyl-benzenemethanimine (1.00 g, 3.5 mmol) in toluene (9.2 mL) was added dropwise a solution of tetrakis(dimethylamido)titanium (0.80 g, 3.5 mmol) in toluene (2.3 mL) at −30° C. The mixture was stirred at room temperature for 30 min and then at 110° C. for 5 hrs. The solvent was then distilled off to give 2-(2,3,4,5-tetramethylcyclopentadienyl)-α-tert-butyl-benzenemethanimidotitanium bis(dimethylamide) (1.21 g, 81.8%).

$^1$H-NMR (C$_6$D$_6$): δ 7.77-6.92 (4H), 3.11 (12H), 2.04 (6H), 1.84 (6H), 1.45 (9H).

Example 48

Synthesis of 2-(2,3,4,5-tetramethylcyclopentadienyl)-α-tert-butyl-benzenemethanimidotitanium dichloride [Complex 15]

To a solution of 2-(2,3,4,5-tetramethylcyclopentadienyl)-α-tert-butyl-benzenemethanimidotitanium bis(dimethylamide) (0.83 g, 2.0 mmol) in pentane (10.6 mL) was added dropwise a solution of trimethylchlorosilane (2.39 g, 22.0 mmol) in pentane (2.7 mL) at 0° C., and the mixture was stirred at room temperature for 15 hrs. A precipitate was formed and then filtered to give 2-(2,3,4,5-tetramethylcyclopentadienyl)-α-tert-butyl-benzenemethanimidotitanium dichloride (0.51 g, yield 63.8%). $^1$H-NMR (C$_6$D$_6$): δ 7.56-6.88 (4H), 2.18 (6H), 1.62 (6H), 1.23 (9H).

Example 49

Synthesis of 2-(2,3,4,5-tetramethylcyclopentadienyl)-α-tert-butylbenzenemethanimidozirconium bis(dimethylamide) [Complex 16]

To a solution of 2-(2,3,4,5-tetramethylcyclopentadienyl)-α-tert-butyl-benzenemethanimine (2.37 g, 8.4 mmol) in toluene (21.9 mL) was added dropwise a solution of tetrakis(dimethylamido)zirconium (2.25 g, 8.4 mmol) in toluene (5.5 mL) at −30° C. The mixture was stirred at room temperature for 30 min and then at 110° C. for 5 hrs. The solvent was then distilled off to give 2-(2,3,4,5-tetramethylcyclopentadienyl)-α-tert-butyl-benzenemethanimidozirconium bis(dimethylamide) (3.12 g, yield 80.8%).

$^1$H-NMR (C$_6$D$_6$): δ 7.84-6.92 (4H), 2.91 (12H), 2.02 (6H), 1.88 (6H), 1.47 (9H).

Example 50

Synthesis of 2-(2,3,4,5-tetramethylcyclopentadienyl)-α-tert-butyl-benzenemethanimidozirconium dichloride [Complex 17]

To a solution of 2-(2,3,4,5-tetramethylcyclopentadienyl)-α-tert-butyl-benzenemethanimidozirconium bis(dimethylamide) (1.00 g, 2.2 mmol) in pentane (12.8 mL) was added dropwise a solution of trimethylchlorosilane (2.60 g, 24.0 mol) in pentane (3.2 mL) at 0° C., and the mixture was stirred at room temperature for 28 hrs. A precipitate was formed and then filtered to give 2-(2,3,4,5-tetramethylcyclopentadienyl)-α-tert-butyl-benzenemethanimidozirconium dichloride (0.35 g, yield 36.5%).

$^1$H-NMR (C$_6$D$_6$): δ7.64-6.78 (4H), 2.22 (3H), 2.18 (3H), 1.94 (3H), 1.92 (3H), 1.46 (9H).

Example 51

Polymerization

An autoclave was charged with toluene (5.0 mL) under nitrogen and the temperature was stabilized at 70° C. It was then charged with ethylene until it was pressurized to 0.60 MPa, and the pressure was stabilized. Thereto a solution of triisobutylaluminum in hexane (100 µL, 1.0M, Kanto Kagaku), triphenylmethyl tetrakis(pentafluorophenyl)borate (0.375 µmol) and 2-(2,3,4,5-tetramethylcyclopentadienyl)-α-phenyl-benzenemethanimidotitanium bis(dimethylamide) (0.125 µmol) were added, and polymerization was carried out for 30 min. As a result of polymerization, a polymer having the molecular weight (Mw) of 897,000 and the molecular weight distribution (Mw/Mn) of 2.3 was produced in an amount of 4.08×10$^4$ g per 1 mol of titanium and per an hour.

Example 52

Polymerization was carried out in a similar manner as in Example 51, except that dimethylanilinium tetrakis(pentafluorophenyl)borate (0.375 µmol) was used instead of triphenylmethyl tetrakis(pentafluorophenyl)borate. As a result of polymerization, a polymer having the molecular weight (Mw) of 657,000 and the molecular weight distribution (Mw/Mn) of 2.5 was produced in an amount of 4.88×10$^4$ g per 1 mol of titanium and per an hour.

Example 53

Polymerization was carried out in a similar manner as in Example 51, except that 2-(2,3,4,5-tetramethylcyclopentadienyl)-α-phenyl-benzenemethanimidotitanium dichloride (0.125 µmol) was used instead of 2-(2,3,4,5-tetramethylcyclopentadienyl)-α-phenyl-benzenemethanimidotitanium bis(dimethylamide). As a result of polymerization, a polymer having the molecular weight (Mw) of 968,000 and the molecular weight distribution (Mw/Mn) of 2.6 was produced in an amount of 5.70×10$^5$ g per 1 mol of titanium and per an hour.

Example 54

Polymerization was carried out in a similar manner as in Example 51, except that 2-(2,3,4,5-tetramethylcyclopentadienyl)-α-phenyl-benzenemethanimidotitanium dichloride (0.125 µmol) was used instead of 2-(2,3,4,5-tetramethylcyclopentadienyl)-α-phenyl-benzenemethanimidotitanium bis (dimethylamide) and that dimethylanilinium tetrakis(pentafluorophenyl)borate (0.375 µmol) was used instead of triphenylmethyl tetrakis(pentafluorophenyl)borate. As a result of polymerization, a polymer having the molecular weight (Mw) of 1,150,000 and the molecular weight distribution (Mw/Mn) of 2.6 was produced in an amount of 4.98×10$^5$ g per 1 mol of titanium and per an hour.

Example 55

Polymerization was carried out in a similar manner as in Example 51, except that 2-(2,3,4,5-tetramethylcyclopentadienyl)-α-tert-butyl-benzenemethanimidotitanium bis(dimethylamide) (0.125 µmol) was used instead of 2-(2,3,4,5-tetramethylcyclopentadienyl)-α-phenyl-benzenemethanimidotitanium bis(dimethylamide). As a result of polymerization, a polymer having the molecular weight (Mw) of 1,370,000 and the molecular weight distribution (Mw/Mn) of 3.9 in an amount of 7.60×10$^4$ g per 1 mol of titanium and per an hour.

Example 56

Polymerization was carried out in a similar manner as in Example 51, except that 2-(2,3,4,5-tetramethylcyclopentadienyl)-α-tert-butyl-benzenemethanimidotitanium bis(dimethylamide) (0.125 µmol) was used instead of 2-(2,3,4,5-tetramethylcyclopentadienyl)-α-phenyl-benzenemethanimidotitanium bis(dimethylamide) and that dimethylanilinium tetrakis(pentafluorophenyl)borate (0.375 µmol) was used instead of triphenylmethyl tetrakis(pentafluorophenyl)borate. As a result of polymerization, a polymer having the molecular weight (Mw) of 1,250,000 and the molecular weight distribution (Mw/Mn) of 3.3 was produced in an amount of 5.68×10$^4$ g per 1 mol of titanium and per an hour.

Example 57

Polymerization was carried out in a similar manner as in Example 51, except that 2-(2,3,4,5-tetramethylcyclopentadienyl)-α-tert-butyl-benzenemethanimidotitanium dichloride (0.125 µmol) was used instead of 2-(2,3,4,5-tetramethylcyclopentadienyl)-α-phenyl-benzenemethanimidotitanium bis (dimethylamide). As a result of polymerization, a polymer having the molecular weight: (Mw) of 1,830,000 and the molecular weight distribution (Mw/Mn) of 1.7 was produced in an amount of 6.23×10$^5$ g per 1 mol of titanium and per an hour.

Example 58

Polymerization was carried out in a similar manner as in Example 51, except that 2-(2,3,4,5-tetramethylcyclopentadienyl)-α-tert-butyl-benzenemethanimidotitanium dichloride (0.125 µmol) was used instead of 2-(2,3,4,5-tetramethylcyclopentadienyl)-α-phenyl-benzenemethanimidotitanium bis (dimethylamide) and that dimethylanilinium tetrakis(pentafluorophenyl)borate (0.375 µmol) was used instead of triphenylmethyl tetrakis(pentafluorophenyl)borate. As a result of polymerization, a polymer having the molecular weight (Mw) of 814,000 and the molecular weight distribution (Mw/Mn) of 2.0 was produced in an amount of 3.81×10$^5$ g per 1 mol of titanium and per an hour.

Example 59

Synthesis of O-methyl-2-(2,3,5-trimethylcyclopentadienyl)benzaldehyde oxime

To a solution of 2-(2,3,5-trimethylcyclopentadienyl)benzaldehyde (11.32 g, 50.0 mmol) in THF (170.0 mL) were added O-methylhydroxylamine hydrochloride (5.43 g, 65.0 mmol), sodium acetate (5.33 g, 65.0 mmol) and water (50.0 mL) at 25° C., and the mixture was stirred for 30 min. After the reaction, ethyl acetate and water were added thereto. The mixture was separated and the aqueous layer was removed.

The obtained organic layer was dried over sodium sulfate and the solvent was distilled off under reduced pressure to give O-methyl-2-(2,3,5-trimethylcyclopentadienyl)benzaldehyde oxime (12.77 g, yield 100%).

$^1$H-NMR (CDCl$_3$): δ 7.97-7.90 (1H), 7.39-7.06 (4H), 3.94 (3H), 3.08-2.70 (1H), 1.90 (3H), 1.84 (3H), 1.68 (3H), 0.88 (3H);

MS (EI) m/z 255 (M$^+$), 240, 224, 209, 194.

Synthesis of 2-(2,3,4,5-tetramethylcyclopentadienyl)benzonitrile

To a solution of diisopropylamine (1.52 g, 15.0 mmol) in THF (17.5 mL) was added dropwise 1.59 M n-butyllithium (9.4 mL, 15.0 mmol) at −78° C. The temperature of the mixture was raised to 20° C. to prepare lithium diisopropylamide. This reaction solution was cooled to −78° C. and a solution of O-methyl-2-(2,3,5-trimethylcyclopentadienyl)benzaldehyde oxime (1.28 g, 5.0 mmol) in tetrahydrofuran (4.3 mL) was added dropwise thereto.

After the temperature of the mixture was raised to room temperature, the reaction was quenched by adding toluene and water. The reaction mixture was separated and the aqueous layer was removed. The obtained organic layer was dried over sodium sulfate and the solvent was distilled off under reduced pressure to give 2-(2,3,4,5-tetramethylcyclopentadienyl)benzonitrile (1.12 g, yield 100%).

$^1$H-NMR (CDCl$_3$): δ 7.66 (1H), 7.52 (1H), 7.33-7.23 (2H), 3.38 (1H), 1.92 (3H), 1.90 (3H), 1.87 (3H), 0.93 (3H);

MS (EI) m/z 223 (M$^+$), 208, 193, 180, 165.

Example 60

To a solution of diisopropylamine (0.96 g, 9.5 mmol) in tetrahydrofuran (34.5 mL) was added dropwise 1.59 M n-butyllithium (6.0 mL, 9.5 mmol) at −78° C. The temperature of the mixture was then raised to 20° C. to prepare lithium diisopropylamide. The reaction solution was cooled to −78° C. and a solution of O-methyl-2-(2,3,5-trimethylcyclopentadienyl)benzaldehyde oxime (2.55 g, 10.0 mmol) in tetrahydrofuran (8.6 mL) was added dropwise thereto. The temperature of the reaction solution was raised to room temperature. According to gas chromatography analysis, 2-(2,3,4,5-tetramethylcyclopentadienyl)benzonitrile was produced in 63.9% yield.

Comparative Example 1

To 2-(2,3,5-trimethylcyclopentadienyl)benzaldehyde (1.13 g, 5.0 mmol) were added acetic acid (22.60 g), sodium acetate (1.64 g, 20.0 mmol) and hydroxylamine hydrochloride (1.39 g, 20.0 mmol). The mixture was heated to 110° C. and stirred to 3 hrs. According to gas chromatography analysis of the reaction solution, 2-(2,3,4,5-tetramethylcyclopentadienyl)benzonitrile was not produced.

Comparative Example 2

To 2-(2,3,5-trimethylcyclopentadienyl)benzaldehyde (1.13 g, 5.0 mmol) were added formic acid (17.0 g) and hydroxylamine hydrochloride (0.45 g, 6.5 mmol). The mixture was heated to 110° C. and stirred for 30 min. According to gas chromatography analysis of the reaction solution, 2-(2,3,4,5-tetramethylcyclopentadienyl)benzonitrile was not produced.

Example 61

Synthesis of [2-(2,3,4,5-tetramethylcyclopentadienyl)phenyl]phenylmethylalkoxytitanium bis(dimethylamide) [Complex 18]

To a solution of [2-(2,3,4,5-tetramethylcyclopentadienyl)phenyl]phenylmethylalcohol (1.00 g, 3.2 mmol) in toluene (9.2 mL) was added a solution of tetrakis(dimethylamido)titanium (0.74 g, 3.2 mmol) in toluene (2.3 mL) at −78° C. The mixture was stirred at room temperature for 30 min and then at 110° C. for 5 hrs. The solvent was distilled off to give [2-(2,3,4,5-tetramethylcyclopentadienyl)phenyl]phenylmethylalkoxytitanium bis(dimethylamide)(1.23 g, yield 86.6%).

$^1$H-NMR (C$_6$D$_6$): δ 7.16-6.96 (4H), 6.45 (1H), 3.09 (6H), 3.04 (6H), 2.07 (3H), 1.97 (3H), 1.88 (3H), 1.85 (3H);

$^{13}$C-NMR (C$_6$D$_6$): δ 147.9-121.4 (aroma), 86.0 (CH), 48.7, 47.5 (NMe$_2$)$_{12.1}$, 11.9, 11.1 (CH$_3$).

Example 62

Synthesis of [2-(2,3,4,5-tetramethylcyclopentadienyl)phenyl]phenylmethylalkoxytitanium dichloride [Complex 19]

To a solution of [2-(2,3,4,5-tetramethylcyclopentadienyl)phenyl]phenylmethylalkoxytitanium bis(dimethylamide) (0.7 g, 1.6 mmol) in pentane (8.9 mL) was added dropwise a solution of tetramethylchlorosilane (1.91 g, 17.6 mmol) in pentane (2.2 mL) at 0° C. The mixture was stirred at room temperature for 15 hrs to give [2-(2,3,4,5-tetramethylcyclopentadienyl)phenyl]phenylmethylalkoxytitanium dichloride (526.6 mg, yield 78.6%) as a yellow solid.

$^1$H-NMR (C$_6$D$_6$): δ 6.85-7.22 (4H), 6.32 (1H), 2.15 (3H), 2.10 (3H), 1.69 (3H), 1.65 (3H);

MS (EI) m/z 420 (M$^+$), 304, 286, 167, 113.

Example 63

Synthesis of [2-(2,3,4,5-tetramethylcyclopentadienyl)phenyl]phenylmethylalkoxyzirconium bis(dimethylamide) [Complex 20]

To a solution of [2-(2,3,4,5-tetramethylcyclopentadienyl)phenyl]phenylmethylalcohol (0.97 g, 3.1 mmol) in toluene (9.0 mL) was added dropwise a solution of tetrakis(dimethylamido)titanium (0.85 g, 3.1 mmol) in toluene (2.2 mL) at −78° C. The mixture was stirred at room temperature for 30 min and then at 110° C. for 5 hrs. The solvent was distilled off to give [2-(2,3,4,5-tetramethylcyclopentadienyl)phenyl]phenylmethylalkoxyzirconium bis(dimethylamide) (1.02 g, yield 67.1%).

$^1$H-NMR (C$_6$D$_6$): δ 6.98-7.37 (4H), 6.35 (1H), 2.87 (6H), 2.85 (6H), 2.03 (3H), 1.96 (3H), 1.89 (3H), 1.85 (3H); $^{13}$C-NMR (C$_6$D$_6$): δ 147.3-117.6 (aroma), 83.2 (CH), 48.7, 43.3 (NMe$_2$), 11.1, 10.8, 10.6 (CH$_3$).

Example 64

Synthesis of N-[2-(1-indenyl)phenylmethyl]-N-phenylamine

To a solution of 2-(1-indenyl)benzaldehyde (7.0 mmol) in ethanol (19.4 mL) was added dropwise aniline (7.3 mmol) under a nitrogen atmosphere. The mixture was stirred at room temperature. After disappearance of the aldehyde was confirmed by gas chromatography, The solvent was distilled off under reduced pressure. After addition of ethanol (19.4 mL), sodium borohydride (4.5 mmol) was added to the solution and the mixture was reacted at room temperature for 3 hrs. Water and toluene were then added to the reaction mixture. The organic layer was dried and concentrated. The obtained oily substance was purified by silica gel column chromatography to give N-[2-(1-indenyl)phenylmethyl]-N-phenylamine (1.48 g, yield 24.0%) as a yellow oily substance.

$^1$H-NMR (CDCl$_3$): δ 7.56-7.52 (3H), 7.36-7.07 (6H), 6.73-6.62 (2H), 6.51-6.47 (3H), 4.26 (2H), 3.91-3.69 (1H), 3.51 (2H);

MS (EI) m/z 297 (M$^+$), 264, 77.

Example 65

Synthesis of N-[2-(1-indenyl)phenylmethyl]-N-phenylamido titanium bis(dimethylamide) [Complex 21]

To a solution of N-[2-(1-indenyl)phenylmethyl]-N-phenylamine (2.8 mmol) in toluene (15.2 mL) was added dropwise a solution of tetrakis(dimethylamino)titanium (2.8 mmol) in toluene (10.1 mL) at −78° C. The mixture was stirred at room temperature for 1 hr and then at 100° C. for 5 hrs to give a red solution. The solvent was distilled off under reduced pressure to give N-[2-(1-indenyl)phenylmethyl]-N-phenylamido titanium bis(dimethylamide) (1.21 g) as a red solid.

$^1$H-NMR (C$_6$D$_6$): δ 7.41-7.00 (14H), 6.28-6.19 (1H), 5.84 (1H), 4.43 (1H), 2.74 (6H), 2.48 (6H).

Example 66

Synthesis of N-[2-(1-indenyl)phenylmethyl]-N-phenylamido titanium dichloride [Complex 22]

To a solution of N-[2-(1-indenyl)phenylmethyl]-N-phenylamido titanium bis(dimethylamide) (2.8 mmol) in pentane (17.5 mL) was added dropwise a solution of trimethylsilyl chloride (30.8 mmol) in pentane (12.0 mL) at 0° C. The mixture was then stirred at room temperature for 16 hrs. A precipitated solid was filtered to give N-[2-(1-indenyl)phenylmethyl]-N-phenylamido titanium dichloride (0.24 g, yield 20.9%) as an orange solid.

$^1$H-NMR (C$_6$D$_6$): δ 7.41-7.00 (14H), 6.18 (1H), 5.21 (1H), 4.23 (1H);

MS (EI) m/z 413 (M$^+$), 377, 297, 204.

Example 67

Synthesis of N-[2-(2,3,4,5-tetramethylcyclopentadienyl)phenylmethyl]-N-(3,5-dimethylphenyl)amine To a solution of 2-(2,3,4,5-tetramethylcyclopentadienyl)benzaldehyde (15.0 mmol) in ethanol (44.6 mL) were added dropwise 3,5-dimethylaniline (15.8 mmol) and acetic acid (1.5 mmol) under a nitrogen atmosphere. The mixture was stirred at room temperature. After disappearance of the aldehyde was confirmed by gas chromatography, sodium borohydride (19.5 mmol) was added to the solution and reacted at room temperature for 3 hrs. Water and toluene were then added to the reaction mixture. The organic layer was dried and concentrated. The obtained oily substance was purified by silica gel column chromatography to give N-[2-(2,3,4,5-tetramethylcyclopentadienyl)phenylmethyl]-N-(3,5-dimethylphenyl)amine (4.88 g, yield 73.3%) as a yellow oily substance.

$^1$H-NMR (CDCl$_3$): δ 7.46-6.15 (7H), 4.30-4.08 (2H), 3.87-3.79 (1H), 3.18-2.72 (1H), 2.33-0.95 (18H);

MS (EI) m/z 331 (M$^+$), 210, 195.

Example 68

Synthesis of N-[2-(2,3,4,5-tetramethylcyclopentadienyl)phenylmethyl]-N-(3,5-dimethylphenyl)amine titanium bis(dimethylamide) [Complex 23]

To a solution of N-[2-(2,3,4,5-tetramethylcyclopentadienyl)phenylmethyl]-N-(3,5-dimethylphenyl)amine (4.0 mmol) in toluene (18.4 mL) was added dropwise a solution of tetrakis(dimethylamino)titanium (4.0 mmol) in toluene (12.2 mL) at −78° C. The mixture was stirred at room temperature for 1 hr and then at 100° C. for 5 hrs to give a red solution. The solvent was distilled off under reduced pressure to synthesize N-[2-(2,3,4,5-tetramethylcyclopentadienyl)phenylmethyl]-N-(3,5-dimethylphenyl)amine titanium bis(dimethylamide) (2.08 g, yield 100%) as a red solid.

$^1$H-NMR (C$_6$D$_6$): δ 7.66-6.74 (7H), 4.48 (2H), 3.05 (12H), 1.94 (6H), 1.74 (6H).

Example 69

Synthesis of N-[2-(2,3,4,5-tetramethylcyclopentadienyl)phenylmethyl]-N-(3,5-dimethylphenyl)amido titanium dichloride [Complex 24]

To a solution of N-[2-(2,3,4,5-tetramethylcyclopentadienyl)phenylmethyl]-N-(3,5-dimethylphenyl)amido titanium bis(dimethylamide) (4.0 mmol) in pentane (29.1 mL) was added dropwise a solution of trimethylsilyl chloride (44.0 mmol) in pentane (19.0 mL) at 0° C. The mixture was then stirred at room temperature for 16 hrs. A precipitated solid was filtered to give N-[2-(2,3,4,5-tetramethylcyclopentadienyl)phenylmethyl]-N-(3,5-dimethylphenyl)amido titanium dichloride (0.31 g, yield 15.6%) as an orange solid.

$^1$H-NMR (C$_6$D$_6$): δ 7.42-6.67 (7H), 4.73 (2H), 2.13 (6H), 2.05 (6H), 1.86 (6H);

MS (EI) m/z 447 (M$^+$), 411, 209.

Example 70

Synthesis of N-[2-(2,3,4,5-tetramethylcyclopentadienyl)phenylmethylene]-N-(2,4,6-trimethylphenyl)amine To a solution of 2-(2,3,4,5-tetramethylcyclopentadienyl)benzaldehyde (10.0 mmol) in ethanol (30.0 mL) were added dropwise acetic acid (1.0 mmol) and 2,4,6-trimethylaniline (10.5 mmol) under a nitrogen atmosphere. The mixture was stirred at room temperature. After disappearance of the aldehyde was confirmed by gas chromatography, the solvent was distilled off under reduced pressure to give N-[2-(2,3,4,5-tetramethylcyclopentadienyl)phenylmethylene]-N-(2,4,6-trimethylphenyl)amine (3.43 g, yield 100%).

$^1$H-NMR (CDCl$_3$): δ 8.37-8.32 (1H), 8.21 (1H), 7.58-7.11 (3H), 6.86 (1H), 3.15-2.67 (1H), 2.27 (3H), 2.12-0.94 (18H).

Example 71

Synthesis of N-[2-(2,3,4,5-tetramethylcyclopentadienyl)phenylmethyl]-N-(2,4,6-trimethylphenyl)amine To a solution of N-[2-(2,3,4,5-tetramethylcyclopentadienyl)phenylmethylene]-N-(2,4,6-trimethylphenyl)amine (10.0 mmol) in acetic acid (7.0 mL) was added sodium borohydride (13.0 mmol). The mixture was reacted at room temperature for 1 hr. Water and toluene were then added the reaction mixture. The organic layer was dried and concentrated. The obtained oily substance was purified by silica gel column chromatography to give N-[2-(2,3,4,5-tetramethylcyclopentadienyl)phenylmethyl]-N-(2,4,6-trimethylphenyl)amine (2.74 g, yield 69.5%) as a yellow oily substance.

$^1$H-NMR (CDCl$_3$): δ 7.67-7.04 (4H), 6.82-6.78 (2H), 3.91-3.77 (2H), 3.10-2.62 (1H), 3.00-2.85 (1H), 2.28-0.88 (21H); MS (EI) m/z 345 (M$^+$), 210, 195.

Example 72

Synthesis of N-[2-(2,3,4,5-tetramethylcyclopentadienyl)phenylmethyl]-N-(2,4,6-trimethylphenyl)amido zirconium bis(dimethylamide) [Complex 25]

To a solution of N-[2-(2,3,4,5-tetramethylcyclopentadienyl)phenylmethyl]-N-(2,4,6-trimethylphenyl)amine (3.1 mmol) in toluene (11.1 mL) was added dropwise a solution of tetrakis(dimethylamino)zirconium (3.1 mmol) in toluene (7.4 mL) at −78° C. The mixture was stirred at room temperature for 1 hr and then at 100° C. for 5 hrs to give a yellow solution. The solvent was distilled off under reduced pressure to give N-[2-(2,3,4,5-tetramethylcyclopentadienyl)phenylmethyl]-N-(2,4,6-trimethylphenyl)amido zirconium bis(dimethylamide) (1.65 g, yield 100%) as a pale yellow solid.

$^1$H-NMR (C$_6$D$_6$): δ 7.37-6.85 (6H), 4.34 (2H), 2.68 (12H), 2.16 (3H), 2.01 (6H), 1.99 (12H); MS (EI) m/z 521 (M$^+$), 476, 432, 210.

Example 73

Synthesis of N-[2-(2,3,4,5-tetramethylcyclopentadienyl)phenylmethyl]-N-(2,4,6-trimethylphenyl)amido zirconium dichloride [Complex 26]

To a solution of N-[2-(2,3,4,5-tetramethylcyclopentadienyl)phenylmethyl]-N-(2,4,6-trimethylphenyl)amido zirconium bis(dimethylamide) (2.5 mmol) in pentane (13.6 mL) was added dropwise a solution of trimethylsilyl chloride (27.5 mmol) in pentane (9.0 mL) at 0° C. The mixture was stirred at room temperature for 16 hrs. A precipitated solid was filtered to give N-[2-(2,3,4,5-tetramethylcyclopentadienyl)phenylmethyl]-N-(2,4,6-trimethylphenyl)amido zirconium dichloride (0.97 g, yield 77.0%) as a white solid.

$^1$H-NMR (C$_6$D$_6$) δ 7.42-7.09 (3H), 6.94-6.89 (1H), 6.80 (2H), 4.35 (2H), 2.15 (6H), 2.07 (6H), 2.00 (3H), 1.86 (6H).

Example 74

Synthesis of N-[2-(2,3,4,5-tetramethylcyclopentadienyl)phenylmethylene]-N-(2,6-diisopropylphenyl)amine To a solution of 2-(2,3,4,5-tetramethylcyclopentadienyl)benzaldehyde (10.0 mmol) in ethanol (30.0 mL) were added dropwise acetic acid (1.0 mmol) and 2,6-diisopropylaniline (10.5 mmol) under a nitrogen atmosphere. The mixture was stirred at room temperature. After disappearance of the aldehyde was confirmed by gas chromatography, the solvent was distilled off under reduced pressure to give N-[2-(2,3,4,5-tetramethylcyclopentadienyl)phenylmethylene]-N-(2,6-diisopropylphenyl)amine (3.85 g, yield 100%).

$^1$H-NMR (CDCl$_3$): δ 8.45-8.28 (1H), 8.14-8.10 (1H), 7.50-6.80 (6H), 3.76-3.00 (1H), 3.00-2.85 (3H), 1.85-0.83 (24H).

Example 75

Synthesis of N-[2-(2,3,4,5-tetramethylcyclopentadienyl)phenylmethyl]-N-(2,6-diisopropylphenyl)amine To a solution of N-[2-(2,3,4,5-tetramethylcyclopentadienyl)phenylmethylene]-N-(2,6-diisopropylphenyl)amine (10.0 mmol) in acetic acid (7.0 mL) was added sodium borohydride (13.0 mmol). The mixture was reacted at room temperature for 1 hr. Water and toluene were then added to the reaction mixture. The organic layer was dried and concentrated. The obtained oily substance was purified by silica gel column chromatography to give N-[2-(2,3,4,5-tetramethylcyclopentadienyl)phenylmethyl]-N-(2,6-diisopropylphenyl)amine (3.19 g, yield 82.4%) as a yellow oily substance.

$^1$H-NMR (CDCl$_3$): δ 7.68-7.06 (7H), 3.91-3.77 (2H), 3.30-2.68 (1H), 3.28-3.08 (2H), 3.08-2.91 (1H), 1.88-0.88 (24H); MS (EI) m/z 387 (M$^+$), 210, 195.

Example 76

Synthesis of N-[2-(2,3,4,5-tetramethylcyclopentadienyl)phenylmethyl]-N-(2,6-diisopropylphenyl)amido zirconium bis(dimethylamide) [Complex 27]

To a solution of N-[2-(2,3,4,5-tetramethylcyclopentadienyl)phenylmethyl]-N-(2,6-diisopropylphenyl)amine (3.0 mmol) in toluene (12.2 mL) was added dropwise a solution of tetrakis(dimethylamino)titanium (3.0 mmol) in toluene (8.1 mL) at −78° C. The mixture was stirred at room temperature 1 hr and then at 100° C. for 5 hrs to give a yellow solution. The solvent was distilled off under reduced pressure to give N-[2-(2,3,4,5-tetramethylcyclopentadienyl)phenylmethyl]-N-(2,6-diisopropylphenyl)amido zirconium bis(dimethylamide) (1.81 g, yield 100%) as a pale yellow solid.

$^1$H-NMR (C$_6$D$_6$): δ 7.31-6.83 (7H), 4.43 (2H), 3.17 (2H), 2.64 (s, 12H), 2.00 (6H), 1.98 (6H), 1.13 (6H), 1.00 (6H); MS (EI) m/z 563 (M$^+$), 518, 473, 431, 387, 210.

Example 77

Synthesis of N-[2-(2,3,4,5-tetramethylcyclopentadienyl)phenylmethyl]-N-(2,6-diisopropylphenyl)amido zirconium dichloride [Complex 28]

To a solution of N-[2-(2,3,4,5-tetramethylcyclopentadienyl)phenylmethyl]-N-(2,6-diisopropylphenyl)amido zirconium bis(dimethylamide) (2.5 mmol) in pentane (14.7 mL) was added dropwise a solution of trimethylsilyl chloride (27.5 mmol) in pentane (10.0 mL) at 0° C. The mixture was then stirred at room temperature for 16 hrs. A precipitated solid was filtered to give N-[2-(2,3,4,5-tetramethylcyclopentadienyl)phenylmethyl]-N-(2,6-diisopropylphenyl)amido zirconium dichloride (0.30 g, yield 22.0%) as a white solid.

$^1$H-NMR (C$_6$D$_6$): δ 7.20-6.76 (7H), 4.64 (2H), 3.01 (2H), 2.06 (6H), 1.87 (6H), 1.43 (6H), 0.93 (6H); MS (EI) m/z 547 (M$^+$), 386, 319, 255, 210, 174.

Example 78

Synthesis of N-[2-(2,3,4,5-tetramethylcyclopentadienyl)phenylmethylene]-N-pentafluorophenylamine Thionyl chloride (50.0 mmol) and pentafluoroaniline (5.0 mmol) were mixed under a nitrogen atmosphere at room temperature, and the volatile component was distilled off under reduced pressure. To the mixture was added dropwise a solution of 2-(2,3,4,5-tetramethylcyclopentadienyl)benzaldehyde (5.0 mmol) in toluene (13.8 mL) at room temperature.

The mixture was stirred at room temperature. After disappearance of the aldehyde was confirmed by gas chromatography, the solvent was distilled off under reduced pressure to give N-[2-(2,3,4,5-tetramethylcyclopentadienyl)phenylmethylene]-N-pentafluorophenylamine (2.10 g, yield 100%).

MS (EI) m/z 391 (M+), 209, 193, 179, 167, 77.

Example 79

Synthesis of N-[2-(2,3,4,5-tetramethylcyclopentadienyl)phenylmethyl]-N-pentafluorophenylamine To a solution of N-[2-(2,3,4,5-tetramethylcyclopentadienyl)phenylmethylene]-N-pentafluorophenylamine (4.0 mmol) in acetic acid-(4.9 mL) was added sodium borohydride (5.2 mmol). The mixture was reacted at room temperature for 3 hrs. Then, 5.0M aqueous NaOH solution and ether were added to the reaction mixture. The organic layer was dried and concentrated. The obtained oily substance was purified by silica gel column chromatography to give N-[2-(2,3,4,5-tetramethylcyclopentadienyl)phenylmethyl]-N-pentafluorophenylamine (0.72 g, yield 34.2%) as a yellow oily substance.

$^1$H-NMR (CDCl$_3$): δ 7.48-7.06 (4H), 4.43-4.27 (2H), 3.85-3.70 (1H), 3.00-2.70 (1H), 1.89-0.90 (12H); MS (EI) m/z 393 (M+), 210, 195, 180, 165.

Example 80

Synthesis of N-[2-(2,3,4,5-tetramethylcyclopentadienyl)phenylmethyl]-N-pentafluorophenylamido titanium bis(dimethylamide) [Complex 29]

To a solution of N-[2-(2,3,4,5-tetramethylcyclopentadienyl)phenylmethyl]-N-pentafluorophenylamine (1.3 mmol) in toluene (7.5 mL) was added dropwise a solution of tetrakis(dimethylamino)titanium (1.3 mmol) in Toluene (5.0 mL) at −78° C. The mixture was stirred at room temperature for 1 hrs and then at 100° C. for 5 hrs to give a red solution. The solvent was distilled off under reduced pressure to give N-[2-(2,3,4,5-tetramethylcyclopentadienyl)phenylmethyl]-N-pentafluorophenylamido titanium bis(dimethylamide) (0.72 g) as a red solid.

Example 81

Synthesis of N-[2-(2,3,4,5-tetramethylcyclopentadienyl)phenylmethyl]-N-pentafluorophenylamido titanium dichloride [Complex 30]

To a solution of N-[2-(2,3,4,5-tetramethylcyclopentadienyl)phenylmethyl]-N-pentafluorophenylamido titanium bis(dimethylamide) (1.3 mmol) obtained by the above reaction in pentane (10.4 mL) was added dropwise a solution of trimethylsilyl chloride (15.1 mmol) in pentane (7.0 mL) at 0° C. The mixture was then stirred at room temperature for 16 hrs. A precipitated solid was filtered off and the obtained solution was concentrated. Pentane was added to the concentrate. A precipitated solid was filtered to give N-[2-(2,3,4,5-tetramethylcyclopentadienyl)phenylmethyl]-N-pentafluorophenylamido titanium dichloride (0.12 g, yield 17.4%) as an orange solid.

$^1$H-NMR (C$_6$D$_6$): δ 7.46-7.43 (2H), 7.20-6.85 (7H), 4.64 (2H), 2.07 (6H), 1.83 (6H);
MS (EI) m/z 509 (M+), 473, 392, 209.

Example 82

Synthesis of 2-(2,3,4,5-tetramethylcyclopentadienyl)benzaldehyde pentafluorophenylhydrazone To a solution of 2-(2,3,4,5-tetramethylcyclopentadienyl)benzaldehyde (10.0 mmol) in ethanol (60.0 mL) was added dropwise pentafluorophenylhydrazine (11.0 mmol) under a nitrogen atmosphere. The mixture was stirred at room temperature for 2 hrs. The solvent was distilled off under reduced pressure and the residue was recrystallized from hexane to give 2-(2,3,4,5-tetramethylcyclopentadienyl)benzaldehyde pentafluorophenylhydrazone (4.00 g, yield 97.0%).

$^1$H-NMR (CDCl$_3$): δ 8.03-8.00 (1H), 7.71-6.91 (5H), 3.17-2.71 (1H), 1.94-0.86 (12H);
MS (EI) m/z 406 (M+), 277, 244, 209.

Example 83

Synthesis of Complex 31

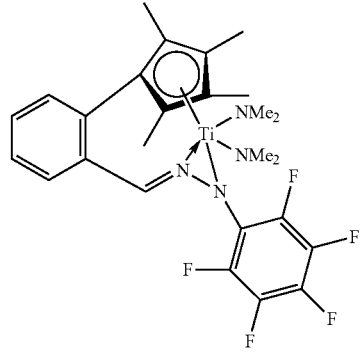

Complex 31

To a solution of 2-(2,3,4,5-tetramethylcyclopentadienyl)benzaldehyde pentafluorophenylhydrazone (4.6 mmol) in toluene (19.0 mL) was added dropwise a solution of tetrakis(dimethylamino)titanium (4.6 mmol) in toluene (13.0 mL) at −78° C. The mixture was stirred at room temperature for 1 hr and then at 100° C. for 5 hrs to give a red solution. The solvent was distilled off under reduced pressure to give Complex 28 (2.37 g, yield 100%) as a red solid.

$^1$H-NMR (C$_6$D$_6$): δ 8.03-8.21 (1H), 7.71-6.99 (4H), 3.27 (12H), 2.77 (6H), 2.60 (6H).

Example 84

Synthesis of Complex 32

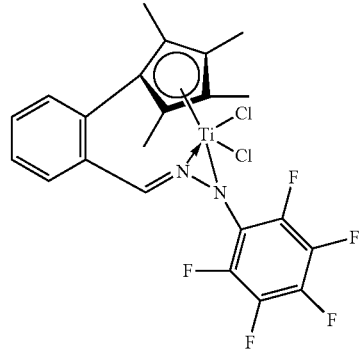

Complex 32

To a solution of Complex 31 (4.4 mmol) in pentane (34.2 mL) was added dropwise a solution of trimethylsilyl chloride (48.0 mmol) in toluene (23.0 mL) at 0° C. The mixture was then stirred at room temperature for 16 hrs. A precipitated solid was filtered to give Complex 29 (0.72 g, yield 31.3%) as an orange solid.

$^1$H-NMR ($C_6D_6$): δ 8.53-8.50 (1H), 7.42-6.91 (4H), 2.16 (6H), 1.61 (6H).

MS (EI) m/z 522 (M$^+$), 406, 342, 222, 209.

Example 85

Synthesis of 2-(2,3,4,5-tetramethylcyclopentadienyl)-α-(2,4,6-trimethylphenyl)-benzenemethanimine To a solution of 2-(2,3,4,5-tetramethylcyclopentadienyl) benzonitrile (6.3 mmol) in tetrahydrofuran (25.5 mL) was added dropwise a solution of 2,4,6-trimethylphenyllithium (12.5 mmol) in tetrahydrofuran (55.6 mL) at −78° C. under a nitrogen atmosphere. The temperature of the mixture was raised to room temperature and the mixture was stirred for 5 hrs. To the reaction mixture solution were added toluene and water to separate an organic layer and an aqueous layer. The organic layer was dried and the solvent was distilled off to give 2-(2,3,4,5-tetramethylcyclopentadienyl)-α-(2,4,6-trimethylphenyl)-benzenemethanimine (2.34 g) as a brown oily substance.

MS (EI) m/z 342, 328, 312, 262.

Example 86

Synthesis of 2-(2,3,4,5-tetramethylcyclopentadienyl)-α-(2,4,6-trimethylphenyl)-benzenemethanimido titanium bis(dimethylamide) [Complex 33]

To a solution of 2-(2,3,4,5-tetramethylcyclopentadienyl)-α-(2,4,6-trimethylphenyl)-benzenemethanimine (1.0 mmol) in toluene (4.0 mL) was added dropwise a solution of tetrakis(dimethylamino)titanium (1.0 mmol) in toluene (2.0 mL) at −78° C. The mixture was stirred at room temperature for 1 hr and then at 100° C. for 5 hrs to give a red solution. The solvent was distilled off under reduced pressure to give 2-(2,3,4,5-tetramethylcyclopentadienyl)-α-(2,4,6-trimethylphenyl)-benzenemethanimido titanium bis(dimethylamide) (0.47 g).

Example 87

Synthesis of 2-(2,3,4,5-tetramethylcyclopentadienyl)-α-(2,4,6-trimethylphenyl)-benzenemethanimido titanium dichloride [Complex 34]

To a solution of 2-(2,3,4,5-tetramethylcyclopentadienyl)-α-(2,4,6-trimethylphenyl)-benzenemethanimido titanium bis(dimethylamide) (1.0 mmol) in pentane (6.9 mL) was added dropwise a solution of trimethylsilyl chloride (11.0 mmol) in pentane (5.0 mL) at 0° C. The mixture was then stirred at room temperature for 16 hrs. A precipitated solid was filtered to give 2-(2,3,4,5-tetramethylcyclopentadienyl)-α-(2,4,6-trimethylphenyl)-benzenemethanimido titanium dichloride (0.19 g, yield 44.0%) as an orange solid.

$^1$H-NMR ($C_6D_6$): δ 7.45-6.67 (6H), 2.43 (6H), 2.15 (3H), 2.08 (6H), 1.67 (6H);

MS (EI) m/z 458 (M$^+$), 423, 340, 278.

Polymerization

Example 88

Polymerization Condition A-1

An autoclave was charged with toluene (5.0 mL) under nitrogen and the temperature was stabilized at 40° C. It was then charged with ethylene until it was pressurized to 0.60 MPa, and the pressure was stabilized. Thereto MMAO (250 μmol, 5.8 wt % Al, Tosoh-Akzo Corporation) (100 μmol) and [2-(2,3,4,5-tetramethylcyclopentadienyl)phenyl]phenylmethylalkoxytitanium dichloride (0.10 μmol) were added and polymerization was carried out for 30 min. As a result of polymerization, a polymer was produced in an amount of $4.00 \times 10^5$ g per 1 mol of titanium and per an hour.

Example 89

Polymerization Condition B-1

Polymerization was carried out in a similar manner as in Example 88, except that a solution of triisobutylaluminum in hexane (40 μL, 1.0M, Kanto Kagaku) and pentafluorophenylborane (0.30 μmol) were used instead of MMAO. As a result of polymerization, a polymer was produced in an amount of $1.00 \times 10^5$ g per 1 mol of titanium and per an hour.

Example 90

Polymerization Condition C-1

Polymerization was carried out in a similar manner as in Example 88, except that a solution of triisobutylaluminum in hexane (40 μL, 1.0 M, Kanto Kagaku) and dimethylanilinium tetrakis(pentafluorophenyl)borate (0.30 μmol) were used instead of MMAO. As a result of polymerization, a polymer having the molecular weight (Mw) of 876,000, the molecular weight distribution (Mw/Mn) of 3.5 and Tm of 126.5° C. was produced in an amount of $3.10 \times 10^6$ g per 1 mol of titanium and per an hour.

Example 91

Polymerization Condition D-1

Polymerization was carried out in a similar manner as in Example 88, except that a solution of triisobutylaluminum in hexane (40 μL, 1.0 M, Kanto Kagaku) and triphenylmethyl tetrakis(pentafluorophenyl)borate (0.30 μmol) were used instead of MMAO. As a result of polymerization, a polymer having the molecular weight (Mw) of 990,000, the molecular weight distribution (Mw/Mn) of 3.6 and Tm of 129.6° C. was produced in an amount of $2.60 \times 10^6$ g per 1 mol of titanium and per an hour.

Example 92

Polymerization Condition A-2

An autoclave was charged with toluene (5.0 mL) under nitrogen and the temperature was stabilized at 40° C. It was then charged with ethylene until it was pressurized to 0.60 MPa, and the pressure was stabilized. Thereto MMAO (250 μmol, 5.8 wt % Al, Tosoh-Akzo Corporation) (100 μmol) and [2-(2,3,4,5-tetramethylcyclopentadienyl)phenylmethyl]-N- phenylamidotitanium dichloride (0.10 μmol) were added and polymerization was carried out for 30 min. As a result of polymerization, a polymer having the molecular weight (Mw) of 285,000, the molecular weight distribution (Mw/Mn) of 4.5 and Tm of 85-9° C. was produced in an amount of $1.59 \times 10^6$ g per 1 mol of titanium and per an hour.

Example 93

Polymerization Condition A-3

Polymerization was carried out in a similar manner as in Example 92, except that the polymerization temperature was 70° C. As a result of polymerization, a polymer having the molecular weight (Mw) of 121,000, the molecular weight distribution (Mw/Mn) of 3.2 and Tm of 90.6° C. was produced in an amount of $1.01 \times 10^7$ g per 1 mol of titanium and per an hour.

Example 94

Polymerization Condition B-2

An autoclave was charged with toluene (5.0 mL) and 1-hexene (0.50 μL) under nitrogen and the temperature was stabilized at 40° C. It was then charged with ethylene until it was pressurized to 0.60 MPa, and the pressure was stabilized. Thereto a solution of triisobutylaluminum in hexane (40 μL, 1.0 M, Kanto Kagaku), pentafluorophenylborane (0.30 μmol) and N-[2-(1-indenyl)phenylmethyl]-N-phenylamido titanium dichloride (0.10 μmol) were added and polymerization was carried out for 30 min. As a result of polymerization, a polymer having the molecular weight (Mw) of 1,360,000, the molecular weight distribution (Mw/Mn) of 8.4 and Tm of 116.1° C. was produced in an amount of $2.25 \times 10^6$ g per 1 mol of titanium and per an hour.

Example 95

Polymerization Condition B-3

Polymerization was carried out in a similar manner as in Example 94, except that the polymerization temperature was 70° C. As a result of polymerization, a polymer having the molecular weight (Mw) of 817,000, the molecular weight distribution (Mw/Mn) of 19.3 and Tm of 122.2° C. was produced in an amount of $1.35 \times 10^7$ g per 1 mol of titanium and per an hour.

Example 96

Polymerization Condition C-2

An autoclave was charged with toluene (5.0 mL) and 1-hexene (0.50 μL) under nitrogen and the temperature was stabilized at 40° C. It was then charged with ethylene until it was pressurized to 0.60 MPa, and the pressure was stabilized. Thereto a solution of triisobutylaluminum in hexane (40 μL, 1.0 M, Kanto Kagaku), dimethylanilinium tetrakis(pentafluorophenyl)borate (0.30 μmol) and [2-(2,3,4,5-tetramethylcyclopentadienyl)phenyl]phenylmethylalkoxytitanium dichloride (0.10 μmol) were added, and polymerization was carried out for 30 min. As a result of polymerization, a polymer having the molecular weight (Mw) of 1,170,000, the molecular weight distribution (Mw/Mn) of 8.4 and Tm of 114.1° C. was produced in an amount of $1.00 \times 10^6$ g per 1 mol of titanium and per an hour.

Example 97

Polymerization Condition C-3

Polymerization was carried out in a similar manner as in Example 96, except that the polymerization temperature was 70° C. As a result of polymerization, a polymer having the molecular weight (Mw) of 530,000, the molecular weight distribution (Mw/Mn) of 7.7 and Tm of 116.0° C. was produced in an amount of $1.50 \times 10^6$ g per 1 mol of titanium and per an hour.

Example 98

Polymerization Condition C-4

Polymerization was carried out in a similar manner as in Example 96, except that the polymerization temperature was 130° C. As a result of polymerization, a polymer was produced in an amount of $2.90 \times 10^5$ g per 1 mol of titanium and per an hour.

Example 99

Polymerization Condition D-2

An autoclave was charged with toluene (5.0 mL) and 1-hexene (0.50 μL) under nitrogen and the temperature was stabilized at 40° C. It was then charged with ethylene until it was pressurized to 0.60 MPa, and the pressure was stabilized. Thereto a solution of triisobutylaluminum in hexane (40 μL, 1.0 M, Kanto Kagaku), triphenylmethyl tetrakis(pentafluorophenyl)borate (0.30 μmol) and [2-(2,3,4,5-tetramethylcyclopentadienyl)phenyl]phenylmethylalkoxytitanium dichloride (0.10 mol) were added, and polymerization was carried out for 30 min. As a result of polymerization, a polymer having the molecular weight (Mw) of 1363,000, the molecular weight distribution (Mw/Mn) of 10.5 and Tm of 115.8° C. was produced in an amount of $1.30 \times 10^6$ g-per 1 mol of titanium and per an hour.

Example 100

Polymerization Condition D-3

Polymerization was carried out in a similar manner as in Example 99, except that the polymerization temperature was 70° C. As a result of polymerization, a polymer having the molecular weight (Mw) of 701,000, the molecular weight distribution (Mw/Mn) of 9.9 and Tm of =117.3° C. was produced in an amount of $1.20 \times 10^6$ g per 1 mol of titanium and per an hour.

Example 101

Polymerization Condition D-4

Polymerization was carried out in a similar manner as in Example 99, except that the polymerization temperature was 130° C. As a result of polymerization, a polymer was produced in an amount of $2.00 \times 10^5$ g per 1 mol of titanium and per an hour.

The catalyst components, polymerization conditions, catalyst activities, reaction results of Examples 102 to 237 are shown in the following Tables 1 to 5.

TABLE 1

Homopolymerization of ethylene

| Example | complex | Polymerization condition | Activity (×10⁶ g PE/mol-cat/hr) |
|---|---|---|---|
| 91 | 2 | D-1 | 1.29 |
| 102 | 3 | A-1 | 1.23 |
| 103 | 3 | C-1 | 1.83 |
| 104 | 3 | D-1 | 3.66 |
| 105 | 4 | A-1 | 12.87 |
| 106 | 4 | B-1 | 4.35 |
| 107 | 4 | C-1 | 9.09 |
| 108 | 4 | D-1 | 4.17 |
| 109 | 7 | C-1 | 1.38 |
| 110 | 7 | D-1 | 1.47 |
| 111 | 8 | A-1 | 2.76 |
| 112 | 8 | C-1 | 6.05 |
| 113 | 8 | D-1 | 6.37 |
| 114 | 5 | A-1 | 1.32 |
| 115 | 6 | C-1 | 5.97 |
| 116 | 6 | D-1 | 7.22 |
| 117 | 12 | C-1 | 5.97 |
| 118 | 12 | D-1 | 7.22 |
| 119 | 15 | C-1 | 1.89 |
| 120 | 15 | D-1 | 2.13 |
| 121 | 10 | C-1 | 2.91 |
| 122 | 10 | D-1 | 3.36 |
| 123 | 18 | C-1 | 3.12 |
| 124 | 18 | D-1 | 2.61 |
| 125 | 30 | A-1 | 4.05 |
| 126 | 30 | C-1 | 22.50 |
| 127 | 30 | D-1 | 21.16 |
| 128 | 22 | A-1 | 26.05 |
| 129 | 22 | B-1 | 8.95 |
| 130 | 22 | C-1 | 6.32 |
| 131 | 22 | D-1 | 5.61 |
| 132 | 25 | A-1 | 5.58 |
| 133 | 25 | C-1 | 7.49 |
| 134 | 25 | D-1 | 13.50 |
| 135 | 27 | A-1 | 3.72 |
| 136 | 27 | C-1 | 17.59 |
| 137 | 27 | D-1 | 19.52 |
| 138 | 26 | A-1 | 8.81 |
| 139 | 26 | C-1 | 15.34 |
| 140 | 26 | D-1 | 6.82 |
| 141 | 28 | A-1 | 5.73 |
| 142 | 28 | C-1 | 23.63 |
| 143 | 28 | D-1 | 34.66 |
| 144 | 24 | A-1 | 4.47 |
| 145 | 24 | B-1 | 3.12 |
| 146 | 24 | C-1 | 7.50 |
| 147 | 24 | D-1 | 9.29 |
| 148 | 31 | A-1 | 1.98 |
| 149 | 31 | C-1 | 2.91 |
| 150 | 31 | D-1 | 3.33 |
| 151 | 34 | C-1 | 12.13 |
| 152 | 34 | D-1 | 7.55 |

TABLE 2

Copolymerization of ethylene-hexene, co-catalyst MMAO

| Example | complex | Polymerization condition | temperature, °C. | activity* | Mw | Mw/Mn | Tm, °C. |
|---|---|---|---|---|---|---|---|
| 153 | 3 | A-2 | 40 | 1.35 | 3,085,000 | 4.7 | 123.2 |
| 154 | 3 | A-3 | 70 | 1.92 | 1,132,000 | 4.8 | 121.1 |
| 155 | 4 | A-2 | 40 | 1.59 | 285,000 | 4.5 | 85.9 |
| 156 | 4 | A-3 | 70 | 10.19 | 121,000 | 3.2 | 90.6 |
| 157 | 8 | A-2 | 40 | 2.70 | 1,444,000 | 4.7 | 117.4 |
| 158 | 8 | A-3 | 70 | 1.95 | 1,173,000 | 10.1 | 119.4 |
| 159 | 5 | A-3 | 70 | 1.92 | 163,000 | 9.5 | 126.9 |
| 160 | 6 | A-2 | 40 | 19.94 | 435,000 | 10.3 | 118.8 |
| 161 | 6 | A-3 | 70 | 54.53 | 66,000 | 5.8 | 106.5 |
| 162 | 30 | A-2 | 40 | 3.42 | 1,624,000 | 7.4 | 109.9 |
| 163 | 30 | A-3 | 70 | 4.87 | 1,486,000 | 39.7 | 112.3 |
| 164 | 22 | A-2 | 40 | 10.88 | 1,759,000 | 10.5 | 107.8 |
| 165 | 22 | A-3 | 70 | 32.77 | 778,000 | 22.1 | 110.1 |
| 166 | 25 | A-2 | 40 | 4.59 | 336,000 | 4.3 | 118.9 |
| 167 | 25 | A-3 | 70 | 19.13 | 93,000 | 3.8 | 125 |
| 168 | 27 | A-2 | 40 | 4.65 | 130,000 | 2.9 | 126.7 |
| 169 | 27 | A-3 | 70 | 27.21 | 44,000 | 3.6 | 123.9 |
| 170 | 26 | A-2 | 40 | 14.23 | 246,000 | 3.2 | 125.9 |
| 171 | 26 | A-3 | 70 | 39.04 | 124,000 | 3 | 124.5 |
| 172 | 28 | A-2 | 40 | 9.12 | 123,000 | 3.2 | 128.6 |
| 173 | 28 | A-3 | 70 | 58.76 | 46,000 | 2.9 | 125.5 |
| 174 | 24 | A-2 | 40 | 3.42 | 1,596,000 | 8.7 | 125 |
| 175 | 24 | A-3 | 70 | 6.44 | 689,000 | 6.7 | 121.7 |

*×10⁶ g polymer/mol-cat/hr

TABLE 3

Copolymerization of ethylene-hexene, co-catalyst TIBA/(C₆F₅)₃B

| Example | complex | Polymerization condition | temperature, °C. | activity | Mw | Mw/Mn | Tm, °C. |
|---|---|---|---|---|---|---|---|
| 176 | 4 | B-3 | 70 | 1.29 | 380,000 | 2.6 | 83.5 |
| 96 | 22 | B-2 | 40 | 2.25 | 1,360,000 | 8.4 | 116.1 |
| 97 | 22 | B-3 | 70 | 13.51 | 817,000 | 19.3 | 122.2 |

* ×10⁶ g polymer/mol-cat/hr

TABLE 4

Copolymerization of ethylene-hexene, co-catalyst TIBA/AB

| Example | complex | Polymerization condition | temperature, °C. | activity* | Mw | Mw/Mn | Tm, °C. |
|---|---|---|---|---|---|---|---|
| 177 | 3 | C-2 | 40 | 1.20 | 3,103,000 | 3.8 | 94.6 |
| 178 | 3 | C-3 | 70 | 1.71 | 2,066,000 | 5.6 | 118.1 |
| 179 | 4 | C-2 | 40 | 37.94 | 567,000 | 4.6 | 130.3 |
| 180 | 4 | C-3 | 70 | 75.10 | 202,000 | 3 | 108.5 |
| 181 | 4 | C-4 | 130 | 47.57 | 178,000 | 3.2 | 100.2 |
| 182 | 7 | C-2 | 40 | 1.23 | 1,526,000 | 5.8 | 117.3 |
| 183 | 7 | C-3 | 70 | 1.32 | 1,041,000 | 3.9 | 119.3 |
| 184 | 8 | C-2 | 40 | 8.24 | 1,204,000 | 4.4 | 116.6 |
| 185 | 8 | C-3 | 70 | 4.07 | 1,337,000 | 5.3 | 117.4 |
| 186 | 6 | C-2 | 40 | 14.23 | 46,000 | 5.9 | 140.3 |
| 187 | 6 | C-3 | 70 | 93.44 | 18,000 | 3.5 | 198.2 |
| 188 | 6 | C-4 | 130 | 19.12 | 114,000 | 6.3 | 119 |
| 189 | 12 | C-3 | 70 | 1.71 | 1,636,000 | 19.9 | 121.8 |
| 190 | 15 | C-2 | 40 | 1.65 | 1,926,000 | 4.5 | 116.5 |
| 191 | 15 | C-3 | 70 | 1.05 | 1,061,000 | 26.7 | 112.9 |
| 192 | 10 | C-2 | 40 | 4.08 | 417,000 | 115.3 | 119.2 |
| 193 | 18 | C-2 | 40 | 0.99 | 1,170,000 | 8.4 | 114.1 |
| 194 | 18 | C-3 | 70 | 1.47 | 530,000 | 7.7 | 116 |
| 195 | 30 | C-2 | 40 | 5.79 | 1,517,000 | 2.4 | 97.5 |
| 196 | 22 | C-2 | 40 | 6.08 | 973,000 | 17.7 | 113.6 |
| 197 | 22 | C-3 | 70 | 61.03 | 603,000 | 23 | 118.2 |
| 198 | 22 | C-4 | 130 | 0.96 | 460,000 | 6.7 | 124 |
| 199 | 25 | C-2 | 40 | 8.29 | 157,000 | 4.2 | 123.8 |
| 200 | 25 | C-3 | 70 | 33.76 | 133,000 | 3 | 124.2 |
| 201 | 27 | C-2 | 40 | 14.46 | 489,000 | 4 | 123.8 |
| 202 | 26 | C-2 | 40 | 19.89 | 156,000 | 3.4 | 128.1 |
| 203 | 26 | C-3 | 70 | 46.80 | 117,000 | 2.7 | 124.7 |
| 204 | 28 | C-2 | 40 | 31.26 | 376,000 | 4.4 | 123 |
| 205 | 28 | C-3 | 70 | 42.77 | 967,000 | 2.5 | 121.6 |
| 206 | 24 | C-2 | 40 | 4.89 | 749,000 | 21 | 121.4 |
| 207 | 24 | C-3 | 70 | 3.72 | 943,000 | 5.4 | 122 |

*×10$^6$ g polymer/mol-cat/hr

TABLE 5

Copolymerization of ethylene-hexene, co-catalyst TIBA/CB

| Example | complex | Polymerization condition | temperature, °C. | activity* | Mw | Mw/Mn | Tm, °C. |
|---|---|---|---|---|---|---|---|
| 208 | 3 | D-2 | 40 | 1.89 | 3,187,000 | 4.3 | 118.5 |
| 209 | 3 | D-3 | 70 | 2.01 | 2,470,000 | 10.3 | 119.1 |
| 210 | 4 | D-2 | 40 | 50.69 | 561,000 | 4.1 | 116.3 |
| 211 | 4 | D-3 | 70 | 70.02 | 208,000 | 3.6 | 111.0 |
| 212 | 4 | D-4 | 130 | 56.70 | 304,000 | 8 | 107.8 |
| 213 | 7 | D-2 | 40 | 0.99 | 1,766,000 | 8.5 | 119.0 |
| 214 | 8 | D-2 | 40 | 6.58 | 1,537,000 | 5.4 | 115.8 |
| 215 | 8 | D-3 | 70 | 3.27 | 1,569,000 | 9.1 | 118.5 |
| 216 | 6 | D-2 | 40 | 75.52 | 97,000 | 15.6 | 119.0 |
| 217 | 6 | D-3 | 70 | 147.27 | 49,000 | 7.1 | 119.6 |
| 218 | 6 | D-4 | 130 | 1.26 | 58,000 | 8.6 | 118.2 |
| 219 | 12 | D-3 | 70 | 1.26 | 1,649,000 | 8.1 | 123.2 |
| 220 | 15 | D-2 | 40 | 1.11 | 1,975,000 | 5.9 | 115.0 |
| 221 | 15 | D-3 | 70 | 0.90 | 1,174,000 | 20 | 116.4 |
| 222 | 10 | D-2 | 40 | 3.00 | 696,648 | 14.2 | 120.9 |
| 223 | 10 | D-3 | 70 | 3.81 | 5,000 | 3 | 121.7 |
| 224 | 18 | D-2 | 40 | 1.29 | 1,363,000 | 10.5 | 115.8 |
| 225 | 18 | D-3 | 70 | 1.23 | 700,000 | 9.9 | 117.3 |
| 226 | 22 | D-2 | 40 | 19.49 | 1,132,000 | 13.3 | 115.2 |
| 227 | 22 | D-3 | 70 | 78.06 | 548,000 | 11.5 | 113.2 |
| 228 | 22 | D-4 | 130 | 1.17 | 564,000 | 6.3 | 123.3 |
| 229 | 25 | D-2 | 40 | 11.39 | 167,000 | 4.4 | 130.3 |
| 230 | 25 | D-3 | 70 | 27.03 | 138,000 | 3 | 124.2 |
| 231 | 27 | D-2 | 40 | 29.16 | 520,000 | 3.9 | 125.7 |
| 232 | 26 | D-2 | 40 | 27.44 | 152,000 | 3.7 | 126.1 |
| 233 | 26 | D-3 | 70 | 55.61 | 108,000 | 2.8 | 125.3 |
| 234 | 28 | D-2 | 40 | 107.08 | 346,000 | 4.4 | 123.6 |
| 235 | 28 | D-3 | 70 | 28.23 | 232,000 | 3.8 | 121.3 |

TABLE 5-continued

Copolymerization of ethylene-hexene, co-catalyst TIBA/CB

| Example | complex | Polymerization condition | temperature, °C. | activity* | Mw | Mw/Mn | Tm, °C. |
|---|---|---|---|---|---|---|---|
| 236 | 24 | D-2 | 40 | 5.07 | 773,000 | 22.1 | 124.0 |
| 237 | 24 | D-3 | 70 | 3.09 | 969,000 | 3.9 | 121.7 |

*×10$^6$ g polymer/mol-cat/hr

Example 238

An autoclave was charged with toluene (5.0 mL) under nitrogen and the temperature was stabilized at 40° C. It was the charged with propylene until it was pressurized to 0.20 MPa, and the pressure was stabilized. Thereto a solution of triisobutylaluminum in hexane (40 µL, 1.0 M, Kanto Kagaku), triphenylmethyl tetrakis(pentafluorophenyl)borate (0.30 µmol) and N-[2-(1-indenyl)phenylmethyl]-N-phenylamido titanium dichloride (0.10 g µmol) were added, and polymerization was carried out for 20 min. As a result of polymerization, a polymer having the molecular weight (Mw) of 712,000, the molecular weight distribution (Mw/Mn) of 3.7 and Tm of 127.7° C. was produced in an amount of 4.41×10$^6$ g per 1 mol of titanium and per an hour.

Example 239

An autoclave was charged with toluene (5.0 mL) under nitrogen and the temperature was stabilized at 40° C. It was then charged with propylene until it was pressurized to 0.20 MPa, and the pressure was stabilized. Thereto a solution of triisobutylaluminum in hexane (40 µL, 1.0 M, Kanto Kagaku), dimethylanilinium tetrakis(pentafluorophenyl)borate (0.30 µmol) and N-[2-(1-indenyl)phenylmethyl]-N-phenylamido titanium dichloride (0.10 µmol) were added, and polymerization was carried out for 20 min. As a result of polymerization, a polymer having the molecular weight (Mw) of 678,000, the molecular weight distribution (Mw/Mn) of 3.8 and Tm of 135.6° C. was produced in an amount of 2.10×10$^6$ g per 1 mol of titanium and per an hour.

INDUSTRIAL APPLICABILITY

According to the present invention, a transition metal complex can be obtained using a ligand intermediate that can be produced and handled more easily, without using a silicon compound that is sensitive to moisture and difficult to be handled as a key intermediate. Since said transition metal complex is useful as a catalyst component for production of various olefin polymers, the present invention especially makes a significant contribution to the art of production of olefin polymers.

The invention claimed is:

1. A transition metal complex represented by the formula (I):

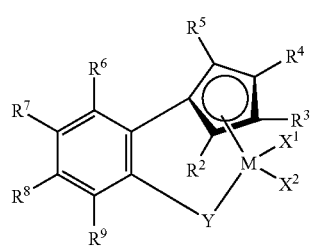

wherein M represents a Group 4 transition metal;
—Y— represents
(c): —C(R$^1$)=A$^1$- or
(d):

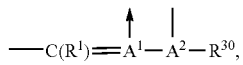

wherein A$^1$ and A$^2$ coordinate to M;
A$^1$ and A$^2$ each represent a Group 15 element;
R$^1$ represents a hydrogen atom,
an optionally substituted C$_{1-10}$ alkyl group,
an optionally substituted C$_{6-20}$ aryl group or
an optionally substituted C$_{7-20}$ aralkyl group;
R$^{30}$ represents a hydrogen atom,
an optionally substituted C$_{1-10}$ alkyl group,
an optionally substituted C$_{6-20}$ aryl group,
an optionally substituted C$_{7-20}$ aralkyl group or
a silyl group optionally substituted with optionally substituted C$_{1-20}$ hydrocarbon group(s);
R$^2$, R$^3$, R$^4$ and R$^5$ are the same or different and each represents a hydrogen atom,
an optionally substituted C$_{1-10}$ alkyl group,
an optionally substituted C$_{1-10}$ alkoxy group,
an optionally substituted C$_{6-20}$ aryl group,
an optionally substituted C$_{6-20}$ aryloxy group,
an optionally substituted C$_{7-20}$ aralkyl group,
an optionally substituted C$_{7-20}$ aralkyloxy group,
a silyl group substituted with optionally substituted C$_{1-20}$ hydrocarbon group(s), or
a C$_{1-20}$ hydrocarbon-substituted amino group;
R$^6$, R$^7$, R$^8$ and R$^9$ are the same or different and each represents a hydrogen atom, a halogen atom,
an optionally substituted C$_{1-10}$ alkyl group,
an optionally substituted C$_{1-10}$ alkoxy group,
an optionally substituted C$_{6-20}$ aryl group,
an optionally substituted C$_{6-20}$ aryloxy group,
an optionally substituted C$_{7-20}$ aralkyl group,
an optionally substituted C$_{7-20}$ aralkyloxy group,
a silyl group substituted with optionally substituted C$_{1-20}$ hydrocarbon group(s), or
a C$_{1-20}$ hydrocarbon-substituted amino group;
X$^1$ and X$^2$ are the same or different and each represents a hydrogen atom, a halogen atom,
an optionally substituted C$_{1-10}$ alkyl group,
an optionally substituted C$_{1-10}$ alkoxy group,
an optionally substituted C$_{6-20}$ aryl group,
an optionally substituted C$_{6-20}$ aryloxy group,
an optionally substituted C$_{7-20}$ aralkyl group,
an optionally substituted C$_{7-20}$ aralkyloxy group or
a C$_{1-20}$ hydrocarbon-substituted amino group, or $X^1$ and $X^2$, the adjacent $R^2$, $R^3$, $R^4$ and $R^5$ or the adjacent $R^6$, $R^7$, $R^8$ and $R^9$ may be linked to each other to form a ring.

2. The transition metal complex according to claim 1, wherein $R^1$ represents a hydrogen atom,
a $C_{1-10}$ alkyl group optionally substituted with halogen atom(s),
a $C_{6-20}$ aryl group optionally substituted with halogen atom(s) or
a $C_{7-20}$ aralkyl group optionally substituted with halogen atom(s);
$R^{30}$ represents a hydrogen atom,
a $C_{1-10}$ alkyl group optionally substituted with halogen atom(s),
a $C_{6-20}$ aryl group optionally substituted with halogen atom(s),
a $C_{7-20}$ aralkyl group optionally substituted with halogen atom(s) or
a silyl group which is optionally substituted with $C_{1-20}$ hydrocarbon(s) optionally substituted with halogen atom(s);
$R^2$, $R^3$, $R^4$ and $R^5$ are the same or different and each represents a hydrogen atom,
a $C_{1-10}$ alkyl group optionally substituted with halogen atom(s),
a $C_{1-10}$ alkoxy group optionally substituted with halogen atom(s),
a $C_{6-20}$ aryl group optionally substituted with halogen atom(s),
a $C_{6-20}$ aryloxy group optionally substituted with halogen atom(s),
a $C_{7-20}$ aralkyl group optionally substituted with halogen atom(s),
a $C_{7-20}$ aralkyloxy group optionally substituted with halogen atom(s),
a silyl group which is substituted with $C_{1-20}$ hydrocarbon group(s) optionally substituted with halogen atom(s) or
a $C_{1-20}$ hydrocarbon-substituted amino group;
$R^6$, $R^7$, $R^8$ and $R^9$ are the same or different and each represents a hydrogen atom, a halogen atom,
a $C_{1-10}$ alkyl group optionally substituted with halogen atom(s),
a $C_{1-10}$ alkoxy group optionally substituted with halogen atom(s),
a $C_{6-20}$ aryl group optionally substituted with halogen atom(s),
a $C_{6-20}$ aryloxy group optionally substituted with halogen atom(s),
a $C_{7-20}$ aralkyl group optionally substituted with halogen atom(s),
a $C_{7-20}$ aralkyloxy group optionally substituted with halogen atom(s),
a silyl group which is substituted with $C_{1-20}$ hydrocarbon group(s) optionally substituted with halogen atom(s), or
a $C_{1-20}$ hydrocarbon-substituted amino group;
$X^1$ and $X^2$ are the same or different and each represents a hydrogen atom, a halogen atom,
a $C_{1-10}$ alkyl group optionally substituted with halogen atom(s),
a $C_{1-10}$ alkoxy group optionally substituted with halogen atom(s),
a $C_{6-20}$ aryl group optionally substituted with halogen atom(s),
a $C_{6-20}$ aryloxy group optionally substituted with halogen atom(s),
a $C_{7-20}$ aralkyl group optionally substituted with halogen atom(s),
a $C_{7-20}$ aralkyloxy group optionally substituted with halogen atom(s), or
a $C_{1-20}$ hydrocarbon-substituted amino group.

3. The transition metal complex according to claim 1, wherein $R^1$ and $R^{30}$ are the same or different and each represents a hydrogen atom,
a $C_{1-10}$ alkyl group,
a $C_{6-20}$ aryl group or
a $C_{7-20}$ aralkyl group;
$R^2$, $R^3$, $R^4$ and $R^5$ are the same or different and each represents a hydrogen atom,
a $C_{1-10}$ alkyl group,
a $C_{1-10}$ alkoxy group,
a $C_{6-20}$ aryl group,
a $C_{6-20}$ aryloxy group,
a $C_{7-20}$ aralkyl group,
a $C_{7-20}$ aralkyloxy group,
a silyl group substituted with $C_{1-20}$ hydrocarbon group(s) or
a $C_{1-20}$ hydrocarbon-substituted amino group;
$R^6$, $R^7$, $R^8$ and $R^9$ are the same or different and each represents a hydrogen atom, a halogen atom,
a $C_{1-10}$ alkyl group,
a $C_{1-10}$ alkoxy group,
a $C_{6-20}$ aryl group,
a $C_{6-20}$ aryloxy group,
a $C_{7-20}$ aralkyl group,
a $C_{7-20}$ aralkyloxy group,
a silyl group substituted with $C_{1-20}$ hydrocarbon group(s) or
a $C_{1-20}$ hydrocarbon-substituted amino group;
$X^1$ and $X^2$ are the same or different and each represents a hydrogen atom, a halogen atom,
a $C_{1-10}$ alkyl group,
a $C_{1-10}$ alkoxy group,
a $C_{6-20}$ aryl group,
a $C_{6-20}$ aryloxy group,
a $C_{7-20}$ aralkyl group,
a $C_{7-20}$ aralkyloxy group or
a $C_{1-20}$ hydrocarbon-substituted amino group.

4. The transition metal complex according to claim 1 or 2, wherein M represents Ti or Zr.

5. The transition metal complex according to claim 1, represented by the formula (I-3), which is the formula (I) wherein —Y— is (d):

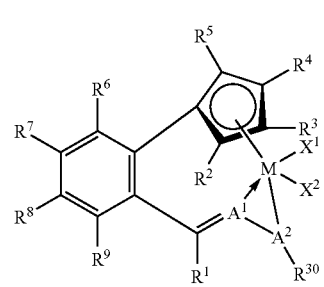

(I-3)

wherein $R^1, R^2, R^3, R^4, R^5, R^6, R^7, R^8, R^9, R^{30}, A^1, A^2, X^1, X^2$ and M have the same meanings as defined in the formula (I).

6. The transition metal complex according to claim 5, wherein $A^1$ and $A^2$ in the formula (I-3) are each a nitrogen atom.

7. The transition metal complex according to claim 1, represented by the formula (I-4), which is the formula (I) wherein —Y— is (c):

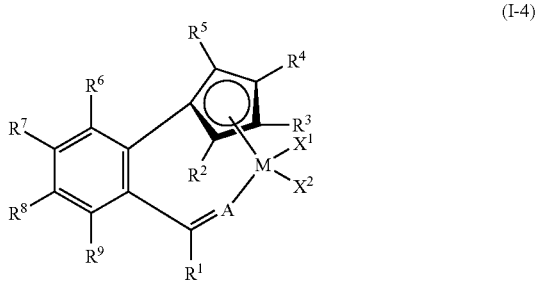
(I-4)

wherein $R^1$, $R^2$, $R^3$, $R^4$, $R^5$, $R^6$, $R^7$, $R^8$, $R^9$, A, $X^1$, $X^2$ and M have the same meanings as defined in the formula (I).

8. The transition metal complex according to claim 7, wherein A in the formula (I-4) is a nitrogen atom.

9. The transition metal complex according to claim 5 or 7, wherein $R^2$, $R^3$, $R^4$ and $R^5$ are the same or different and each represents a hydrogen atom or a $C_{1-5}$ alkyl group.

10. The transition metal complex according to claim 5 or 7, wherein $X^1$ and $X^2$ are the same or different and each represents a halogen atom, a $C_{1-10}$ alkyl group, a $C_{7-20}$ aralkyl group, a $C_{6-20}$ aryl group or a $C_{1-20}$ hydrocarbon-substituted amino group.

11. The transition metal complex according to claim 10, wherein $X^1$ and $X^2$ are each a halogen atom or a $C_{1-10}$ hydrocarbon-substituted amino group, $R^2$, $R^3$, $R^4$ and $R^5$ are each a methyl group, and $R^6$, $R^7$, $R^8$ and $R^9$ are each a hydrogen atom.

12. A catalyst for olefin polymerization comprising the transition metal complex of any one of claims 1, 5 and 7 in combination with the following compound (A), wherein (A) represents at least one compound selected from the following compounds (A1) to (A3):
(A1): an organic aluminum compound represented by the formula $E1_a Al(Z)_{(3-a)}$,
(A2): cyclic aluminoxane having the structure represented by the formula $\{-Al(E2)-O-\}_b$,
(A3): linear aluminoxane having the structure represented by the formula $E3\{-Al(E3)-O-\}_c Al(E3)_2$,
wherein E1 to E3 are the same or different and each represents a C1-8 hydrocarbon group;
Z is the same or different and represents a hydrogen atom or a halogen atom;
a is 1, 2 or 3, b is an integer of not less than 2, and c is an integer of not less than 1.

13. The catalyst for olefin polymerization according to claim 12, which further comprises (B), wherein (B) represents at least one compound selected from the following compounds (B1) to (B3):
(B1): a boron compound represented by the formula $BQ_1Q_2Q_3$,
(B2): a boron compound represented by the formula $Z^+(BQ_1Q_2Q_3Q_4)^-$,
(B3): a boron compound represented by the formula $(L-H)^+(BQ_1Q_2Q_3Q_4)^-$,
wherein B is a boron atom in a trivalent valence state;
Q1 to Q4 are the same or different and each represents a halogen atom,
a $C_{1-20}$ hydrocarbon group,
a $C_{1-20}$ halogenated hydrocarbon group,
a silyl group substituted with $C_{1-20}$ hydrocarbon group(s),
a $C_{1-20}$ alkoxy group or
an amino group substituted with two $C_{2-20}$ hydrocarbon groups;
L-H represents a Brønsted acid;
Z are the same or different and represents a hydrogen atom or a halogen atom.

14. A process for producing an olefin polymer, which comprises polymerizing olefin using the catalyst for olefin polymerization according to claim 12.

15. A process for producing the transition metal complex represented by the formula (I) according to claim 1, wherein $X^1$ and $X^2$ are as defined below, which comprises reacting a substituted cyclopentadiene compound represented by the formula (II)

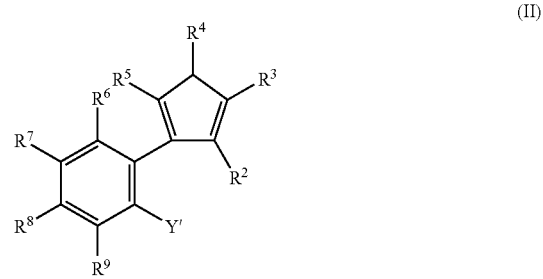
(II)

wherein —Y' represents
(c'): $-C(R^1)=A^1-H$ or
(d'):

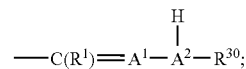

$R^1$, $R^2$, $R^3$, $R^4$, $R^5$, $R^6$, $R^7$, $R^8$, $R^9$, $R^{20}$, $R^{30}$, A, $A^1$ and $A^2$ have the same meanings as defined in claim 1;
provided that 1) when —Y' represents (a'), neither $R^2$ and $R^3$ nor $R^4$ and $R^5$ are linked to each other and taken together with the cyclopentadiene ring to form a fluorene ring or an indenyl ring, and 2) the compound represented by the formula (II) is not 2-(4-methoxyinden-1-yl)benzonitrile,
with a transition metal compound represented by the formula (III)

$$MX^1X^2X^3X^4 \quad (III)$$

wherein M represents a Group 4 transition metal;
$X^1$, $X^2$, $X^3$ and $X^4$ are the same or different and each represents a hydrogen atom,
a $C_{1-10}$ alkyl group,
a $C_{1-10}$ alkoxy group,
a $C_{6-20}$ aryl group,
a $C_{6-20}$ aryloxy group,
a $C_{7-20}$ aralkyl group,
a $C_{7-20}$ aralkyloxy group or
a $C_{1-20}$ hydrocarbon-substituted amino group.

16. The process for producing the transition metal complex represented by the formula (I) according to claim 15, wherein $X^1$, $X^2$, $X^3$ and $X^4$ in the formula (III) each represent a $C_{1-5}$ hydrocarbon-substituted amino group.

17. A process for producing an olefin polymer, which comprises polymerizing olefin using the catalyst for olefin polymerization according to claim 13.

18. A process for producing the transition metal complex represented by the formula (I) according to claim 1 wherein at least one of $X^1$ and $X^2$ is halogen, which comprises reacting a transition metal complex represented by the formula (I) according to claim 1 wherein at least one of $X^1$ and $X^2$ is a $C_{1-20}$ hydrocarbon-substituted amino group, with a halogen compound selected from a chlorosilane compound and hydrogen chloride.

* * * * *